United States Patent
Suzuki et al.

(10) Patent No.: US 7,064,124 B2
(45) Date of Patent: Jun. 20, 2006

(54) NF-κB INHIBITOR CONTAINING SUBSTITUTED BENZOIC ACID DERIVATIVE AS ACTIVE INGREDIENT

(75) Inventors: Kenji Suzuki, Osaka (JP); Yoichi Nunokawa, Toyonaka (JP); Naohisa Ogou, Ibaraki (JP)

(73) Assignees: Daiichi Suntory Pharma Co., Ltd., Tokyo (JP); Daiichi Suntory Biomedical Research Co., Ltd., Osaka (JP)

( * ) Notice: Subject to any disclaimer, the term of this patent is extended or adjusted under 35 U.S.C. 154(b) by 355 days.

(21) Appl. No.: 10/296,810

(22) PCT Filed: Mar. 27, 2002

(86) PCT No.: PCT/JP02/03017

§ 371 (c)(1),
(2), (4) Date: Nov. 27, 2002

(87) PCT Pub. No.: WO02/076918

PCT Pub. Date: Oct. 3, 2002

(65) Prior Publication Data

US 2004/0122244 A1 Jun. 24, 2004

(30) Foreign Application Priority Data

Mar. 27, 2001 (JP) ........................... 2001-091003

(51) Int. Cl.
| A61K 31/535 | (2006.01) |
| A61K 31/445 | (2006.01) |
| C07D 413/00 | (2006.01) |
| C07C 69/76 | (2006.01) |
| C07C 50/04 | (2006.01) |

(52) U.S. Cl. .................. 514/239.5; 514/256; 514/317; 514/318; 514/319; 514/326; 514/330; 514/336; 514/354; 514/355; 514/396; 514/397; 514/399; 514/532; 514/568; 514/688; 514/689; 544/111; 544/124; 544/125; 544/128; 544/129; 546/192; 546/193; 546/194; 546/208; 546/218; 546/221; 546/268.1; 546/276.4; 546/281.7; 546/289; 546/314; 552/293; 552/307; 552/309; 552/310; 560/8; 560/55; 560/57

(58) Field of Classification Search .............. 552/293, 552/309, 310, 307; 546/289, 192, 194, 208, 546/218, 221, 268.1, 276.4, 281.7, 314; 560/8, 560/55, 57; 544/111, 124, 125, 128, 129; 514/231.2, 231.5, 239.5, 256, 317, 318, 319, 514/326, 330, 336, 354, 355, 396, 397, 399, 514/532, 568, 688, 689

See application file for complete search history.

(56) References Cited

FOREIGN PATENT DOCUMENTS

| JP | 62286949 | 12/1987 |
| JP | 04226937 | 8/1992 |
| JP | 07291859 | 11/1995 |
| JP | 0955372 | 11/1999 |
| WO | 99/48491 | 9/1999 |

OTHER PUBLICATIONS

Lewis Mander et al, "Studies on Reductive Alkylation. Regiocontrolled Synthesis of Anthracene Derivatives," Aust. J. Chem., 34, 1981, pp. 2249–2252.

*Primary Examiner*—Cecilia J. Tsang
*Assistant Examiner*—Raymond Covington
(74) *Attorney, Agent, or Firm*—Burns, Doane, Swecker & Mathis, LLP

(57) ABSTRACT

A NF-κB inhibitor represented by the following formula (I) is provided:

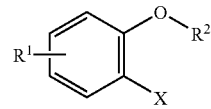

(I)

12 Claims, 4 Drawing Sheets

NF-κB INHIBITOR CONTAINING SUBSTITUTED BENZOIC ACID DERIVATIVE AS ACTIVE INGREDIENT

FIELD OF INVENTION

The present invention relates to a novel substituted benzoic acid derivative and, more specifically, the present invention relates to a preventive or therapeutic agent for diseases caused by the activation of NF-κB, which is an NF-κB inhibitor containing a substituted benzoic acid derivative or a hydroquinone form or a pharmaceutically acceptable salt thereof, as an active ingredient.

BACKGROUND ART

NF-κB is a protein that regulates the gene expression and is one of the so-called transcription factors. When normal cells are stimulated by an inflammatory cytokine such as interleukin-1 (IL-1) and TNF-α or by lipopolysaccharide, or ultraviolet rays, NF-κB is activated and migrates from the cytosol into the nucleus to bind to its specific nucleotide sequences on the genome DNA and thereby participate in the expression of various genes (see, T. S. Blackwell and J. W. Christman, *Am. J. Respir. Cell. Mol. Biol.,* 17, 3–9 (1997)).

Among the genes of which the expression is under the control of NF-κB, many genes participate in an immunoinflammatory reaction, such as inflammatory cytokines (e.g., IL-1, IL-6, IL-8, TNF-α), cell adhesion molecules (e.g., ICAM-1, VCAM-1, ELAM-1) and inducible NO-synthase (iNOS) (see, T. Collins, M. A. Read, A. S. Neish, M. Z. Whitley, D. Thanos and T. Maniatis, *Faseb. J.,* 899–909 (1995)). Furthermore, the inflammatory cytokine bound to its receptor is known to transduce a signal for activating NF-κB through various pathways and this is considered to make the inflammation worse. As such, in an inflammation, the activation of NF-κB is understood to be a cause or an exacerbation factor of a disease (see, P. A. Baeuerle and V. R. Baichwal, *Adv. Immunol.,* 65, 111–137 (1997)).

In recent years, it has also been reported that HIV, HTLV-1, CMV and adenovirus activate NF-κB in host cells (see, B. J. Dezube, A. B. Pardee, L. A. Beckett, C. M. Ahlers, L. Ecto, J. Allen-Ryan, Z. A. Anisowicz, R. Sager and C. S. Crumpacker, *J. Acquir. Immune Defic. Syndr.,* 5, 1099–1104 (1992); G. Nabel and D. Baltimore, *Nature* 326, 711–713 (1987); F. Fazely, B. J. Dezube, J. Allen-Ryan, A. B. Pardee and R. M. Ruprecht, *Blood,* 77, 1653–1656 (1991); and E. Munoz and A. Israel, *Immunobiology,* 193, 128–136 (1995)) and this activation of NF-κB is considered to participate in the self replication or increase of virus in the infected host cell.

Accordingly, the expression and induction of the inflammatory cytokines, the cell adhesion molecules gene and the viruses can be prevented altogether by inhibiting the activation of NF-κB and the NF-κB activation inhibitor is thought to be promising as a therapeutic agent for diseases directly or indirectly caused by the activation of NF-κB, particularly various inflammatory diseases and autoimmune diseases, or as a immunosuppressant or as a therapeutic agent for viral diseases.

At present, many antiinflammatory drugs are clinically used for the purpose of treating osteoarthritis, lumbago, rheumatoid arthritis and the like, however, there has been not found an effective for inhibiting the production of various inflammatory cytokines or the expression of cell adhesion molecules. NSAIDs (non-steroidal antiinflammatory drugs), which are very often used, inhibit cyclooxygenase in the metabolic pathway of arachidonic acid cascade and thereby inhibit the production of prostaglandins, however, in general, they do not directly inhibit the production of cytokines. Steroids inhibit the production of a plurality of cytokines but these are known to bring about grave side effects such as undesired hormone activity, aggravation of infectious diseases, onset of peptic ulcers, and central effect and therefore are not amenable to a long-term administration.

It has also been reported in recent years that antiinflammatory drugs at high doses suppress the activation of NF-κB. (see, N. Auphan, J. A. DiDonato, C. Rosette, A. Helmberg and M. Karin, *Science,* 270, 286–290 (1995); R. E. Shackelford, P. B. Alford, Y. Xue, S. F. Thai, D. O. Adams and S. Pizzo, *Mol. Phamacol.,* 52, 421–429 (1997); and V. Bitko, A. Velazquez, L. Yang, Y. C. Yang and S. Barik, *Virology,* 232, 369–378 (1997)). For example, benzoic acid derivatives such as salicylic acid and aspirin have been reported to inhibit the activation of NF-κB (see, *Science,* 265, 956–959 (1994)), however, insufficient efficacy and side effects due to various pharmacological actions have been pointed out as problems.

Accordingly, development of medicines capable of more specifically inhibiting the activation of NF-κB and having higher safety is required and many researchers are making investigations for NF-κB activation inhibitors.

As the NF-κB activation inhibitors, there have been recently proposed, for example, isocarbazole derivatives (see, Japanese Unexamined Patent Publication (Kokai) Nos. 8-319238 and 2000-169479), isoquinoline derivatives (see, Kokai Nos. 10-87491 and 11-180873), benzoquinone derivatives (see, Kokai Nos. 7-291859 and 11-266872), β-lactam derivatives (see, Kokai No. 11-71278), lignan derivatives (see, Kokai No. 10-175861), benzylidene derivatives (see, PCT/JP98/04774), pyrimidine-5-carboxamide derivatives (see, WO97/09315 and WO97/09325), cyclopentabenzofuran derivatives (see, WO00/08007), benzene derivatives (see, WO00/15603), pyrrolidine dithiocarbonate (PDTC) (see, *Eur. J. Immunol.,* 29, 1890–1900 (1999)), 3-deazaadenosine (DZA) (see, *J. Biol. Chem.,* 274, 27, 18981–18988 (1999)) and 2,2'-bi-1H-pyrrole derivatives (see, *J. Immunol.,* 162, 7102–7109 (1999)).

In many cases, the mechanisms of action inhibiting the activation are not clearly known, however, as for the substances considered to inhibit the activation by antioxidant effects or activities of inhibiting protein phosphorylation, the stability or the specificity seems to be a problem. Furthermore, at present, drugs having a enough potency to inhibit transcription factor NF-κB activation are not found.

On the other hand, Kokai No. 7-291859 discloses the following benzoquinone derivative (A) as an NF-κB activation inhibitor:

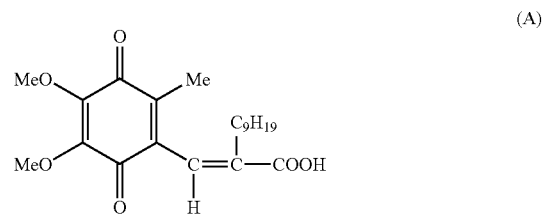

(A)

Also, Kokai No. 11-266872 discloses a novel method for screening substances capable of inhibiting the activation of NF-κB and a substance capable of inhibiting the activation of NF-κB found by the method, the following benzoquinone derivative (B) was described:

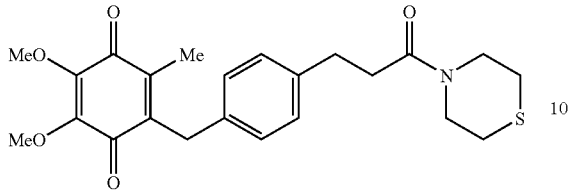

(B)

However, these compounds are not sufficiently high in efficacy as NF-κB activation inhibitors. A substance having a stronger NF-κB inhibitory activity is required.

DISCLOSURE OF THE INVENTION

The present invention provides a preventive and therapeutic agent for diseases caused by the activation of NF-κB such as, for example, diseases caused by the excess production of various inflammation mediators or increase of viruses, by inhibiting the activation of NF-κB. More specifically, the present invention provides a preventive and therapeutic agent for diseases considered caused by the excess production of NO or TNF-α, for example, septic shock, osteoarthritis, rheumatold arthritis, cachexia, multiple organ failure, inflammatory bowel disease, malaria, acquired immune deficiency syndrome, human T-cell leukemia, meningitis, hepatitis, myocarditis, type II diabetes, multiple sclerosis, Behcet disease, systemic lupus erythematosus and ischemic heart disease, and the like.

As a result of extensive investigations on substances capable of inhibiting the activation of NF-κB, the present inventors have found that novel substituted benzoic acid derivatives represented by formula (I), or its hydroquinone forms, or pharmaceutically acceptable salts thereof, strongly inhibit the activation of NF-κB. The present invention has been accomplished based on this finding.

More specifically, the present invention provides novel substituted benzoic acid derivatives represented by the following formula (I):

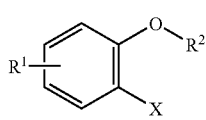

(I)

(wherein
$R^1$ is the following formula (II):

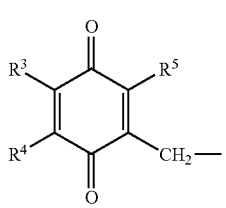

(II)

or the following formula (III):

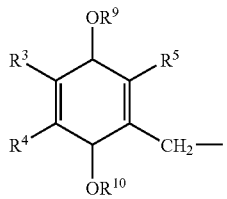

(III)

[wherein $R^3$, $R^4$ and $R^5$ each independently represents a hydrogen atom, an alkyl group having from 1 to 6 carbons or an alkoxy group having from 1 to 6 carbons, and $R^9$ and $R^{10}$ each independently represents a hydrogen atom, an alkyl group having from 1 to 6 carbons or an acyl group having from 2 to 11 carbons);

$R^2$ represents a hydrogen atom, a lower alkyl group having from 1 to 6 carbons, which may be substituted, an aryl group having from 6 to 12 carbons, which may be substituted, a heteroaryl group having from 4 to 11 carbons, which may be substituted, an aralkyl group having from 7 to 14 carbons, which may be substituted, a heteroarylalkyl group having from 5 to 13 carbons, which may be substituted, or an acyl group having from 2 to 11 carbons; and X represents a carboxyl group which may be esterified or amidated], NF-κB inhibitors comprising the novel substituted benzoic acid derivatives or its hydroquinone form or pharmaceutically acceptable salts thereof as active ingredients, and application thereof to a preventive or therapeutic agent for inflammatory diseases, autoimmune diseases and viral diseases, which are used as an inhibitor of gene expression of one or more substances selected from the group consisting of IL-1, TNF-α, IL-2, IL-6, IL-8, iNOS, granulocyte colony-stimulating factor, interferon-γ, ICAM-1, VCAM-1, ELAM-1, major histocompatibility system class I, major histocompatibility system class II, β-2 microglobulin, immunoglobulin light chain, serum amyloid A, angiotensinogen, complement B, complement C4, c-myc, HIV, HTLV-1, SV-40, CMV and adenovirus.

The present invention also provides a preventive or therapeutic agent for diseases caused by the activation of NF-κB, comprising a novel substituted benzoic acid derivative represented by formula (I), or its hydroquinone form, or pharmaceutically acceptable salt thereof, as an active ingredient.

MODE FOR CARRYING OUT THE INVENTION

Figure 1:
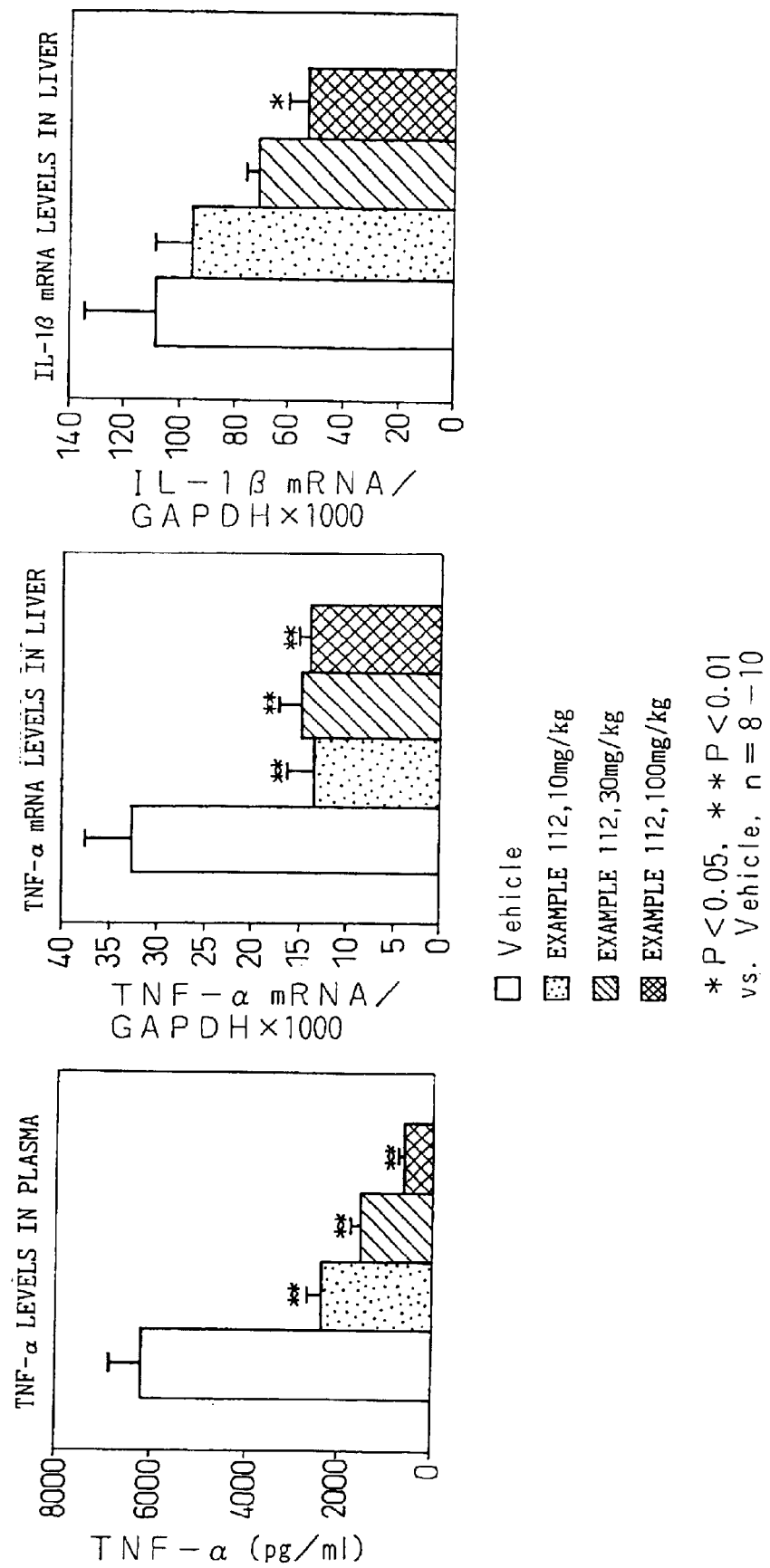
FIG. 1 shows the results when a 7-week-old C3H/HeN female mouse was intraperitoneally administered with GalN/LPS and immediately thereafter, administered with the compound of Example 112, the liver was removed 60 minutes after the stimulation and the TNF-α mRNA levels (center in the Figure) and the IL-1β mRNA levels (right in the Figure) in liver were measured, in addition 90 minutes after the stimulation, blood was collected from the heart and the TNF-α levels (left in the Figure) in plasma were also measured.

When the substituted benzoic acid derivative, as an active ingredient of the present invention, has a benzoquinone ring within the molecule, a corresponding hydroquinone form can be easily obtained by the reduction. Accordingly, in the present invention, a hydroquinone form resulting from the reduction of a benzoquinone ring of a substituted benzoic acid derivative as an active ingredient of the present invention can also be used as an active ingredient of the present invention. The "hydroquinone form" means a compound that is formed by converting an oxo at the 1-position and/or the 4-position of the benzoquinone ring of the benzoquinone derivative of the present invention to a hydroxy group chemically with a catalyst etc., or biochemically with an enzyme etc., or by converting with reduction in vivo and that still has an activity equivalent to that of the benzoquinone derivative.

As for the pharmaceutically acceptable salt for use in the present invention, examples thereof include salts with an inorganic acid such as hydrochloric acid, nitric acid, sulfuric acid, phosphoric acid and hydrobromic acid, an organic acid such as maleic acid, fumaric acid, tartaric acid, lactic acid, citric acid, acetic acid, methanesulfonic acid, p-toluenesulfonic acid, adipic acid, palmitic acid and tannic acid, an inorganic metal such as alkali metal (e.g., lithium, sodium, potassium) and alkali earth metal (e.g., calcium, magnesium), and a basic amino acid such as lysine.

In the formula, $R^1$ represents the following formula (II):

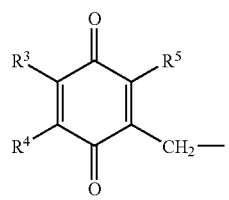

(II)

or the following formula (III):

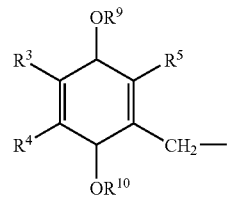

(III)

In the formulae, $R^3$, $R^4$ and $R^5$ each independently represents a hydrogen atom, an alkyl group having from 1 to 6 carbons or an alkoxy group having from 1 to 6 carbons. Preferred examples of the alkyl group include a straight or branched saturated aliphatic hydrocarbon group having from 1 to 6 carbons, such as methyl, ethyl, propyl, isopropyl, n-butyl, sec-butyl, tert-butyl, pentyl, isopentyl, neopentyl, tert-pentyl and n-hexyl, a saturated alicyclic hydrocarbon group such as cyclopropyl, cyclobutyl, cyclopentyl and cyclohexyl, and a saturated alicyclic hydrocarbon group-aliphatic hydrocarbon group such as cyclopropylmethyl, cyclopropylethyl and cyclobutylmethyl. The alkoxy group means a group resulting from bonding of the above-described alkyl group to an oxygen atom and preferred examples of the alkoxy group include a straight or branched alkoxy group having from 1 to 6 carbons, such as methoxy, ethoxy, propoxy, isopropoxy, n-butoxy, isobutoxy, sec-butoxy and tert-butoxy.

$R^9$ and $R^{10}$ each independently represents a hydrogen atom, an alkyl group having from 1 to 6 carbons or an acyl group having from 2 to 11 carbons. Preferred examples of the alkyl group include a straight or branched saturated aliphatic hydrocarbon group having from 1 to 6 carbons, such as methyl, ethyl, propyl, isopropyl, n-butyl, sec-butyl, tert-butyl, pentyl, isopentyl, neopentyl, tert-pentyl and n-hexyl, a saturated alicyclic hydrocarbon group such as cyclopropyl, cyclobutyl, cyclopentyl and cyclohexyl, and a saturated alicyclic hydrocarbon group-aliphatic hydrocarbon group such as cyclopropylmethyl, cyclopropylethyl and cyclobutylmethyl. Preferred examples of the acyl group include an acetyl group, a propanoyl group, a butanoyl group, a cyclopropylcarbonyl group, a cyclopentylcarbonyl group, a cyclohexylcarbonyl group, a benzoyl group, a 2-pyridinecarbonyl group, a 3-pyridinecarbonyl group and a 4-pyridinecarbonyl group.

$R^2$ represents a hydrogen atom, a lower alkyl group having from 1 to 6 carbons, which may be substituted, an aryl group having from 6 to 12 carbons, which may be substituted, a heteroaryl group having from 4 to 11 carbons, which may be substituted, an aralkyl group having from 7 to 14 carbons, which may be substituted, a heteroarylalkyl group having from 5 to 13 carbons, which may be substituted, or an acyl group having from 2 to 11 carbons.

In the present invention, specific examples of the substituent for a group "which may be substituted" include an aryl group, a heteroaryl group, a hydroxy group, an alkoxy group, an acyloxy group, a carboxyl group, an alkoxycarbonyl group, an aryloxycarbonyl group, a carbamoyl group which may be substituted, an amino group which may be substituted, a cyano group and a halogen atom.

Accordingly, preferred examples of the alkyl group include those described above and preferred examples of the substituted lower alkyl group having from 1 to 6 carbons include a hydroxymethyl group, an alkoxymethyl group, an aminomethyl group, a mono- or di-substituted aminomethyl group (e.g., N-methylaminomethyl, N,N-dimethylaminomethyl), a cyanomethyl group, a carboxymethyl group, a methoxycarbonylmethyl group, an ethoxycarbonylmethyl group and a carbamoylmethyl group.

Preferred examples of the aryl group having from 6 to 12 carbons, which may be substituted, include a phenyl group, a 4-methoxyphenyl group, a 3-methoxyphenyl group, a 2-methoxyphenyl group, a 3,4-dimethoxyphenyl group, a 3,4,5-trimethoxyphenyl group, a 4-trifluoromethylphenyl group, a 4-morpholinophenyl group, a 4-cyanophenyl group, a 4-chlorophenyl group, a 4-nitrophenyl group and a 1-naphthyl group.

Preferred examples of the heteroaryl group having from 4 to 11 carbons, which may be substituted, include a 2-pyridyl group, a 3-pyridyl group, a 4-pyridyl group, a 2-furanyl group, a 2-thienyl group, a 2-pyrimidinyl group, a 2-quinolyl group and a 3-isoquinolyl group.

Preferred examples of the aralkyl group having from 7 to 14 carbons, which may be substituted, include a benzyl group, a 4-nitrobenzyl group, a 3-nitrobenzyl group, a 4-methoxybenzyl group, a 3-methoxybenzyl group, a 4-chlorobenzyl group, a 2-phenethyl group and a 3-phenylpropyl group.

Preferred examples of the heteroarylalkyl group having from 5 to 13 carbons, which may be substituted, include a 4-pyridylmethyl group, a 3-pyridylmethyl group, a 2-pyridylmethyl group, a 2-(pyridin-4-yl)ethyl group, a 2-(pyridin-3-yl)ethyl group, a 2-quinolylmethyl group and a 3-isoquinolylmethyl group.

Preferred examples of the acyl group having from 2 to 11 carbons include a straight or branched alkylcarbonyl group having from 2 to 11 carbons, an arylcarbonyl group having from 7 to 11 carbons, which may be substituted, and a heteroarylcarbonyl group having from 4 to 10 carbons, which may be substituted. In the arylcarbonyl group, the aryl group which may be substituted indicates an aromatic hydrocarbon group such as phenyl, naphthyl and indenyl, and in the heteroarylcarbonyl group, the heteroaryl group which may be substituted indicates an aromatic heterocyclic group such as 2-pyridyl, 3-pyridyl and 2-pyrimidyl (in this case, the aromatic ring may be substituted by one or two substituent(s) selected from a lower alkyl group such as methyl, ethyl and propyl, an alkoxy group such as methoxy and ethoxy, a halogen atom such as chlorine atom, fluorine atom, and a carboxyl group which may be esterified or amidated). Preferred examples thereof include an acetyl group, a propanoyl group, a butanoyl group, a pentanoyl group, a benzoyl group, a p-chlorobenzoyl group, a nicotinoyl group, an isonicotinoyl group and a picolinoyl group.

$R^2$ is preferably a hydrogen atom, a methyl group, an isopropyl group, a phenyl group, a 3-methoxyphenyl group, a 3-pyridyl group, a 4-pyridyl group, a benzyl group, a 3-pyridylmethyl group, a 4-pyridylmethyl group, an acetyl group, a carboxymethyl group, a methoxycarbonylmethyl group or a tert-butoxycarbonylmethyl group.

X represents a carboxyl group which may be esterified or amidated. Preferred examples of the carboxyl group which may be esterified or amidated include a group —COOR$^6$ (wherein R$^6$ represents a hydrogen atom, an alkyl group having from 1 to 6 carbons, which may be substituted, or an aralkyl group having from 7 to 14 carbons, which may be substituted), a group —CONR$^7$R$^8$ (wherein R$^7$ and R$^8$ each independently represents a hydrogen atom, an alkyl group having from 1 to 6 carbons, which may be substituted, an aryl group having from 6 to 12 carbons, which may be substituted, a heteroaryl group having from 4 to 11 carbons, which may be substituted, an aralkyl group having from 7 to 14 carbons, which may be substituted, or a heteroarylalkyl group having from 5 to 13 carbons, which may be substituted, or R$^7$ and R$^8$, together with the nitrogen atom to which they are attached, represent a heterocyclic ring which may further contain a nitrogen atom, an oxygen atom, and or a sulfur atom or may be condensed) and a group —CONR$^7$R$^8$ (wherein R$^7$ and R$^8$, together with nitrogen atom to which they are attached represent a 5- to 8-membered nitrogen-containing heterocyclic ring which may contain from 1 to 3 heteroatoms selected from the group consist of a nitrogen atom, an oxygen atom and a sulfur atom, in addition to the carbon atom and nitrogen atom which may be substituted, and the carbon atom or sulfur atom on the ring may be converted into an oxide form).

Specific preferred examples of the substituents $R^6$, $R^7$ and $R^8$ in these functional groups include the following. Preferred examples of the alkyl group having from 1 to 6 carbons include a straight or branched saturated aliphatic hydrocarbon group such as methyl, ethyl, propyl, isopropyl, butyl, isobutyl, sec-butyl, tert-butyl, pentyl, isopentyl, neopentyl and hexyl, a saturated alicyclic hydrocarbon group such as cyclopropyl, cyclobutyl, cyclopentyl and cyclohexyl, and a saturated alicyclic hydrocarbon group-aliphatic hydrocarbon group such as cyclopropylmethyl, cyclopropylethyl, cyclobutylmethyl and cyclopentylmethyl.

Preferred examples of the substituted alkyl group having from 1 to 6 carbons include an alkyl group substituted by a group selected from the group consisting of a) an aryl group such as phenyl and naphthyl (in this case, the aromatic ring may be substituted by one or two substituent(s) selected from an alkyl group such as methyl, ethyl and propyl, a halogen atom such as chlorine atom and fluorine atom, and a carboxyl group which may be esterified or amidated), b) a heteroaryl group such as 2-pyridyl, 3-pyridyl and 2-pyrimidinyl, c) a carboxyl group which may be esterified or amidated, d) a hydroxyl group, e) an alkoxy group, f) an amino group which may be substituted and g) a cyano group. Particularly preferred specific examples thereof include a carboxymethyl group, a methoxycarbonylmethyl group, a carboxyethyl group, a carbamoylmethyl group, a 2-hydroxyethyl group, a 3-hydroxypropyl group, a 4-hydroxybutyl group, a 2-(diethylamino)ethyl group, a cyanomethyl group and a cyanoethyl group.

Preferred examples of the aralkyl group having from 7 to 14 carbons, which may be substituted, include a benzyl group, a 4-nitrobenzyl group, a 3-nitrobenzyl group, a 4-methoxybenzyl group, a 3-methoxybenzyl group, a 4-chlorobenzyl group, a 2-phenethyl group and a 3-phenylpropyl group.

Preferred examples of the aryl group having from 6 to 12 carbons, which may be substituted, include an aromatic hydrocarbon group such as phenyl, naphthyl and indenyl. In this case, the aromatic ring may be substituted by one, two or three substituent(s) selected from an alkyl group which may be substituted, such as methyl, ethyl, propyl, trifluoromethyl and cyanomethyl, an alkoxy group which may be substituted, such as methoxy, ethoxy, isopropoxy and trifluoromethoxy, a hydroxyl group, a nitro group, an amino group which may be substituted, such as amino, N-methylamino, N,N-dimethylamino, morpholino and alkoxycarbamoyl, a trifluoromethanesulfonyl group, a heterocyclic ring such as imidazol-1-yl and 1H-pyrazol-3-yl, a halogen atom such as chlorine atom and fluorine atom, and a carboxyl group which may be esterified or amidated.

Preferred examples of the heteroaryl group having from 4 to 11 carbons, which may be substituted, include an aromatic heterocyclic group such as pyridin-2-yl, pyridin-3-yl, pyridin-4-yl and pyrimidin-4-yl. In this case, the aromatic heterocyclic ring may be substituted by one, two or three substituent(s) selected from an alkyl group which may be substituted, such as methyl, ethyl, propyl, trifluoromethyl and cyanomethyl, an alkoxy group which may be substituted, such as methoxy, ethoxy, isopropoxy and trifluoromethoxy, a hydroxyl group, a nitro group, an amino group which may be substituted, such as amino, N-methylamino, N,N-dimethylamino, morpholino and alkoxycarbamoyl, a trifluoromethanesulfonyl group, a heterocyclic ring such as imidazol-1-yl and 1H-pyrazol-3-yl, a halogen atom such as chlorine atom and fluorine atom, and a carboxyl group which may be esterified or amidated.

For example, in the case of an amidated carboxyl group, when in the group —CONR$^7$R$^8$, R$^7$ and R$^8$, together with the nitrogen atom to which they are attached, represent a heterocyclic ring which may further contain a nitrogen atom, an oxygen atom and/or a sulfur atom or may be condensed, preferred specific examples of the heterocyclic ring include a piperidino group, a pyrrolidino group, a morpholino group, a thiomorpholino group, a piperazino group and a homopiperazino group.

The carbon atom or sulfur atom on this ring may be converted into an oxide or the ring may have thereon one or two substituent(s) selected from an alkyl group such as methyl, ethyl and propyl, an aryl group which may be substituted, such as phenyl, 4-methoxyphenyl, 4-chlorophenyl and naphthyl, a heteroaryl group which may be substituted, such as 2-pyridyl, 3-pyridyl and 2-pyrimidyl, a carboxyl group, a carbamoyl group which may be substituted, such as carbamoyl and dimethylaminocarbamoyl, and an aralkyl group which may be substituted, such as benzyl, 4-chlorobenzyl, 2-pyridylmethyl and 3-pyridylmethyl.

Examples of the amino group which may be substituted include a group —NR$^a$R$^b$ (wherein R$^a$ and R$^b$ each independently represents a hydrogen atom or a lower alkyl group having from 1 to 6 carbons, which may be substituted, or R$^a$ and R$^b$, together with the nitrogen atom to which they are attached represent a heterocyclic ring which may further contain a nitrogen atom, an oxygen atom or a sulfur atom or may be condensed), a group —NHCOR$^c$ (wherein R$^c$ represents a hydrogen atom, a lower alkyl group having from 1 to 6 carbons, which may be substituted, or an aryl group having from 6 to 12 carbons, which may be substituted), a group —NHCOCH$_2$NR$^d$R$^e$ (wherein R$^d$ and R$^e$ each independently represents a hydrogen atom, an alkyl group having from 1 to 6 carbons, which may be substituted, or an aryl group having from 6 to 12 carbons, which may be substituted, or R$^d$ and R$^e$, together with the nitrogen atom to which they are attached represent a heterocyclic ring which may further contain a nitrogen atom, an oxygen atom or a sulfur atom or may be condensed), a group —NHSO$_2$R$^f$ (wherein R$^f$ represents a lower alkyl group having from 1 to 6 carbons, which may be substituted, or an aryl group having from 6 to 12 carbons, which may be substituted), a group —NR$^g$COOR$^h$ (wherein R$^g$ represents a hydrogen atom or a lower alkyl group having from 1 to 6 carbons, which may be substituted, and R$^h$ represents a lower alkyl group having from 1 to 6 carbons, which may be substituted, or an aryl group having from 6 to 12 carbons, which may be substituted), a group —NHCONR$^i$R$^j$ (wherein R$^i$ and R$^j$ each independently represents a hydrogen atom, a lower alkyl group having from 1 to 6 carbons, which may be substituted, or an aryl group having from 6 to 12 carbons, which may be substituted, or R$^i$ and R$^j$, together with the nitrogen atom to which they are attached represent a heterocyclic ring which may further contain a nitrogen atom, an oxygen atom or a sulfur atom or may be condensed), and a group —NHC(=NH)NR$^k$R$^l$ (wherein R$^k$ and R$^l$ each independently represents a hydrogen atom or a lower alkyl group having from 1 to 6 carbons, which may be substituted).

Preferred examples of the lower alkyl group having from 1 to 6 carbons, which may be substituted, include a straight or branched saturated aliphatic hydrocarbon group such as methyl, ethyl, propyl, isopropyl, n-butyl, sec-butyl, tert-butyl, pentyl, isopentyl, neopentyl, tert-pentyl and n-hexyl, a saturated alicyclic hydrocarbon group such as cyclopropyl, cyclobutyl, cyclopentyl and cyclohexyl, and a saturated alicyclic hydrocarbon group-aliphatic hydrocarbon group such as cyclopropylmethyl, cyclopropylethyl and cyclobutylmethyl.

Preferred examples of the aryl group having from 6 to 12 carbons, which may be substituted, include a phenyl group, a 4-methoxyphenyl group, a 3-methoxyphenyl group, a 2-methoxyphenyl group, a 3,4-dimethoxyphenyl group, a 3,4,5-trimethoxyphenyl group, a 4-trifluoromethylphenyl group, a 4-morpholinophenyl group, a 4-cyanophenyl group, a 4-chlorophenyl group, a 4-nitrophenyl group and a 1-naphthyl group.

In this case, specific preferred examples include an amino group, a methylamino group, an ethylamino group, an n-propylamino group, a dimethylamino group, a diethylamino group, a (2-hydroxyethyl)amino group, a (3-hydroxypropyl)amino group, a (4-hydroxybutyl)amino group, a di(2-hydroxyethyl)amino group, a (2-diethylaminoethyl)amino group, a (carboxymethyl)amino group, a di(carboxymethyl)amino group, an (ethoxycarbonylmethyl)amino group, a di(ethoxycarbonylmethyl)amino group, a benzylamino group, a benzyl(methyl)amino group, an acetylamino group, an n-propionylamino group, a (2-chloroacetyl)amino group, a (2-aminoacetyl)amino group, a (2-morpholinoacetyl)amino group, a (2-pyrrolidinoacetyl)amino group, a (2-piperazinoacetyl)amino group, a (2-isopropylaminoacetyl)amino group, a (2-cyclohexylaminoacetyl)amino group, a (2-phenylaminoacetyl)amino group, a benzoylamino group, a (4-methylbenzoyl)amino group, a (4-chlorobenzoyl)amino group, a (4-aminobenzoyl)amino group, a (methoxycarbonyl)amino group, a (tert-butoxycarbonyl) amino group, a (benzyloxycarbonyl)amino group, an (aminocarbonyl)amino group, a (dimethylaminocarbonyl) amino group, an (anilinocarbonyl)amino group, a methanesulfonylamino group, a benzenesulfonylamino group and a toluenesulfonylamino group. For example, in the group —NR$^a$R$^b$, when R$^a$ and R$^b$, together with the nitrogen atom to which they are attached represent a heterocyclic ring which may further contain a nitrogen atom, an oxygen atom or a sulfur atom or may be condensed, preferred specific examples of the heterocyclic ring include a piperidino group, a pyrrolidino group, a morpholino group, a thiomorpholino group, a piperazino group, an N-methylpiperazino group, an N-phenylpiperazino group and a homopiperazino group.

Preferred examples of the heteroaryl group having from 4 to 11 carbons, which may be substituted, include a 2-pyridyl group, a 3-pyridyl group, a 4-pyridyl group, a 2-furanyl group, a 2-thienyl group, a 2-pyrimidinyl group, a 2-quinolyl group and a 3-isoquinolyl group.

Preferred examples of the aralkyl group having from 7 to 14 carbons, which may be substituted, include a benzyl group, a 4-nitrobenzyl group, a 3-nitrobenzyl group, a 4-methoxybenzyl group, a 3-methoxybenzyl group, a 4-chlorobenzyl group, a 2-phenethyl group and a 3-phenylpropyl group.

Preferred examples of the heteroarylalkyl group having from 5 to 13 carbons, which may be substituted, include a 4-pyridylmethyl group, a 3-pyridylmethyl group, a 2-pyridylmethyl group, a 2-(pyridin-4-yl)ethyl group, a 2-(pyridin-3-yl)ethyl group, a 2-quinolylmethyl group and a 3-isoquinolylmethyl group.

Examples of the halogen atom include a fluorine atom, a chlorine atom, a bromine atom and an iodine atom.

The compounds of the present invention are preferably compounds where in the following formula (I):

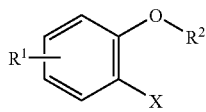

(I)

wherein $R^1$ is the following formula (II)

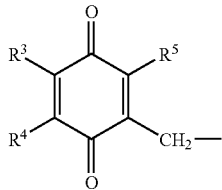

(II)

(wherein $R^3$ and $R^4$ each represents a methyl group or a methoxy group and $R^5$ represents a methyl group); $R^2$ represents a hydrogen atom, a methyl group, an isopropyl group, a phenyl group, a 3-methoxyphenyl group, a 3-pyridyl group, a 4-pyridyl group, a benzyl group, a 3-pyridylmethyl group, a 4-pyridylmethyl group, an acetyl group, a carboxymethyl group, a methoxycarbonylmethyl group or tert-butoxycarbonylmethyl group; and X represents a carboxyl group which may be esterified or amidated).

Particularly preferred specific examples of the compounds include the following compounds:

4-(3,4,5,6-tetramethoxy-2-methylbenzyl)-2-benzyloxybenzoic acid,
6-(3,4,5,6-tetramethoxy-2-methylbenzyl)-2-benzyloxybenzoic acid,
5-(3,4,5,6-tetramethoxy-2-methylbenzyl)-2-benzyloxybenzoic acid,
3-(3,4,5,6-tetramethoxy-2-methylbenzyl)-2-benzyloxybenzoic acid,
N-[4-(3,4,5,6-tetramethoxy-2-methylbenzyl)-2-benzyloxybenzoyl]piperidine,
N-[5-(3,4,5,6-tetramethoxy-2-methylbenzyl)-2-benzyloxybenzoyl]piperidine,
N-[5-(3,4,5,6-tetramethoxy-2-methylbenzyl)-2-benzyloxybenzoyl]morpholine,
N-[5-(3,4,5,6-tetramethoxy-2-methylbenzyl)-2-benzyloxybenzoyl]-4-methoxyaniline,
4-(3,4,5,6-tetramethoxy-2-methylbenzyl)-2-hydroxybenzoic acid,
5-(3,4,5,6-tetramethoxy-2-methylbenzyl)-2-hydroxybenzoic acid,
3-(3,4,5,6-tetramethoxy-2-methylbenzyl)-2-hydroxybenzoic acid,
4-(3,4,5,6-tetramethoxy-2-methylbenzyl)-2-acetoxybenzoic acid,
5-(3,4,5,6-tetramethoxy-2-methylbenzyl)-2-acetoxybenzoic acid,
3-(3,4,5,6-tetramethoxy-2-methylbenzyl)-2-acetoxybenzoic acid,
methyl 5-(3,4,5,6-tetramethoxy-2-methylbenzyl)-2-hydroxybenzoate,
5-(3,4,5,6-tetramethoxy-2-methylbenzyl)-2-methoxybenzoic acid,
5-(3,4,5,6-tetramethoxy-2-methylbenzyl)-2-isopropoxybenzoic acid,
methyl 5-(3,4,5,6-tetramethoxy-2-methylbenzyl)-2-phenoxybenzoate,
methyl 5-(3,4,5,6-tetramethoxy-2-methylbenzyl)-2-(3-methoxyphenoxy)benzoate,
methyl 5-(3,4,5,6-tetramethoxy-2-methylbenzyl)-2-(3-pyridylmethyloxy)benzoate,
methyl 5-(3,4,5,6-tetramethoxy-2-methylbenzyl)-2-(4-pyridylmethyloxy)benzoate,
methyl 5-(3,4,5,6-tetramethoxy-2-methylbenzyl)-2-(tert-butoxycarbonylmethyloxy)benzoate,
5-(3,4,5,6-tetramethoxy-2-methylbenzyl)-2-phenoxybenzoic acid,
5-(3,4,5,6-tetramethoxy-2-methylbenzyl)-2-(3-methoxyphenoxy)benzoic acid,
5-(3,4,5,6-tetramethoxy-2-methylbenzyl)-2-(3-pyridylmethyloxy)benzoic acid,
5-(3,4,5,6-tetramethoxy-2-methylbenzyl)-2-(4-pyridylmethyloxy)benzoic acid,
N-[5-(3,4,5,6-tetramethoxy-2-methylbenzyl)-2-hydroxybenzoyl]piperidine,
N-[5-(3,4,5,6-tetramethoxy-2-methylbenzyl)-2-hydroxybenzoyl]morpholine,
N-[5-(3,4,5,6-tetramethoxy-2-methylbenzyl)-2-(3-pyridylmethyloxy)benzoyl]piperidine,
N-[5-(3,4,5,6-tetramethoxy-2-methylbenzyl)-2-(4-pyridylmethyloxy)benzoyl]piperidine,
N-[5-(3,4,5,6-tetramethoxy-2-methylbenzyl)-2-(3-pyridyloxy)benzoyl]piperidine,
N-[5-(3,4,5,6-tetramethoxy-2-methylbenzyl)-2-(4-pyridyloxy)benzoyl]piperidine,
N-[5-(3,4,5,6-tetramethoxy-2-methylbenzyl)-2-(methoxycarbonylmethyloxy)benzoyl]piperidine,
N-[5-(3,4,5,6-tetramethoxy-2-methylbenzyl)-2-(3-tert-butoxycarbonylmethyloxy)benzoyl]piperidine,
N-[5-(3,4,5,6-tetramethoxy-2-methylbenzyl)-2-(3-pyridylmethyloxy)benzoyl]morpholine,
N-[5-(3,4,5,6-tetramethoxy-2-methylbenzyl)-2-(4-(pyridylmethyloxy)benzoyl]morpholine,
N-[5-(3,4,5,6-tetramethoxy-2-methylbenzyl)-2-(3-pyridyloxy)benzoyl]morpholine,
N-[5-(3,4,5,6-tetramethoxy-2-methylbenzyl)-2-(4-pyridyloxy)benzoyl]morpholine,
N-[5-(3,4,5,6-tetramethoxy-2-methylbenzyl)-2-(methoxycarbonylmethyloxy)benzoyl]morpholine,
N-[5-(3,4,5,6-tetramethoxy-2-methylbenzyl)-2-(tert-butoxycarbonylmethyloxy)benzoyl]morpholine,
4-(5,6-dimethoxy-3-methyl-1,4-benzoquinon-2-yl)methyl-2-benzyloxybenzoic acid,
6-(5,6-dimethoxy-3-methyl-1,4-benzoquinon-2-yl)methyl-2-benzyloxybenzoic acid,
5-(5,6-dimethoxy-3-methyl-1,4-benzoquinon-2-yl)methyl-2-benzyloxybenzoic acid,
3-(5,6-dimethoxy-3-methyl-1,4-benzoquinon-2-yl)methyl-2-benzyloxybenzoic acid,
4-(5,6-dimethoxy-3-methyl-1,4-benzoquinon-2-yl)methyl-2-acetoxybenzoic acid,
5-(5,6-dimethoxy-3-methyl-1,4-benzoquinon-2-yl)methyl-2-acetoxybenzoic acid, 3-(5,6-dimethoxy-3-methyl-1,4-benzoquinon-2-yl)methyl-2-acetoxybenzoic acid,
4-(5,6-dimethoxy-3-methyl-1,4-benzoquinon-2-yl)methyl-2-hydroxybenzoic acid,
5-(5,6-dimethoxy-3-methyl-1,4-benzoquinon-2-yl)methyl-2-hydroxybenzoic acid,
3-(5,6-dimethoxy-3-methyl-1,4-benzoquinon-2-yl)methyl-2-hydroxybenzoic acid,
5-(5,6-dimethoxy-3-methyl-1,4-benzoquinon-2-yl)methyl-2-methoxybenzoic acid,
5-(5,6-dimethoxy-3-methyl-1,4-benzoquinon-2-yl)methyl-2-isopropoxybenzoic acid,
5-(5,6-dimethoxy-3-methyl-1,4-benzoquinon-2-yl)methyl-2-phenoxybenzoic acid,
5-(5,6-dimethoxy-3-methyl-1,4-benzoquinon-2-yl)methyl-2-(3-methoxyphenoxy)benzoic acid,
5-(5,6-dimethoxy-3-methyl-1,4-benzoquinon-2-yl)methyl-2-(3-pyridylmethyloxy)benzoic acid,
5-(5,6-dimethoxy-3-methyl-1,4-benzoquinon-2-yl)methyl-2-(4-pyridylmethyloxy)benzoic acid,
N-[4-(5,6-dimethoxy-3-methyl-1,4-benzoquinon-2-yl)methyl-2-benzyloxybenzoyl]piperidine,
N-[4-(5,6-dimethoxy-3-methyl-1,4-benzoquinon-2-yl)methyl-2-benzyloxybenzoyl]morpholine,
N-[4-(5,6-dimethoxy-3-methyl-1,4-benzoquinon-2-yl)methyl-2-benzyloxybenzoyl]-4-methoxyaniline,
N-[6-(5,6-dimethoxy-3-methyl-1,4-benzoquinon-2-yl)methyl-2-benzyloxybenzoyl]-4-methoxyaniline,
N-[5-(5,6-dimethoxy-3-methyl-1,4-benzoquinon-2-yl)methyl-2-benzyloxybenzoyl]piperidine,
N-[5-(5,6-dimethoxy-3-methyl-1,4-benzoquinon-2-yl)methyl-2-benzyloxybenzoyl]morpholine,
N-[5-(5,6-dimethoxy-3-methyl-1,4-benzoquinon-2-yl)methyl-2-benzyloxybenzoyl]-4-methoxyaniline,
N-[3-(5,6-dimethoxy-3-methyl-1,4-benzoquinon-2-yl)methyl-2-benzyloxybenzoyl]piperidine,
N-[3-(5,6-dimethoxy-3-methyl-1,4-benzoquinon-2-yl)methyl-2-benzyloxybenzoyl]morpholine,
N-[3-(5,6-dimethoxy-3-methyl-1,4-benzoquinon-2-yl)methyl-2-benzyloxybenzoyl]-4-methoxyaniline,
N-[4-(5,6-dimethoxy-3-methyl-1,4-benzoquinon-2-yl)methyl-2-acetoxybenzoyl]-4-methoxyaniline,
N-[5-(5,6-dimethoxy-3-methyl-1,4-benzoquinon-2-yl)methyl-2-acetoxybenzoyl]piperidine,
N-[5-(5,6-dimethoxy-3-methyl-1,4-benzoquinon-2-yl)methyl-2-acetoxybenzoyl]morpholine,
N-[5-(5,6-dimethoxy-3-methyl-1,4-benzoquinon-2-yl)methyl-2-acetoxybenzoyl]-4-methoxyaniline,
N-[3-(5,6-dimethoxy-3-methyl-1,4-benzoquinon-2-yl)methyl-2-acetoxybenzoyl]piperidine,
N-[3-(5,6-dimethoxy-3-methyl-1,4-benzoquinon-2-yl)methyl-2-acetoxybenzoyl]morpholine,
N-[3-(5,6-dimethoxy-3-methyl-1,4-benzoquinon-2-yl)methyl-2-acetoxybenzoyl]-4-methoxyaniline,
N-[5-(5,6-dimethoxy-3-methyl-1,4-benzoquinon-2-yl)methyl-2-hydroxybenzoyl]piperidine,
N-[5-(5,6-dimethoxy-3-methyl-1,4-benzoquinon-2-yl)methyl-2-hydroxybenzoyl]morpholine,
N-[5-(5,6-dimethoxy-3-methyl-1,4-benzoquinon-2-yl)methyl-2-hydroxybenzoyl]-4-methoxyaniline,
N-[3-(5,6-dimethoxy-3-methyl-1,4-benzoquinon-2-yl)methyl-2-hydroxybenzoyl]piperidine,
N-[3-(5,6-dimethoxy-3-methyl-1,4-benzoquinon-2-yl)methyl-2-hydroxybenzoyl]morpholine,
N-[3-(5,6-dimethoxy-3-methyl-1,4-benzoquinon-2-yl)methyl-2-hydroxybenzoyl]-4-methoxyaniline,
N-[5-(5,6-dimethoxy-3-methyl-1,4-benzoquinon-2-yl)methyl-2-methoxybenzoyl]piperidine,
N-[5-(5,6-dimethoxy-3-methyl-1,4-benzoquinon-2-yl)methyl-2-methoxybenzoyl]morpholine,
N-[5-(5,6-dimethoxy-3-methyl-1,4-benzoquinon-2-yl)methyl-2-methoxybenzoyl]-4-methoxyaniline,
N-[5-(5,6-dimethoxy-3-methyl-1,4-benzoquinon-2-yl)methyl-2-isopropoxybenzoyl]piperidine,
N-[5-(5,6-dimethoxy-3-methyl-1,4-benzoquinon-2-yl)methyl-2-isopropoxybenzoyl]morpholine,
N-[5-(5,6-dimethoxy-3-methyl-1,4-benzoquinon-2-yl)methyl-2-isopropoxybenzoyl]-4-methoxyaniline,
N-[5-(5,6-dimethoxy-3-methyl-1,4-benzoquinon-2-yl)methyl-2-phenoxybenzoyl]piperidine,
N-[5-(5,6-dimethoxy-3-methyl-1,4-benzoquinon-2-yl)methyl-2-phenoxybenzoyl]morpholine,
N-[5-(5,6-dimethoxy-3-methyl-1,4-benzoquinon-2-yl)methyl-2-phenoxybenzoyl]-4-methoxyaniline,
N-[5-(5,6-dimethoxy-3-methyl-1,4-benzoquinon-2-yl)methyl-2-(3-methoxyphenoxy)benzoyl]piperidine,
N-[5-(5,6-dimethoxy-3-methyl-1,4-benzoquinon-2-yl)methyl-2-(3-methoxyphenoxy)benzoyl]morpholine,
N-[5-(5,6-dimethoxy-3-methyl-1,4-benzoquinon-2-yl)methyl-2-(3-methoxyphenoxy)benzoyl]-4-methoxyaniline,
N-[5-(5,6-dimethoxy-3-methyl-1,4-benzoquinon-2-yl)methyl-2-(3-pyridylmethyloxy)benzoyl]piperidine,
N-[5-(5,6-dimethoxy-3-methyl-1,4-benzoquinon-2-yl)methyl-2-(3-pyridylmethyloxy)benzoyl]morpholine,
N-[5-(5,6-dimethoxy-3-methyl-1,4-benzoquinon-2-yl)methyl-2-(3-pyridylmethyloxy)benzoyl]-4-methoxyaniline,
N-[5-(5,6-dimethoxy-3-methyl-1,4-benzoquinon-2-yl)methyl-2-(4-pyridylmethyloxy)benzoyl]piperidine,
N-[5-(5,6-dimethoxy-3-methyl-1,4-benzoquinon-2-yl)methyl-2-(4-pyridylmethyloxy)benzoyl]morpholine,
N-[5-(5,6-dimethoxy-3-methyl-1,4-benzoquinon-2-yl)methyl-2-(4-pyridylmethyloxy)benzoyl]-4-methoxyaniline,
N-[5-(5,6-dimethoxy-3-methyl-1,4-benzoquinon-2-yl)methyl-2-(3-pyridyloxy)benzoyl]piperidine,
N-[5-(5,6-dimethoxy-3-methyl-1,4-benzoquinon-2-yl)methyl-2-(3-pyridyloxy)benzoyl]morpholine,
N-[5-(5,6-dimethoxy-3-methyl-1,4-benzoquinon-2-yl)methyl-2-(4-pyridyloxy)benzoyl]piperidine,
N-[5-(5,6-dimethoxy-3-methyl-1,4-benzoquinon-2-yl)methyl-2-(4-pyridyloxy)benzoyl]morpholine,
N-[5-(5,6-dimethoxy-3-methyl-1,4-benzoquinon-2-yl)methyl-2-(methoxycarbonylmethyloxy)benzoyl]piperidine,
N-[5-(5,6-dimethoxy-3-methyl-1,4-benzoquinon-2-yl)methyl-2-(methoxycarbonylmethyloxy)benzoyl]morpholine,
N-[5-(5,6-dimethoxy-3-methyl-1,4-benzoquinon-2-yl)methyl-2-(tert-butoxycarbonylmethyloxy)benzoyl]piperidine,
N-[5-(5,6-dimethoxy-3-methyl-1,4-benzoquinon-2-yl)methyl-2-(tert-butoxycarbonylmethyloxy)benzoyl]morpholine,
N-[5-(5,6-dimethoxy-3-methyl-1,4-benzoquinon-2-yl)methyl-2-acetoxybenzoyl]-3,4-dimethoxyaniline,
N-[5-(5,6-dimethoxy-3-methyl-1,4-benzoquinon-2-yl)methyl-2-acetoxybenzoyl]-3,4,5-trimethoxyaniline,
N-[5-(5,6-dimethoxy-3-methyl-1,4-benzoquinon-2-yl)methyl-2-acetoxybenzoyl]-4-acetylaniline,
N-[5-(5,6-dimethoxy-3-methyl-1,4-benzoquinon-2-yl)methyl-2-acetoxybenzoyl]-4-chloroaniline,
N-[5-(5,6-dimethoxy-3-methyl-1,4-benzoquinon-2-yl)methyl-2-acetoxybenzoyl]-4-morpholinoaniline, N-[5-(5,6-dimethoxy-3-methyl-1,4-benzoquinon-2-yl)methyl-2-acetoxybenzoyl]-4-cyanoaniline,
N-[5-(5,6-dimethoxy-3-methyl-1,4-benzoquinon-2-yl)methyl-2-acetoxybenzoyl]-4-trifluoromethylaniline,
N-[5-(5,6-dimethoxy-3-methyl-1,4-benzoquinon-2-yl)methyl-2-acetoxybenzoyl]-3,5-bistrifluoromethylaniline,
N-[5-(5,6-dimethoxy-3-methyl-1,4-benzoquinon-2-yl)methyl-2-hydroxybenzoyl]-3,4-dimethoxyaniline,
N-[5-(5,6-dimethoxy-3-methyl-1,4-benzoquinon-2-yl)methyl-2-hydroxybenzoyl]-3,4,5-trimethoxyaniline,
N-[5-(5,6-dimethoxy-3-methyl-1,4-benzoquinon-2-yl)methyl-2-hydroxybenzoyl]-4-acetylaniline,
N-[5-(5,6-dimethoxy-3-methyl-1,4-benzoquinon-2-yl)methyl-2-hydroxybenzoyl]-4-chloroaniline,
N-[5-(5,6-dimethoxy-3-methyl-1,4-benzoquinon-2-yl)methyl-2-hydroxybenzoyl]-4-morpholinoaniline,
N-[5-(5,6-dimethoxy-3-methyl-1,4-benzoquinon-2-yl)methyl-2-hydroxybenzoyl]-4-cyanoaniline,
N-[5-(5,6-dimethoxy-3-methyl-1,4-benzoquinon-2-yl)methyl-2-hydroxybenzoyl]-4-trifluoromethylaniline,
N-[5-(5,6-dimethoxy-3-methyl-1,4-benzoquinon-2-yl)methyl-2-hydroxybenzoyl]-3,5-bistrifluoromethylaniline,
N-[5-(5,6-dimethoxy-3-methyl-1,4-benzoquinon-2-yl)methyl-2-hydroxybenzoyl]-(S)-1-phenylethylamine,
N-[5-(5,6-dimethoxy-3-methyl-1,4-benzoquinon-2-yl)methyl-2-hydroxybenzoyl]-(R)-1-phenylethylamine,
N-[5-(5,6-dimethoxy-3-methyl-1,4-benzoquinon-2-yl)methyl-2-phenoxybenzoyl]-1,2,3,4-tetrahydroquinoline,
N-[5-(5,6-dimethoxy-3-methyl-1,4-benzoquinon-2-yl)methyl-2-phenoxybenzoyl]-2-methylpiperidine,
N-[5-(5,6-dimethoxy-3-methyl-1,4-benzoquinon-2-yl)methyl-2-(3-pyridylmethyloxy)benzoyl]-1,2,3,4-tetrahydroquinoline,
N-[5-(5,6-dimethoxy-3-methyl-1,4-benzoquinon-2-yl)methyl-2-(3-pyridylmethyloxy)benzoyl]-4-methylpiperidine,
N-[5-(5,6-dimethoxy-3-methyl-1,4-benzoquinon-2-yl)methyl-2-(3-pyridylmethyloxy)benzoyl]-3,4,5-trimethoxyaniline,
N-[5-(5,6-dimethoxy-3-methyl-1,4-benzoquinon-2-yl)methyl-2-(3-pyridylmethyloxy)benzoyl]-4-acetylaniline,
methyl 5-(5,6-dimethoxy-3-methyl-1,4-benzoquinon-2-yl)methyl-2-(tert-butoxycarbonylmethyloxy)benzoate,
N-(6-chloropyridin-3-yl)-4-(5,6-dimethoxy-3-methyl-1,4-benzoquinon-2-yl)methyl-2-hydroxybenzamide,
N-(2-chloropyridin-3-yl)-4-(5,6-dimethoxy-3-methyl-1,4-benzoquinon-2-yl)methyl-2-acetoxybenzamide,
N-(2-chloropyridin-3-yl)-4-(5,6-dimethoxy-3-methyl-1,4-benzoquinon-2-yl)methyl-2-hydroxybenzamide,
N-(6-methoxypyridin-3-yl)-4-(5,6-dimethoxy-3-methyl-1,4-benzoquinon-2-yl)methyl-2-acetoxybenzamide,
N-(6-methoxypyridin-3-yl)-4-(5,6-dimethoxy-3-methyl-1,4-benzoquinon-2-yl)methyl-2-hydroxybenzamide,
N-[4-(5,6-dimethoxy-3-methyl-1,4-benzoquinon-2-yl)methyl-2-acetoxybenzoyl]-4-(trifluoromethylsulfonyl)aniline,
N-[4-(5,6-dimethoxy-3-methyl-1,4-benzoquinon-2-yl)methyl-2-hydroxybenzoyl]-4-(trifluoromethylsulfonyl)aniline,
N-(pyridin-3-yl)-4-(5,6-dimethoxy-3-methyl-1,4-benzoquinon-2-yl)methyl-2-acetoxybenzamide,
N-(pyridin-3-yl)-4-(5,6-dimethoxy-3-methyl-1,4-benzoquinon-2-yl)methyl-2-hydroxybenzamide,
N-(pyridin-4-yl)-4-(5,6-dimethoxy-3-methyl-1,4-benzoquinon-2-yl)methyl-2-hydroxybenzamide,
N-[5-(5,6-dimethoxy-3-methyl-1,4-benzoquinon-2-yl)methyl-2-acetoxybenzoyl]-4-fluoroaniline,
N-[5-(5,6-dimethoxy-3-methyl-1,4-benzoquinon-2-yl)methyl-2-hydroxybenzoyl]-4-fluoroaniline,
N-[5-(5,6-dimethoxy-3-methyl-1,4-benzoquinon-2-yl)methyl-2-acetoxybenzoyl]-3-nitroaniline,
N-[5-(5,6-dimethoxy-3-methyl-1,4-benzoquinon-2-yl)methyl-2-hydroxybenzoyl]-3-nitroaniline,
N-[5-(5,6-dimethoxy-3-methyl-1,4-benzoquinon-2-yl)methyl-2-acetoxybenzoyl]-2-trifluoromethylaniline,
N-[5-(5,6-dimethoxy-3-methyl-1,4-benzoquinon-2-yl)methyl-2-hydroxybenzoyl]-2-trifluoromethylaniline,
ethyl N-[5-(5,6-dimethoxy-3-methyl-1,4-benzoquinon-2-yl)methyl-2-acetoxybenzoyl]-4-aminobenzoate,
ethyl N-[5-(5,6-dimethoxy-3-methyl-1,4-benzoquinon-2-yl)methyl-2-hydroxybenzoyl]-4-aminobenzoate,
N-[5-(5,6-dimethoxy-3-methyl-1,4-benzoquinon-2-yl)methyl-2-acetoxybenzoyl]-4-cyanomethylaniline,
N-[5-(5,6-dimethoxy-3-methyl-1,4-benzoquinon-2-yl)methyl-2-hydroxybenzoyl]-4-cyanomethylaniline,
N-[5-(5,6-dimethoxy-3-methyl-1,4-benzoquinon-2-yl)methyl-2-acetoxybenzoyl]-3-trifluoromethylaniline,
N-[5-(5,6-dimethoxy-3-methyl-1,4-benzoquinon-2-yl)methyl-2-hydroxybenzoyl]-3-trifluoromethylaniline,
N-[5-(5,6-dimethoxy-3-methyl-1,4-benzoquinon-2-yl)methyl-2-acetoxybenzoyl]-2-nitroaniline,
N-[5-(5,6-dimethoxy-3-methyl-1,4-benzoquinon-2-yl)methyl-2-hydroxybenzoyl]-2-nitroaniline,
N-(pyridin-2-yl)-5-(5,6-dimethoxy-3-methyl-1,4-benzoquinon-2-yl)methyl-2-acetoxybenzamide,
N-(pyridin-2-yl)-5-(5,6-dimethoxy-3-methyl-1,4-benzoquinon-2-yl)methyl-2-hydroxybenzamide,
N-(pyridin-4-yl)-5-(5,6-dimethoxy-3-methyl-1,4-benzoquinon-2-yl)methyl-2-hydroxybenzamide,
N-(pyridin-3-yl)-5-(5,6-dimethoxy-3-methyl-1,4-benzoquinon-2-yl)methyl-2-hydroxybenzamide,
N-cyclopropyl-5-(5,6-dimethoxy-3-methyl-1,4-benzoquinon-2-yl)methyl-2-acetoxybenzamide,
N-cyclopropyl-5-(5,6-dimethoxy-3-methyl-1,4-benzoquinon-2-yl)methyl-2-hydroxybenzamide,
N-cyclohexyl-5-(5,6-dimethoxy-3-methyl-1,4-benzoquinon-2-yl)methyl-2-acetoxybenzamide
N-cyclohexyl-5-(5,6-dimethoxy-3-methyl-1,4-benzoquinon-2-yl)methyl-2-hydroxybenzamide
N-methyl-N-[5-(5,6-dimethoxy-3-methyl-1,4-benzoquinon-2-yl)methyl-2-acetoxybenzoyl]-4-methoxyaniline,
N-methyl-N-[5-(5,6-dimethoxy-3-methyl-1,4-benzoquinon-2-yl)methyl-2-hydroxybenzoyl]-4-methoxyaniline,
N-[3-(5,6-dimethoxy-3-methyl-1,4-benzoquinon-2-yl)methyl-2-acetoxybenzoyl]-4-trifluoromethylaniline,
N-[3-(5,6-dimethoxy-3-methyl-1,4-benzoquinon-2-yl)methyl-2-hydroxybenzoyl]-4-trifluoromethylaniline,
ethyl N-[5-(5,6-dimethoxy-3-methyl-1,4-benzoquinon-2-yl)methyl-2-(3-pyridylmethyloxy)benzoyl]-4-aminobenzoate,
N-(pyridin-4-yl)-5-(5,6-dimethoxy-3-methyl-1,4-benzoquinon-2-yl)methyl-2-(3-pyridylmethyloxy)benzamide,
N-(pyridin-3-yl)-5-(5,6-dimethoxy-3-methyl-1,4-benzoquinon-2-yl)methyl-2-(3-pyridylmethyloxy)benzamide,
N-cyclopropyl-5-(5,6-dimethoxy-3-methyl-1,4-benzoquinon-2-yl)methyl-2-(3-pyridylmethyloxy)benzamide,
N-cyclohexyl-5-(5,6-dimethoxy-3-methyl-1,4-benzoquinon-2-yl)methyl-2-(3-pyridylmethyloxy)benzamide,
N-[5-(5,6-dimethoxy-3-methyl-1,4-benzoquinon-2-yl)methyl-2-(3-pyridylmethyloxy)benzoyl]-4-trifluoromethylaniline, N-[5-(5,6-dimethoxy-3-methyl-1,4-benzoquinon-2-yl)methyl-2-acetoxybenzoyl]-4-(trifluoromethylsulfonyl)aniline, N-[5-(5,6-dimethoxy-3-methyl-1,4-benzoquinon-2-yl)methyl-2-hydroxybenzoyl]-4-(trifluoromethylsulfonyl)aniline, N-[3-(5,6-dimethoxy-3-methyl-1,4-benzoquinon-2-yl)methyl-2-acetoxybenzoyl]-4-(trifluoromethylsulfonyl)aniline, N-[3-(5,6-dimethoxy-3-methyl-1,4-benzoquinon-2-yl)methyl-2-acetoxybenzoyl]-2,4-dichloroaniline, N-[3-(5,6-dimethoxy-3-methyl-1,4-benzoquinon-2-yl)methyl-2-hydroxybenzoyl]-2,4-dichloroaniline, N-[3-(5,6-dimethoxy-3-methyl-1,4-benzoquinon-2-yl)methyl-2-acetoxybenzoyl]-4-morpholinoaniline, N-[3-(5,6-dimethoxy-3-methyl-1,4-benzoquinon-2-yl)methyl-2-hydroxybenzoyl]-4-morpholinoaniline, N-(6-methoxypyridin-3-yl)-5-(5,6-dimethoxy-3-methyl-1,4-benzoquinon-2-yl)methyl-2-acetoxybenzamide, N-(6-methoxypyridin-3-yl)-5-(5,6-dimethoxy-3-methyl-1,4-benzoquinon-2-yl)methyl-2-hydroxybenzamide, N-(2,6-dimethoxypyridin-3-yl)-5-(5,6-dimethoxy-3-methyl-1,4-benzoquinon-2-yl)methyl-2-acetoxybenzamide, N-(2,6-dimethoxypyridin-3-yl)-5-(5,6-dimethoxy-3-methyl-1,4-benzoquinon-2-yl)methyl-2-hydroxybenzamide, N-(6-chloropyridin-3-yl)-5-(5,6-dimethoxy-3-methyl-1,4-benzoquinon-2-yl)methyl-2-acetoxybenzamide, N-(6-chloropyridin-3-yl)-5-(5,6-dimethoxy-3-methyl-1,4-benzoquinon-2-yl)methyl-2-hydroxybenzamide, N-(2-chloropyridin-3-yl)-5-(5,6-dimethoxy-3-methyl-1,4-benzoquinon-2-yl)methyl-2-acetoxybenzamide, N-(2-chloropyridin-3-yl)-5-(5,6-dimethoxy-3-methyl-1,4-benzoquinon-2-yl)methyl-2-hydroxybenzamide, tert-butyl N-[5-(5,6-dimethoxy-3-methyl-1,4-benzoquinon-2-yl)methyl-2-acetoxybenzoyl]-4-aminobenzoate, N-[5-(5,6-dimethoxy-3-methyl-1,4-benzoquinon-2-yl)methyl-2-acetoxybenzoyl]-4-aminobenzoic acid, N-[5-(5,6-dimethoxy-3-methyl-1,4-benzoquinon-2-yl)methyl-2-hydroxybenzoyl]-4-aminobenzoic acid, N-[5-(5,6-dimethoxy-3-methyl-1,4-benzoquinon-2-yl)methyl-2-hydroxybenzoyl]-4-nitroaniline, N-[5-(5,6-dimethoxy-3-methyl-1,4-benzoquinon-2-yl)methyl-2-hydroxybenzoyl]-2,6-dichloro-4-trifluoromethoxyaniline, N-(3-tert-butoxycarbonylpyridin-2-yl)-5-(5,6-dimethoxy-3-methyl-1,4-benzoquinon-2-yl)methyl-2-acetoxybenzamide, N-(3-hydroxycarbonylpyridin-2-yl)-5-(5,6-dimethoxy-3-methyl-1,4-benzoquinon-2-yl)methyl-2-acetoxybenzamide, N-(3-hydroxycarbonylpyridin-2-yl)-5-(5,6-dimethoxy-3-methyl-1,4-benzoquinon-2-yl)methyl-2-hydroxybenzamide, N-(5-tert-butoxycarbonylpyridin-2-yl)-5-(5,6-dimethoxy-3-methyl-1,4-benzoquinon-2-yl)methyl-2-acetoxybenzamide, N-(5-hydroxycarbonylpyridin-2-yl)-5-(5,6-dimethoxy-3-methyl-1,4-benzoquinon-2-yl)methyl-2-acetoxybenzamide, N-(5-hydroxycarbonylpyridin-2-yl)-5-(5,6-dimethoxy-3-methyl-1,4-benzoquinon-2-yl)methyl-2-hydroxybenzamide, N-[5-(5,6-dimethoxy-3-methyl-1,4-benzoquinon-2-yl)methyl-2-acetoxybenzoyl]-4-tert-butoxycarbonylaminoaniline, N-[5-(5,6-dimethoxy-3-methyl-1,4-benzoquinon-2-yl)methyl-2-hydroxybenzoyl]-4-tert-butoxycarbonylaminoaniline, N-(pyridin-3-yl)-5-(5,6-dimethoxy-3-methyl-1,4-benzoquinon-2-yl)methyl-2-acetoxybenzamide, N-(pyridin-3-yl)-5-(5,6-dimethoxy-3-methyl-1,4-benzoquinon-2-yl)methyl-2-hydroxybenzamide (methanesulfonate), N-(pyridin-4-yl)-5-(5,6-dimethoxy-3-methyl-1,4-benzoquinon-2-yl)methyl-2-hydroxybenzamide (methanesulfonate), N-[5-(5,6-dimethoxy-3-methyl-1,4-benzoquinon-2-yl)methyl-2-hydroxybenzoyl]-p-phenylenediamine, N-[5-(5,6-dimethoxy-3-methyl-1,4-benzoquinon-2-yl)methyl-2-hydroxybenzoyl]-p-phenylenediamine (hydrochloride), N-(pyridin-3-yl)-3-(5,6-dimethoxy-3-methyl-1,4-benzoquinon-2-yl)methyl-2-acetoxybenzamide, N-(pyridin-3-yl)-3-(5,6-dimethoxy-3-methyl-1,4-benzoquinon-2-yl)methyl-2-hydroxybenzamide, N-[5-(5,6-dimethoxy-3-methyl-1,4-benzoquinon-2-yl)methyl-2-acetoxybenzoyl]-4-(imidazol-1-yl)aniline, N-[5-(5,6-dimethoxy-3-methyl-1,4-benzoquinon-2-yl)methyl-2-hydroxybenzoyl]-4-(imidazol-1-yl)aniline, N-[5-(5,6-dimethoxy-3-methyl-1,4-benzoquinon-2-yl)methyl-2-acetoxybenzoyl]-4-(1H-pyrazol-3-yl)aniline, N-[5-(5,6-dimethoxy-3-methyl-1,4-benzoquinon-2-yl)methyl-2-hydroxybenzoyl]-4-(1H-pyrazol-3-yl)aniline, N-methyl-N-[5-(5,6-dimethoxy-3-methyl-1,4-benzoquinon-2-yl)methyl-2-acetoxybenzoyl]-4-trifluoromethylaniline, N-methyl-N-[5-(5,6-dimethoxy-3-methyl-1,4-benzoquinon-2-yl)methyl-2-hydroxybenzoyl]-4-trifluoromethylaniline, t-butyl N-[5-(5,6-dimethoxy-3-methyl-1,4-benzoquinon-2-yl)methyl-2-hydroxybenzoyl]-4-aminobenzoate, N-(2-methoxypyridin-3-yl)-5-(5,6-dimethoxy-3-methyl-1,4-benzoquinon-2-yl)methyl-2-acetoxybezamide, N-(2-methoxypyridin-3-yl)-5-(5,6-dimethoxy-3-methyl-1,4-benzoquinon-2-yl)methyl-2-hydroxybezamide, N-(2-dimethylaminopyridin-3-yl)-5-(5,6-dimethoxy-3-methyl-1,4-benzoquinon-2-yl)methyl-2-acetoxybezamide, N-(2-dimethylaminopyridin-3-yl)-5-(5,6-dimethoxy-3-methyl-1,4-benzoquinon-2-yl)methyl-2-hydroxybezamide, N-[5-(5,6-dimethoxy-3-methyl-1,4-benzoquinon-2-yl)methyl-2-acetoxybenzoyl]-2,5-dimethoxyaniline, N-[5-(5,6-dimethoxy-3-methyl-1,4-benzoquinon-2-yl)methyl-2-hydroxybenzoyl]-2,5-dimethoxyaniline, N-(2-chloropyridin-3-yl)-5-(5,6-dimethoxy-3-methyl-1,4-benzoquinon-2-yl)methyl-2-methoxybenzamide, N-(2-morpholinopyridin-3-yl)-5-(5,6-dimethoxy-3-methyl-1,4-benzoquinon-2-yl)methyl-2-acetoxybenzamide, N-(2-morpholinopyridin-3-yl)-5-(5,6-dimethoxy-3-methyl-1,4-benzoquinon-2-yl)methyl-2-hydroxybenzamide, N-(6-morpholinopyridin-3-yl)-5-(5,6-dimethoxy-3-methyl-1,4-benzoquinon-2-yl)methyl-2-acetoxybenzamide, N-(6-morpholinopyridin-3-yl)-5-(5,6-dimethoxy-3-methyl-1,4-benzoquinon-2-yl)methyl-2-hydroxybenzamide, N-(2-chloropyridin-4-yl)-5-(5,6-dimethoxy-3-methyl-1,4-benzoquinon-2-yl)methyl-2-acetoxybenzamide, N-(2-chloropyridin-4-yl)-5-(5,6-dimethoxy-3-methyl-1,4-benzoquinon-2-yl)methyl-2-hydroxybenzamide, N-(6-methoxypyrimidin-4-yl)-5-(5,6-dimethoxy-3-methyl-1,4-benzoquinon-2-yl)methyl-2-acetoxybenzamide, N-(6-methoxypyrimidin-4-yl)-5-(5,6-dimethoxy-3-methyl-1,4-benzoquinon-2-yl)methyl-2-hydroxybenzamide, N-(2-methoxypyridin-4-yl)-5-(5,6-dimethoxy-3-methyl-1,4-benzoquinon-2-yl)methyl-2-acetoxybenzamide, N-(2-methoxypyridin-4-yl)-5-(5,6-dimethoxy-3-methyl-1,4-benzoquinon-2-yl)methyl-2-hydroxybenzamide,
5-(2,5-dimethoxy-3,4,6-trimethylbenzyl)-2-acetoxybenzoic acid,
5-(3,5,6-trimethyl-1,4-benzoquinon-2-yl)methyl-2-acetoxybenzoic acid,
N-[5-(3,5,6-trimethyl-1,4-benzoquinon-2-yl)methyl-2-acetoxybenzoyl]-4-trifluoromethylaniline,
N-[5-(3,5,6-trimethyl-1,4-benzoquinon-2-yl)methyl-2-hydroxybenzoyl]-4-trifluoromethylaniline,
N-(2-chloropyridin-3-yl)-5-(3,5,6-trimethyl-1,4-benzoquinon-2-yl)methyl-2-acetoxybenzamide,
N-(2-chloropyridin-3-yl)-5-(3,5,6-trimethyl-1,4-benzoquinon-2-yl)methyl-2-hydroxybenzamide,
N-(pyridin-4-yl)-5-(3,5,6-trimethyl-1,4-benzoquinon-2-yl)methyl-2-hydroxybenzamide.

Examples of the production method of the compounds for practicing the present invention are described below. However, the production method of the compound as an active ingredient of the present invention is not limited thereto.

[General Production Method]

The substituted benzoic acid derivative represented by formula (I), which is used as an active ingredient of the present invention, can be produced using a synthetic intermediate which can be prepared according to the method described in K. Suzuki, T. Tatsuoka, T. Ishihara, R. Ogino, T. Miyazaki, F. Satoh, S. Miyano and K. Sumoto, *Chem. Pharm. Bull.*, 45, 668–674 (1997), or a method based thereupon.

More specifically, an aldehyde compound represented by formula (IV):

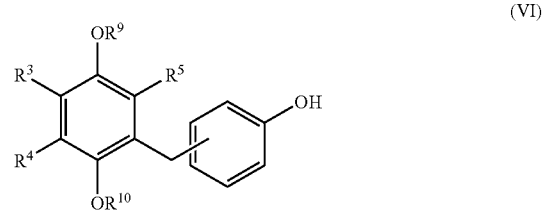

(IV)

(wherein $R^3$ to $R^5$, $R^9$ and $R^{10}$ are as defined above) is allowed to react with a Grignard reagent or an organic lithium reagent prepared from a bromophenol derivative to afford a compound represented by formula (V):

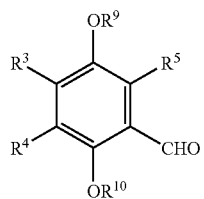

(V)

(wherein $R^3$ to $R^5$, $R^9$ and $R^{10}$ are as defined above, and Bn represents a benzyl group, which may be substituted), and this compound is reduced with a reducing agent such as triethylsilane in the presence of catalyst such as Lewis acid or trimethylsilyl trifluoromethanesulfonate and then catalytically reduced by stirring it in a hydrogen stream in the presence of catalyst such as palladium-carbon to obtain a phenol derivative represented by formula (VI):

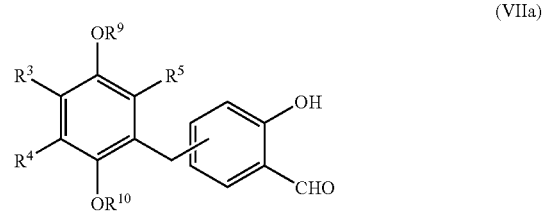

(VI)

(wherein $R^3$ to $R^5$, $R^9$ and $R^{10}$ are as defined above).

The obtained compound is stirred together with hexamethylenetetramine in a solvent such as trifluoroacetic acid at a temperature from room temperature to 100° C. and then hydrolyzed to obtain a compound represented by formula (VIIa):

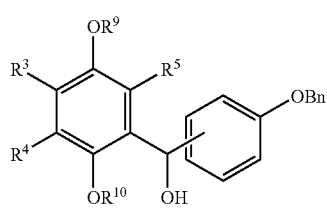

(VIIa)

(wherein $R^3$ to $R^5$, $R^9$ and $R^{10}$ are as defined above).

This compound is stirred together with an alkylating agent such as dimethyl sulfate or benzyl bromide at a temperature from room temperature to 50° C. in the presence of a base such as potassium carbonate or sodium hydroxide in a solvent not participating in the reaction, such as acetone, to obtain a compound represented by formula (VIIb):

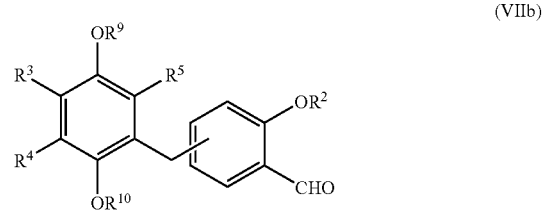

(VIIb)

(wherein $R^3$ to $R^5$, $R^9$ and $R^{10}$ are as defined above and $R^2$ represents a lower alkyl group having from 1 to 6 carbons or an aralkyl group having from 7 to 14 carbons).

The resulting compound is dissolved in a solvent not participating in the reaction, such as acetonitrile, and then stirred at a temperature of 0 to 50° C. in the presence of an oxidizing agent such as sodium chlorite and aqueous hydrogen peroxide, in a mixed solution with a phosphate buffer solution to obtain a substituted benzoic acid derivative represented by formula (Ia):

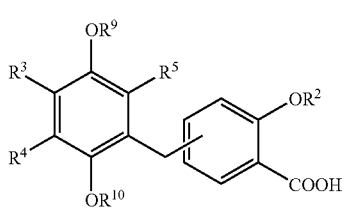

(wherein $R^3$ to $R^5$, $R^9$ and $R^{10}$ are as defined above and $R^2$ represents a lower alkyl group having from 1 to 6 carbons or an aralkyl group having from 7 to 14 carbons).

This carboxylic acid compound is treated with diazomethane or (trimethylsilyl)diazomethane in a solvent not participating in the reaction, such as methanol, or condensed with an alcohol represented by formula (VIII):

$R^6$—OH (VIII)

(wherein $R^6$ represents a lower alkyl group having from 1 to 6 carbons or an aralkyl group having from 7 to 14 carbons) or an amine represented by formula (IX):

(wherein $R^7$ and $R^8$ are as defined above) using a condensing agent such as 1-ethyl-3-(3-dimethylaminopropyl)carbodiimide hydrochloride or as an acid chloride form with oxalyl chloride or the like in the presence or absence of catalyst such as 4-dimethylaminopyridine in a solvent not participating in the reaction, such as methylene chloride, whereby a compound represented by formula (Ib):

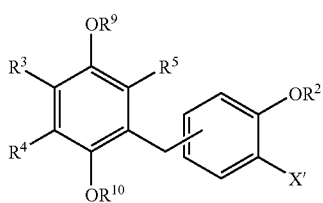

(wherein $R^2$ to $R^5$, $R^9$ and $R^{10}$ are as defined above and X' represents an esterified or amidated carboxyl group) can be obtained.

The compound where in formula (Ib), $R^2$ is a benzyl group which may be substituted is stirred at a temperature from room temperature to 50° C. in a hydrogen stream in the presence of catalyst such as palladium-carbon, whereby a compound represented by formula (Ic):

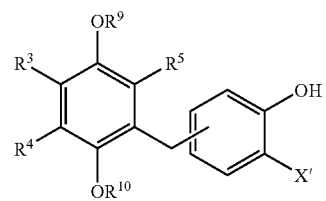

(wherein $R^3$ to $R^5$, $R^9$, $R^{10}$ and X' are as defined above) can be obtained.

The compound (IC) is:
1) stirred together with an alkylating agent such as alkyl halide at a temperature of 0 to 100° C. in the presence of a base such as potassium carbonate in a solvent not participating in the reaction, such as acetone,
2) stirred together with a boronic acid derivative represented by formula (X):

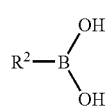

(wherein $R^2$ represents an aryl group which may be substituted, or a heteroaryl group which may be substituted) in the presence of catalyst such as copper acetate in a solvent not participating in the reaction, such as methylene chloride or acetonitrile, or
3) stirred together with an alcohol represented by formula (XI):

$R^{2'}$—OH (XI)

(wherein $R^{2'}$ represents a lower alkyl group which may be substituted, an aralkyl group which may be substituted, or a heteroarylalkyl group which may be substituted) in the presence of, for example, triphenylphosphine (or tributylphosphine) and diethylazodicaroxylate (or N,N,N', N'-tetramethylazodicarboxylate) in a solvent not participating in the reaction, such as tetrahydrofuran, under the conditions of normal [Mitsunobu reaction] (or a modified method thereof), whereby a compound represented by formula (Ib'):

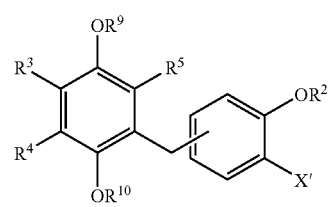

(wherein $R^{2'}$ represents a lower alkyl group having from 1 to 6 carbons, which may be substituted, an aryl group having from 6 to 12 carbons, which may be substituted, a heteroaryl group having from 4 to 11 carbons, which may be substituted, an aralkyl group having from 7 to 14 carbons, which may be substituted, or a heteroarylalkyl group having from 5 to 13 carbons, which may be substituted, and $R^3$ to $R^5$, $R^9$, $R^{10}$ and X' are as defined above) can be obtained.

The compounds (Ia), (Ib) and (Ib') each is oxidized with an oxidizing agent such as ammonium cerium(IV) nitrate in a solvent not participating in the reaction, such as a mixed solvent of acetonitrile and water, whereby a benzoquinone derivative represented by formula (Id):

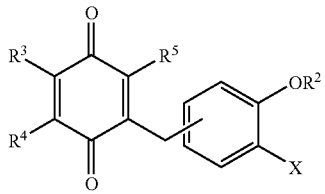

(Id)

(wherein $R^2$ to $R^5$ and X are as defined above) can be obtained.

Also, the compound where in formula (Ia), $R^2$ is a benzyl group which may be substituted is stirred at a temperature from room temperature to 50° C. in a hydrogen stream in the presence of catalyst such as palladium-carbon to remove benzyl group and then reacted with an acylating agent such as acetic anhydride or benzoic anhydride, whereby a compound represented by formula (Ie):

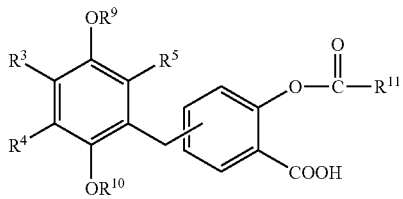

(Ie)

(wherein $R^3$ to $R^5$, $R^9$ and $R^{10}$ are as defined above and $R^{11}$ represents a lower alkyl group having from 1 to 6 carbons, which may be substituted, or an aryl group having from 6 to 12 carbons, which may be substituted) can be obtained.

This compound is oxidized with an oxidizing agent such as ammonium cerium(IV) nitrate in a solvent not participating in the reaction, such as a mixed solvent of acetonitrile and water, whereby a carboxylic acid compound represented by formula (If):

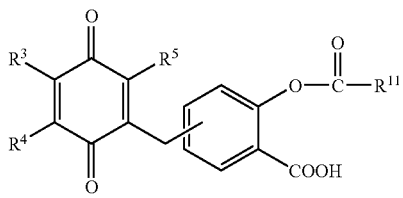

(If)

(wherein $R^3$ to $R^5$ and $R^{11}$ are as defined above) can be obtained. Then, this carboxylic acid compound is condensed with an alcohol or an amine using a condensing agent in the presence or absence of catalyst such as 4-dimethylaminopyridine in a solvent not participating in the reaction, such as methylene chloride, whereby a compound represented by formula (Ig):

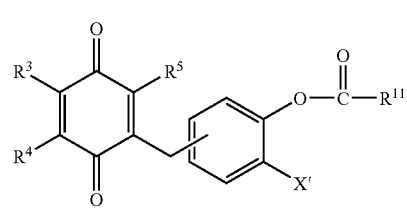

(Ig)

(wherein $R^3$ to $R^5$ and $R^{11}$ are as defined above and X' represents an esterified or amidated carboxyl group) can be obtained.

Also, the compound of formula (Ic) is:

1) reacted with an acid anhydride such as acetic anhydride in the presence of a base such as pyridine or triethylamine,
2) condensed with a benzoic acid derivative which may be substituted or with a heteroaryl carboxylic acid derivative such as nicotinic acid or picolinic acid using a condensing agent in the presence or absence of catalyst such as 4-dimethylaminopyridine, or
3) reacted with an acid chloride such as acetyl chloride or benzoyl chloride in the presence of a base such as pyridine or triethylamine, whereby a compound represented by formula (Ih):

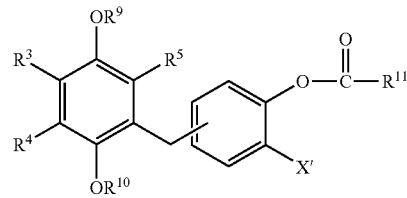

(Ih)

(wherein $R^3$ to $R^5$, $R^9$ and $R^{10}$ are as defined above, $R^{11'}$ represents a lower alkyl group having from 1 to 6 carbons, which may be substituted, an aryl group having from 6 to 12 carbons, which may be substituted, or a heteroaryl group having from 4 to 11 carbons, which may be substituted, and X' represents an esterified or amidated carboxyl group) can be obtained.

This compound is oxidized with an oxidizing agent such as ammonium cerium(IV) nitrate in a solvent not participating in the reaction, such as a mixed solvent of acetonitrile and water, whereby a compound represented by formula (Ii):

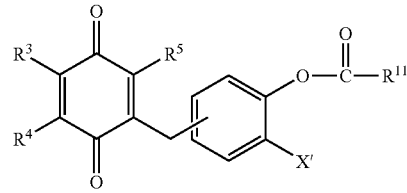

(Ii)

(wherein $R^3$ to $R^5$, $R^{11'}$ and X' are as defined above) can be obtained.

The compounds (Ig) and (Ii) each is hydrolyzed by stirring it in the presence of a base such as sodium hydrogencarbonate in a solvent not participating in the reaction, such as a mixed solvent of methanol and water, whereby a compound represented by formula (Ij):

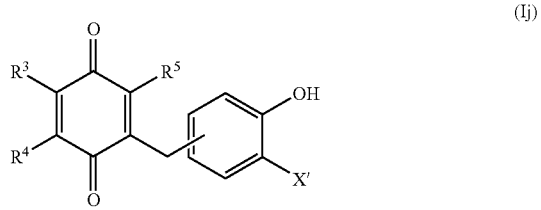

(wherein $R^3$ to $R^5$ and X' are as defined above) can be obtained.

The substances represented by formulae (Ia) to (Ij) of the present invention can inhibit the activation of NF-κB and therefore, are useful as a preventive or therapeutic agent for diseases caused by the activation of NF-κB, for example, diseases caused by excess production of various inflammation mediators or viral propagation. More specifically, these substances are useful as a preventive or therapeutic agent for diseases considered to be caused by the excess production of NO or TNF-α, for example, septic shock, osteoarthritis, rheumatoid arthris, cachexia, multiple organ failure, inflammatory bowel disease, malaria, acquired immune deficiency syndrome, human T-cell leukemia, meningitis, hepatitis, myocarditis, type II diabetes, multiple sclerosis, Behcet disease, systemic lupus erythematosus and ischemic heart disease, and the like.

In the case of using the compound of the present invention as the above-described medical composition, the compound can be used orally in the preparation form of tablets, capsules, elixirs, microcapsules or the like, or parenterally in the preparation form of injections such as a solution with water or other pharmaceutically acceptable solution or a suspension. For example, the medical composition can be produced by mixing the compound with physiologically acceptable carriers, flavoring agents, excipients, stabilizers and the like in a generally admitted form. Examples of the additive which can be mixed in tablets include a binder such as gelatin, swelling agents such as corn starch, excipients such as crystalline cellulose, and lubricants such as magnesium stearate. When formulated into capsules, the above-described composition may further contain liquid carriers. The aseptic composition for injection can also be formulated in the conventional manner.

Examples of the aqueous solution for injection include an isotonic solution containing glucose. An appropriate solubilizer such as polyethylene glycol may be used in combination. Also, buffer, stabilizers, preservatives, antioxidants, soothing agents and the like may be blended. The preparation thus obtained can be administered, for example, to mammals including humans. The dosage varies depending on the symptom and the like but in the case of oral administration, the daily dose for adult is generally from about 0.01 to 100 mg, preferably from about 0.1 to 50 mg, more preferably from about 1.0 to 25 mg. In the case of parenteral administration, for example, in the case of injection, the preparation is preferably administered by phleboclysis and the daily dose for adult is generally on the order from about 0.001 to 50 mg, preferably from about 0.01 to 25 mg, more preferably from about 0.1 to 10 mg.

The effect of NF-κB inhibition can be examined by directly or indirectly measuring the expression of genes regulated by the activation of NF-κB.

The effect of inhibiting the excess production of inflammatory proteins can be examined by directly or indirectly measuring the levels of inflammatory protein increasing in the culture medium or the body fluid when the cells or animals are stimulated with a cytokine such as IL-1 or TNF-α or with a lipopolysaccharide. As for the method of confirming the conventional anti-inflammatory effect, the effect of inhibiting the edema caused by carrageenin or dextran can be examined.

In these models, it is confirmed that the production of NO or TNF-α is effectively inhibited (see, M. C. Filion and N. C. Phillips, *Br. J. Pharmacol.*, 122, 551–557 (1997); P. W. Tsao, T. Suzuki, R. Totsuka, T. Murata, T. Takagi, Y. Ohmachi, H. Fujiwara and I. Takata, *Clin. Immunol. Immunopathol.*, 83, 173–178 (1997); S. Cuzzocrea, B. Zingarelli, P. Hake, A. L. Salzman and C. Szabo, *Free Radic. Biol. Med.*, 24, 450–459 (1998)).

For specific diseases, the efficacy as a therapeutic agent for sepsis can be evaluated by administering a lipopolysaccharide to an animal such as mice and measuring the effect of improving the survival ratio or the levels of inflammatory cytokines in blood. The effect as a therapeutic agent for rheumatoid arthritis can be evaluated in animal models suffering from arthritis caused by adjuvant or collagen (see, Y. Iigo et al., *J. Immunol.*, 147, 4167 (1991)).

The effect as a therapeutic agent for intractable inflammation such as Crohn's disease, hepatitis and nephritis can be presumed using an animal model prepared by a known method or in accordance with the method (see, K. Nishikawa et al., *J. Exp. Med.*, 180, 95 (1994); K. Kawasaki et al., *J. Immunol.*, 150, 1074 (1992)). Furthermore, the effect as an organ transplant rejection inhibitor can be evaluated using, for example, GVH (Graft versus Host) disease or various organ transplant model animals (see. A. B. Cosimi et al., *J. Immunol.*, 142, 2617 (1990); and M. Isobe et al., *Science*, 255, 1125 (1992)).

As such, the effect of the NF-κB inhibitor as a therapeutic agent for diseases can be confirmed using various animal models which can be prepared by a known method or according to the method.

The present invention is described in more detail with reference to Examples and Experiments, however, it should be noted that the present invention is not limited by them in any way.

REFERENCE EXAMPLE 1

3-(Benzyloxy)bromobenzene

3-Bromophenol (50 g, 0.289 mol) was dissolved in acetone (500 ml) and after adding thereto in sequence anhydrous potassium carbonate (80 g, 0.580 mmol) and benzyl bromide (59 g, 0.345 mol), the solution was refluxed under heating for 3 hours. The reaction mixture was filtered and the filtrate was concentrated under reduced pressure. The obtained crude product was recrystallized (the recrystallization operation was performed twice using hexane as a solvent) to obtain the titled compound (45.0 g, 0.171 mol, 59%).

REFERENCE EXAMPLE 2

4-(Benzyloxy)bromobenzene

4-Bromophenol (100 g, 0.587 mol) was dissolved in acetone (1,100 ml) and after adding thereto in sequence anhydrous potassium carbonate (159.53 g, 1.156 mmol) and benzyl bromide (103.78 g, 0.607 mol), the solution was refluxed under heating for 3 hours. The reaction mixture was filtered and the filtrate was concentrated under reduced pressure. The obtained crude product was recrystallized (the recrystallization operation was performed using hexane as a solvent) to obtain the titled compound (120.76 g, 0.459 mol, 79%).

REFERENCE EXAMPLE 3

2-(Benzyloxy)bromobenzene

2-Bromophenol (50.0 g, 0.289 mol) was dissolved in acetone (400 ml) and after adding thereto in sequence anhydrous potassium carbonate (79.89 g, 0.578 mmol) and benzyl bromide (59.32 g, 0.347 mol), the solution was refluxed under heating for 3 hours. The reaction mixture was filtered and the filtrate was concentrated under reduced pressure. The obtained crude product was purified by silica gel column chromatography (hexane:AcOEt=95:5) to obtain the titled compound (30.0 g, 0.114 mol, 40%).

REFERENCE EXAMPLE 4

1-(3,4,5,6-Tetramethoxy-2-methylphenyl)-1-(3-benzyloxyphenyl)methanol

An anhydrous tetrahydrofuran (50 ml) solution of 3,4,5,6-tetramethoxy-2-methylbenzaldehyde (14 g, 0.058 mol) was added dropwise under ice cooling to a Grignard reagent (150 ml tetrahydrofuran solution) prepared from 3-(benzyloxy)bromobenzene (18.4 g, 0.070 mol) and magnesium (1.87 g, 0.077 mol), and the resulting solution was stirred for 2 hours. The reaction solution was poured in an aqueous solution of saturated ammonium chloride and extracted with ether. The extract was washed with saturated brine and then dried. The reaction solution was filtered, the filtrate was concentrated and the obtained crude product was purified by silica gel column chromatography (hexand:ethyl acetate=4:1) to obtain the titled compound (23.5 g, 0.055 mol, 95%).

REFERENCE EXAMPLE 5

1-(3,4,5,6-Tetramethoxy-2-methylphenyl)-1-(4-benzyloxyphenyl)methanol

An anhydrous tetrahydrofuran (20 ml) solution of 3,4,5,6-tetramethoxy-2-methylbenzaldehyde (3.65 g, 0.015 mol) was added dropwise under ice cooling to a Grignard reagent (30 ml tetrahydrofuran solution) prepared from 4-(benzyloxy)bromobenzene (8.00 g, 0.030 mol) and magnesium (0.81 g, 0.033 mol), and the resulting solution was stirred for 2 hours. The reaction solution was poured in an aqueous solution of saturated ammonium chloride and extracted with ether. The extract was washed with saturated brine and then dried. The reaction solution was filtered, the filtrate was concentrated and the obtained crude product was purified by silica gel column chromatography (hexand:ethyl acetate=4:1) to obtain the titled compound (5.93 g, 0.014 mol, 92%).

REFERENCE EXAMPLE 6

1-(3,4,5,6-Tetramethoxy-2-methylphenyl)-1-(2-benzyloxyphenyl)methanol

An anhydrous tetrahydrofuran (30 ml) solution of 3,4,5,6-tetramethoxy-2-methylbenzaldehyde (5.00 g, 0.021 mol) was added dropwise under ice cooling to a Grignard reagent (35 ml tetrahydrofuran solution) prepared from 2-(benzyloxy)bromobenzene (11.50 g, 0.044 mol) and magnesium (1.16 g, 0.048 mol), and the resulting solution was stirred for 2 hours. The reaction solution was poured in an aqueous solution of saturated ammonium chloride and extracted with ether. The extract was washed with saturated brine and then dried. The reaction solution was filtered, the filtrate was concentrated and the obtained crude product was purified by silica gel column chromatography (hexand:ethyl acetate=4:1) to obtain the titled compound (8.80 g, 0.021 mol, 99%).

REFERENCE EXAMPLE 7

3-(3,4,5,6-Tetramethoxy-2-methylbenzyl)phenol

A methylene chloride solution of the compound obtained in Reference Example 4 (25.3 g, 59.67 mmol) was added dropwise to a methylene chloride solution (1,000 ml) of triethylsilane (8.33 g, 71.64 mmol) and TMSOTf (2.65 g, 11.92 mmol) and the resulting solution was stirred at room temperature for 1 hour. The reaction solution was washed with water and then dried, and the solvent was removed by distillation. The residue was dissolved in ethanol (100 ml) and dioxane (150 ml) and then added to an ethanol suspension (50 ml) of 5% Pd—C (3 g) and thereafter, the solution was stirred at room temperature for 16 hours in a hydrogen stream. The reaction solution was filtered, the filtrate was concentrated and the obtained residue was purified by silica gel column chromatography (hexand:ethyl acetate=3:1) to obtain the titled compound (18.4 g, 57.9 mmol, 97%).

REFERENCE EXAMPLE 8

4-(3,4,5,6-Tetramethoxy-2-methylbenzyl)phenol

A methylene chloride solution (70 ml) of the compound obtained in Reference Example 5 (3.00 g, 7.08 mmol) was added dropwise to a methylene chloride solution (80 ml) of triethylsilane (0.99 g, 8.52 mmol) and TMSOTf (0.31 g, 1.39 mmol) and the resulting solution was stirred at room temperature for 1 hour. The reaction solution was washed with water and then dried, and the solvent was removed by distillation. The residue was dissolved in ethanol (50 ml) and then added to an ethanol suspension (250 ml) of 5% Pd—C (500 mg) and thereafter, the solution was stirred at room temperature for 16 hours in a hydrogen stream. The reaction solution was filtered, the filtrate was concentrated and the obtained residue was purified by silica gel column chromatography (hexand:ethyl acetate=4:1) to obtain the titled compound (1.96 g, 6.15 mmol, 87%).

REFERENCE EXAMPLE 9

2-(3,4,5,6-Tetramethoxy-2-methylbenzyl)phenol

A methylene chloride solution (130 ml) of the compound obtained in Reference Example 6 (9.00 g, 21.23 mmol) was added dropwise to a methylene chloride solution (150 ml) of triethylsilane (2.95 g, 25.43 mmol) and TMSOTf (0.94 g, 4.23 mmol) and the resulting solution was stirred at room temperature for 1 hour. The reaction solution was washed with water and then dried, and the solvent was removed by distillation. The residue was dissolved in ethanol (50 ml) and then added to an ethanol suspension (350 ml) of 5% Pd—C (1.5 g) and thereafter, the solution was stirred at room temperature for 16 hours in a hydrogen stream. The reaction solution was filtered, the filtrate was concentrated and the obtained residue was purified by silica gel column chromatography (hexand:ethyl acetate=4:1) to obtain the titled compound (5.67 g, 17.83 mmol, 84%).

REFERENCE EXAMPLE 10

4-(3,4,5,6-Tetramethoxy-2-methylbenzyl)-2-hydroxybenzaldehyde (A) and 6-(3,4,5,6-tetramethoxy-2-methylbenzyl)-2-hydroxybenzaldehyde (B)

3-(3,4,5,6-Tetramethoxy-2-methylbenzyl)phenol (11.17 g, 35.13 mmol) and hexamethylenetetramine (6.39 g, 0.046 mol) were dissolved in trifluoroacetic acid (100 ml) and the solution was stirred under heating at 80° C. for 4 hours. After the completion of reaction, the solvent was removed by distillation and to the obtained residue, water (100 ml) was added. The resulting solution was stirred for 30 minutes and extracted with methylene chloride. The extract was washed with water and then dried, the solvent was removed by distillation and the obtained residue was purified by silica gel column chromatography (hexand:ethyl acetate=9:1) to obtain the titled compound A (3.35 g, 9.68 mmol, 28%) and compound B (2.03 g, 18%).

REFERENCE EXAMPLE 11

5-(3,4,5,6-Tetramethoxy-2-methylbenzyl)-2-hydroxybenzaldehyde 4-(3,4,5,6-Tetramethoxy-2-methylbenzyl)phenol (14.5 g, 45.60 mmol) and hexamethylenetetramine (8.30 g, 59.29 mmol) were dissolved in trifluoroacetic acid (100 ml) and the solution was stirred under heating at 80° C. for 4 hours. After the completion of reaction, the solvent was removed by distillation and to the obtained residue, water (100 ml) was added. The resulting solution was stirred for 30 minutes and extracted with methylene chloride. The extract was washed with water and then dried, the solvent was removed by distillation and the obtained residue was purified by silica gel column chromatography (hexand:ethyl acetate=4:1) to obtain the titled compound (12.20 g, 35.26 mmol, 78%).

REFERENCE EXAMPLE 12

3-(3,4,5,6-Tetramethoxy-2-methylbenzyl)-2-hydroxybenzaldehyde 2-(3,4,5,6-Tetramethoxy-2-methylbenzyl)phenol (8.64 g, 27.17 mmol) and hexamethylenetetramine (5.00 g, 35.67 mmol) were dissolved in trifluoroacetic acid (100 ml) and the solution was stirred under heating at 80° C. for 4 hours. After the completion of reaction, the solvent was removed by distillation and to the obtained residue, water (100 ml) was added. The resulting solution was stirred for 30 minutes and extracted with methylene chloride. The extract was washed with water and then dried, the solvent was removed by distillation and the obtained residue was purified by silica gel column chromatography (hexand:ethyl acetate=4:1) to obtain the titled compound (2.50 g, 7.23 mmol, 27%).

REFERENCE EXAMPLE 13

4-(3,4,5,6-Tetramethoxy-2-methylbenzyl)-2-benzyloxybenzaldehyde 4-(3,4,5,6-Tetramethoxy-2-methylbenzyl)-2-hydroxybenzaldehyde (743 mg, 2.14 mmol) was dissolved in acetone (50 ml) and after adding thereto anhydrous sodium carbonate (593 mg, 4.30 mmol) and benzyl bromide (477 mg, 2.79 mmol), the solution was stirred at room temperature for 16 hours. The reaction solution was filtered, the filtrate was concentrated and the obtained residue was purified by silica gel column chromatography (hexand:ethyl acetate=3:1) to obtain the titled compound (864 mg, 1.98 mmol, 93%).

REFERENCE EXAMPLE 14

6-(3,4,5,6-Tetramethoxy-2-methylbenzyl)-2-benzyloxybenzaldehyde 6-(3,4,5,6-Tetramethoxy-2-methylbenzyl)-2-hydroxybenzaldehyde (187 mg, 0.54 mmol) was dissolved in acetone (20 ml) and after adding thereto anhydrous sodium carbonate (149 mg, 1.08 mmol) and benzyl bromide (120 mg, 0.70 mmol), the solution was stirred at room temperature for 16 hours. The reaction solution was filtered, the filtrate was concentrated and the obtained residue was purified by silica gel column chromatography (hexand:ethyl acetate=3:1) to obtain the titled compound (221 mg, 0.51 mmol, 94%).

REFERENCE EXAMPLE 15

5-(3,4,5,6-Tetramethoxy-2-methylbenzyl)-2-benzyloxybenzaldehyde 5-(3,4,5,6-Tetramethoxy-2-methylbenzyl)-2-hydroxybenzaldehyde (0.100 g, 0.290 mol) was dissolved in acetone (10 ml) and after adding thereto anhydrous sodium carbonate (0.080 g, 0.579 mmol) and benzyl bromide (0.059 g, 0.347 mmol), the solution was refluxed under heating for 3 hours. The reaction solution was filtered, the filtrate was concentrated and the obtained residue was purified by silica gel column chromatography (hexand:ethyl acetate=4:1) to obtain the titled compound (0.114 g, 0.261 mmol, 90%).

REFERENCE EXAMPLE 16

3-(3,4,5,6-Tetramethoxy-2-methylbenzyl)-2-benzyloxybenzaldehyde 3-(3,4,5,6-Tetramethoxy-2-methylbenzyl)-2-hydroxybenzaldehyde (1.16 g, 3.35 mol) was dissolved in acetone (5 ml) and after adding thereto anhydrous sodium carbonate (1.02 g, 7.38 mmol) and benzyl bromide (0.69 g, 4.02 mmol), the solution was refluxed under heating for 3 hours. The reaction solution was filtered, the filtrate was concentrated and the obtained residue was purified by silica gel column chromatography (hexand:ethyl acetate=2:1) to obtain the titled compound (1.45 g, 3.32 mmol, 99%).

REFERENCE EXAMPLE 17

5-(3,4,5,6-Tetramethoxy-2-methylbenzyl)-2-methoxybenzaldehyde 5-(3,4,5,6-Tetramethoxy-2-methylbenzyl)-2-hydroxybenzaldehyde (0.500 g, 1.45 mmol) was dissolved in ethanol (15 ml) and after adding thereto in sequence sodium hydroxide (0.064 g, 1.59 mmol) and dimethyl sulfate (0.200 g, 1.59 mmol), the solution was stirred at room temperature for 12 hours. After the completion of reaction, the reaction solution was poured into a cold diluted hydrochloric acid solution and extracted with ethyl acetate. The extract was washed with water and then dried, the solvent was removed by distillation and the obtained residue was purified by silica gel column chromatography (hexand:ethyl acetate=4:1) to obtain the titled compound (0.359 g, 0.998 mmol, 69%).

REFERENCE EXAMPLE 18

5-(3,4,5,6-Tetramethoxy-2-methylbenzyl)-2-isopropoxybenzaldehyde 5-(3,4,5,6-Tetramethoxy-2-methylbenzyl)-2-hydroxybenzaldehyde (0.500 g, 1.45 mmol) was dissolved in DMF (15 ml) and after adding thereto in sequence anhydrous potassium carbonate (0.359 g, 2.60 mmol) and isopropyl bromide (0.320 g, 2.60 mmol), the solution was refluxed under heating for 3 hours. The reaction mixture was filtered, the filtrate was concentrated and the obtained residue was purified by silica gel column chromatography (hexand:ethyl acetate=4:1) to obtain the titled compound (0.530 g, 1.37 mmol, 94%).

EXAMPLE 1

4-(3,4,5,6-Tetramethoxy-2-methylbenzyl)-2-benzyloxybenzoic acid

An aqueous solution (2 ml) of sodium dihydrogenphosphate (157 mg, 1.31 mmol), an aqueous solution (7 ml) of sodium chlorite (795 mg, 80%, 7.07 mmol) and aqueous hydrogen peroxide (0.5 ml, 30%) were added to an acetonitrile solution (5 ml) of 4-(3,4,5,6-tetramethoxy-2-methylbenzyl)-2-benzyloxybenzaldehyde (735 mg, 1.69 mmol) and the resulting solution was stirred at room temperature for 16 hours. The reaction solution was diluted with water and then extracted with ethyl acetate. The extract was washed with an aqueous 10% sodium hydrosulfite ($Na_2S_2O_4$) solution and saturated brine, then dried and concentrated to obtain the titled compound (603 mg, 1.33 mmol, 79%).

EXAMPLE 2

6-(3,4,5,6-Tetramethoxy-2-methylbenzyl)-2-benzyloxybenzoic acid

An aqueous solution (1 ml) of sodium dihydrogenphosphate (24 mg, 0.20 mmol), an aqueous solution (3.5 ml) of sodium chlorite (123 mg, 80%, 1.09 mmol) and aqueous hydrogen peroxide (0.08 ml, 30%) were added to an acetonitrile solution (2.5 ml) of 6-(3,4,5,6-tetramethoxy-2-methylbenzyl)-2-benzyloxybenzaldehyde (112 mg, 0.26 mmol) and the resulting solution was stirred at room temperature for 16 hours. The reaction solution was diluted with water and then extracted with ethyl acetate. The extract was washed with an aqueous 10% sodium hydrosulfite ($Na_2S_2O_4$) solution and saturated brine, then dried and concentrated to obtain the titled compound (106 mg, 0.23 mmol, 91%).

EXAMPLE 3

5-(3,4,5,6-Tetramethoxy-2-methylbenzyl)-2-benzyloxybenzoic acid

An aqueous solution (10 ml) of sodium dihydrogenphosphate (12.0 g, 0.100 mol), an aqueous solution (30 ml) of sodium chlorite (5.19 g, 0.0577 mol) and aqueous hydrogen peroxide (1.701 ml, 30%) were added to an acetonitrile solution (30 ml) of 5-(3,4,5,6-tetramethoxy-2-methylbenzyl)-2-benzyloxybenzaldehyde (5.60 g, 0.0128 mol) and the resulting solution was stirred at room temperature for 5 hours. The reaction solution was diluted with water and then extracted with ethyl acetate. The extract was washed with an aqueous saturated sodium hydrosulfite ($Na_2S_2O_4$) solution and saturated brine, then dried and concentrated to obtain the titled compound (5.20 g, 0.0115 mol, 90%).

EXAMPLE 4

3-(3,4,5,6-Tetramethoxy-2-methylbenzyl)-2-benzyloxybenzoic acid

An aqueous solution (7 ml) of sodium dihydrogenphosphate (4.01 g, 33.42 mmol), an aqueous solution (7 ml) of sodium chlorite (1.74 g, 19.33 mmol) and aqueous hydrogen peroxide (1.89 ml, 30%) were added to an acetonitrile solution (12 ml) of 3-(3,4,5,6-tetramethoxy-2-methylbenzyl)-2-benzyloxybenzaldehyde (1.87 g, 4.28 mmol) and the resulting solution was stirred at room temperature for 5 hours. The reaction solution was diluted with water and then extracted with ethyl acetate. The extract was washed with an aqueous saturated sodium hydrosulfite ($Na_2S_2O_4$) solution and saturated brine, then dried and concentrated to obtain the titled compound (1.90 g, 4.20 mmol, 98%).

EXAMPLE 5

N-[4-(3,4,5,6-Tetramethoxy-2-methylbenzyl)-2-benzyloxybenzoyl]piperidine

Piperidine (56 mg, 0.6576 mmol) and 1-ethyl-3-(3-dimethylaminopropyl)carbodiimide hydrochloride (169 mg, 0.8815 mmol) were added to a methylene chloride solution (20 ml) of 4-(3,4,5,6-tetramethoxy-2-methylbenzyl)-2-benzyloxybenzoic acid (173 mg, 0.3827 mmol) and the resulting solution was stirred at room temperature for 8 hours. The reaction solution was poured into ice water and then extracted with methylene chloride. The extract was washed with water and then dried, and the solvent was removed by distillation. The obtained residue was purified by flash column chromatography (hexand:ethyl acetate=2:1) to obtain the titled compound (129 mg, 0.2485 mmol, 65%).

EXAMPLE 6

N-[5-(3,4,5,6-Tetramethoxy-2-methylbenzyl)-2-benzyloxybenzoyl]piperidine

Piperidine (0.358 g, 4.20 mmol) and 1-ethyl-3-(3-dimethylaminopropyl)carbodiimide hydrochloride (1.21 g, 6.30 mmol) were added to a methylene chloride solution (50 ml) of 5-(3,4,5,6-tetramethoxy-2-methylbenzyl)-2-benzyloxybenzoic acid (0.95 g, 2.10 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by silica gel column chromatography (chloroform:methanol=50:1) to obtain the titled compound (1.02 g, 2.09 mmol, 99%).

EXAMPLE 7

N-[5-(3,4,5,6-Tetramethoxy-2-methylbenzyl)-2-benzyloxybenzoyl]morpholine

Morpholine (0.451 g, 5.17 mmol) and 1-ethyl-3-(3-dimethylaminopropyl)carbodiimide hydrochloride (1.49 g, 7.76 mmol) were added to a methylene chloride solution (80 ml) of 5-(3,4,5,6-tetramethoxy-2-methylbenzyl)-2-benzyloxybenzoic acid (1.17 g, 2.59 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by silica gel column chromatography (chloroform:methanol=50:1) to obtain the titled compound (1.27 g, 2.59 mmol, 99%).

EXAMPLE 8

N-[5-(3,4,5,6-Tetramethoxy-2-methylbenzyl)-2-benzyloxybenzoyl]-4-methoxyaniline p-Methoxyaniline (0.250 g, 2.03 mmol), triethylamine (0.206 g, 2.03 mmol) and 2-chloro-1,3- dimethylimidazolinium chloride (0.344 g, 2.03 mmol) were added to a methylene chloride solution (40 ml) of 5-(3,4,5,6-tetramethoxy-2-methylbenzyl)-2-benzyloxybenzoic acid (0.460 g, 1.02 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (ethyl acetate:hexane=1:2) and recrystallized from ether to obtain the titled compound (0.211 g, 0.379 mmol, 37%).

EXAMPLE 9

4-(3,4,5,6-Tetramethoxy-2-methylbenzyl)-2-hydroxybenzoic acid

10% Pd—C (50 mg) was added to an ethanol (10 ml) and dioxane (10 ml) mixed solution of 4-(3,4,5,6-tetramethoxy-2-methylbenzyl)-2-benzyloxybenzoic acid (150 mg, 0.3554 mmol) and the resulting solution was stirred at room temperature for 16 hours in a hydrogen stream. The reaction solution was filtered, the filtrate was concentrated under reduced pressure, and the residue was washed with hexane to obtain the titled compound (97 mg, 0.2679 mmol, 75%).

EXAMPLE 10

5-(3,4,5,6-Tetramethoxy-2-methylbenzyl)-2-hydroxybenzoic acid 5-(3,4,5,6-Tetramethoxy-2-methylbenzyl)-2-benzyloxybenzoic acid (159.53 g, 1.156 mmol) was dissolved in ethanol (20 ml) and after adding thereto an ethanol suspension (3 ml) of 5% Pd—C (0.250 g), the solution was stirred at room temperature for 16 hours in a hydrogen stream. The reaction solution was filtered, the filtrate was concentrated, and the obtained residue was recrystallized from ether to obtain the titled compound (0.630 g, 1.74 mmol, 79%).

EXAMPLE 11

3-(3,4,5,6-Tetramethoxy-2-methylbenzyl)-2-hydroxybenzoic acid 3-(3,4,5,6-Tetramethoxy-2-methylbenzyl)-2-benzyloxybenzoic acid (0.52 g, 1.15 mmol) was dissolved in ethanol (10 ml) and after adding thereto an ethanol suspension (3 ml) of 5% Pd—C (0.15 g), the solution was stirred at room temperature for 16 hours in a hydrogen stream. The reaction solution was filtered, the filtrate was concentrated, and the obtained residue was purified by silica gel column chromatography (chloroform:methanol=9:1) to obtain the titled compound (0.41 g, 1.13 mmol, 98%).

EXAMPLE 12

4-(3,4,5,6-Tetramethoxy-2-methylbenzyl)-2-acetoxybenzoic acid 4-(3,4,5,6-Tetramethoxy-2-methylbenzyl)-2-hydroxybenzoic acid (97 mg, 0.2679 mmol) was dissolved in acetic anhydride (20 ml) and the resulting solution was refluxed under heating for 2 hours. The reaction solution was concentrated and the residue was purified by silica gel column chromatography (5% methanol-methylene chloride) to obtain the titled compound (65 mg, 0.1608 mmol, 60%).

EXAMPLE 13

5-(3,4,5,6-Tetramethoxy-2-methylbenzyl)-2-acetoxybenzoic acid 5-(3,4,5,6-Tetramethoxy-2-methylbenzyl)-2-hydroxybenzoic acid (1.30 g, 3.59 mmol) was dissolved in acetic anhydride (5 ml) and the resulting solution was stirred under heating at 65° C. for 3 hours. The reaction solution was cooled and after adding thereto water (20 ml) and stirring at room temperature for 1 hour, extracted with ethyl acetate. The extract was washed with saturated brine and then dried, and the solvent was removed by distillation. The residue was purified by silica gel column chromatography (chloroform:methanol=10:1) to obtain the titled compound (0.99 g, 2.45 mmol, 68%).

EXAMPLE 14

3-(3,4,5,6-Tetramethoxy-2-methylbenzyl)-2-acetoxybenzoic acid 3-(3,4,5,6-Tetramethoxy-2-methylbenzyl)-2-hydroxybenzoic acid (0.288 g, 0.795 mmol) was dissolved in acetic anhydride (5 ml) and the resulting solution was stirred under heating at 65° C. for 3 hours. The reaction solution was cooled and after adding thereto water (20 ml) and stirring at room temperature for 1 hour, extracted with ethyl acetate. The extract was washed with saturated brine and then dried, and the solvent was removed by distillation. The residue was purified by silica gel column chromatography (chloroform:methanol=9:1) to obtain the titled compound (0.245 g, 0.541 mmol, 68%).

EXAMPLE 15

Methyl 5-(3,4,5,6-tetramethoxy-2-methylbenzyl)-2-hydroxybenzoate 5-(3,4,5,6-Tetramethoxy-2-methylbenzyl)-2-hydroxybenzoic acid (0.800 g, 2.21 mmol) was dissolved in a mixed solvent of methanol (4 ml) and benzene (28 ml) and after adding thereto trimethylsilyldiazomethane (10% hexane solution) (0.303 g, 2.65 mmol), the solution was stirred at room temperature for 3 hours. The reaction solution was concentrated and the obtained residue was purified by silica gel column chromatography (hexand:ethyl acetate=3:1) to obtain the titled compound (0.800 g, 2.13 mmol, 96%).

EXAMPLE 16

5-(3,4,5,6-Tetramethoxy-2-methylbenzyl)-2-methoxybenzoic acid

An aqueous solution (5 ml) of sodium dihydrogenphosphate (1.06 g, 8.86 mmol), an aqueous solution (7 ml) of sodium chlorite (0.460 g, 5.11 mmol) and aqueous hydrogen peroxide (0.502 ml, 30%) were added to an acetonitrile solution (10 ml) of 5-(3,4,5,6-tetramethoxy-2-methylbenzyl)-2-methoxybenzaldehyde (0.409 g, 1.14 mmol) and the resulting solution was stirred at room temperature for 5 hours. The reaction solution was diluted with water and then extracted with ethyl acetate. The extract was washed with an aqueous saturated sodium hydrosulfite ($Na_2S_2O_4$) solution and saturated brine, then dried and concentrated. The obtained residue was purified by silica gel column chromatography (hexane:ethyl acetate=2:1) to obtain the titled compound (0.260 g, 0.691 mmol, 61%).

EXAMPLE 17

5-(3,4,5,6-Tetramethoxy-2-methylbenzyl)-2-isopropoxybenzoic acid

An aqueous solution (5 ml) of sodium dihydrogenphosphate (1.28 g, 10.65 mmol), an aqueous solution (7 ml) of sodium chlorite (0.533 g, 6.15 mmol) and aqueous hydrogen peroxide (0.18 ml, 30%) were added to an acetonitrile solution (5 ml) of 5-(3,4,5,6-tetramethoxy-2-methylbenzyl)-2-isopropoxybenzaldehyde (0.530 g, 1.37 mol) and the resulting solution was stirred at room temperature for 5 hours. The reaction solution was diluted with water and then extracted with ethyl acetate. The extract was washed with an aqueous saturated sodium hydrosulfite ($Na_2S_2O_4$) solution and saturated brine, then dried and concentrated to obtain the titled compound (0.475 g, 1.18 mmol, 86%).

EXAMPLE 18

Methyl 5-(3,4,5,6-tetramethoxy-2-methylbenzyl)-2-phenoxybenzoate

Methyl 5-(3,4,5,6-tetramethoxy-2-methylbenzyl)-2-hydroxybenzoate (0.510 g, 1.18 mmol) was dissolved in methylene chloride (12 ml) and after adding thereto in sequence copper acetate (0.215 g, 1.18 mmol), phenylboronic acid (0.289 g, 2.37 mmol), Molecular Sieves 4A (0.300 g), triethylamine (0.299 g, 2.96 mmol) and pyridine (0.234 g, 2.96 mmol), the solution was stirred at room temperature for 12 hours. The reaction solution was filtered and the filtrate was poured into water and then extracted with methylene chloride. The extract was washed with saturated brine, then dried and concentrated. The obtained residue was purified by silica gel column chromatography (hexand:ethyl acetate=3:1) to obtain the titled compound (0.220 g, 0.487 mmol, 41%).

EXAMPLE 19

Methyl 5-(3,4,5,6-tetramethoxy-2-methylbenzyl)-2-(3-methoxyphenoxy)benzoate

Methyl 5-(3,4,5,6-tetramethoxy-2-methylbenzyl)-2-hydroxybenzoate (0.805 g, 2.14 mmol) was dissolved in methylene chloride (50 ml) and after adding thereto in sequence copper acetate (0.429 g, 2.36 mmol), 3-methoxyphenylboronic acid (0.651 g, 4.28 mmol), Molecular Sieves 4A (0.500 g), triethylamine (0.541 g, 5.35 mmol) and pyridine (0.423 g, 5.35 mmol), the solution was stirred at room temperature for 12 hours. The reaction solution was filtered and the filtrate was poured into water and then extracted with methylene chloride. The extract was washed with saturated brine, then dried and concentrated. The obtained residue was purified by silica gel column chromatography (hexand:ethyl acetate=4:1) to obtain the titled compound (0.200 g, 0.414 mmol, 19%).

EXAMPLE 20

Methyl 5-(3,4,5,6-tetramethoxy-2-methylbenzyl)-2-(3-pyridylmethyloxy)benzoate

3-Pyridinemethanol (0.084 g, 0.774 mmol), tri-n-butylphosphine (0.156 g, 0.774 mmol) and N,N,N',N'-tetramethylazodicarboxamide (0.133 g, 0.774 mmol) were added to a benzene solution of methyl 5-(3,4,5,6-tetramethoxy-2-methylbenzyl)-2-hydroxybenzoate (0.194 g, 0.516 mmol) and the solution was stirred at room temperature for 12 hours. The reaction solution was poured into an aqueous 2N sodium hydroxide solution (15 ml) and then extracted with methylene chloride. The extract was washed with water and then dried, and the solvent was removed by distillation. The obtained residue was purified by silica gel column chromatography (hexand:ethyl acetate=2:3) to obtain the titled compound (0.167 g, 0.358 mmol, 69%).

EXAMPLE 21

Methyl 5-(3,4,5,6-tetramethoxy-2-methylbenzyl)-2-(4-pyridylmethyloxy)benzoate

4-Pyridinemethanol (0.232 g, 2.13 mmol), tri-n-butylphosphine (0.430 g, 2.13 mmol) and N,N,N',N'-tetramethylazodicarboxamide (0.366 g, 2.13 mmol) were added to a benzene solution of methyl 5-(3,4,5,6-tetramethoxy-2-methylbenzyl)-2-hydroxybenzoate (0.500 g, 1.33 mmol) and the solution was stirred at room temperature for 12 hours. The reaction solution was poured into an aqueous 2N sodium hydroxide solution (15 ml) and then extracted with methylene chloride. The extract was washed with water and then dried, and the solvent was removed by distillation. The obtained residue was purified by silica gel column chromatography (hexand:ethyl acetate=2:3) to obtain the titled compound (0.610 g, 1.31 mmol, 98%).

EXAMPLE 22

Methyl 5-(3,4,5,6-tetramethoxy-2-methylbenzyl)-2-(tert-butoxycarbonylmethyloxy)benzoate Methyl 5-(3,4,5,6-tetramethoxy-2-methylbenzyl)-2-hydroxybenzoate (1.09 g, 2.53 mmol) was dissolved in acetone (50 ml) and after adding thereto anhydrous sodium carbonate (0.420 g, 3.03 mmol) and tert-butyl bromoacetate (0.592 g, 3.03 mmol), the solution was refluxed under heating for 3 hours. The reaction solution was filtered, the filtrate was concentrated, and the obtained residue was purified by silica gel column chromatography (hexand:ethyl acetate=2:1) to obtain the titled compound (0.650 g, 1.33 mmol, 53%).

EXAMPLE 23

5-(3,4,5,6-Tetramethoxy-2-methylbenzyl)-2-phenoxybenzoic acid

Methyl 5-(3,4,5,6-tetramethoxy-2-methylbenzyl)-2-phenoxybenzoate (0.220 g, 0.487 mmol) was dissolved in a mixed solution of an aqueous 1N NaOH solution (3 ml) and 1,4-dioxane (5 ml) and the resulting solution was stirred at room temperature for 12 hours. The reaction solution was diluted with water, rendered acidic with concentrated hydrochloric acid and then extracted with ether. The extract was washed with water and then dried, and the solvent was removed by distillation. The residue was purified by silica gel column chromatography (hexane:ethyl acetate=2:1) to obtain the titled compound (0.210 g, 0.479 mmol, 98%).

EXAMPLE 24

5-(3,4,5,6-Tetramethoxy-2-methylbenzyl)-2-(3-methoxyphenoxy)benzoic acid

Methyl 5-(3,4,5,6-tetramethoxy-2-methylbenzyl)-2-(3-methoxyphenoxy)benzoate (0.200 g, 0.414 mmol) was dissolved in a mixed solution of an aqueous 1N NaOH solution (3 ml) and 1,4-dioxane (3 ml) and the resulting solution was stirred at room temperature for 6 hours. The reaction solution was diluted with water, rendered acidic with concentrated hydrochloric acid and then extracted with ether. The extract was washed with water and then dried, and the solvent was removed by distillation. The residue was recrystallized from ether to obtain the titled compound (0.190 g, 0.408 mmol, 99%).

EXAMPLE 25

5-(3,4,5,6-Tetramethoxy-2-methylbenzyl)-2-(3-pyridylmethyloxy)benzoic acid

Methyl 5-(3,4,5,6-tetramethoxy-2-methylbenzyl)-2-(3-pyridylmethyloxy)benzoate (0.165 g, 0.353 mmol) was dissolved in a mixed solution of an aqueous 1N NaOH solution (3 ml) and 1,4-dioxane (3 ml) and the resulting solution was stirred at room temperature for 6 hours. The reaction solution was diluted with water, rendered acidic with concentrated hydrochloric acid and then extracted with ether. The extract was washed with water and then dried, and the solvent was removed by distillation. The obtained residue was purified by silica gel column chromatography (hexand:ethyl acetate=2:3) to obtain the titled compound (0.150 g, 0.331 mmol, 88%).

EXAMPLE 26

5-(3,4,5,6-Tetramethoxy-2-methylbenzyl)-2-(4-pyridylmethyloxy)benzoic acid

Methyl 5-(3,4,5,6-tetramethoxy-2-methylbenzyl)-2-(4-pyridylmethyloxy)benzoate (0.600 g, 1.28 mmol) was dissolved in a mixed solution of an aqueous 1N NaOH solution (3 ml) and 1,4-dioxane (3 ml) and the resulting solution was stirred at room temperature for 6 hours. The reaction solution was diluted with water, rendered acidic with concentrated hydrochloric acid and then extracted with ether. The extract was washed with water and then dried, and the solvent was removed by distillation. The obtained residue was purified by silica gel column chromatography (hexand:ethyl acetate=1:2) to obtain the titled compound (0.500 g, 1.10 mmol, 86%).

EXAMPLE 27

N-[5-(3,4,5,6-Tetramethoxy-2-methylbenzyl)-2-hydroxybenzoyl]piperidine

N-[5-(3,4,5,6-Tetramethoxy-2-methylbenzyl)-2-benzyloxybenzoyl]piperidine (1.02 g, 2.09 mmol) was dissolved in ethanol (50 ml) and the resulting solution was added to an ethanol suspension (5 ml) of 5% Pd—C (0.200 g) and stirred at room temperature for 16 hours in a hydrogen stream. The reaction solution was filtered, the filtrate was concentrated and the obtained residue was recrystallized from ether to obtain the titled compound (0.760 g, 1.95 mmol, 93%).

EXAMPLE 28

N-[5-(3,4,5,6-Tetramethoxy-2-methylbenzyl)-2-hydroxybenzoyl]morpholine

N-[5-(3,4,5,6-Tetramethoxy-2-methylbenzyl)-2-benzyloxybenzoyl]morpholine (1.27 g, 2.59 mmol) was dissolved in ethanol (50 ml) and the resulting solution was added to an ethanol suspension (5 ml) of 5% Pd—C (0.200 g) and stirred at room temperature for 16 hours in a hydrogen stream. The reaction solution was filtered, the filtrate was concentrated and the obtained residue was recrystallized from ether to obtain the titled compound (1.00 g, 2.49 mmol, 96%).

EXAMPLE 29

N-[5-(3,4,5,6-Tetramethoxy-2-methylbenzyl)-2-(3-pyridylmethyloxy)benzoyl]piperidine 3-Pyridinemethanol (0.102 g, 0.932 mmol), triphenylphosphine (0.293 g, 1.12 mmol) and diethylazodicarboxylate (0.195 g, 1.12 mmol) were added to a benzene solution (30 ml) of N-[5-(3,4,5,6-tetramethoxy-2-methylbenzyl)-2-hydroxybenzoyl]piperidine (0.320 g, 0.746 mmol) and the resulting solution was stirred at room temperature for 12 hours. The reaction solution was poured into an aqueous 2N sodium hydroxide solution (15 ml) and then extracted with methylene chloride. The extract was washed with water and then dried, and the solvent was removed by distillation. The obtained residue was purified by silica gel column chromatography (hexand:ethyl acetate= 1.5:8.5) to obtain the titled compound (0.350 g, 0.673 mmol, 90%).

EXAMPLE 30

N-[5-(3,4,5,6-Tetramethoxy-2-methylbenzyl)-2-(4-pyridylmethyloxy)benzoyl]piperidine 4-Pyridinemethanol (0.254 g, 2.33 mmol), triphenylphosphine (0.611 g, 2.33 mmol) and diethylazodicarboxylate (0.406 g, 2.33 mmol) were added to a benzene solution (30 ml) of N-[5-(3,4,5,6-tetramethoxy-2-methylbenzyl)-2-hydroxybenzoyl]piperidine (0.500 g, 1.17 mmol) and the resulting solution was stirred at room temperature for 12 hours. The reaction solution was poured into an aqueous 2N sodium hydroxide solution (15 ml) and then extracted with methylene chloride. The extract was washed with water and then dried, and the solvent was removed by distillation. The obtained residue was purified by silica gel column chromatography (hexand:ethyl acetate=1:5) to obtain the titled compound (0.375 g, 0.721 mmol, 62%).

EXAMPLE 31

N-[5-(3,4,5,6-Tetramethoxy-2-methylbenzyl)-2-(3-pyridyloxy)benzoyl]piperidine

N-[5-(3,4,5,6-Tetramethoxy-2-methylbenzyl)-2-hydroxybenzoyl]piperidine (0.150 g, 0.350 mmol) was dissolved in methylene chloride (3.5 ml) and after adding thereto in sequence copper acetate (0.064 g, 0.350 mmol), 3-pyridylboronic acid (0.114 g, 0.700 mmol), Molecular Sieves 4A (0.150 g), triethylamine (0.088 g, 0.874 mmol) and pyridine (0.069 g, 0.874 mmol), the solution was stirred at room temperature for 12 hours. The reaction solution was filtered and the filtrate was poured into water and then extracted with methylene chloride. The extract was washed with saturated brine, then dried and concentrated. The obtained residue was purified by silica gel column chromatography (chloroform:methanol=9:1) to obtain the titled compound (0.063 g, 0.125 mmol, 36%).

EXAMPLE 32

N-[5-(3,4,5,6-Tetramethoxy-2-methylbenzyl)-2-(4-pyridyloxy)benzoyl]piperidine

N-[5-(3,4,5,6-Tetramethoxy-2-methylbenzyl)-2-hydroxybenzoyl]piperidine (0.150 g, 0.350 mmol) was dissolved in methylene chloride (3.5 ml) and after adding thereto in sequence copper acetate (0.064 g, 0.350 mmol), 4-pyridylboronic acid (0.086 g, 0.700 mmol), Molecular Sieves 4A (0.150 g), triethylamine (0.088 g, 0.874 mmol) and pyridine (0.069 g, 0.874 mmol), the solution was stirred at room temperature for 12 hours. The reaction solution was filtered and the filtrate was poured into water and then extracted with methylene chloride. The extract was washed with saturated brine, then dried and concentrated. The obtained residue was purified by silica gel column chromatography (chloroform:methanol=9:1) to obtain the titled compound (0.055 g, 0.109 mmol, 31%).

EXAMPLE 33

N-[5-(3,4,5,6-Tetramethoxy-2-methylbenzyl)-2-(methoxycarbonylmethyloxy)benzoyl]piperidine N-[5-(3,4,5,6-Tetramethoxy-2-methylbenzyl)-2-hydroxybenzoyl]piperidine (0.200 g, 0.465 mmol) was dissolved in acetone (30 ml) and after adding thereto anhydrous sodium carbonate (0.077 g, 0.558 mmol) and methyl bromoacetate (0.078 g, 0.512 mmol), the solution was refluxed under heating for 3 hours. The reaction solution was filtered, the filtrate was concentrated and the obtained residue was purified by silica gel column chromatography (hexand:ethyl acetate=1:1) to obtain the titled compound (0.230 g, 0.459 mmol, 99%).

EXAMPLE 34

N-[5-(3,4,5,6-Tetramethoxy-2-methylbenzyl)-2-(tert-butoxycarbonylmethyloxy benzoyl]piperidine N-[5-(3,4,5,6-Tetramethoxy-2-methylbenzyl)-2-hydroxybenzoyl]piperidine (0.200 g, 0.467 mmol) was dissolved in acetone (30 ml) and after adding thereto anhydrous sodium carbonate (0.078 g, 0.561 mmol) and tert-butyl bromoacetate (0.109 g, 0.561 mmol), the solution was refluxed under heating for 3 hours. The reaction solution was filtered, the filtrate was concentrated and the obtained residue was purified by silica gel column chromatography (hexand:ethyl acetate=2:1) to obtain the titled compound (0.205 g, 0.378 mmol, 81%).

EXAMPLE 35

N-[5-(3,4,5,6-Tetramethoxy-2-methylbenzyl)-2-(3-pyridylmethyloxy)benzoyl]morpholine 3-Pyridinemethanol (0.080 g, 0.731 mmol), triphenylphosphine (0.192 g, 0.731 mmol) and diethylazodicarboxylate (0.127 g, 0.731 mmol) were added to a benzene solution of N-[5-(3,4,5,6-tetramethoxy-2-methylbenzyl)-2-hydroxybenzoyl]morpholine (0.210 g, 0.487 mmol) and the solution was stirred at room temperature for 12 hours. The reaction solution was poured into an aqueous 2N sodium hydroxide solution (15 ml) and then extracted with methylene chloride. The extract was washed with water and then dried, and the solvent was removed by distillation. The obtained residue was purified by silica gel column chromatography (hexane:ethyl acetate=1.5:8.5) to obtain the titled compound (0.195 g, 0.374 mmol, 77%).

EXAMPLE 36

N-[5-(3,4,5,6-Tetramethoxy-2-methylbenzyl)-2-(4-pyridylmethyloxy)benzoyl]morpholine 4-Pyridinemethanol (0.253 g, 2.32 mmol), triphenylphosphine (0.609 g, 2.32 mmol) and diethylazodicarboxylate (0.404 g, 2.32 mmol) were added to a benzene solution of N-[5-(3,4,5,6-tetramethoxy-2-methylbenzyl)-2-hydroxybenzoyl]morpholine (0.500 g, 1.16 mmol) and the solution was stirred at room temperature for 12 hours. The reaction solution was poured into an aqueous 2N sodium hydroxide solution (15 ml) and then extracted with methylene chloride. The extract was washed with water and then dried, and the solvent was removed by distillation. The obtained residue was purified by silica gel column chromatography (hexane:ethyl acetate=1:5) to obtain the titled compound (0.380 g, 0.728 mmol, 63%).

EXAMPLE 37

N-[5-(3,4,5,6-Tetramethoxy-2-methylbenzyl)-2-(3-pyridyloxy)benzoyl]morpholine

N-[5-(3,4,5,6-Tetramethoxy-2-methylbenzyl)-2-hydroxybenzoyl]morpholine (0.100 g, 0.232 mmol) was dissolved in methylene chloride (2.5 ml) and after adding thereto in sequence copper acetate (0.042 g, 0.232 mmol), 3-pyridylboronic acid (0.076 g, 0.464 mmol), Molecular Sieves 4A (0.100 g), triethylamine (0.059 g, 0.580 mmol) and pyridine (0.046 g, 0.580 mmol), the solution was stirred at room temperature for 12 hours. The reaction solution was filtered and the filtrate was poured into water and then extracted with methylene chloride. The extract was washed with saturated brine, then dried and concentrated. The obtained residue was purified by silica gel column chromatography (chloroform:methanol=9:1) to obtain the titled compound (0.050 g, 0.0984 mmol, 42%).

EXAMPLE 38

N-[5-(3,4,5,6-Tetramethoxy-2-methylbenzyl)-2-(4-pyridyloxy)benzoyl]morpholine

N-[5-(3,4,5,6-Tetramethoxy-2-methylbenzyl)-2-hydroxybenzoyl]morpholine (0.150 g, 0.348 mmol) was dissolved in methylene chloride (3.5 ml) and after adding thereto in sequence copper acetate (0.070 g, 0.383 mmol), 4-pyridylboronic acid (0.086 g, 0.696 mmol), Molecular Sieves 4A (0.150 g), triethylamine (0.088 g, 0.870 mmol) and pyridine (0.069 g, 0.870 mmol), the solution was stirred at room temperature for 12 hours. The reaction solution was filtered and the filtrate was poured into water and then extracted with methylene chloride. The extract was washed with saturated brine, then dried and concentrated. The obtained residue was purified by silica gel column chromatography (chloroform:methanol=9:1) to obtain the titled compound (0.052 g, 0.102 mmol, 29%).

EXAMPLE 39

N-[5-(3,4,5,6-Tetramethoxy-2-methylbenzyl)-2-(methoxycarbonylmethyloxy)benzoyl]morpholine N-[5-(3,4,5,6-Tetramethoxy-2-methylbenzyl)-2-hydroxybenzoyl]morpholine (0.200 g, 0.465 mmol) was dissolved in acetone (30 ml) and after adding thereto anhydrous sodium carbonate (0.077 g, 0.558 mmol) and methyl bromoacetate (0.078 g, 0.512 mmol), the solution was refluxed under heating for 3 hours. The reaction solution was filtered, the filtrate was concentrated and the obtained residue was purified by silica gel column chromatography (hexand:ethyl acetate=1:1) to obtain the titled compound (0.230 g, 0.398 mmol, 86%).

EXAMPLE 40

N-[5-(3,4,5,6-Tetramethoxy-2-methylbenzyl)-2-(tert-butoxycarbonylmethyloxy)benzoyl]morpholine N-[5-(3,4,5,6-Tetramethoxy-2-methylbenzyl)-2-hydroxybenzoyl]morpholine (0.200 g, 0.465 mmol) was dissolved in acetone (30 ml) and after adding thereto anhydrous sodium carbonate (0.077 g, 0.558 mmol) and tert-butyl bromoacetate (0.109 g, 0.558 mol), the solution was refluxed under heating for 3 hours. The reaction solution was filtered, the filtrate was concentrated and the obtained residue was purified by silica gel column chromatography (hexand:ethyl acetate=2:1) to obtain the titled compound (0.198 g, 0.363 mmol, 78%).

EXAMPLE 41

4-(5,6-Dimethoxy-3-methyl-1,4-benzoquinon-2-yl)methyl-2-benzyloxybenzoic acid 4-(3,4,5,6-Tetramethoxy-2-methylbenzyl)-2-benzyloxybenzoic acid (312 mg, 0.6902 mmol) was dissolved in a mixed solution of acetonitrile (15 ml) and water (5 ml) and after adding thereto ammonium cerium(IV) nitrate (hereinafter simply referred to as "CAN") (946 mg, 1.7262 mmol) at room temperature, the solution was stirred at room temperature for 1 hour. The reaction solution was diluted with water and then extracted with ether. The extract was washed with water and then dried, and the solvent was removed by distillation. The residue was recrystallized from ether to obtain the titled compound (187 mg, 0.4431 mmol, 64%).

EXAMPLE 42

6-(5,6-Dimethoxy-3-methyl-1,4-benzoquinon-2-yl) methyl-2-benzyloxybenzoic acid 6-(3,4,5,6-Tetramethoxy-2-methylbenzyl)-2-benzyloxybenzoic acid (106 mg, 0.2345 mmol) was dissolved in a mixed solution of acetonitrile (6 ml) and water (2 ml) and after adding thereto CAN (321 mg, 0.5857 mmol) at room temperature, the solution was stirred at room temperature for 1 hour. The reaction solution was diluted with water and then extracted with ether. The extract was washed with water and then dried, and the solvent was removed by distillation. The residue was recrystallized from ether to obtain the titled compound (62 mg, 0.1469 mmol, 64%).

EXAMPLE 43

5-(5,6-Dimethoxy-3-methyl-1,4-benzoquinon-2-yl) methyl-2-benzyloxybenzoic acid 5-(3,4,5,6-Tetramethoxy-2-methylbenzyl)-2-benzyloxybenzoic acid (0.490 g, 1.08 mmol) was dissolved in a mixed solution of acetonitrile (15 ml) and water (3 ml) and after adding thereto CAN (1.48 g, 2.71 mmol) at room temperature, the solution was stirred at room temperature for 1 hour. The reaction solution was diluted with water and then extracted with ether. The extract was washed with water and then dried, and the solvent was removed by distillation. The residue was recrystallized from ether to obtain the titled compound (0.217 g, 0.514 mmol, 48%).

EXAMPLE 44

3-(5,6-Dimethoxy-3-methyl-1,4-benzoquinon-2-yl) methyl-2-benzyloxybenzoic acid 3-(3,4,5,6-Tetramethoxy-2-methylbenzyl)-2-benzyloxybenzoic acid (0.55 g, 1.21 mmol) was dissolved in a mixed solution of acetonitrile (9 ml) and water (3 ml) and after adding thereto CAN (1.67 g, 3.03 mmol) at room temperature, the solution was stirred at room temperature for 2 hours. The reaction solution was diluted with water and then extracted with ether. The extract was washed with water and then dried, and the solvent was removed by distillation. The residue was recrystallized from ether to obtain the titled compound (0.250 g, 0.592 mmol, 49%).

EXAMPLE 45

4-(5,6-Dimethoxy-3-methyl-1,4-benzoquinon-2-yl methyl-2-acetoxybenzoic acid 4-(3,4,5,6-Tetramethoxy-2-methylbenzyl)-2-acetoxybenzoic acid (60 mg, 0.1485 mmol) was dissolved in a mixed solution of acetonitrile (15 ml) and water (5 ml) and after adding thereto CAN (203 mg, 0.3704 mmol) at room temperature, the solution was stirred at room temperature for 3 hours. The reaction solution was diluted with water and then extracted with ether. The extract was washed with water and then dried, and the solvent was removed by distillation. The residue was purified by preparative thin-layer chromatography (5% methanol-methylene chloride) to obtain the titled compound (38 mg, 0.1016 mmol, 68%).

EXAMPLE 46

5-(5,6-Dimethoxy-3-methyl-1,4-benzoquinon-2-yl) methyl-2-acetoxybenzoic acid 5-(3,4,5,6-Tetramethoxy-2-methylbenzyl)-2-acetoxybenzoic acid (0.200 g, 0.495 mmol) was dissolved in a mixed solution of acetonitrile (9 ml) and water (3 ml) and after adding thereto CAN (0.678 g, 1.24 mmol) at room temperature, the solution was stirred at room temperature for 1 hour. The reaction solution was diluted with water and then extracted with ether. The extract was washed with water and then dried, and the solvent was removed by distillation. The residue was recrystallized from ether to obtain the titled compound (0.160 g, 0.425 mmol, 86%).

EXAMPLE 47

3-(5,6-Dimethoxy-3-methyl-1,4-benzoquinon-2-yl) methyl-2-acetoxybenzoic acid 3-(3,4,5,6-Tetramethoxy-2-methylbenzyl)-2-acetoxybenzoic acid (0.300 g, 0.663 mmol) was dissolved in a mixed solution of acetonitrile (9 ml) and water (3 ml) and after adding thereto CAN (0.909 g, 1.658 mmol) at room temperature, the solution was stirred at room temperature for 1 hour. The reaction solution was diluted with water and then extracted with ether. The extract was washed with water and then dried, and the solvent was removed by distillation. The residue was recrystallized from ether to obtain the titled compound (0.248 g, 0.662 mmol, 99%).

EXAMPLE 48

4-(5,6-Dimethoxy-3-methyl-1,4-benzoquinon-2-yl) methyl-2-hydroxybenzoic acid 4-(5,6-Dimethoxy-3-methyl-1,4-benzoquinon-2-yl) methyl-2-acetoxybenzoic acid (22 mg, 0.059 mmol) was dissolved in methanol (2 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=10:1) and then recrystallized from ether to obtain the titled compound (12 mg, 0.0361 mmol, 61%).

EXAMPLE 49

5-(5,6-Dimethoxy-3-methyl-1,4-benzoquinon-2-yl) methyl-2-hydroxybenzoic acid 5-(5,6-Dimethoxy-3-methyl-1,4-benzoquinon-2-yl) methyl-2-acetoxybenzoic acid (0.150 g, 0.401 mmol) was dissolved in methanol (2 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=10:1) and then recrystallized from ether to obtain the titled compound (0.055 g, 0.166 mmol, 42%).

EXAMPLE 50

3-(5,6-Dimethoxy-3-methyl-1,4-benzoquinon-2-yl) methyl-2-hydroxybenzoic acid 3-(5,6-Dimethoxy-3-methyl-1,4-benzoquinon-2-yl) methyl-2-acetoxybenzoic acid (0.036 g, 0.0963 mmol) was dissolved in methanol (2 ml) and after adding thereto an aqueous saturated sodium hydrogencarbonate solution (2 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=9:1) and then recrystallized from diisopropyl ether to obtain the titled compound (0.010 g, 0.0301 mmol, 31%).

EXAMPLE 51

5-(5,6-Dimethoxy-3-methyl-1,4-benzoquinon-2-yl) methyl-2-methoxybenzoic acid 5-(3,4,5,6-Tetramethoxy-2-methylbenzyl)-2-methoxybenzoic acid (0.257 g, 0.684 mmol) was dissolved in a mixed solution of acetonitrile (9 ml) and water (3 ml) and after adding thereto CAN (0.937 g, 1.71 mmol) at room temperature, the solution was stirred at room temperature for 1 hour. The reaction solution was diluted with water and then extracted with ether. The extract was washed with water and then dried, and the solvent was removed by distillation. The residue was recrystallized from ether to obtain the titled compound (0.237 g, 0.683 mmol, 99%).

EXAMPLE 52

5-(5,6-Dimethoxy-3-methyl-1,4-benzoquinon-2-yl) methyl-2-isopropoxybenzoic acid 5-(3,4,5,6-Tetramethoxy-2-methylbenzyl)-2-isopropoxybenzoic acid (0.472 g, 1.17 mmol) was dissolved in a mixed solution of acetonitrile (9 ml) and water (3 ml) and after adding thereto CAN (1.60 g, 2.92 mmol) at room temperature, the solution was stirred at room temperature for 1 hour. The reaction solution was diluted with water and then extracted with ether. The extract was washed with water and then dried, and the solvent was removed by distillation. The residue was recrystallized from ether to obtain the titled compound (0.364 g, 0.972 mmol, 83%).

EXAMPLE 53

5-(5,6-Dimethoxy-3-methyl-1,4-benzoquinon-2-yl) methyl-2-phenoxybenzoic acid 5-(3,4,5,6-Tetramethoxy-2-methylbenzyl)-2-phenoxybenzoic acid (0.220 g, 0.502 mmol) was dissolved in a mixed solution of acetonitrile (12 ml) and water (4 ml) and after adding thereto CAN (0.688 g, 1.26 mmol) at room temperature, the solution was stirred at room temperature for 1 hour. The reaction solution was diluted with water and then extracted with ether. The extract was washed with water and then dried, and the solvent was removed by distillation. The residue was recrystallized from ether to obtain the titled compound (0.100 g, 0.245 mmol, 49%).

EXAMPLE 54

5-(5,6-Dimethoxy-3-methyl-1,4-benzoquinon-2-yl methyl-2-(3-methoxyphenoxy)benzoic acid 5-(3,4,5,6-Tetramethoxy-2-methylbenzyl)-2-(3-methoxyphenoxy)benzoic acid (0.194 g, 0.408 mmol) was dissolved in a mixed solution of acetonitrile (9 ml) and water (3 ml) and after adding thereto CAN (0.638 g, 1.02 mmol) at room temperature, the solution was stirred at room temperature for 1 hour. The reaction solution was diluted with water and then extracted with ether. The extract was washed with water and then dried, and the solvent was removed by distillation. The residue was recrystallized from ether to obtain the titled compound (0.159 g, 0.365 mmol, 89%).

EXAMPLE 55

5-(5,6-Dimethoxy-3-methyl-1,4-benzoquinon-2-yl) methyl-2-(3-pyridylmethyloxy)benzoic acid 5-(3,4,5,6-Tetramethoxy-2-methylbenzyl)-2-(3-pyridylmethyloxy)benzoic acid (0.100 g, 0.221 mmol) was dissolved in a mixed solution of acetonitrile (9 ml) and water (3 ml) and after adding thereto CAN (0.303 g, 0.552 mmol) at room temperature, the solution was stirred at room temperature for 1 hour. The reaction solution was diluted with water and then extracted with ether. The extract was washed with water and then dried, and the solvent was removed by distillation. The residue was purified by silica gel column chromatography (chloroform:methanol=1:2) and then recrystallized from ether to obtain the titled compound (0.071 g, 0.168 mmol, 76%).

EXAMPLE 56

5-(5,6-Dimethoxy-3-methyl-1,4-benzoquinon-2-yl) methyl-2-(4-pyridylmethyloxy)benzoic acid 5-(3,4,5,6-Tetramethoxy-2-methylbenzyl)-2-(4-pyridylmethyloxy)benzoic acid (0.425 g, 0.938 mmol) was dissolved in a mixed solution of acetonitrile (18 ml) and water (6 ml) and after adding thereto CAN (1.29 g, 2.35 mmol) at room temperature, the solution was stirred at room temperature for 1 hour. The reaction solution was diluted with water and then extracted with ether. The extract was washed with water and then dried, and the solvent was removed by distillation. The residue was purified by silica gel column chromatography (chloroform:methanol=9:1) and then recrystallized from ether to obtain the titled compound (0.376 g, 0.868 mmol, 93%).

EXAMPLE 57

N-[4-(5,6-Dimethoxy-3-methyl-1,4-benzoquinon-2-yl)methyl-2-benzyloxybenzoyl]piperidine N-[4-(3,4,5,6-Tetramethoxy-2-methylbenzyl)-2-benzyloxybenzoyl]piperidine (129 mg, 0.2485 mmol) was dissolved in a mixed solution of acetonitrile (15 ml) and water (5 ml) and after adding thereto CAN (341 mg, 0.6222 mmol) at room temperature, the solution was stirred at room temperature for 1 hour. The reaction solution was diluted with water and then extracted with ether. The extract was washed with water and then dried, and the solvent was removed by distillation. The residue was purified by flash column chromatography (hexand:ethyl acetate=2:1) to obtain the titled compound (85 mg, 0.1738 mmol, 70%).

EXAMPLE 58

N-[4-(5,6-Dimethoxy-3-methyl-1,4-benzoquinon-2-yl)methyl-2-benzyloxybenzoyl]morpholine Morpholine (19 mg, 0.2183 mmol) and 1-ethyl-3-(3-dimethylaminopropyl)carbodiimide hydrochloride (55 mg, 0.2869 mmol) were added to a methylene chloride solution (10 ml) of 4-(5,6-dimethoxy-3-methyl-1,4-benzoquinon-2-yl)methyl-2-benzyloxybenzoic acid (60 mg, 0.1421 mmol) and the resulting solution was stirred at room temperature for 16 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:2) to obtain the titled compound (55 mg, 0.1120 mmol, 79%).

EXAMPLE 59

N-[4-(5,6-Dimethoxy-3-methyl-1,4-benzoquinon-2-yl)methyl-2-benzyloxybenzoyl]-4-methoxyaniline p-Methoxyaniline (26 mg, 0.2113 mmol), triethylamine (29 mg, 0.2871 mmol) and 2-chloro-1,3-dimethylimidazolinium chloride (48 mg, 0.2840 mmol) were added to a methylene chloride solution (10 ml) of 4-(5,6-dimethoxy-1,4-benzoquinon-2-yl)methyl-2-benzyloxybenzoic acid (60 mg, 0.1421 mmol) and the resulting solution was stirred at room temperature for 3 hours. The reaction solution was poured into ice water and then extracted with ether. The extract was washed with water and then dried, and the solvent was removed by distillation. The obtained residue was purified by preparative thin-layer chromatography (hexand:ethyl acetate=1:1) to obtain the titled compound (55 mg, 0.1143 mmol, 73%).

EXAMPLE 60

N-[6-(5,6-Dimethoxy-3-methyl-1,4-benzoquinon-2-yl)methyl-2-benzyloxybenzoyl]-4-methoxyaniline p-Methoxyaniline (13 mg, 0.1056 mmol), triethylamine (15 mg, 0.1485 mmol) and 2-chloro-1,3-dimethylimidazolinium chloride (24 mg, 0.1420 mmol) were added to a methylene chloride solution (3 ml) of 6-(5,6-dimethoxy-1,4-benzoquinon-2-yl)methyl-2-benzyloxybenzoic acid (29 mg, 0.0687 mmol) and the resulting solution was stirred at room temperature for 3 hours. The reaction solution was poured into ice water and then extracted with ether. The extract was washed with water and then dried, and the solvent was removed by distillation. The obtained residue was purified by preparative thin-layer chromatography (hexand:ethyl acetate=1:1) to obtain the titled compound (20 mg, 0.0687 mmol, 55%).

EXAMPLE 61

N-[5-(5,6-Dimethoxy-3-methyl-1,4-benzoquinon-2-yl)methyl-2-benzyloxybenzoyl]piperidine Piperidine (0.025 g, 0.296 mmol) and 1-ethyl-3-(3-dimethylaminopropyl)carbodiimide hydrochloride (0.068 g, 0.355 mmol) were added to a methylene chloride solution (5 ml) of 5-(5,6-dimethoxy-3-methyl-1,4-benzoquinon-2-yl)methyl-2-benzyloxybenzoic acid (0.050 g, 0.118 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) to obtain the titled compound (0.025 g, 0.0511 mmol, 43%).

EXAMPLE 62

N-[5-(5,6-Dimethoxy-3-methyl-1,4-benzoquinon-2-yl)methyl-2-benzyloxybenzoyl]morpholine Oxalyl chloride (0.150 g, 1.18 mmol) was added to a methylene chloride solution (5 ml) of 5-(5,6-dimethoxy-3-methyl-1,4-benzoquinon-2-yl)methyl-2-benzyloxybenzoic acid (0.050 g, 0.118 mmol) and the resulting solution was stirred at room temperature for 1 hour. The reaction solution was concentrated and after adding a THF solution of morpholine (0.036 g, 0.414 mmol) to the obtained residue, the solution was stirred at room temperature for 30 minutes. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:1) to obtain the titled compound (0.058 g, 0.117 mmol, 99%).

EXAMPLE 63

N-[5-(5,6-Dimethoxy-3-methyl-1,4-benzoquinon-2-yl)methyl-2-benzyloxybenzoyl]-4-methoxyaniline p-Methoxyaniline (0.038 g, 0.308 mmol), triethylamine (0.031 g, 0.308 mmol) and 2-chloro-1,3-dimethylimidazolinium chloride (0.052 g, 0.308 mmol) were added to a methylene chloride solution (5 ml) of 5-(5,6-dimethoxy-3-methyl-1,4-benzoquinon-2-yl)methyl-2-benzyloxybenzoic acid (0.065 g, 0.154 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:2) to obtain the titled compound (0.066 g, 0.125 mmol, 81%).

EXAMPLE 64

N-[3-(5,6-Dimethoxy-3-methyl-1,4-benzoquinon-2-yl)methyl-2-benzyloxybenzoyl]piperidine Piperidine (0.038 g, 0.45 mmol) and 1-ethyl-3-(3-dimethylaminopropyl)carbodiimide hydrochloride (0.129 g, 0.68 mmol) were added to a methylene chloride solution (10 ml) of 3-(5,6-dimethoxy-3-methyl-1,4-benzoquinon-2-yl)methyl-2-benzyloxybenzoic acid (0.095 g, 0.23 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:1) to obtain the titled compound (0.060 g, 0.12 mmol, 55%).

EXAMPLE 65

N-[3-(5,6-Dimethoxy-3-methyl-1,4-benzoquinon-2-yl)methyl-2-benzyloxybenzoyl]morpholine Morpholine (0.033 g, 0.38 mmol) and 1-ethyl-3-(3-dimethylaminopropyl)carbodiimide hydrochloride (0.109 g, 0.57 mmol) were added to a methylene chloride solution (10 ml) of 3-(5,6-dimethoxy-3-methyl-1,4-benzoquinon-2-yl) methyl-2-benzyloxybenzoic acid (0.080 g, 0.19 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:1) to obtain the titled compound (0.057 g, 0.12 mmol, 61%).

EXAMPLE 66

N-[3-(5,6-Dimethoxy-3-methyl-1,4-benzoquinon-2-yl)methyl-2-benzyloxybenzoyl]-4-methoxyaniline p-Methoxyaniline (0.035 g, 0.28 mmol), triethylamine (0.029 g, 0.28 mmol) and 2-chloro-1,3-dimethylimidazolinium chloride (0.048 g, 0.28 mmol) were added to a methylene chloride solution (5 ml) of 3-(5,6-dimethoxy-3-methyl-1,4-benzoquinon-2-yl)methyl-2-benzyloxybenzoic acid (0.060 g, 0.14 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:1) to obtain the titled compound (0.038 g, 0.072 mmol, 51%).

EXAMPLE 67

N-[4-(5,6-Dimethoxy-3-methyl-1,4-benzoquinon-2-yl)methyl-2-acetoxybenzoyl]-4-methoxyaniline p-Methoxyaniline (4.3 mg, 0.0349 mmol), triethylamine (5.9 mg, 0.0584 mmol) and 2-chloro-1,3-dimethylimidazolinium chloride (9.9 mg, 0.0585 mmol) were added to a methylene chloride solution (3 ml) of 4-(5,6-dimethoxy-1,4-benzoquinon-2-yl)methyl-2-acetoxybenzoic acid (11 mg, 0.0294 mmol) and the resulting solution was stirred at room temperature for 6 hours. The reaction solution was poured into ice water and then extracted with ether. The extract was washed with water and then dried, and the solvent was removed by distillation. The obtained residue was purified by preparative thin-layer chromatography (hexand:ethyl acetate=1:3) to obtain the titled compound (6 mg, 0.0125 mmol, 43%).

EXAMPLE 68

N-[5-(5,6-Dimethoxy-3-methyl-1,4-benzoquinon-2-yl)methyl-2-acetoxybenzoyl]piperidine Piperidine (0.027 g, 0.321 mmol) and 1-ethyl-3-(3-dimethylaminopropyl)carbodiimide hydrochloride (0.062 g, 0.321 mmol) were added to a methylene chloride solution (5 ml) of 5-(5,6-dimethoxy-3-methyl-1,4-benzoquinon-2-yl) methyl-2-acetoxybenzoic acid (0.040 g, 0.107 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) to obtain the titled compound (0.008 g, 0.0181 mmol, 17%).

EXAMPLE 69

N-[5-(5,6-Dimethoxy-3-methyl-1,4-benzoquinon-2-yl, methyl-2-acetoxybenzoyl]morpholine Morpholine (0.034 g, 0.385 mmol) and 1-ethyl-3-(3-dimethylaminopropyl)carbodiimide hydrochloride (0.074 g, 0.385 mmol) were added to a methylene chloride solution (5 ml) of 5-(5,6-dimethoxy-3-methyl-1,4-benzoquinon-2-yl) methyl-2-acetoxybenzoic acid (0.048 g, 0.128 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) to obtain the titled compound (0.017 g, 0.0383 mmol, 30%).

EXAMPLE 70

N-[5-(5,6-Dimethoxy-3-methyl-1,4-benzoquinon-2-yl)methyl-2-acetoxybenzoyl]-4-methoxyaniline p-Methoxyaniline (0.046 g, 0.374 mmol), triethylamine (0.038 g, 0.374 mmol) and 2-chloro-1,3-dimethylimidazolinium chloride (0.063 g, 0.374 mmol) were added to a methylene chloride solution (5 ml) of 5-(5,6-dimethoxy-3-methyl-1,4-benzoquinon-2-yl)methyl-2-acetoxybenzoic acid (0.070 g, 0.187 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from ether to obtain the titled compound (0.043 g, 0.0897 mmol, 48%).

EXAMPLE 71

N-[3-(5,6-Dimethoxy-3-methyl-1,4-benzoquinon-2-yl)methyl-2-acetoxybenzoyl]piperidine Piperidine (0.133 g, 1.56 mmol) and 1-ethyl-3-(3-dimethylaminopropyl)carbodiimide hydrochloride (0.448 g, 2.34 mmol) were added to a methylene chloride solution (30 ml) of 3-(5,6-dimethoxy-3-methyl-1,4-benzoquinon-2-yl) methyl-2-acetoxybenzoic acid (0.293 g, 0.783 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=30:1) to obtain the titled compound (0.152 g, 0.345 mmol, 44%).

EXAMPLE 72

N-[3-(5,6-Dimethoxy-3-methyl-1,4-benzoquinon-2-yl)methyl-2-acetoxybenzoyl]morpholine Morpholine (0.176 g, 2.02 mmol) and 1-ethyl-3-(3-dimethylaminopropyl)carbodiimide hydrochloride (0.581 g, 3.03 mmol) were added to a methylene chloride solution (50 ml) of 3-(5,6-dimethoxy-3-methyl-1,4-benzoquinon-2-yl) methyl-2-acetoxybenzoic acid (0.380 g, 1.01 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=30:1) to obtain the titled compound (0.175 g, 0.394 mmol, 39%).

EXAMPLE 73

N-[3-(5,6-Dimethoxy-3-methyl-1,4-benzoquinon-2-yl)methyl-2-acetoxybenzoyl]-4-methoxyaniline p-Methoxyaniline (0.104 g, 0.845 mmol), triethylamine (0.085 g, 0.845 mmol) and 2-chloro-1,3-dimethylimidazolinium chloride (0.143 g, 0.845 mmol) were added to a methylene chloride solution (20 ml) of 3-(5,6-dimethoxy-3-methyl-1,4-benzoquinon-2-yl)methyl-2-acetoxybenzoic acid (0.158 g, 0.422 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=30:1) and then recrystallized from isopropyl ether to obtain the titled compound (0.066 g, 0.138 mmol, 33%).

EXAMPLE 74

N-[5-(5,6-Dimethoxy-3-methyl-1,4-benzoquinon-2-yl)methyl-2-hydroxybenzoyl]piperidine N-[5-(5,6-Dimethoxy-3-methyl-1,4-benzoquinon-2-yl)methyl-2-acetoxybenzoyl]piperidine (0.040 g, 0.0906 mmol) was dissolved in methanol (2 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=10:1) to obtain the titled compound (0.025 g, 0.0626 mmol, 69%).

EXAMPLE 75

N-[5-(5,6-Dimethoxy-3-methyl-1,4-benzoquinon-2-yl)methyl-2-hydroxybenzoyl]morpholine N-[5-(5,6-Dimethoxy-3-methyl-1,4-benzoquinon-2-yl)methyl-2-acetoxybenzoyl]morpholine (0.045 g, 0.101 mmol) was dissolved in methanol (2 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=10:1) to obtain the titled compound (0.020 g, 0.0498 mmol, 49%).

EXAMPLE 76

N-[5-(5,6-Dimethoxy-3-methyl-1,4-benzoquinon-2-yl)methyl-2-hydroxybenzoyl]-4-methoxyaniline N-[5-(5,6-Dimethoxy-3-methyl-1,4-benzoquinon-2-yl)methyl-2-acetoxybenzoyl]-4-methoxyaniline (0.073 g, 0.152 mmol) was dissolved in methanol (2 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (hexand:ethyl acetate=1:1) and then recrystallized from ether to obtain the titled compound (0.043 g, 0.0983 mmol, 65%).

EXAMPLE 77

N-[3-(5,6-Dimethoxy-3-methyl-1,4-benzoquinon-2-yl)methyl-2-hydroxybenzoyl]piperidine N-[3-(5,6-Dimethoxy-3-methyl-1,4-benzoquinon-2-yl)methyl-2-acetoxybenzoyl]piperidine (0.050 g, 0.113 mmol) was dissolved in methanol (3 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=9:1) to obtain the titled compound (0.017 g, 0.0426 mmol, 38%).

EXAMPLE 78

N-[3-(5,6-Dimethoxy-3-methyl-1,4-benzoquinon-2-yl)methyl-2-hydroxybenzoyl]morpholine N-[3-(5,6-Dimethoxy-3-methyl-1,4-benzoquinon-2-yl)methyl-2-acetoxybenzoyl]morpholine (0.050 g, 0.113 mmol) was dissolved in methanol (3 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=9:1) to obtain the titled compound (0.022 g, 0.0542 mmol, 48%).

EXAMPLE 79

N-[3-(5,6-Dimethoxy-3-methyl-1,4-benzoquinon-2-yl)methyl-2-hydroxybenzoyl]-4-methoxyaniline N-[3-(5,6-Dimethoxy-3-methyl-1,4-benzoquinon-2-yl)methyl-2-acetoxybenzoyl]-4-methoxyaniline (0.040 g, 0.0834 mmol) was dissolved in methanol (3 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=30:1) to obtain the titled compound (0.025 g, 0.0528 mmol, 69%).

EXAMPLE 80

N-[5-(5,6-Dimethoxy-3-methyl-1,4-benzoquinon-2-yl)methyl-2-methoxybenzoyl]piperidine Piperidine (0.027 g, 0.318 mmol) and 1-ethyl-3-(3-dimethylaminopropyl)carbodiimide hydrochloride (0.091 g, 0.477 mmol) were added to a methylene chloride solution (5 ml) of 5-(5,6-dimethoxy-3-methyl-1,4-benzoquinon-2-yl)methyl-2-methoxybenzoic acid (0.055 g, 0.159 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (ethyl acetate) to obtain the titled compound (0.0175 g, 0.0423 mmol, 27%).

EXAMPLE 81

N-[5-(5,6-Dimethoxy-3-methyl-1,4-benzoquinon-2-yl)methyl-2-methoxybenzoyl]morpholine Morpholine (0.025 g, 0.289 mmol) and 1-ethyl-3-(3-dimethylaminopropyl)carbodiimide hydrochloride (0.083 g, 0.434 mmol) were added to a methylene chloride solution (5 ml) of 5-(5,6-dimethoxy-3-methyl-1,4-benzoquinon-2-yl)methyl-2-methoxybenzoic acid (0.050 g, 0.145 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (ethyl acetate) to obtain the titled compound (0.033 g, 0.0794 mmol, 55%).

EXAMPLE 82

N-[5-(5,6-Dimethoxy-3-methyl-1,4-benzoquinon-2-yl)methyl-2-methoxybenzoyl]-4-methoxyaniline p-Methoxyaniline (0.043 g, 0.347 mmol), triethylamine (0.035 g, 0.347 mmol) and 2-chloro-1,3-dimethylimidazolinium chloride (0.059 g, 0.347 mmol) were added to a methylene chloride solution (5 ml) of 5-(5,6-dimethoxy-3-methyl-1,4-benzoquinon-2-yl)methyl-2-methoxybenzoic acid (0.060 g, 0.173 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (ethyl acetate) to obtain the titled compound (0.044 g, 0.0975 mmol, 56%).

EXAMPLE 83

N-[5-(5,6-Dimethoxy-3-methyl-1,4-benzoquinon-2-yl)methyl-2-isopropoxybenzoyl]piperidine Piperidine (0.030 g, 0.353 mmol) and 1-ethyl-3-(3-dimethylaminopropyl)carbodiimide hydrochloride (0.101 g, 0.529 mmol) were added to a methylene chloride solution (5 ml) of 5-(5,6-dimethoxy-3-methyl-1,4-benzoquinon-2-yl)methyl-2-isopropoxybenzoic acid (0.066 g, 0.176 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:6) to obtain the titled compound (0.030 g, 0.068 mmol, 39%).

EXAMPLE 84

N-[5-(5,6-Dimethoxy-3-methyl-1,4-benzoquinon-2-yl)methyl-2-isopropoxybenzoyl]morpholine Morpholine (0.030 g, 0.348 mmol) and 1-ethyl-3-(3-dimethylaminopropyl)carbodiimide hydrochloride (0.100 g, 0.521 mmol) were added to a methylene chloride solution (5 ml) of 5-(5,6-dimethoxy-3-methyl-1,4-benzoquinon-2-yl)methyl-2-isopropoxybenzoic acid (0.065 g, 0.174 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:6) to obtain the titled compound (0.026 g, 0.0586 mmol, 34%).

EXAMPLE 85

N-[5-(5,6-Dimethoxy-3-methyl-1,4-benzoquinon-2-yl)methyl-2-isopropoxybenzoyl]-4-methoxyaniline p-Methoxyaniline (0.077 g, 0.626 mmol), triethylamine (0.063 g, 0.626 mmol) and 2-chloro-1,3-dimethylimidazolinium chloride (0.106 g, 0.626 mmol) were added to a methylene chloride solution (10 ml) of 5-(5,6-dimethoxy-3-methyl-1,4-benzoquinon-2-yl)methyl-2-isopropoxybenzoic acid (0.117 g, 0.313 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexane:ethyl acetate=1:2) to obtain the titled compound (0.095 g, 0.198 mmol, 63%).

EXAMPLE 86

N-[5-(5,6-Dimethoxy-3-methyl-1,4-benzoquinon-2-yl)methyl-2-phenoxybenzoyl]piperidine Piperidine (0.054 g, 0.634 mmol) and 1-ethyl-3-(3-dimethylaminopropyl)carbodiimide hydrochloride (0.182 g, 0.950 mmol) were added to a methylene chloride solution (10 ml) of 5-(5,6-dimethoxy-3-methyl-1,4-benzoquinon-2-yl)methyl-2-phenoxybenzoic acid (0.129 g, 0.317 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:1) to obtain the titled compound (0.060 g, 0.126 mmol, 40%).

EXAMPLE 87

N-[5-(5,6-Dimethoxy-3-methyl-1,4-benzoquinon-2-yl)methyl-2-phenoxybenzoyl]morpholine Morpholine (0.030 g, 0.343 mmol) and 1-ethyl-3-(3-dimethylaminopropyl)carbodiimide hydrochloride (0.099 g, 0.515 mmol) were added to a methylene chloride solution (5 ml) of 5-(5,6-dimethoxy-3-methyl-1,4-benzoquinon-2-yl)methyl-2-phenoxybenzoic acid (0.070 g, 0.172 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) to obtain the titled compound (0.040 g, 0.0839 mmol, 49%).

EXAMPLE 88

N-[5-(5,6-Dimethoxy-3-methyl-1,4-benzoquinon-2-yl)methyl-2-phenoxybenzoyl]-4-methoxyaniline p-Methoxyaniline (0.045 g, 0.368 mmol), triethylamine (0.037 g, 0.368 mmol) and 2-chloro-1,3-dimethylimidazolinium chloride (0.062 g, 0.368 mmol) were added to a methylene chloride solution (5 ml) of 5-(5,6-dimethoxy-3-methyl-1,4-benzoquinon-2-yl)methyl-2-phenoxybenzoic acid (0.075 g, 0.184 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=9:1) to obtain the titled compound (0.040 g, 0.0780 mmol, 42%).

EXAMPLE 89

N-[5-(5,6-Dimethoxy-3-methyl-1,4-benzoquinon-2-yl)methyl-2-(3-methoxyphenoxy)benzoyl]piperidine Piperidine (0.096 g, 1.128 mmol) and 1-ethyl-3-(3-dimethylaminopropyl)carbodiimide hydrochloride (0.324 g, 1.692 mmol) were added to a methylene chloride solution (5 ml) of 5-(5,6-dimethoxy-3-methyl-1,4-benzoquinon-2-yl)methyl-2-(3-methoxyphenoxy)benzoic acid (0.247 g, 0.564 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) to obtain the titled compound (0.165 g, 0.327 mmol, 58%).

EXAMPLE 90

N-[5-(5,6-Dimethoxy-3-methyl-1,4-benzoquinon-2-yl)methyl-2-(3-methoxyphenoxy)benzoyl]morpholine Morpholine (0.106 g, 1.225 mmol) and 1-ethyl-3-(3-dimethylaminopropyl)carbodiimide hydrochloride (0.352 g, 1.838 mmol) were added to a methylene chloride solution (50 ml) of 5-(5,6-dimethoxy-3-methyl-1,4-benzoquinon-2-yl)methyl-2-(3-methoxyphenoxy)benzoic acid (0.250 g, 0.613 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) to obtain the titled compound (0.173 g, 0.341 mmol, 51%).

EXAMPLE 91

N-[5-(5,6-Dimethoxy-3-methyl-1,4-benzoquinon-2-yl)methyl-2-(3-methoxyphenoxy)benzoyl]-4-methoxyaniline p-Methoxyaniline (0.056 g, 0.457 mmol), triethylamine (0.046 g, 0.457 mmol) and 2-chloro-1,3-dimethylimidazolinium chloride (0.077 g, 0.457 mmol) were added to a methylene chloride solution (10 ml) of 5-(5,6-dimethoxy-3-methyl-1,4-benzoquinon-2-yl)methyl-2-(3-methoxyphenoxy)benzoic acid (0.100 g, 0.228 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=2:3) to obtain the titled compound (0.058 g, 0.107 mmol, 47%).

EXAMPLE 92

N-[5-(5,6-Dimethoxy-3-methyl-1,4-benzoquinon-2-yl)methyl-2-(3-pyridylmethyloxy)benzoyl]piperidine N-[5-(3,4,5,6-Tetramethoxy-2-methylbenzyl)-2-(3-pyridylmethyloxy)benzoyl]piperidine (0.380 g, 0.731 mmol) was dissolved in a mixed solution of acetonitrile (12 ml) and water (4 ml) and after adding thereto CAN (1.00 g, 1.83 mmol) at room temperature, the solution was stirred at room temperature for 1 hour. The reaction solution was diluted with water and then extracted with ether. The extract was washed with water and then dried, and the solvent was removed by distillation. The residue was purified by silica gel column chromatography (chloroform:methanol=9:1) to obtain the titled compound (0.222 g, 0.453 mmol, 62%).

EXAMPLE 93

N-[5-(5,6-Dimethoxy-3-methyl-1,4-benzoquinon-2-yl)methyl-2-(3-pyridylmethyloxy)benzoyl]morpholine N-[5-(3,4,5,6-Tetramethoxy-2-methylbenzyl-2-(3-pyridylmethyloxy)benzoyl]morpholine (0.263 g, 0.506 mmol) was dissolved in a mixed solution of acetonitrile (12 ml) and water (4 ml) and after adding thereto CAN (0.693 g, 1.26 mmol) at room temperature, the solution was stirred at room temperature for 1 hour. The reaction solution was diluted with water and then extracted with ether. The extract was washed with water and then dried, and the solvent was removed by distillation. The residue was purified by silica gel column chromatography (chloroform:methanol=9:1) to obtain the titled compound (0.153 g, 0.311 mmol, 61%).

EXAMPLE 94

N-[5-(5,6-Dimethoxy-3-methyl-1,4-benzoquinon-2-yl)methyl-2-(3-pyridylmethyloxy)benzoyl]-4-methoxyaniline p-Methoxyaniline (0.078 g, 0.639 mmol), triethylamine (0.066 g, 0.639 mmol) and 2-chloro-1,3-dimethylimidazolinium chloride (0.108 g, 0.639 mmol) were added to a methylene chloride solution (20 ml) of 5-(5,6-dimethoxy-3-methyl-1,4-benzoquinon-2-yl)methyl-2-(3-pyridylmethyloxy)benzoic acid (0.135 g, 0.318 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=9:1) and then recrystallized from ether to obtain the titled compound (0.040 g, 0.0756 mmol, 24%).

EXAMPLE 95

N-[5-(5,6-Dimethoxy-3-methyl-1,4-benzoquinon-2-yl)methyl-2-(4-pyridylmethyloxy)benzoyl]piperidine N-[5-(3,4,5,6-Tetramethoxy-2-methylbenzyl)-2-(4-pyridylmethyloxy)benzoyl]piperidine (0.550 g, 1.06 mmol)

was dissolved in a mixed solution of acetonitrile (15 ml) and water (5 ml) and after adding thereto CAN (1.45 g, 2.64 mmol) at room temperature, the solution was stirred at room temperature for 1 hour. The reaction solution was diluted with water and then extracted with ether. The extract was washed with water and then dried, and the solvent was removed by distillation. The residue was purified by silica gel column chromatography (chloroform:methanol=9:1) to obtain the titled compound (0.320 g, 0.652 mmol, 62%).

EXAMPLE 96

N-[5-(5,6-Dimethoxy-3-methyl-1,4-benzoquinon-2-yl)methyl-2-(4-pyridylmethyloxy)benzoyl]morpholine N-[5-(3,4,5,6-Tetramethoxy-2-methylbenzyl)-2-(4-pyridylmethyloxy)benzoyl]morpholine (0.460 g, 0.885 mmol) was dissolved in a mixed solution of acetonitrile (15 ml) and water (5 ml) and after adding thereto CAN (1.21 g, 2.21 mmol) at room temperature, the solution was stirred at room temperature for 1 hour. The reaction solution was diluted with water and then extracted with ether. The extract was washed with water and then dried, and the solvent was removed by distillation. The residue was purified by silica gel column chromatography (chloroform:methanol=9:1) to obtain the titled compound (0.270 g, 0.548 mmol, 62%).

EXAMPLE 97

N-[5-(5,6-Dimethoxy-3-methyl-1,4-benzoquinon-2-yl)methyl-2-(4-pyridylmethyloxy)benzoyl]-4-methoxyaniline p-Methoxyaniline (0.078 g, 0.639 mmol), triethylamine (0.066 g, 0.639 mmol) and 2-chloro-1,3-dimethylimidazolinium chloride (0.108 g, 0.639 mmol) were added to a methylene chloride solution (10 ml) of 5-(5,6-dimethoxy-3-methyl-1,4-benzoquinon-2-yl)methyl-2-(4-pyridylmethyloxy)benzoic acid (0.135 g, 0.318 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=9:1) and then recrystallized from ether to obtain the titled compound (0.054 g, 0.102 mmol, 32%).

EXAMPLE 98

N-[5-(5,6-Dimethoxy-3-methyl-1,4-benzoquinon-2-yl)methyl-2-(3-pyridyloxy)benzoyl]piperidine N-[5-(3,4,5,6-Tetramethoxy-2-methylbenzyl)-2-(3-pyridyloxy)benzoyl]piperidine (0.050 g, 0.099 mmol) was dissolved in a mixed solution of acetonitrile (12 ml) and water (4 ml) and after adding thereto CAN (0.135 g, 0.247 mmol) at room temperature, the solution was stirred at room temperature for 1 hour. The reaction solution was diluted with water and then extracted with ether. The extract was washed with water and then dried, and the solvent was removed by distillation. The obtained residue was purified by preparative thin-layer chromatography (chloroform:methanol=9:1) to obtain the titled compound (0.025 g, 0.0525 mmol, 53%).

EXAMPLE 99

N-[5-(5,6-Dimethoxy-3-methyl-1,4-benzoquinon-2-yl)methyl-2-(3-pyridyloxy)benzoyl]morpholine N-[5-(3,4,5,6-Tetramethoxy-2-methylbenzyl)-2-(3-pyridyloxy)benzoyl]morpholine (0.022 g, 0.0435 mmol) was dissolved in a mixed solution of acetonitrile (6 ml) and water (2 ml) and after adding thereto CAN (0.060 g, 0.109 mmol) at room temperature, the solution was stirred at room temperature for 1 hour. The reaction solution was diluted with water and then extracted with ether. The extract was washed with water and then dried, and the solvent was removed by distillation. The obtained residue was purified by preparative thin-layer chromatography (chloroform:methanol=9:1) to obtain the titled compound (0.012 g, 0.0251 mmol, 58%).

EXAMPLE 100

N-[5-(5,6-Dimethoxy-3-methyl-1,4-benzoquinon-2-yl)methyl-2-(4-pyridyloxy)benzoyl]piperidine N-[5-(3,4,5,6-Tetramethoxy-2-methylbenzyl)-2-(4-pyridyloxy)benzoyl]piperidine (0.021 g, 0.0415 mmol) was dissolved in a mixed solution of acetonitrile (6 ml) and water (2 ml) and after adding thereto CAN (0.057 g, 0.104 mmol) at room temperature, the solution was stirred at room temperature for 1 hour. The reaction solution was diluted with water and then extracted with ether. The extract was washed with water and then dried, and the solvent was removed by distillation. The obtained residue was purified by preparative thin-layer chromatography (chloroform:methanol=9:1) to obtain the titled compound (0.013 g, 0.580 mmol, 66%).

EXAMPLE 101

N-[5-(5,6-Dimethoxy-3-methyl-1,4-benzoquinon-2-yl)methyl-2-(4-pyridyloxy)benzoyl]morpholine N-[5-(3,4,5,6-Tetramethoxy-2-methylbenzyl)-2-(4-pyridyloxy)benzoyl]morpholine (0.042 g, 0.0827 mmol) was dissolved in a mixed solution of acetonitrile (9 ml) and water (3 ml) and after adding thereto CAN (0.113 g, 0.207 mmol) at room temperature, the solution was stirred at room temperature for 1 hour. The reaction solution was diluted with water and then extracted with ether. The extract was washed with water and then dried, and the solvent was removed by distillation. The obtained residue was purified by preparative thin-layer chromatography (hexand:ethyl acetate:methanol=3:6:1) to obtain the titled compound (0.025 g, 0.0523 mmol, 63%).

EXAMPLE 102

N-[5-(5,6-Dimethoxy-3-methyl-1,4-benzoquinon-2-yl)methyl-2-(methoxycarbonylmethyloxy)benzoyl]piperidine N-[5-(3,4,5,6-Tetramethoxy-2-methylbenzyl)-2-(methoxycarbonylmethyloxy)benzoyl]piperidine (0.260 g, 0.520 mmol) was dissolved in a mixed solution of acetonitrile (12 ml) and water (4 ml) and after adding thereto CAN (0.713 g, 1.30 mmol) at room temperature, the solution was stirred at room temperature for 1 hour. The reaction solution was diluted with water and then extracted with ether. The extract was washed with water and then dried, and the solvent was removed by distillation. The obtained residue was purified by preparative thin-layer chromatography (hexand:ethyl acetate=1:3) to obtain the titled compound (0.180 g, 0.382 mmol, 73%).

EXAMPLE 103

N-[5-(5,6-Dimethoxy-3-methyl-1,4-benzoquinon-2-yl)methyl-2-(methoxycarbonylmethyloxy)benzoyl]morpholine N-[5-(3,4,5,6-Tetramethoxy-2-methylbenzyl)-2-(methoxycarbonylmethyloxy)benzoyl]morpholine (0.240 g, 0.478 mmol) was dissolved in a mixed solution of acetonitrile (12 ml) and water (4 ml) and after adding thereto CAN (0.655 g, 1.20 mmol) at room temperature, the solution was stirred at room temperature for 1 hour. The reaction solution was diluted with water and then extracted with ether. The extract was washed with water and then dried, and the solvent was removed by distillation. The obtained residue was purified by preparative thin-layer chromatography (hexand:ethyl acetate=1:3) to obtain the titled compound (0.180 g, 0.381 mmol, 80%).

EXAMPLE 104

N-[5-(5,6-Dimethoxy-3-methyl-1,4-benzoquinon-2-yl)methyl-2-(tert-butoxycarbonylmethyloxy)benzoyl]piperidine N-[5-(3,4,5,6-Tetramethoxy-2-methylbenzyl)-2-(tert-butoxycarbonylmethyloxy)benzoyl]piperidine (0.292 g, 0.538 mmol) was dissolved in a mixed solution of acetonitrile (12 ml) and water (4 ml) and after adding thereto CAN (0.737 g, 1.34 mmol) at room temperature, the solution was stirred at room temperature for 1 hour. The reaction solution was diluted with water and then extracted with ether. The extract was washed with water and then dried, and the solvent was removed by distillation. The obtained residue was purified by preparative thin-layer chromatography (hexand:ethyl acetate=2:1) to obtain the titled compound (0.175 g, 0.341 mmol, 63%).

EXAMPLE 105

N-[5-(5,6-Dimethoxy-3-methyl-1,4-benzoquinon-2-yl)methyl-2-(tert-butoxycarbonylmethyloxy)benzoyl]morpholine N-[5-(3,4,5,6-Tetramethoxy-2-methylbenzyl)-2-(tert-butoxycarbonylmethyloxy)benzoyl]morpholine (0.290 g, 0.533 mmol) was dissolved in a mixed solution of acetonitrile (12 ml) and water (4 ml) and after adding thereto CAN (0.731 g, 1.33 mmol) at room temperature, the solution was stirred at room temperature for 1 hour. The reaction solution was diluted with water and then extracted with ether. The extract was washed with water and then dried, and the solvent was removed by distillation. The obtained residue was purified by preparative thin-layer chromatography (hexand:ethyl acetate=2:1) to obtain the titled compound (0.170 g, 0.330 mmol, 62%).

EXAMPLE 106

N-[5-(5,6-Dimethoxy-3-methyl-1,4-benzoquinon-2-yl)methyl-2-acetoxybenzoyl]-3,4,5-trimethoxyaniline 3,4,5-Trimethoxyaniline (0.216 g, 1.18 mmol), triethylamine (0.119 g, 1.18 mmol) and 2-chloro-1,3-dimethylimidazolinium chloride (0.199 g, 1.18 mmol) were added to a methylene chloride solution (20 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) to obtain the titled compound (0.109 g, 0.202 mmol, 38%).

EXAMPLE 107

N-[5-(5,6-Dimethoxy-3-methyl-1,4-benzoquinon-2-yl)methyl-2-acetoxybenzoyl]-3,4-dimethoxyaniline 3,4-Dimethoxyaniline (0.246 g, 1.604 mmol), triethylamine (0.162 g, 1.604 mmol) and 2-chloro-1,3-dimethylimidazolinium chloride (0.271 g, 1.604 mmol) were added to a methylene chloride solution (20 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:2) to obtain the titled compound (0.110 g, 0.216 mmol, 40%).

EXAMPLE 108

N-[5-(5,6-Dimethoxy-3-methyl-1,4-benzoquinon-2-yl)methyl-2-acetoxybenzoyl]-4-acetylaniline 4-Acetylaniline (0.159 g, 1.18 mmol), triethylamine (0.119 g, 1.18 mmol) and 2-chloro-1,3-dimethylimidazolinium chloride (0.199 g, 1.18 mmol) were added to a methylene chloride solution (20 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=1:2) to obtain the titled compound (0.160 g, 0.326 mmol, 61%).

EXAMPLE 109

N-[5-(5,6-Dimethoxy-3-methyl-1,4-benzoquinon-2-yl)methyl-2-acetoxybenzoyl]-4-chloroaniline 4-Chloroaniline (0.150 g, 1.18 mmol), triethylamine (0.119 g, 1.18 mmol) and 2-chloro-1,3-dimethylimidazolinium chloride (0.199 g, 1.18 mmol) were added to a methylene chloride solution (20 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:2) to obtain the titled compound (0.115 g, 0.238 mmol, 44%).

EXAMPLE 110

N-[5-(5,6-Dimethoxy-3-methyl-1,4-benzoquinon-2-yl)methyl-2-acetoxybenzoyl]-4-morpholinoaniline 4-Morpholinoaniline (0.286 g, 1.60 mmol), triethylamine (0.162 g, 1.60 mmol) and 2-chloro-1,3-dimethylimidazolinium chloride (0.271 g, 1.60 mmol) were added to a methylene chloride solution (20 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:2) and then recrystallized from ether to obtain the titled compound (0.077 g, 0.144 mmol, 27%).

EXAMPLE 111

N-[5-(5,6-Dimethoxy-3-methyl-1,4-benzoquinon-2-yl)methyl-2-acetoxybenzoyl]-4-cyanoaniline 4-Cyanoaniline (0.189 g, 1.60 mmol), triethylamine (0.162 g, 1.60 mmol) and 2-chloro-1,3-dimethylimidazolinium chloride (0.271 g, 1.60 mmol) were added to a methylene chloride solution (20 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:2) to obtain the titled compound (0.141 g, 0.297 mmol, 56%).

EXAMPLE 112

N-[5-(5,6-Dimethoxy-3-methyl-1,4-benzoquinon-2-yl)methyl-2-acetoxybenzoyl]-4-trifluoromethylaniline 4-Trifluoromethylaniline (0.258 g, 1.60 mmol), triethylamine (0.162 g, 1.60 mmol) and 2-chloro-1,3-dimethylimidazolinium chloride (0.271 g, 1.60 mmol) were added to a methylene chloride solution (20 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:2) to obtain the titled compound (0.123 g, 0.238 mmol, 44%).

EXAMPLE 113

N-[5-(5,6-Dimethoxy-3-methyl-1,4-benzoquinon-2-yl)methyl-2-acetoxybenzoyl]-3,5-bistrifluoromethylaniline 3,5-Bistrifluoromethylaniline (0.368 g, 1.604 mmol), triethylamine (0.162 g, 1.604 mmol) and 2-chloro-1,3-dimethylimidazolinium chloride (0.271 g, 1.604 mmol) were added to a methylene chloride solution (20 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:2) and then recrystallized from ether to obtain the titled compound (0.196 g, 0.335 mmol, 63%).

EXAMPLE 114

N-[5-(5,6-Dimethoxy-3-methyl-1,4-benzoquinon-2-yl)methyl-2-hydroxybenzoyl]-3,4,5-trimethoxyaniline N-[5-(5,6-Dimethoxy-3-methyl-1,4-benzoquinon-2-yl)methyl-2-acetoxybenzoyl]-3,4,5-trimethoxyaniline (0.100 g, 0.185 mmol) was dissolved in methanol (6 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (hexand:ethyl acetate=1:2) and then recrystallized from ether to obtain the titled compound (0.050 g, 0.101 mmol, 55%).

EXAMPLE 115

N-[5-(5,6-Dimethoxy-3-methyl-1,4-benzoquinon-2-yl)methyl-2-hydroxybenzoyl]-3,4-dimethoxyaniline N-[5-(5,6-Dimethoxy-3-methyl-1,4-benzoquinon-2-yl)methyl-2-acetoxybenzoyl]-3,4-dimethoxyaniline (0.100 g, 0.196 mmol) was dissolved in methanol (6 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (hexand:ethyl acetate=1:2) and then recrystallized from ether to obtain the titled compound (0.032 g, 0.0685 mmol, 35%).

EXAMPLE 116

N-[5-(5,6-Dimethoxy-3-methyl-1,4-benzoquinon-2-yl)methyl-2-hydroxybenzoyl]-4-acetylaniline N-[5-(5,6-Dimethoxy-3-methyl-1,4-benzoquinon-2-yl)methyl-2-acetoxybenzoyl]-4-acetylaniline (0.100 g, 0.204 mmol) was dissolved in methanol (6 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (hexand:ethyl acetate=1:2) and then recrystallized from ether to obtain the titled compound (0.060 g, 0.133 mmol, 65%).

EXAMPLE 117

N-[5-(5,6-Dimethoxy-3-methyl-1,4-benzoquinon-2-yl methyl-2-hydroxybenzoyl]-4-chloroaniline N-[5-(5,6-Dimethoxy-3-methyl-1,4-benzoquinon-2-yl)methyl-2-acetoxybenzoyl]-4-chloroaniline (0.072 g, 0.149 mmol) was dissolved in methanol (6 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (hexand:ethyl acetate=1:2) and then recrystallized from ether to obtain the titled compound (0.046 g, 0.104 mmol, 70%).

EXAMPLE 118

N-[5-(5,6-Dimethoxy-3-methyl-1,4-benzoquinon-2-yl)methyl-2-hydroxybenzoyl]-4-morpholinoaniline N-[5-(5,6-Dimethoxy-3-methyl-1,4-benzoquinon-2-yl)methyl-2-acetoxybenzoyl]-4-morpholinoaniline (0.060 g, 0.110 mmol) was dissolved in methanol (6 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (hexand:ethyl acetate=1:2) and then recrystallized from ether to obtain the titled compound (0.037 g, 0.0752 mmol, 68%).

EXAMPLE 119

N-[5-(5,6-Dimethoxy-3-methyl-1,4-benzoquinon-2-yl)methyl-2-hydroxybenzoyl]-4-cyanoaniline N-[5-(5,6-Dimethoxy-3-methyl-1,4-benzoquinon-2-yl) methyl-2-acetoxybenzoyl]-4-cyanoaniline (0.100 g, 0.211 mmol) was dissolved in methanol (6 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (hexand:ethyl acetate=1:2) and then recrystallized from ether to obtain the titled compound (0.063 g, 0.146 mmol, 69%).

EXAMPLE 120

N-[5-(5,6-Dimethoxy-3-methyl-1,4-benzoquinon-2-yl)methyl-2-hydroxybenzoyl]-4-trifluoromethylaniline N-[5-(5,6-Dimethoxy-3-methyl-1,4-benzoquinon-2-yl) methyl-2-acetoxybenzoyl]-4-trifluoromethylaniline (0.087 g, 0.168 mmol) was dissolved in methanol (6 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (hexand:ethyl acetate=1:2) and then recrystallized from ether to obtain the titled compound (0.056 g, 0.118 mmol, 70%).

EXAMPLE 121

N-[5-(5,6-Dimethoxy-3-methyl-1,4-benzoquinon-2-yl)methyl-2-hydroxybenzoyl]-3,5-bistrifluoromethylaniline N-[5-(5,6-Dimethoxy-3-methyl-1,4-benzoquinon-2-yl) methyl-2-acetoxybenzoyl]-3,5-bistrifluoromethylaniline (0.130 g, 0.222 mmol) was dissolved in methanol (6 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (hexand:ethyl acetate=1:2) and then recrystallized from ether to obtain the titled compound (0.050 g, 0.0921 mmol, 41%).

EXAMPLE 122

N-[5-(5,6-Dimethoxy-3-methyl-1,4-benzoquinon-2-yl)methyl-2-hydroxybenzoyl]-(S)-1-phenylethylamine (S)-Phenethylamine (0.130 g, 1.07 mmol), dimethylaminopyridine (0.013 g, 0.107 mmol) and 1-ethyl-3-(3-dimethylaminopropyl)carbodiimide hydrochloride (0.308 g, 1.60 mmol) were added to a methylene chloride solution (30 ml) of 5-(5,6-dimethoxy-3-methyl-1,4-benzoquinon-2-yl) methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=2:1) and then recrystallized from ether to obtain the titled compound (0.135 g, 0.283 mmol, 53%).

EXAMPLE 123

N-[5-(5,6-Dimethoxy-3-methyl-1,4-benzoquinon-2-yl)methyl-2-hydroxybenzoyl]-(R)-1-phenylethylamine (R)-Phenethylamine (0.162 g, 1.337 mmol), dimethylaminopyridine (0.016 g, 0.134 mmol) and 1-ethyl-3-(3-dimethylaminopropyl)carbodiimide hydrochloride (0.384 g, 2.005 mmol) were added to a methylene chloride solution (30 ml) of 5-(5,6-dimethoxy-3-methyl-1,4-benzoquinon-2-yl) methyl-2-acetoxybenzoic acid (0.250 g, 0.668 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=2:1) and then recrystallized from ether to obtain the titled compound (0.167 g, 0.350 mmol, 52%).

EXAMPLE 124

N-[5-(5,6-Dimethoxy-3-methyl-1,4-benzoquinon-2-yl)methyl-2-phenoxybenzoyl]-1,2,3,4-tetrahydroquinoline 1,2,3,4-Tetrahydroquinoline (0.049 g, 0.367 mmol) and 1-ethyl-3-(3-dimethylaminopropyl)carbodiimide hydrochloride (0.105 g, 0.550 mmol) were added to a methylene chloride solution (10 ml) of 5-(5,6-dimethoxy-3-methyl-1, 4-benzoquinon-2-yl)methyl-2-phenoxybenzoic acid (0.075 g, 0.183 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=9:1) to obtain the titled compound (0.050 g, 0.0955 mmol, 52%).

EXAMPLE 125

N-[5-(5,6-Dimethoxy-3-methyl-1,4-benzoquinon-2-yl)methyl-2-phenoxybenzoyl]-2-methylpiperidine 2-Methylpiperidine (0.039 g, 0.391 mmol) and 1-ethyl-3-(3-dimethylaminopropyl)carbodiimide hydrochloride (0.112 g, 0.587 mmol) were added to a methylene chloride solution (5 ml) of 5-(5,6-dimethoxy-3-methyl-1,4-benzoquinon-2-yl)methyl-2-phenoxybenzoic acid (0.080 g, 0.196 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=9:1) to obtain the titled compound (0.045 g, 0.0919 mmol, 47%).

EXAMPLE 126

N-[5-(5,6-Dimethoxy-3-methyl-1,4-benzoquinon-2-yl)methyl-2-(3-pyridylmethyloxy)benzoyl]-1,2,3,4-tetrahydroquinoline 1,2,3,4-Tetrahydroquinoline (0.126 g, 0.946 mmol) and 1-ethyl-3-(3-dimethylaminopropyl)carbodiimide hydrochloride (0.272 g, 1.42 mmol) were added to a methylene chloride solution (20 ml) of 5-(5,6-dimethoxy-3-methyl-1,4-benzoquinon-2-yl)methyl-2-(3-pyridylmethyloxy)benzoic acid (0.200 g, 0.473 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=9:1) to obtain the titled compound (0.100 g, 0.186 mmol, 39%).

EXAMPLE 127

N-[5-(5,6-Dimethoxy-3-methyl-1,4-benzoquinon-2-yl)methyl-2-(3-pyridylmethyloxy)benzoyl]-4-methylpiperidine 4-Methylpiperidine (0.094 g, 0.946 mmol) and 1-ethyl-3-(3-dimethylaminopropyl)carbodiimide hydrochloride (0.272 g, 1.42 mmol) were added to a methylene chloride solution (20 ml) of 5-(5,6-dimethoxy-3-methyl-1,4-benzoquinon-2-yl)methyl-2-(3-pyridylmethyloxy)benzoic acid (0.200 g, 0.473 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=9:1) to obtain the titled compound (0.100 g, 0.198 mmol, 42%).

EXAMPLE 128

N-[5-(5,6-Dimethoxy-3-methyl-1,4-benzoquinon-2-yl)methyl-2-(3-pyridylmethyloxy)benzoyl]-3,4,5-trimethoxyaniline 3,4,5-Trimethoxyaniline (0.260 g, 1.42 mmol), triethylamine (0.144 g, 1.42 mmol) and 2-chloro-1,3-dimethylimidazolinium chloride (0.240 g, 1.42 mmol) were added to a methylene chloride solution (20 ml) of 5-(5,6-dimethoxy-3-methyl-1,4-benzoquinon-2-yl)methyl-2-(3-pyridylmethyloxy)benzoic acid (0.200 g, 0.473 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from ether to obtain the titled compound (0.050 g, 0.085 mmol, 18%).

EXAMPLE 129

N-[5-(5,6-Dimethoxy-3-methyl-1,4-benzoquinon-2-yl)methyl-2-(3-pyridylmethyloxy)benzoyl]-4-acetylaniline 4-Acetylaniline (0.128 g, 0.946 mmol), triethylamine (0.096 g, 0.946 mmol) and 2-chloro-1,3-dimethylimidazolinium chloride (0.160 g, 0.946 mmol) were added to a methylene chloride solution (20 ml) of 5-(5,6-dimethoxy-3-methyl-1,4-benzoquinon-2-yl)methyl-2-(3-pyridylmethyloxy)benzoic acid (0.200 g, 0.473 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from ether to obtain the titled compound (0.080 g, 0.148 mmol, 31%).

EXAMPLE 130

Methyl 5-(5,6-Dimethoxy-3-methyl-1,4-benzoquinon-2-yl)methyl-2-(tert-butoxycarbonylmethyloxy)benzoate Methyl 5-(3,4,5,6-tetramethoxy-2-methylbenzyl)-2-(tert-butoxycarbonylmethyloxy)benzoate (1.25 g, 2.56 mmol) was dissolved in a mixed solution of acetonitrile (30 ml) and water (10 ml) and after adding thereto CAN (3.50 g, 6.39 mmol) at room temperature, the solution was stirred at room temperature for 1 hour. The reaction solution was diluted with water and then extracted with ether. The extract was washed with water and then dried, and the solvent was removed by distillation. The obtained residue was purified by silica gel column chromatography (hexand:ethyl acetate=2:1) to obtain the titled compound (0.800 g, 1.74 mmol, 68%).

EXAMPLE 131

N-(6-Chloropyridin-3-yl)-4-(5,6-dimethoxy-3-methyl-1,4-benzoquinon-2-yl)methyl-2-hydroxybenzamide 2-Chloro-1,3-dimethylimidazolinium chloride (61 mg, 0.361 mmol), 5-amino-2-chloropyridine (46 mg, 0.361 mmol) and triethylamine (36 mg, 0.361 mmol) were added to a methylene chloride solution (3 ml) of 4-(5,6-dimethoxy-3-methyl-1,4-benzoquinon-2-yl)methyl-2-acetoxybenzoic acid (45 mg, 0.120 mmol) in a nitrogen atmosphere and the resulting solution was stirred all the night through. The reaction solution was diluted with chloroform, then washed with water and dried, and the solvent was removed by distillation. The residue was purified by silica gel column chromatography (hexand:ethyl acetate=3:1) to obtain the titled compound (10 mg, 0.021 mmol, 17%).

EXAMPLE 132

N-(2-Chloropyridin-3-yl)-4-(5,6-dimethoxy-3-methyl-1,4-benzoquinon-2-yl)methyl-2-acetoxybenzamide 2-Chloro-1,3-dimethylimidazolinium chloride (89 mg, 0.524 mmol), 3-amino-2-chloropyridine (51 mg, 0.390 mmol) and triethylamine (53 mg, 0.524 mmol) were added to a methylene chloride solution (10 ml) of 4-(5,6-dimethoxy-3-methyl-1,4-benzoquinon-2-yl)methyl-2-acetoxybenzoic acid (98 mg, 0.120 mmol) in a nitrogen atmosphere and the resulting solution was stirred all the night through. The reaction solution was diluted with chloroform, then washed with water and dried, and the solvent was removed by distillation. The residue was purified by silica gel column chromatography (hexand:ethyl acetate=3:1) to obtain the titled compound (29 mg, 0.060 mmol, 23%).

EXAMPLE 133

N-(2-Chloropyridin-3-yl)-4-(5,6-dimethoxy-3-methyl-1,4-benzoquinon-2-yl methyl-2-hydroxybenzamide An aqueous saturated sodium hydrogencarbonate solution (1 ml) was added to a methanol solution (2 ml) of N-(2-chloropyridin-3-yl)-4-(5,6-dimethoxy-3-methyl-1,4-benzoquinon-2-yl)methyl-2-acetoxybenzamide (20 mg, 0.0412 mmol) and the resulting solution was stirred for 1 hour. The reaction solution was extracted with ethyl acetate, then washed with water and dried, and the solvent was removed by distillation. The residue was recrystallized from an ethyl acetate-diisopropyl ether mixed solvent to obtain the titled compound (18 mg, 0.0406 mmol, 99%).

EXAMPLE 134

N-(6-Methoxypyridin-3-yl)-4-(5,6-dimethoxy-3-methyl-1,4-benzoquinon-2-yl)methyl-2-acetoxybenzamide 2-Chloro-1,3-dimethylimidazolinium chloride (93 mg, 0.555 mmol), 5-amino-2-methoxypyridine (55 mg, 0.440 mmol) and triethylamine (44 mg, 0.440 mmol) were added to a methylene chloride solution (5 ml) of 4-(5,6-dimethoxy-3-methyl-1,4-benzoquinon-2-yl)methyl-2-acetoxybenzoic acid (137 mg, 0.366 mmol) in a nitrogen atmosphere and the resulting solution was stirred all the night through. The reaction solution was diluted with chloroform, then washed with water and dried, and the solvent was removed by distillation. The residue was purified by silica gel column chromatography (hexand:ethyl acetate=3:1) to obtain the titled compound (31 mg, 0.065 mmol, 18%).

EXAMPLE 135

N-(6-Methoxypyridin-3-yl)-4-(5,6-dimethoxy-3-methyl-1,4-benzoquinon-2-yl)methyl-2-hydroxybenzamide An aqueous saturated sodium hydrogencarbonate solution (4 ml) was added to a methanol solution (8 ml) of N-(6-methoxypyridin-3-yl)-5-(5,6-dimethoxy-3-methyl-1,4-benzoquinon-2-yl)methyl-2-acetoxybenzamide (48 mg, 0.100 mmol) and the resulting solution was stirred for 1 hour. The reaction solution was extracted with ethyl acetate, then washed with water and dried, and the solvent was removed by distillation. The residue was recrystallized from an ethyl acetate-diisopropyl ether mixed solvent to obtain the titled compound (29 mg, 0.066 mmol, 66%).

EXAMPLE 136

N-[4-(5,6-Dimethoxy-3-methyl-1,4-benzoquinon-2-yl)methyl-2-acetoxybenzoyl]-4-(trifluoromethylsulfonyl)aniline 2-Chloro-1,3-dimethylimidazolinium chloride (130 mg, 0.77 mmol), 4-(trifluoromethylsulfonyl)aniline (173 mg, 0.77 mmol) and triethylamine (78 mg, 0.77 mmol) were added to a methylene chloride solution (8 ml) of 4-[(5,6-dimethoxy-3-methyl-1,4-benzoquinon-2-yl)methyl]-2-acetoxybenzoic acid (240 mg, 0.64 mmol) in a nitrogen atmosphere and the resulting solution was stirred for 2 hours. The reaction solution was diluted with chloroform, then washed with water and dried, and the solvent was removed by distillation. The residue was purified by silica gel column chromatography (methylene chloride:methanol= 60:1) to obtain the titled compound (146 mg, 0.251 mmol, 39%).

EXAMPLE 137

N-[4-(5,6-Dimethoxy-3-methyl-1,4-benzoquinon-2-yl)methyl-2-hydroxybenzoyl]-4-(trifluoromethylsulfonyl)aniline An aqueous saturated sodium hydrogencarbonate solution (7 ml) was added to a methanol solution (15 ml) of N-[4-(5,6-dimethoxy-3-methyl-1,4-benzoquinon-2-yl)methyl-2-acetoxybenzoyl]-4-(trifluoromethylsulfonyl)aniline (114 mg, 0.196 mmol) and the resulting solution was stirred for 1 hour. The reaction solution was extracted with ethyl acetate, then washed with water and dried, and the solvent was removed by distillation. The residue was purified by silica gel column chromatography (hexand:ethyl acetate= 4:1) to obtain the titled compound (35 mg, 0.065 mmol, 33%).

EXAMPLE 138

N-(Pyridin-3-yl)-4-(5,6-dimethoxy-3-methyl-1,4-benzoquinon-2-yl)methyl-2-acetoxybenzamide 2-Chloro-1,3-dimethylimidazolinium chloride (39 mg, 0.23 mmol), 3-aminopyridine (21 mg, 0.23 mmol) and triethylamine (23 mg, 0.23 mmol) were added to a methylene chloride solution (5 ml) of 4-(5,6-dimethoxy-3-methyl-1,4-benzoquinon-2-yl)methyl-2-acetoxybenzoic acid (57 mg, 0.152 mmol) in a nitrogen atmosphere and the resulting solution was stirred all the night through. The reaction solution was diluted with chloroform, then washed with water and dried, and the solvent was removed by distillation. The residue was purified by silica gel column chromatography (benzene:acetone=3:1) to obtain the titled compound (12 mg, 0.027 mmol, 18%).

EXAMPLE 139

N-(Pyridin-3-yl)-4-(5,6-dimethoxy-3-methyl-1,4-benzoquinon-2-yl)methyl-2-hydroxybenzamide An aqueous saturated sodium hydrogencarbonate solution (4 ml) was added to a methanol solution (10 ml) of N-(pyridin-3-yl)-4-(5,6-dimethoxy-3-methyl-1,4-benzoquinon-2-yl)methyl-2-acetoxybenzamide (55 mg, 0.122 mmol) and the resulting solution was stirred for 1 hour. The reaction solution was extracted with ethyl acetate, then washed with water and dried, and the solvent was removed by distillation. The residue was purified by silica gel column chromatography (benzene:acetone=3:1) to obtain the titled compound (28 mg, 0.0686 mmol, 56%).

EXAMPLE 140

N-(Pyridin-4-yl)-4-(5,6-dimethoxy-3-methyl-1,4-benzoquinon-2-yl)methyl-2-hydroxybenzamide 2-Chloro-1,3-dimethylimidazolinium chloride (43 mg, 0.257 mmol), 4-aminopyridine (24 mg, 0.257 mmol) and triethylamine (26 mg, 0.257 mmol) were added to a methylene chloride solution (5 ml) of 4-(5,6-dimethoxy-3-methyl-1,4-benzoquinon-2-yl)methyl-2-acetoxybenzoic acid (64 mg, 0.171 mmol) in a nitrogen atmosphere and the resulting solution was stirred all the night through. The reaction solution was diluted with chloroform, then washed with water and dried, and the solvent was removed by distillation. Subsequently, an aqueous saturated sodium hydrogencarbonate solution (10 ml) was added to a methanol solution (4 ml) of the obtained residue and the resulting solution was stirred for 1 hour. The reaction solution was extracted with ethyl acetate, then washed with water and dried, and the solvent was removed by distillation. The residue was purified by silica gel column chromatography (methylene chloride:methanol=30:1) to obtain the titled compound (5 mg, 0.012 mmol, 7.2%).

EXAMPLE 141

N-[5-(5,6-Dimethoxy-3-methyl-1,4-benzoquinon-2-yl)methyl-2-acetoxybenzoyl]-4-fluoroaniline 4-Fluoroaniline (0.178 g, 1.604 mmol), triethylamine (0.162 g, 1.604 mmol) and 2-chloro-1,3-dimethylimidazolinium chloride (0.271 g, 1.604 mmol) were added to a methylene chloride solution (50 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:1) and then recrystallized from ether to obtain the titled compound (0.125 g, 0.268 mmol, 50%).

EXAMPLE 142

N-[5-(5,6-Dimethoxy-3-methyl-1,4-benzoquinon-2-yl)methyl-2-hydroxybenzoyl]-4-fluoroaniline N-[5-(5,6-dimethoxy-3-methyl-1,4-benzoquinon-2-yl)methyl-2-acetoxybenzoyl]-4-fluoroaniline (0.068 g, 0.145 mmol) was dissolved in methanol (6 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (hexane:ethyl acetate=1:2) and then recrystallized from ether to obtain the titled compound (0.030 g, 0.0705 mmol, 48%).

EXAMPLE 143

N-[5-(5,6-Dimethoxy-3-methyl-1,4-benzoquinon-2-yl)methyl-2-acetoxybenzoyl]-3-nitroaniline 3-Nitroaniline (0.222 g, 1.604 mmol), triethylamine (0.162 g, 1.604 mmol) and 2-chloro-1,3-dimethylimidazolinium chloride (0.271 g, 1.604 mmol) were added to a methylene chloride solution (50 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:1) and then recrystallized from ether to obtain the titled compound (0.149 g, 0.301 mmol, 56%).

EXAMPLE 144

N-[5-(5,6-Dimethoxy-3-methyl-1,4-benzoquinon-2-yl)methyl-2-hydroxybenzoyl]-3-nitroaniline N-[5-(5,6-Dimethoxy-3-methyl-1,4-benzoquinon-2-yl)methyl-2-acetoxybenzoyl]-3-nitroaniline (0.070 g, 0.142 mmol) was dissolved in methanol (6 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was recrystallized from ether to obtain the titled compound (0.060 g, 0.133 mmol, 94%).

EXAMPLE 145

N-[5-(5,6-Dimethoxy-3-methyl-1,4-benzoquinon-2-yl)methyl-2-acetoxybenzoyl]-2-trifluoromethylaniline 2-Trifluoromethylaniline (0.483 g, 3.000 mmol), triethylamine (0.304 g, 3.000 mmol) and 2-chloro-1,3-dimethylimidazolinium chloride (0.507 g, 3.000 mmol) were added to a methylene chloride solution (100 ml) of 5-(5,6-dimethoxy-3-methyl-1,4-benzoquinon-2-yl)methyl-2-acetoxybenzoic acid (0.374 g, 1.000 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from ether to obtain the titled compound (0.259 g, 0.500 mmol, 50%).

EXAMPLE 146

N-[5-(5,6-Dimethoxy-3-methyl-1,4-benzoquinon-2-yl)methyl-2-hydroxybenzoyl]-2-trifluoromethylaniline N-[5-(5,6-Dimethoxy-3-methyl-1,4-benzoquinon-2-yl)methyl-2-acetoxybenzoyl]-2-trifluoromethylaniline (0.100 g, 0.193 mmol) was dissolved in methanol (6 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=10:1) and then recrystallized from ether to obtain the titled compound (0.090 g, 0.189 mmol, 98%).

EXAMPLE 147

Ethyl N-[5-(5,6-dimethoxy-3-methyl-1,4-benzoquinon-2-yl)methyl-2-acetoxybenzoyl]-4-aminobenzoate Ethyl 4-aminobenzoate (0.265 g, 1.604 mmol), triethylamine (0.162 g, 1.604 mmol) and 2-chloro-1,3- dimethylimidazolinium chloride (0.271 g, 1.604 mmol) were added to a methylene chloride solution (50 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:1) and then recrystallized from ether to obtain the titled compound (0.165 g, 0.316 mmol, 59%).

EXAMPLE 148

Ethyl N-[5-(5,6-dimethoxy-3-methyl-1,4-benzoquinon-2-yl methyl-2-hydroxybenzoyl]-4-aminobenzoate Ethyl N-[5-(5,6-dimethoxy-3-methyl-1,4-benzoquinon-2-yl)methyl-2-acetoxybenzoyl]-4-aminobenzoate (0.060 g, 0.115 mmol) was dissolved in methanol (6 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=10:1) and then recrystallized from ether to obtain the titled compound (0.040 g, 0.0834 mmol, 73%).

EXAMPLE 149

N-[5-(5,6-Dimethoxy-3-methyl-1,4-benzoquinon-2-yl)methyl-2-acetoxybenzoyl]-4-cyanomethylaniline 4-Cyanomethylaniline (0.212 g, 1.604 mmol), triethylamine (0.162 g, 1.604 mmol) and 2-chloro-1,3-dimethylimidazolinium chloride (0.271 g, 1.604 mmol) were added to a methylene chloride solution (50 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:1) and then recrystallized from a mixed solvent of ether and hexane (3:1) to obtain the titled compound (0.110 g, 0.225 mmol, 42%).

EXAMPLE 150

N-[5-(5,6-Dimethoxy-3-methyl-1,4-benzoquinon-2-yl)methyl-2-hydroxybenzoyl]-4-cyanomethylaniline N-[5-(5,6-Dimethoxy-3-methyl-1,4-benzoquinon-2-yl) methyl-2-acetoxybenzoyl]-4-cyanomethylaniline (0.060 g, 0.123 mmol) was dissolved in methanol (6 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=10:1) and then recrystallized from ether to obtain the titled compound (0.040 g, 0.0897 mmol, 73%).

EXAMPLE 151

N-[5-(5,6-Dimethoxy-3-methyl-1,4-benzoquinon-2-yl)methyl-2-acetoxybenzoyl]-3-trifluoromethylaniline 3-Trifluoromethylaniline (0.483 g, 3.000 mmol), triethylamine (0.304 g, 3.000 mmol) and 2-chloro-1,3-dimethylimidazolinium chloride (0.507 g, 3.000 mmol) were added to a methylene chloride solution (100 ml) of 5-(5,6-dimethoxy-3-methyl-1,4-benzoquinon-2-yl)methyl-2-acetoxybenzoic acid (0.374 g, 1.000 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from ether to obtain the titled compound (0.235 g, 0.454 mmol, 45%).

EXAMPLE 152

N-[5-(5,6-Dimethoxy-3-methyl-1,4-benzoquinon-2-yl)methyl-2-hydroxybenzoyl]-3-trifluoromethylaniline N-[5-(5,6-Dimethoxy-3-methyl-1,4-benzoquinon-2-yl) methyl-2-acetoxybenzoyl]-3-trifluoromethylaniline (0.100 g, 0.193 mmol) was dissolved in methanol (6 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=10:1) and then recrystallized from ether to obtain the titled compound (0.088 g, 0.185 mmol, 96%).

EXAMPLE 153

N-[5-(5,6-Dimethoxy-3-methyl-1,4-benzoquinon-2-yl)methyl-2-acetoxybenzoyl]-2-nitroaniline 2-Nitroaniline (0.222 g, 1.604 mmol), triethylamine (0.162 g, 1.604 mmol) and 2-chloro-1,3-dimethylimidazolinium chloride (0.271 g, 1.604 mmol) were added to a methylene chloride solution (50 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:1) and then recrystallized from ether to obtain the titled compound (0.140 g, 0.283 mmol, 53%).

EXAMPLE 154

N-[5-(5,6-Dimethoxy-3-methyl-1,4-benzoquinon-2-yl)methyl-2-hydroxybenzoyl]-2-nitroaniline N-[5-(5,6-Dimethoxy-3-methyl-1,4-benzoquinon-2-yl) methyl-2-acetoxybenzoyl]-2-nitroaniline (0.070 g, 0.142 mmol) was dissolved in methanol (6 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was recrystallized from ether to obtain the titled compound (0.063 g, 0.139 mmol, 98%).

EXAMPLE 155

N-(Pyridin-2-yl)-5-(5,6-dimethoxy-3-methyl-1,4-benzoquinon-2-yl)methyl-2-acetoxybenzamide 2-Aminopyridine (0.282 g, 3.000 mmol), triethylamine (0.304 g, 3.000 mmol) and 2-chloro-1,3-dimethylimidazolinium chloride (0.507 g, 3.000 mmol) were added to a methylene chloride solution (50 ml) of 5-(5,6-dimethoxy-3-methyl-1,4-benzoquinon-2-yl)methyl-2-acetoxybenzoic acid (0.374 g, 1.000 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:1) and then recrystallized from ether to obtain the titled compound (0.140 g, 0.311 mmol, 31%).

EXAMPLE 156

N-(Pyridin-2-yl)-5-(5,6-dimethoxy-3-methyl-1,4-benzoquinon-2-yl)methyl-2-hydroxybenzamide N-(Pyridin-2-yl)-5-(5,6-dimethoxy-3-methyl-1,4-benzoquinon-2-yl)methyl-2-acetoxybenzamide (0.050 g, 0.111 mmol) was dissolved in methanol (6 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was recrystallized from ether to obtain the titled compound (0.023 g, 0.0564 mmol, 51%).

EXAMPLE 157

N-(Pyridin-4-yl)-5-(5,6-dimethoxy-3-methyl-1,4-benzoquinon-2-yl)methyl-2-hydroxybenzamide 4-Aminopyridine (0.282 g, 3.000 mmol), triethylamine (0.304 g, 3.000 mmol) and 2-chloro-1,3-dimethylimidazolinium chloride (0.507 g, 3.000 mmol) were added to a methylene chloride solution (50 ml) of 5-(5,6-dimethoxy-3-methyl-1,4-benzoquinon-2-yl)methyl-2-acetoxybenzoic acid (0.374 g, 1.000 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from ether to obtain the titled compound (0.050 g, 0.123 mmol, 12%).

EXAMPLE 158

N-(Pyridin-3-yl)-5-(5,6-dimethoxy-3-methyl-1,4-benzoquinon-2-yl)methyl-2-hydroxybenzamide 3-Aminopyridine (0.151 g, 1.604 mmol), triethylamine (0.162 g, 1.604 mmol) and 2-chloro-1,3-dimethylimidazolinium chloride (0.271 g, 1.604 mmol) were added to a methylene chloride solution (50 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from ether to obtain the titled compound (0.065 g, 0.159 mmol, 30%).

EXAMPLE 159

N-Cyclopropyl-5-(5,6-dimethoxy-3-methyl-1,4-benzoquinon-2-yl)methyl-2-acetoxybenzamide Cyclopropylamine (0.0916 g, 1.604 mmol), triethylamine (0.162 g, 1.604 mmol) and 2-chloro-1,3-dimethylimidazolinium chloride (0.271 g, 1.604 mmol) were added to a methylene chloride solution (50 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:1) and then recrystallized from ether to obtain the titled compound (0.089 g, 0.215 mmol, 40%).

EXAMPLE 160

N-Cyclopropyl-5-(5,6-dimethoxy-3-methyl-1,4-benzoquinon-2-yl)methyl-2-hydroxybenzamide N-Cyclopropyl-5-(5,6-dimethoxy-3-methyl-1,4-benzoquinon-2-yl)methyl-2-acetoxybenzamide (0.050 g, 0.121 mmol) was dissolved in methanol (3 ml) and after adding thereto an aqueous saturated sodium hydrogencarbonate solution (1.5 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (hexand:ethyl acetate=1:1) and then recrystallized from ether to obtain the titled compound (0.023 g, 0.0673 mmol, 56%).

EXAMPLE 161

N-Cyclohexyl-5-(5,6-dimethoxy-3-methyl-1,4-benzoquinon-2-yl)methyl-2-acetoxybenzamide Cyclohexylamine (0.159 g, 1.604 mmol), triethylamine (0.162 g, 1.604 mmol) and 2-chloro-1,3-dimethylimidazolinium chloride (0.271 g, 1.604 mmol) were added to a methylene chloride solution (50 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexane:ethyl acetate=1:1) and

EXAMPLE 162

N-Cyclohexyl-5-(5,6-dimethoxy-3-methyl-1,4-benzoquinon-2-yl)methyl-2-hydroxybenzamide N-Cyclohexyl-5-(5,6-dimethoxy-3-methyl-1,4-benzoquinon-2-yl)methyl-2-acetoxybenzamide (0.070 g, 0.154 mmol) was dissolved in methanol (3 ml) and after adding thereto an aqueous saturated sodium hydrogencarbonate solution (1.5 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was recrystallized from ether to obtain the titled compound (0.035 g, 0.0846 mmol, 55%).

EXAMPLE 163

N-Methyl-[5-(5,6-dimethoxy-3-methyl-1,4-benzoquinon-2-yl)methyl-2-acetoxybenzoyl]-4-methoxyaniline N-Methyl-4-methoxyaniline (0.220 g, 1.604 mmol), triethylamine (0.162 g, 1.604 mmol) and 2-chloro-1,3-dimethylimidazolinium chloride (0.271 g, 1.604 mmol) were added to a methylene chloride solution (50 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:2) to obtain the titled compound (0.142 g, 0.288 mmol, 54%).

EXAMPLE 164

N-Methyl-[5-(5,6-dimethoxy-3-methyl-1,4-benzoquinon-2-yl)methyl-2-hydroxybenzoyl]-4-methoxyaniline N-Methyl-[5-(5,6-dimethoxy-3-methyl-1,4-benzoquinon-2-yl)methyl-2-acetoxybenzoyl]-4-methoxyaniline (0.070 g, 0.142 mmol) was dissolved in methanol (3 ml) and after adding thereto an aqueous saturated sodium hydrogencarbonate solution (2 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (hexand:ethyl acetate=1:2) to obtain the titled compound (0.050 g, 0.111 mmol, 78%).

EXAMPLE 165

N-[3-(5,6-Dimethoxy-3-methyl-1,4-benzoquinon-2-yl)methyl-2-acetoxybenzoyl]-4-trifluoromethylaniline 4-Trifluoromethylaniline (0.159 g, 1.604 mmol), triethylamine (0.162 g, 1.604 mmol) and 2-chloro-1,3-dimethylimidazolinium chloride (0.271 g, 1.604 mmol) were added to a methylene chloride solution (50 ml) of 3-(5,6-dimethoxy-3-methyl-1,4-benzoquinon-2-yl)methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (hexand:ethyl acetate=1:1) and then recrystallized from ether to obtain the titled compound (0.140 g, 0.271 mmol, 51%).

EXAMPLE 166

N-[3-(5,6-Dimethoxy-3-methyl-1,4-benzoquinon-2-yl)methyl-2-hydroxybenzoyl]-4-trifluoromethylaniline N-[3-(5,6-Dimethoxy-3-methyl-1,4-benzoquinon-2-yl)methyl-2-acetoxybenzoyl]-4-trifluoromethylaniline (0.150 g, 0.290 mmol) was dissolved in methanol (3 ml) and after adding thereto an aqueous saturated sodium hydrogencarbonate solution (2 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was recrystallized from ether to obtain the titled compound (0.080 g, 0.168 mmol, 58%).

EXAMPLE 167

Ethyl N-[5-(5,6-dimethoxy-3-methyl-1,4-benzoquinon-2-yl)methyl-2-(3-pyridylmethyloxy)benzoyl]-4-aminobenzoate Ethyl 4-aminobenzoate (0.248 g, 1.500 mmol), triethylamine (0.152 g, 1.500 mmol) and 2-chloro-1,3-dimethylimidazolinium chloride (0.254 g, 1.500 mmol) were added to a methylene chloride solution (100 ml) of 5-(5,6-dimethoxy-3-methyl-1,4-benzoquinon-2-yl)methyl-2-(3-pyridylmethyloxy)benzoic acid (0.2115 g, 0.500 mmol) and the resulting solution was stirred at room temperature for 10 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from ether to obtain the titled compound (0.020 g, 0.0351 mmol, 7%).

EXAMPLE 168

N-(Pyridin-4-yl)-5-(5,6-dimethoxy-3-methyl-1,4-benzoquinon-2-yl)methyl-2-(3-pyridylmethyloxy)benzamide 4-Aminopyridine (0.141 g, 1.500 mmol), triethylamine (0.152 g, 1.500 mmol) and 2-chloro-1,3-dimethylimidazolinium chloride (0.254 g, 1.500 mmol) were added to a methylene chloride solution (100 ml) of 5-(5,6-dimethoxy-3-methyl-1,4-benzoquinon-2-yl)methyl-2-(3-pyridylmethyloxy)benzoic acid (0.2115 g, 0.500 mmol) and the resulting solution was stirred at room temperature for 10 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from ether to obtain the titled compound (0.023 g, 0.0460 mmol, 9%).

EXAMPLE 169

N-(Pyridin-3-yl)-5-(5,6-dimethoxy-3-methyl-1,4-benzoquinon-2-yl)methyl-2-(3-pyridylmethyloxy)benzamide 3-Aminopyridine (0.141 g, 1.500 mmol), triethylamine (0.152 g, 1.500 mmol) and 2-chloro-1,3-dimethylimidazolinium chloride (0.254 g, 1.500 mmol) were added to a methylene chloride solution (100 ml) of 5-(5,6-dimethoxy-3-methyl-1,4-benzoquinon-2-yl)methyl-2-(3-pyridylmethyloxy)benzoic acid (0.2115 g, 0.500 mmol) and the resulting solution was stirred at room temperature for 10 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from ether to obtain the titled compound (0.024 g, 0.0480 mmol, 10%).

EXAMPLE 170

N-Cyclopropyl-5-(5,6-dimethoxy-3-methyl-1,4-benzoquinon-2-yl)methyl-2-(3-pyridylmethyloxy)benzamide Cyclopropylamine (0.0857 g, 1.500 mmol), triethylamine (0.152 g, 1.500 mmol) and 2-chloro-1,3-dimethylimidazolinium chloride (0.254 g, 1.500 mmol) were added to a methylene chloride solution (100 ml) of 5-(5,6-dimethoxy-3-methyl-1,4-benzoquinon-2-yl)methyl-2-(3-pyridylmethyloxy)benzoic acid (0.2115 g, 0.500 mmol) and the resulting solution was stirred at room temperature for 13 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from ether to obtain the titled compound (0.029 g, 0.0627 mmol, 13%).

EXAMPLE 171

N-Cyclohexyl-5-(5,6-dimethoxy-3-methyl-1,4-benzoquinon-2-yl)methyl-2-(3-pyridylmethyloxy)benzamide Cyclohexylamine (0.149 g, 1.500 mmol), triethylamine (0.152 g, 1.500 mmol) and 2-chloro-1,3-dimethylimidazolinium chloride (0.254 g, 1.500 mmol) were added to a methylene chloride solution (100 ml) of 5-(5,6-dimethoxy-3-methyl-1,4-benzoquinon-2-yl)methyl-2-(3-pyridylmethyloxy)benzoic acid (0.215 g, 0.500 mmol) and the resulting solution was stirred at room temperature for 10 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from ether to obtain the titled compound (0.032 g, 0.0634 mmol, 13%).

EXAMPLE 172

N-[5-(5,6-Dimethoxy-3-methyl-1,4-benzoquinon-2-yl)methyl-2-(3-pyridylmethyloxy)benzoyl]-4-trifluoromethylaniline 4-Trifluoromethylaniline (0.242 g, 1.500 mmol), triethylamine (0.152 g, 1.500 mmol) and 2-chloro-1,3-dimethylimidazolinium chloride (0.254 g, 1.500 mmol) were added to a methylene chloride solution (100 ml) of 5-(5,6-dimethoxy-3-methyl-1,4-benzoquinon-2-yl)methyl-2-(3-pyridylmethyloxy)benzoic acid (0.215 g, 0.500 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from ether to obtain the titled compound (0.035 g, 0.0618 mmol, 12%).

EXAMPLE 173

N-[5-(5,6-Dimethoxy-3-methyl-1,4-benzoquinon-2-yl)methyl-2-acetoxybenzoyl]-4-(trifluoromethylsulfonyl)aniline 4-(Trifluoromethylsulfonyl)aniline (0.452 g, 2.005 mmol), triethylamine (0.203 g, 2.005 mmol) and 2-chloro-1,3-dimethylimidazolinium chloride (0.339 g, 2.005 mmol) were added to a methylene chloride solution (70 ml) of 5-(5,6-dimethoxy-3-methyl-1,4-benzoquinon-2-yl)methyl-2-acetoxybenzoic acid (0.250 g, 0.668 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from ether to obtain the titled compound (0.140 g, 0.241 mmol, 36%).

EXAMPLE 174

N-[5-(5,6-Dimethoxy-3-methyl-1,4-benzoquinon-2-yl)methyl-2-hydroxybenzoyl]-4-(trifluoromethylsulfonyl)aniline N-[5-(5,6-Dimethoxy-3-methyl-1,4-benzoquinon-2-yl)methyl-2-acetoxybenzoyl]-4-(trifluoromethylsulfonyl)aniline (0.060 g, 0.103 mmol) was dissolved in methanol (3 ml) and after adding thereto an aqueous saturated sodium hydrogencarbonate solution (2 ml), the solution was stirred at room temperature for 2 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=10:1) and then recrystallized from ether to obtain the titled compound (0.021 g, 0.0389 mmol, 38%).

EXAMPLE 175

N-[3-(5,6-Dimethoxy-3-methyl-1,4-benzoquinon-2-yl)methyl-2-acetoxybenzoyl]-4-(trifluoromethylsulfonyl)aniline 4-(Trifluoromethylsulfonyl)aniline (0.361 g, 1.604 mmol), triethylamine (0.162 g, 1.604 mmol) and 2-chloro- 1,3-dimethylimidazolinium chloride (0.271 g, 1.604 mmol) were added to a methylene chloride solution (50 ml) of 3-(5,6-dimethoxy-3-methyl-1,4-benzoquinon-2-yl)methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from ether to obtain the titled compound (0.084 g, 0.144 mmol, 27%).

EXAMPLE 176

N-[3-(5,6-Dimethoxy-3-methyl-1,4-benzoquinon-2-yl)methyl-2-acetoxybenzoyl]-2,4-dichloroaniline 2,4-Dichloroaniline (0.383 g, 2.366 mmol), triethylamine (0.239 g, 2.366 mmol) and 2-chloro-1,3-dimethylimidazolinium chloride (0.400 g, 2.366 mmol) were added to a methylene chloride solution (100 ml) of 3-(5,6-dimethoxy-3-methyl-1,4-benzoquinon-2-yl)methyl-2-acetoxybenzoic acid (0.295 g, 0.789 mmol) and the resulting solution was stirred at room temperature for 10 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from ether to obtain the titled compound (0.150 g, 0.289 mmol, 37%).

EXAMPLE 177

N-[3-(5,6-Dimethoxy-3-methyl-1,4-benzoquinon-2-yl)methyl-2-hydroxybenzoyl]-2,4-dichloroaniline N-[3-(5,6-Dimethoxy-3-methyl-1,4-benzoquinon-2-yl) methyl-2-acetoxybenzoyl]-2,4-dichloroaniline (0.075 g, 0.145 mmol) was dissolved in methanol (2 ml) and after adding thereto an aqueous saturated sodium hydrogencarbonate solution (1.5 ml), the solution was stirred at room temperature for 2 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=10:1) and then recrystallized from ether to obtain the titled compound (0.035 g, 0.0735 mmol, 51%).

EXAMPLE 178

N-[3-(5,6-Dimethoxy-3-methyl-1,4-benzoquinon-2-yl)methyl-2-acetoxybenzoyl]-4-morpholinoaniline 4-Morpholinoaniline (0.214 g, 1.203 mmol), triethylamine (0.122 g, 1.203 mmol) and 2-chloro-1,3-dimethylimidazolinium chloride (0.203 g, 1.203 mmol) were added to a methylene chloride solution (40 ml) of 3-(5,6-dimethoxy-3-methyl-1,4-benzoquinon-2-yl)methyl-2-acetoxybenzoic acid (0.150 g, 0.401 mmol) and the resulting solution was stirred at room temperature for 10 hours. The reaction solution was poured into ice water and then extracted with methylene chloride. The extract was washed with water and then dried, and the solvent was removed by distillation. The obtained residue was purified by preparative thin-layer chromatography (ethyl acetate) and then recrystallized from ether to obtain the titled compound (0.109 g, 0.203 mmol, 51%).

EXAMPLE 179

N-[3-(5,6-Dimethoxy-3-methyl-1,4-benzoquinon-2-yl)methyl-2-hydroxybenzoyl]-4-morpholinoaniline N-[3-(5,6-Dimethoxy-3-methyl-1,4-benzoquinon-2-yl) methyl-2-acetoxybenzoyl]-4-morpholinoaniline (0.075 g, 0.145 mmol) was dissolved in methanol (5 ml) and after adding thereto an aqueous saturated sodium hydrogencarbonate solution (1.5 ml), the solution was stirred at room temperature for 1.5 hours. After the completion of reaction, the reaction solution was diluted with water and then extracted with ethyl acetate. The extract was washed with water and then dried, and the solvent was removed by distillation. The obtained residue was purified by preparative thin-layer chromatography (ethyl acetate) and then recrystallized from ether to obtain the titled compound (0.048 g, 0.0975 mmol, 74%).

EXAMPLE 180

N-(6-Methoxypyridin-3-yl)-5-(5,6-dimethoxy-3-methyl-1,4-benzoquinon-2-yl methyl-2-acetoxybenzamide 5-Amino-2-methoxypyridine (0.199 g, 1.604 mmol), triethylamine (0.162 g, 1.604 mmol) and 2-chloro-1,3-dimethylimidazolinium chloride (0.271 g, 1.604 mmol) were added to a methylene chloride solution (100 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 10 hours. The reaction solution was poured into ice water and then extracted with methylene chloride. The extract was washed with water and then dried, and the solvent was removed by distillation. The obtained residue was purified by preparative thin-layer chromatography (ethyl acetate) and then recrystallized from ether to obtain the titled compound (0.109 g, 0.227 mmol, 42%).

EXAMPLE 181

N-(6-Methoxypyridin-3-yl)-5-(5,6-dimethoxy-3-methyl-1,4-benzoquinon-2-yl)methyl-2-hydroxybenzamide N-(6-Methoxypyridin-3-yl)-5-(5,6-dimethoxy-3-methyl-1,4-benzoquinon-2-yl)methyl-2-acetoxybenzamide (0.065 g, 0.135 mmol) was dissolved in methanol (3 ml) and after adding thereto an aqueous saturated sodium hydrogencarbonate solution (1.5 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (ethyl acetate) and then recrystallized from ether to obtain the titled compound (0.050 g, 0.114 mmol, 84%).

EXAMPLE 182

N-(2,6-Dimethoxypyridin-3-yl)-5-(5,6-dimethoxy-3-methyl-1,4-benzoquinon-2-yl)methyl-2-acetoxybenzamide 3-Amino-2,6-dimethoxypyridine hydrochloride (0.306 g, 1.604 mmol), triethylamine (0.162 g, 1.604 mmol) and 2-chloro-1,3-dimethylimidazolinium chloride (0.271 g, 1.604 mmol) were added to a methylene chloride solution (100 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 10 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from ether to obtain the titled compound (0.160 g, 0.313 mmol, 59%).

EXAMPLE 183

N-(2,6-Dimethoxypyridin-3-yl)-5-(5,6-dimethoxy-3-methyl-1,4-benzoquinon-2-yl)methyl-2-hydroxybenzamide N-(2,6-Dimethoxypyridin-3-yl)-5-(5,6-dimethoxy-3-methyl-1,4-benzoquinon-2-yl)methyl-2-acetoxybenzamide (0.100 g, 0.196 mmol) was dissolved in methanol (3 ml) and after adding thereto an aqueous saturated sodium hydrogencarbonate solution (1.5 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=10:1) and then recrystallized from ether to obtain the titled compound (0.079 g, 0.169 mmol, 87%).

EXAMPLE 184

N-(6-Chloropyridin-3-yl)-5-(5,6-dimethoxy-3-methyl-1,4-benzoquinon-2-yl)methyl-2-acetoxybenzamide 5-Amino-2-chloropyridine (0.206 g, 1.604 mmol), triethylamine (0.162 g, 1.604 mmol) and 2-chloro-1,3-dimethylimidazolinium chloride (0.271 g, 1.604 mmol) were added to a methylene chloride solution (100 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 10 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from ether to obtain the titled compound (0.142 g, 0.293 mmol, 55%).

EXAMPLE 185

N-(6-Chloropyridin-3-yl)-5-(5,6-dimethoxy-3-methyl-1,4-benzoquinon-2-yl)methyl-2-hydroxybenzamide N-(6-Chloropyridin-3-yl)-5-(5,6-dimethoxy-3-methyl-1,4-benzoquinon-2-yl)methyl-2-acetoxybenzamide (0.070 g, 0.144 mmol) was dissolved in methanol (3 ml) and after adding thereto an aqueous saturated sodium hydrogencarbonate solution (1.5 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=10:1) and then recrystallized from ether to obtain the titled compound (0.056 g, 0.126 mmol, 88%).

EXAMPLE 186

N-(2-Chloropyridin-3-yl)-5-(5,6-dimethoxy-3-methyl-1,4-benzoquinon-2-yl)methyl-2-acetoxybenzamide 3-Amino-2-chloropyridine (0.206 g, 1.604 mmol), triethylamine (0.162 g, 1.604 mmol) and 2-chloro-1,3-dimethylimidazolinium chloride (0.271 g, 1.604 mmol) were added to a methylene chloride solution (100 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 10 hours. The reaction solution was poured into ice water and then extracted with methylene chloride. The extract was washed with water and then dried, and the solvent was removed by distillation. The obtained residue was purified by preparative thin-layer chromatography (ethyl acetate:hexane=1:1) to obtain the titled compound (0.140 g, 0.289 mmol, 54%).

EXAMPLE 187

N-(2-Chloropyridin-3-yl)-5-(5,6-dimethoxy-3-methyl-1,4-benzoquinon-2-yl)methyl-2-hydroxybenzamide N-(2-Chloropyridin-3-yl)-5-(5,6-dimethoxy-3-methyl-1,4-benzoquinon-2-yl)methyl-2-acetoxybenzamide (0.070 g, 0.144 mmol) was dissolved in methanol (3 ml) and after adding thereto an aqueous saturated sodium hydrogencarbonate solution (1.5 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (ethyl acetate:hexane=1:1) and then recrystallized from ether to obtain the titled compound (0.040 g, 0.0903 mmol, 63%).

EXAMPLE 188 tert-Butyl N-[5-(5,6-dimethoxy-3-methyl-1,4-benzoquinon-2-yl)methyl-2-acetoxybenzoyl]-4-aminobenzoate tert-Butyl 4-aminobenzoate (0.620 g, 6.209 mmol), triethylamine (0.325 g, 3.209 mmol) and 2-chloro-1,3-dimethylimidazolinium chloride (0.542 g, 3.209 mmol) were added to a methylene chloride solution (150 ml) of 5-(5,6-dimethoxy-3-methyl-1,4-benzoquinon-2-yl)methyl-2-acetoxybenzoic acid (0.400 g, 1.070 mmol) and the resulting solution was stirred at room temperature for 6 hours. The reaction solution was poured into ice water and then extracted with methylene chloride. The extract was washed with water and then dried, and the solvent was removed by distillation. The obtained residue was purified by preparative thin-layer chromatography (ethyl acetate:hexane=1:2→1:0) to obtain the titled compound (0.302 g, 0.549 mmol, 57%).

EXAMPLE 189

N-[5-(5,6-Dimethoxy-3-methyl-1,4-benzoquinon-2-yl)methyl-2-acetoxybenzoyl]-4-aminobenzoic acid tert-Butyl N-[5-(5,6-dimethoxy-3-methyl-1,4-benzoquinon-2-yl)methyl-2-acetoxybenzoyl]-4- aminobenzoate (0.250 g, 0.455 mmol) was dissolved in formic acid (3.0 ml) and the resulting solution was stirred at room temperature for 12 hours. The reaction solution was concentrated and the obtained residue was recrystallized from methanol to obtain the titled compound (0.129 g, 0.261 mmol, 57%).

EXAMPLE 190

N-[5-(5,6-Dimethoxy-3-methyl-1,4-benzoquinon-2-yl)methyl-2-hydroxybenzoyl]-4-aminobenzoic acid N-[5-(5,6-Dimethoxy-3-methyl-1,4-benzoquinon-2-yl)methyl-2-acetoxybenzoyl]-4-aminobenzoic acid (0.070 g, 0.142 mmol) was dissolved in methanol (3 ml) and after adding thereto an aqueous saturated sodium hydrogencarbonate solution (1.5 ml), the solution was stirred at room temperature for 3 hours. After the completion of reaction, the reaction solution was diluted with a 2N hydrochloric acid solution and the aqueous layer was rendered acidic (pH=1 to 2) and then extracted with ethyl acetate. The extract was washed with water and then dried, and the solvent was removed by distillation. The obtained residue was purified by preparative thin-layer chromatography (chloroform:methanol=10:1) and then recrystallized from methanol to obtain the titled compound (0.049 g, 0.109 mmol, 77%).

EXAMPLE 191

N-[5-(5,6-Dimethoxy-3-methyl-1,4-benzoquinon-2-yl)methyl-2-hydroxybenzoyl]-4-nitroaniline 4-Nitroaniline (0.414 g, 3.000 mmol), triethylamine (0.304 g, 3.000 mmol) and 2-chloro-1,3-dimethylimidazolinium chloride (0.507 g, 3.000 mmol) were added to a methylene chloride solution (100 ml) of 5-(5,6-dimethoxy-3-methyl-1,4-benzoquinon-2-yl)methyl-2-acetoxybenzoic acid (0.374 g, 1.000 mmol) and the resulting solution was stirred at room temperature for 12 hours. The reaction solution was poured into ice water and then extracted with methylene chloride. The extract was washed with water and then dried, and the solvent was removed by distillation. The obtained residue was dissolved in methanol (3 ml) and after adding thereto an aqueous saturated sodium hydrogencarbonate solution (1.5 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=10:1) and then recrystallized from ether to obtain the titled compound (0.080 g, 0.177 mmol, 18%).

EXAMPLE 192

N-[5-(5,6-Dimethoxy-3-methyl-1,4-benzoquinon-2-yl)methyl-2-hydroxybenzoyl]-2,6-dichloro-4-trifluoromethoxyaniline 2,6-Dichloro-4-trifluoromethoxyaniline (0.395 g, 1.604 mmol), triethylamine (0.162 g, 1.604 mmol) and 2-chloro-1,3-dimethylimidazolinium chloride (0.271 g, 1.604 mmol) were added to a methylene chloride solution (100 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 10 hours. The reaction solution was poured into ice water and then extracted with methylene chloride. The extract was washed with water and then dried, and the solvent was removed by distillation. The obtained residue was purified by preparative thin-layer chromatography (ethyl acetate:hexane=1:2) and then recrystallized from ether to obtain the titled compound (0.099 g, 0.177 mmol, 33%).

EXAMPLE 193

N-(3-tert-Butoxycarbonylpyridin-2-yl)-5-(5,6-dimethoxy-3-methyl-1,4-benzoquinon-2-yl)methyl-2-acetoxybenzamide tert-Butyl 2-aminonicotinate (0.311 g, 1.604 mmol), triethylamine (0.162 g, 1.604 mmol) and 2-chloro-1,3-dimethylimidazolinium chloride (0.271 g, 1.604 mmol) were added to a methylene chloride solution (100 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 10 hours. The reaction solution was poured into ice water and then extracted with methylene chloride. The extract was washed with water and then dried, and the solvent was removed by distillation. The obtained residue was purified by preparative thin-layer chromatography (chloroform:methanol=15:1) to obtain the titled compound (0.157 g, 0.285 mmol, 53%).

EXAMPLE 194

N-(3-Hydroxycarbonylpyridin-2-yl)-5-(5,6-dimethoxy-3-methyl-1,4-benzoquinon-2-yl)methyl-2-acetoxybenzamide N-(3-tert-Butoxycarbonylpyridin-2-yl)-5-(5,6-dimethoxy-3-methyl-1,4-benzoquinon-2-yl)methyl-2-acetoxybenzamide (0.140 g, 0.254 mmol) was dissolved in formic acid (2.0 ml) and the resulting solution was stirred at room temperature for 12 hours. The reaction solution was concentrated and the obtained residue was purified by silica gel chromatography (chloroform:methanol=10:1) and then recrystallized from ether to obtain the titled compound (0.110 g, 0.222 mmol, 87%).

EXAMPLE 195

N-(3-Hydroxycarbonylpyridin-2-yl)-5-(5,6-dimethoxy-3-methyl-1,4-benzoquinon-2-yl)methyl-2-hydroxybenzamide N-(3-Hydroxycarbonylpyridin-2-yl)-5-(5,6-dimethoxy-3-methyl-1,4-benzoquinon-2-yl)methyl-2-acetoxybenzamide (0.080 g, 0.162 mmol) was dissolved in methanol (6 ml) and after adding thereto an aqueous saturated sodium hydrogencarbonate solution (2 ml), the solution was stirred at room temperature for 3 hours. After the completion of reaction, the reaction solution was diluted with a 2N hydrochloric acid solution and the aqueous layer was rendered acidic (pH=3 to 4) and then extracted with ethyl acetate. The extract was washed with water and then dried, and the solvent was removed by distillation. The obtained residue was recrystallized from ether to obtain the titled compound (0.051 g, 0.113 mmol, 70%).

EXAMPLE 196

N-(5-tert-Butoxycarbonylpyridin-2-yl)-5-(5,6-dimethoxy-3-methyl-1,4-benzoquinon-2-yl)methyl-2-acetoxybenzamide tert-Butyl 6-aminonicotinate (0.467 g, 2.406 mmol), triethylamine (0.244 g, 2.406 mmol) and 2-chloro-1,3- dimethylimidazolinium chloride (0.407 g, 2.406 mmol) were added to a methylene chloride solution (100 ml) of 5-(5,6-dimethoxy-3-methyl-1,4-benzoquinon-2-yl)methyl-2-acetoxybenzoic acid (0.300 g, 0.802 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) to obtain the titled compound (0.240 g, 0.436 mmol, 54%).

EXAMPLE 197

N-(5-Hydroxycarbonylpyridin-2-yl)-5-(5,6-dimethoxy-3-methyl-1,4-benzoquinon-2-yl)methyl-2-acetoxybenzamide N-(5-tert-Butoxycarbonylpyridin-2-yl)-5-(5,6-dimethoxy-3-methyl-1,4-benzoquinon-2-yl)methyl-2-acetoxybenzamide (0.170 g, 0.309 mmol) was dissolved in formic acid (3.0 ml) and the resulting solution was stirred at room temperature for 12 hours. The reaction solution was concentrated and the obtained residue was purified by silica gel chromatography (chloroform:methanol=10:1) and then recrystallized from ether to obtain the titled compound (0.109 g, 0.220 mmol, 71%).

EXAMPLE 198

N-(5-Hydroxycarbonylpyridin-2-yl)-5-(5,6-dimethoxy-3-methyl-1,4-benzoquinon-2-yl)methyl-2-hydroxybenzamide N-(5-Hydroxycarbonylpyridin-2-yl)-5-(5,6-dimethoxy-3-methyl-1,4-benzoquinon-2-yl)methyl-2-acetoxybenzamide (0.085 g, 0.172 mmol) was dissolved in methanol (6 ml) and after adding thereto an aqueous saturated sodium hydrogencarbonate solution (2 ml), the solution was stirred at room temperature for 3 hours. After the completion of reaction, the reaction solution was diluted with a 2N hydrochloric acid solution and the aqueous layer was rendered acidic (pH=3 to 4) and then extracted with ethyl acetate. The extract was washed with water and then dried, and the solvent was removed by distillation. The obtained residue was recrystallized from ether to obtain the titled compound (0.062 g, 0.137 mmol, 79%).

EXAMPLE 199

N-[5-(5,6-Dimethoxy-3-methyl-1,4-benzoquinon-2-yl)methyl-2-acetoxybenzoyl]-4-(tert-butoxycarbonyl)aminoaniline N-(tert-Butoxycarbonyl)-p-phenylenediamine (0.209 g, 1.002 mmol), triethylamine (0.101 g, 1.002 mmol) and 2-chloro-1,3-dimethylimidazolinium chloride (0.279 g, 1.002 mmol) were added to a methylene chloride solution (100 ml) of 5-(5,6-dimethoxy-3-methyl-1,4-benzoquinon-2-yl)methyl-2-acetoxybenzoic acid (0.250 g, 0.668 mmol) and the resulting solution was stirred at room temperature for 6 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from ethanol to obtain the titled compound (0.180 g, 0.319 mmol, 48%).

EXAMPLE 200

N-[5-(5,6-Dimethoxy-3-methyl-1,4-benzoquinon-2-yl)methyl-2-hydroxybenzoyl]-4-(tert-butoxycarbonyl)aminoaniline N-[5-(5,6-Dimethoxy-3-methyl-1,4-benzoquinon-2-yl)methyl-2-acetoxybenzoyl]-4-(tert-butoxycarbonyl)aminoaniline (0.140 g, 0.248 mmol) was dissolved in methanol (6 ml) and after adding thereto an aqueous saturated sodium hydrogencarbonate solution (2 ml), the solution was stirred at room temperature for 3 hours. After the completion of reaction, the reaction solution was diluted with water and extracted with ethyl acetate. The extract was washed with water and then dried, and the solvent was removed by distillation. The obtained residue was purified by preparative thin-layer chromatography (chloroform:methanol=10:1) and then recrystallized from a mixed solvent of ether and hexane (3:1) to obtain the titled compound (0.095 g, 0.182 mmol, 73%).

EXAMPLE 201

N-(Pyridin-3-yl)-5-(5,6-dimethoxy-3-methyl-1,4-benzoquinon-2-yl)methyl-2-acetoxybenzamide 3-Aminopyridine (0.424 g, 4.492 mmol), triethylamine (0.440 g, 4.342 mmol) and 2-chloro-1,3-dimethylimidazolinium chloride (0.735 g, 4.342 mmol) were added to a methylene chloride solution (200 ml) of 5-(5,6-dimethoxy-3-methyl-1,4-benzoquinon-2-yl)methyl-2-acetoxybenzoic acid (1.120 g, 2.995 mmol) and the resulting solution was stirred at room temperature for 6 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) to obtain the titled compound (0.710 g, 1.576 mmol, 53%).

EXAMPLE 202

N-(Pyridin-3-yl)-5-(5,6-dimethoxy-3-methyl-1,4-benzoquinon-2-yl)methyl-2-hydroxybenzamide (methanesulfonate)

Methanesulfonic acid (0.00732 g, 0.0762 mmol) was added to a methanol solution (2 ml) of N-(pyridin-3-yl)-5-(5,6-dimethoxy-3-methyl-1,4-benzoquinon-2-yl)methyl-2-acetoxybenzamide (0.0327 g, 0.0726 mmol), and the solvent was removed by distillation. The obtained residue was recrystallized from a mixed solvent of methanol, hexane and toluene (1:2:0.2) to obtain the titled compound (0.030 g, 0.0595 mmol, 82%).

EXAMPLE 203

N-(Pyridin-4-yl)-5-(5,6-dimethoxy-3-methyl-1,4-benzoquinon-2-yl)methyl-2-hydroxybenzamide (methanesulfonate)

Methanesulfonic acid (0.00914 g, 0.0951 mmol) was added to a methanol:dichloromethane mixed solution (1:1, 2 ml) of N-(pyridin-4-yl)-5-(5,6-dimethoxy-3-methyl-1,4-benzoquinon-2-yl)methyl-2-hydroxybenzamide (0.0370 g, 0.0906 mmol), and the solvent was removed by distillation. The obtained residue was recrystallized from a mixed solvent of methanol, ether and ethyl acetate (2:1:0.5) to obtain the titled compound (0.019 g, 0.0377 mmol, 42%).

EXAMPLE 204

N-[5-(5,6-Dimethoxy-3-methyl-1,4-benzoquinon-2-yl)methyl-2-hydroxybenzoyl]-p-phenylenediamine Trifluoroacetic acid (0.5 ml) was added to a methylene chloride solution (10 ml) of N-[5-(5,6-dimethoxy-3-methyl- 1,4-benzoquinon-2-yl)methyl-2-hydroxybenzoyl]-4-tert-butoxycarbonylaminoaniline (0.205 g, 0.309 mmol) and the resulting solution was stirred at room temperature for 10 hours. The reaction solution was concentrated and the obtained residue was purified by silica gel column chromatography (chloroform:methanol=95:5) to obtain the titled compound (0.150 g, 0.355 mmol, 91%).

EXAMPLE 205

N-[5-(5,6-Dimethoxy-3-methyl-1,4-benzoquinon-2-yl)methyl-2-hydroxybenzoyl]-p-phenylenediamine (hydrochloride)

A 4N hydrochloric acid-dioxane solution (0.045 g, 0.180 mmol) was added to a methylene chloride solution (3 ml) of N-[5-(5,6-dimethoxy-3-methyl-1,4-benzoquinon-2-yl)methyl-2-hydroxybenzoyl]-p-phenylenediamine (0.0724 g, 0.171 mmol) and the solvent was removed by distillation. The obtained residue was recrystallized from a methanol ether mixed solvent (1:10) to obtain the titled compound (0.070 g, 0.153 mmol, 89%).

EXAMPLE 206

N-(Pyridin-3-yl)-3-(5,6-dimethoxy-3-methyl-1,4-benzoquinon-2-yl)methyl-2-acetoxybenzamide 3-Aminopyridine (0.076 g, 0.802 mmol), triethylamine (0.081 g, 0.802 mmol) and 2-chloro-1,3-dimethylimidazolinium chloride (0.136 g, 0.802 mmol) were added to a methylene chloride solution (100 ml) of 3-(5,6-dimethoxy-3-methyl-1,4-benzoquinon-2-yl)methyl-2-acetoxybenzoic acid (0.200 g, 0.535 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) to obtain the titled compound (0.100 g, 0.222 mmol, 41%).

EXAMPLE 207

N-(Pyridin-3-yl)-3-(5,6-dimethoxy-3-methyl-1,4-benzoquinon-2-yl)methyl-2-hydroxybenzamide N-(Pyridin-3-yl)-3-(5,6-dimethoxy-3-methyl-1,4-benzoquinon-2-yl)methyl-2-acetoxybenzamide (0.060 g, 0.133 mmol) was dissolved in methanol (2 ml) and after adding thereto an aqueous saturated sodium hydrogencarbonate solution (1.5 ml), the solution was stirred at room temperature for 2 hours. After the completion of reaction, the reaction solution was diluted with water and then extracted with ethyl acetate. The extract was washed with water and then dried, and the solvent was removed by distillation. The obtained residue was purified by preparative thin-layer chromatography (ethyl acetate:hexane=4:1) and then recrystallized from methanol to obtain the titled compound (0.035 g, 0.0857 mmol, 64%).

EXAMPLE 208

N-[5-(5,6-Dimethoxy-3-methyl-1,4-benzoquinon-2-yl)methyl-2-acetoxybenzoyl]-4-(imidazol-1-yl) aniline 4-(1H-Imidazol-1-yl)aniline (0.159 g, 1.003 mmol), triethylamine (0.101 g, 1.003 mmol) and 2-chloro-1,3-dimethylimidazolinium chloride (0.170 g, 1.003 mmol) were added to a methylene chloride solution (100 ml) of 5-(5,6-dimethoxy-3-methyl-1,4-benzoquinon-2-yl)methyl-2-acetoxybenzoic acid (0.250 g, 0.668 mmol) and the resulting solution was stirred at room temperature for 3 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from a mixed solvent of ethyl acetate and hexane (2:1) to obtain the titled compound (0.140 g, 0.272 mmol, 41%).

EXAMPLE 209

N-[5-(5,6-Dimethoxy-3-methyl-1,4-benzoquinon-2-yl)methyl-2-hydroxybenzoyl]-4-(imidazol-1-yl) aniline N-[5-(5,6-Dimethoxy-3-methyl-1,4-benzoquinon-2-yl)methyl-2-acetoxybenzoyl]-4-(imidazol-1-yl)aniline (0.070 g, 0.136 mmol) was dissolved in methanol (5 ml) and after adding thereto an aqueous saturated sodium hydrogencarbonate solution (3 ml), the solution was stirred at room temperature for 3 hours. After the completion of reaction, the reaction solution was diluted with water and extracted with ethyl acetate. The extract was washed with water and then dried, and the solvent was removed by distillation. The obtained residue was recrystallized from ether to obtain the titled compound (0.063 g, 0.133 mmol, 98%).

EXAMPLE 210

N-[5-(5,6-Dimethoxy-3-methyl-1,4-benzoquinon-2-yl)methyl-2-acetoxybenzoyl]-4-(1H-pyrazol-3-yl) aniline 4-(1H-Pyrazol-3-yl)aniline (0.159 g, 1.003 mmol), triethylamine (0.101 g, 1.003 mmol) and 2-chloro-1,3-dimethylimidazolinium chloride (0.170 g, 1.003 mmol) were added to a methylene chloride solution (100 ml) of 5-(5,6-dimethoxy-3-methyl-1,4-benzoquinon-2-yl)methyl-2-acetoxybenzoic acid (0.250 g, 0.668 mmol) and the resulting solution was stirred at room temperature for 3 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) to obtain the titled compound (0.180 g, 0.350 mmol, 52%).

EXAMPLE 211

N-[5-(5,6-Dimethoxy-3-methyl-1,4-benzoquinon-2-yl)methyl-2-hydroxybenzoyl]-4-(1H-pyrazol-3-yl) aniline N-[5-(5,6-Dimethoxy-3-methyl-1,4-benzoquinon-2-yl)methyl-2-acetoxybenzoyl]-4-(1H-pyrazol-3-yl)aniline (0.090 g, 0.175 mmol) was dissolved in a mixed solvent of methanol (2 ml) and dichloromethane (1 ml), and after adding thereto an aqueous saturated sodium hydrogencarbonate solution (2 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=10:1) and then recrystallized from a mixed solvent of ethyl acetate and hexane (1:1) to obtain the titled compound (0.049 g, 0.104 mmol, 59%).

EXAMPLE 212

N-Methyl-N-[5-(5,6-dimethoxy-3-methyl-1,4-benzoquinon-2-yl)methyl-2-acetoxybenzoyl]-4-trifluoromethylaniline N-Methyl-4-trifluoromethylaniline (0.200 g, 1.143 mmol), triethylamine (0.116 g, 1.143 mmol) and 2-chloro-1,3-dimethylimidazolinium chloride (0.193 g, 1.143 mmol) were added to a methylene chloride solution (100 ml) of 5-(5,6-dimethoxy-3-methyl-1,4-benzoquinon-2-yl)methyl-2-acetoxybenzoic acid (0.285 g, 0.762 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) to obtain the titled compound (0.140 g, 0.263 mmol, 35%).

EXAMPLE 213

N-Methyl-N-[5-(5,6-dimethoxy-3-methyl-1,4-benzoquinon-2-yl)methyl-2-hydroxybenzoyl]-4-trifluoromethylaniline N-Methyl-N-[5-(5,6-dimethoxy-3-methyl-1,4-benzoquinon-2-yl)methyl-2-acetoxybenzoyl]-4-trifluoromethylaniline (0.138 g, 0.260 mmol) was dissolved in methanol (3 ml) and after adding thereto an aqueous saturated sodium hydrogencarbonate solution (2 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (ethyl acetate:hexane=1:2) to obtain the titled compound (0.075 g, 0.153 mmol, 59%).

EXAMPLE 214 tert-Butyl N-[5-(5,6-dimethoxy-3-methyl-1,4-benzoquinon-2-yl)methyl-2-hydroxybenzoyl]-4-aminobenzoate tert-Butyl N-[5-(5,6-dimethoxy-3-methyl-1,4-benzoquinon-2-yl)methyl-2-acetoxybenzoyl]-4-aminobenzoate (0.240 g, 0.437 mmol) was dissolved in methanol (5 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=95:5) and then recrystallized from ether to obtain the titled compound (0.115 g, 0.227 mmol, 52%).

EXAMPLE 215

N-(2-Methoxypyridin-3-yl)-5-(5,6-dimethoxy-3-methyl-1,4-benzoquinon-2-yl)methyl-2-acetoxybenzamide 3-Amino-2-methoxypyridine (0.149 g, 1.203 mmol), triethylamine (0.122 g, 1.203 mmol) and 2-chloro-1,3-dimethylimidazolinium chloride (0.203 g, 1.203 mmol) were added to a methylene chloride solution (150 ml) of 5-(5,6-dimethoxy-3-methyl-1,4-benzoquinon-2-yl)methyl-2-acetoxybenzoic acid (0.300 g, 0.802 mmol) and the resulting solution was stirred at room temperature for 4 hours. The reaction solution was poured into ice water and then extracted with methylene chloride. The extract was washed with water and then dried, and the solvent was removed by distillation. The obtained residue was purified by preparative thin-layer chromatography (chloroform:methanol=50:1) to obtain the titled compound (0.250 g, 0.520 mmol, 65%).

EXAMPLE 216

N-(2-Methoxypyridin-3-yl)-5-(5,6-dimethoxy-3-methyl-1,4-benzoquinon-2-yl)methyl-2-hydroxybenzamide N-(2-Methoxypyridin-3-yl)-5-(5,6-dimethoxy-3-methyl-1,4-benzoquinon-2-yl)methyl-2-acetoxybenzamide (0.150 g, 0.312 mmol) was dissolved in methanol (5 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (ethyl acetate:hexane=3:1) to obtain the titled compound (0.112 g, 0.255 mmol, 82%).

EXAMPLE 217

N-(2-Dimethylaminopyridin-3-yl)-5-(5,6-dimethoxy-3-methyl-1,4-benzoquinon-2-yl)methyl-2-acetoxybenzamide 3-Amino-2-dimethylaminopyridine (0.154 g, 1.125 mmol), triethylamine (0.114 g, 1.125 mmol) and 2-chloro-1,3-dimethylimidazolinium chloride (0.190 g, 1.125 mmol) were added to a methylene chloride solution (100 ml) of 5-(5,6-dimethoxy-3-methyl-1,4-benzoquinon-2-yl)methyl-2-acetoxybenzoic acid (0.281 g, 0.750 mmol) and the resulting solution was stirred at room temperature for 4 hours. The reaction solution was poured into ice water and then extracted with methylene chloride. The extract was washed with water and then dried, and the solvent was removed by distillation. The obtained residue was purified by preparative thin-layer chromatography (chloroform:methanol=95:5) to obtain the titled compound (0.139 g, 0.282 mmol, 38%).

EXAMPLE 218

N-(2-Dimethylaminopyridin-3-yl)-5-(5,6-dimethoxy-3-methyl-1,4-benzoquinon-2-yl)methyl-2-hydroxybenzamide N-(2-Dimethylaminopyridin-3-yl)-5-(5,6-dimethoxy-3-methyl-1,4-benzoquinon-2-yl)methyl-2-acetoxybenzamide (0.074 g, 0.0933 mmol) was dissolved in methanol (3 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (ethyl acetate:hexane=1:1) to obtain the titled compound (0.042 g, 0.0930 mmol, 99%).

EXAMPLE 219

N-[5-(5,6-Dimethoxy-3-methyl-1,4-benzoquinon-2-yl)methyl-2-acetoxybenzoyl]-2,5-dimethoxyaniline 2,5-Dimethoxyaniline (0.172 g, 1.125 mmol), triethylamine (0.114 g, 1.125 mmol) and 2-chloro-1,3-dimethylimidazolinium chloride (0.190 g, 1.125 mmol) were added to a methylene chloride solution (100 ml) of 5-(5,6-dimethoxy-3-methyl-1,4-benzoquinon-2-yl)methyl-2-acetoxybenzoic acid (0.281 g, 0.750 mmol) and the resulting solution was stirred at room temperature for 4 hours. The reaction solution was poured into ice water and then extracted with methylene chloride. The extract was washed with water and then dried, and the solvent was removed by distillation. The obtained residue was purified by preparative thin-layer chromatography (chloroform:methanol=95:5) to obtain the titled compound (0.149 g, 0.292 mmol, 39%).

EXAMPLE 220

N-[5-(5,6-Dimethoxy-3-methyl-1,4-benzoquinon-2-yl)methyl-2-hydroxybenzoyl]-2,5-dimethoxyaniline N-[5-(5,6-Dimethoxy-3-methyl-1,4-benzoquinon-2-yl)methyl-2-acetoxybenzoyl]-2,5-dimethoxyaniline (0.075 g, 0.147 mmol) was dissolved in methanol (3 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was recrystallized from a mixed solvent of ether and hexane (1:1) to obtain the titled compound (0.048 g, 0.103 mmol, 70%).

EXAMPLE 221

N-(2-Chloropyridin-3-yl)-5-(5,6-dimethoxy-3-methyl-1,4-benzoquinon-2-yl)methyl-2-methoxybenzamide N-(2-Chloropyridin-3-yl)-5-(5,6-dimethoxy-3-methyl-1,4-benzoquinon-2-yl)methyl-2-hydroxybenzamide (0.050 g, 0.113 mmol) was dissolved in methanol (5 ml) and after adding thereto 10% trimethylsilyldiazomethane (hexane solution) (3.5 ml), the solution was stirred at room temperature for 2 hours. The reaction solution was concentrated and the obtained residue was recrystallized from a mixed solvent of ether and hexane (1:1) to obtain the titled compound (0.051 g, 0.112 mmol, 99%).

EXAMPLE 222

N-(2-Morpholinopyridin-3-yl)-5-(5,6-dimethoxy-3-methyl-1,4-benzoquinon-2-yl)methyl-2-acetoxybenzamide 3-Amino-2-morpholinopyridine (0.269 g, 1.500 mmol), triethylamine (0.197 g, 1.950 mmol) and 2-chloro-1,3-dimethylimidazolinium chloride (0.165 g, 0.975 mmol) were added to a methylene chloride solution (100 ml) of 5-(5,6-dimethoxy-3-methyl-1,4-benzoquinon-2-yl)methyl-2-acetoxybenzoic acid (0.281 g, 0.750 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (ethyl acetate:hexane=2:1) to obtain the titled compound (0.249 g, 0.465 mmol, 62%).

EXAMPLE 223

N-(2-Morpholinopyridin-3-yl)-5-(5,6-dimethoxy-3-methyl-1,4-benzoquinon-2-yl)methyl-2-hydroxybenzamide N-(2-Morpholinopyridin-3-yl)-5-(5,6-dimethoxy-3-methyl-1,4-benzoquinon-2-yl)methyl-2-acetoxybenzamide (0.110 g, 0.205 mmol) was dissolved in methanol (3 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was recrystallized from ether to obtain the titled compound (0.100 g, 0.203 mmol, 99%).

EXAMPLE 224

N-(6-Morpholinopyridin-3-yl)-5-(5,6-dimethoxy-3-methyl-1,4-benzoquinon-2-yl)methyl-2-acetoxybenzamide 3-Amino-6-morpholinopyridine (0.269 g, 1.500 mmol), triethylamine (0.197 g, 1.950 mmol) and 2-chloro-1,3-dimethylimidazolinium chloride (0.165 g, 0.975 mmol) were added to a methylene chloride solution (100 ml) of 5-(5,6-dimethoxy-3-methyl-1,4-benzoquinon-2-yl)methyl-2-acetoxybenzoic acid (0.281 g, 0.750 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) to obtain the titled compound (0.239 g, 0.446 mmol, 59%).

EXAMPLE 225

N-(6-Morpholinopyridin-3-yl)-5-(5,6-dimethoxy-3-methyl-1,4-benzoquinon-2-yl)methyl-2-hydroxybenzamide N-(6-Morpholinopyridin-3-yl)-5-(5,6-dimethoxy-3-methyl-1,4-benzoquinon-2-yl)methyl-2-acetoxybenzamide (0.100 g, 0.187 mmol) was dissolved in methanol (3 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was recrystallized from ether to obtain the titled compound (0.089 g, 0.180 mmol, 96%).

EXAMPLE 226

N-(2-Chloropyridin-4-yl)-5-(5,6-dimethoxy-3-methyl-1,4-benzoquinon-2-yl)methyl-2-acetoxybenzamide 4-Amino-2-chloropyridine (0.103 g, 1.802 mmol), triethylamine (0.0812 g, 0.802 mmol) and 2-chloro-1,3-dimethylimidazolinium chloride (0.136 g, 0.802 mmol)

were added to a methylene chloride solution (100 ml) of 5-(5,6-dimethoxy-3-methyl-1,4-benzoquinon-2-yl)methyl-2-acetoxybenzoic acid (0.200 g, 0.535 mmol) and the resulting solution was stirred in an oil bath at 50° C. for 8 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) to obtain the titled compound (0.078 g, 0.161 mmol, 30%).

EXAMPLE 227

N-(2-Chloropyridin-4-yl)-5-(5,6-dimethoxy-3-methyl-1,4-benzoquinon-2-yl)methyl-2-hydroxybenzamide N-(2-Chloropyridin-4-yl)-5-(5,6-dimethoxy-3-methyl-1,4-benzoquinon-2-yl)methyl-2-acetoxybenzamide (0.079 g, 0.163 mmol) was dissolved in methanol (3 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was recrystallized from ether to obtain the titled compound (0.057 g, 0.129 mmol, 79%).

EXAMPLE 228

N-(6-Methoxypyrimidin-4-yl)-5-(5,6-dimethoxy-3-methyl-1,4-benzoquinon-2-yl)methyl-2-acetoxybenzamide 4-Amino-6-methoxypyrimidine (0.134 g, 1.070 mmol), triethylamine (0.141 g, 1.390 mmol) and 2-chloro-1,3-dimethylimidazolinium chloride (0.118 g, 0.695 mmol) were added to a methylene chloride solution (100 ml) of 5-(5,6-dimethoxy-3-methyl-1,4-benzoquinon-2-yl)methyl-2-acetoxybenzoic acid (0.200 g, 0.535 mmol) and the resulting solution was stirred at room temperature for 10 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) to obtain the titled compound (0.120 g, 0.249 mmol, 47%).

EXAMPLE 229

N-(6-Methoxypyrimidin-4-yl)-5-(5,6-dimethoxy-3-methyl-1,4-benzoquinon-2-yl)methyl-2-hydroxybenzamide N-(6-Methoxypyrimidin-4-yl)-5-(5,6-dimethoxy-3-methyl-1,4-benzoquinon-2-yl)methyl-2-acetoxybenzamide (0.060 g, 0.125 mmol) was dissolved in methanol (3 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=10:1) and then recrystallized from ether to obtain the titled compound (0.040 g, 0.0910 mmol, 73%).

EXAMPLE 230

N-(2-Methoxypyridin-4-yl)-5-(5,6-dimethoxy-3-methyl-1,4-benzoquinon-2-yl)methyl-2-acetoxybenzamide 4-Amino-2-methoxypyridine (0.167 g, 1.340 mmol), triethylamine (0.176 g, 1.740 mmol) and 2-chloro-1,3-dimethylimidazolinium chloride (0.147 g, 0.869 mmol) were added to a methylene chloride solution (100 ml) of 5-(5,6-dimethoxy-3-methyl-1,4-benzoquinon-2-yl)methyl-2-acetoxybenzoic acid (0.250 g, 0.668 mmol) and the resulting solution was stirred at room temperature for 10 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from ether to obtain the titled compound (0.200 g, 0.416 mmol, 62%).

EXAMPLE 231

N-(2-Methoxypyridin-4-yl)-5-(5,6-dimethoxy-3-methyl-1,4-benzoquinon-2-yl)methyl-2-hydroxybenzamide N-(2-Methoxypyridin-4-yl)-5-(5,6-dimethoxy-3-methyl-1,4-benzoquinon-2-yl)methyl-2-acetoxybenzamide (0.100 g, 0.208 mmol) was dissolved in methanol (3 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=10:1) and then recrystallized from ether to obtain the titled compound (0.050 g, 0.114 mmol, 55%).

EXAMPLE 232

5-(2,5-Dimethoxy-3,4,6-trimethylbenzyl)-2-acetoxybenzoic acid 5-(2,5-Dimethoxy-3,4,6-trimethylbenzyl)-2-hydroxybenzoic acid (0.150 g, 0.455 mmol) was dissolved in acetic anhydride (3 ml) and the resulting solution was stirred at 80° C. for 1 hour. The reaction solution was diluted with water and then extracted with ethyl acetate. The extract was washed with water and then dried, and the solvent was removed by distillation. The obtained residue was purified by silica gel column chromatography (hexand:ethyl acetate=2:1) to obtain the titled compound (0.170 g, 0.454 mmol, 99%).

EXAMPLE 233

5-(3,5,6-Trimethyl-1,4-benzoquinon-2-yl)methyl-2-acetoxybenzoic acid 5-(2,5-Dimethoxy-3,4,6-trimethylbenzyl)-2-etoxybenzoic acid (1.25 g, 2.56 mmol) was dissolved in a mixed solution of acetonitrile (30 ml) and water (10 ml) and after adding thereto CAN (3.50 g, 6.39 mmol), the solution was stirred at room temperature for 1 hour. The reaction solution was diluted with water and then extracted with ether. The extract was washed with water and then dried, and the solvent was removed by distillation. The obtained residue was purified by silica gel column chromatography (hexand:ethyl acetate=2:1) and then recrystallized from ether to obtain the titled compound (0.800 g, 1.74 mmol, 68%).

EXAMPLE 234

N-[5-(3,5,6-Trimethyl-1,4-benzoquinon-2-yl)methyl-2-acetoxybenzoyl]-4-trifluoromethylaniline 4-Trifluoromethylaniline (0.176 g, 1.096 mmol), triethylamine (0.111 g, 1.096 mmol) and 2-chloro-1,3-dimethylimidazolinium chloride (0.185 g, 1.096 mmol) were added to a methylene chloride solution (100 ml) of 5-(3,5,6-trimethyl-1,4-benzoquinon-2-yl)methyl-2-acetoxybenzoic acid (0.250 g, 0.730 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from a mixed solvent of ethyl acetate and hexane (1:2) to obtain the titled compound (0.220 g, 0.453 mmol, 62%).

EXAMPLE 235

N-[5-(3,5,6-Trimethyl-1,4-benzoquinon-2-yl)methyl-2-hydroxybenzoyl]-4-trifluoromethylaniline N-[5-(3,5,6-Trimethyl-1,4-benzoquinon-2-yl)methyl-2-acetoxybenzoyl]-4-trifluoromethylaniline (0.070 g, 0.144 mmol) was dissolved in methanol (4 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was recrystallized from a mixed solvent of ethyl acetate and hexane (1:1) to obtain the titled compound (0.060 g, 0.135 mmol, 94%).

EXAMPLE 236

N-(2-Chloropyridin-3-yl)-5-(3,5,6-trimethyl-1,4-benzoquinon-2-yl)methyl-2-acetoxybenzamide 3-Amino-2-chloropyridine (0.141 g, 1.096 mmol), triethylamine (0.111 g, 1.096 mmol) and 2-chloro-1,3-dimethylimidazolinium chloride (0.185 g, 1.096 mmol) were added to a methylene chloride solution (100 ml) of 5-(3,5,6-trimethyl-1,4-benzoquinon-2-yl)methyl-2-acetoxybenzoic acid (0.250 g, 0.730 mmol) and the resulting solution was stirred at room temperature for 12 hours. The reaction solution was poured into ice water and then extracted with methylene chloride. The extract was washed with water and then dried, and the solvent was removed by distillation. The obtained residue was purified by preparative thin-layer chromatography (chloroform:methanol=10:1) and then recrystallized from a mixed solvent of ethyl acetate and hexane (2:1) to obtain the titled compound (0.149 g, 0.329 mmol, 45%).

EXAMPLE 237

N-(2-Chloropyridin-3-yl)-5-(3,5,6-trimethyl-1,4-benzoquinon-2-yl methyl-2-hydroxybenzamide N-(2-Chloropyridin-3-yl)-5-(3,5,6-trimethyl-1,4-benzoquinon-2-yl)methyl-2-acetoxybenzamide (0.055 g, 0.121 mmol) was dissolved in methanol (4 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was recrystallized from a mixed solvent of ethyl acetate and hexane (1:1) to obtain the titled compound (0.035 g, 0.0852 mmol, 70%).

EXAMPLE 238

N-(Pyridin-4-yl)-5-(3,5,6-trimethyl-1,4-benzoquinon-2-yl)methyl-2-hydroxybenzamide 4-Aminopyridine (0.103 g, 1.096 mmol), triethylamine (0.111 g, 1.096 mmol) and 2-chloro-1,3-dimethylimidazolinium chloride (0.185 g, 1.096 mmol) were added to a methylene chloride solution (100 ml) of 5-(3,5,6-trimethyl-1,4-benzoquinon-2-yl)methyl-2-acetoxybenzoic acid (0.250 g, 0.730 mmol) and the resulting solution was stirred at room temperature for 12 hours. The reaction solution was poured into ice water and then extracted with methylene chloride. The extract was washed with water and then dried, and the solvent was removed by distillation. The obtained residue was dissolved in methanol (3 ml) and after adding thereto an aqueous saturated sodium hydrogencarbonate solution (3 ml), the solution was stirred at room temperature for 3 hours. After the completion of reaction, the reaction solution was diluted with water and then extracted with ethyl acetate. The extract was washed with water and then dried, and the solvent was removed by distillation. The obtained residue was purified by preparative thin-layer chromatography (chloroform:methanol=95:5) to obtain the titled compound (0.020 g, 0.049 mmol, 7%).

TABLE 1

| Re. Ex. No. | Structure | Appearance | FABMS(m/z) |
|---|---|---|---|
| ref. 4 | (structure shown) | colorless powder 80–82° C. | 424(M+) 90(100) |

TABLE 1-continued

| | | | |
|---|---|---|---|
| ref. 5 | [structure: tetramethoxy-methyl-benzene with CH(OH) linked to 4-(benzyloxy)phenyl] | colorless powder 54–56° C. | 424(M+) 90(100) |
| ref. 6 | [structure: tetramethoxy-methyl-benzene with CH(OH) linked to 2-(benzyloxy)phenyl] | colorless oil | 424(M+) 91(100) |
| ref. 7a | [structure: tetramethoxy-methyl-benzene with CH2 linked to 3-(benzyloxy)phenyl] | colorless powder 77–78° C. | 408(M+) 91(100) |

| NMR(CDCl$_3$, δ) | IR (cm$^{-1}$) |
|---|---|
| 2.23 (3H,s), 3.27 (3H,s), 3.81 (3H,s), 3.85 (3H, s), 3.94 (3H,s), 4.03 (1H,d,J = 10.8 Hz), 5.05 (2H,s), 5.93 (1H,d,J = 10.8 Hz), 6.80–7.00 (3H, m),7.15–7.40 (6H,m) | 3514, 1610, 1582 (KBr) |
| 2.23 (3H,s), 3.35 (3H,s), 3.80 (3H,s), 3.86 (3H, s), 3.94 (3H,s), 4.07 (1H,d, J = 10.8 Hz), 5.05 (2H,s), 5.93 (1H,d,J = 10.8 Hz), 6.93(2H,d, J = 8.69 Hz), 7.19 (2H,d,J = 8.60 Hz), 7.25–7.45 (5H,m) | 3568, 2933, 1509 (KBr) |
| 2.16 (3H,s), 3.38 (3H,s), 3.72 (3H,s), 3.75– 3.79 (1H,m), 3.86 (3H.s), 3.93 (3H,s), 5.03 (1H, d,J = 12.40 Hz), 5.09 (1H,d,J = 12.36 Hz), 6.31 (1H,d,J = 8.32 Hz), 6.83 (1H,d,J = 8.12 Hz). 6.94 (1H,t,J = 7.52 Hz), 7.11–7.18 (3H,m),7.23–7.30 (3H,m), 7.36 (1H,d,J = 7.52 Hz) | 3500, 2937, 1599, 1464 (KBr) |
| 2.06 (3H,s), 3.67 (3H,s), 3.78 (3H,s), 3.91 (3H, s), 3.94 (3H, s), 3.98 (2H,s), 5.00 (2H,s), 6.65– 6.80 (3H,m), 7.05–7.45 (6H,m) | 1601, 1468 (KBr) |

TABLE 2

| Re. Ex. No. | Structure | Appearance | FABMS(m/z) |
|---|---|---|---|
| ref. 8a | [structure: tetramethoxy-methyl-benzene with CH2 linked to 4-(benzyloxy)phenyl] | colorless oil | 408(M+) 91(100) |

TABLE 2-continued

| Re. Ex. No. | Structure | Appearance | FABMS(m/z) |
|---|---|---|---|
| ref. 9a | 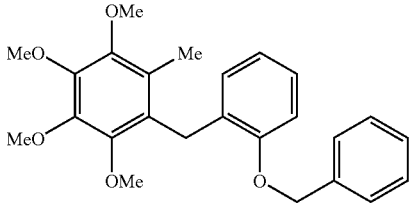 | colorless oil | 408(M+, 100) |
| ref. 7 | 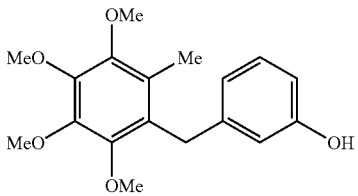 | colorless oil | 318(M+, 100) |
| ref. 8 | 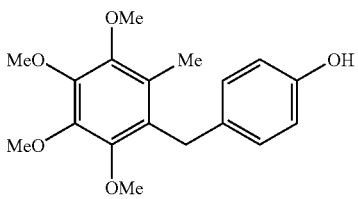 | colorless powder 80–81° C. | 318(M+, 100) |

| NMR(CDCl$_3$, δ) | IR (cm$^{-1}$) |
|---|---|
| 2.08 (3H,s), 3.69 (3H,s), 3.78 (3H,s), 3.91 (3H, s), 3.93 (3H,s), 3.94 (2H,s), 5.01 (2H,s), 6.86 (2H,d,J = 8.64 Hz), 7.01 (2H,d,J = 8.52 Hz), 7.30–7.42 (5H,m) | 2935, 1513, 1406 (KBr) |
| 1.94 (3H,s), 3.59 (3H,s), 3.70 (3H,s), 3.84 (3H, s), 3.87 (3H,s), 3.98 (2H,s), 5.06 (2H,s), 6.65 (1H,d,J = 7.48 Hz), 7.71 (1H,t,J = 7.52 Hz), 6.82 (1H,d,J = 8.12 Hz), 7.03 (1H,t,J = 8.08 Hz), 7.20–7.31(3H,m), 7.38 (2H,d,J = 7.32 Hz) | 2935, 1599, 1465 (NaCl) |
| 2.07 (3H,s), 3.70 (3H,s), 3.78 (3H,s), 3.91 (3H, s), 3.93 (3H,s), 3.96 (2H,s), 4.76 (1H,s), 6.54 (1H,s), 6.60 (1H,d), 6.68 (1H,d), 7.09 (1H,t) | 3387, 1589 (NaCl) |
| 2.08 (3H,s), 3.69 (3H,s), 3.78 (3H,s), 3.92 (3H, s), 3.93 (5H,s), 6.68 (2H,d,J = 8.52 Hz), 6.94 (2H,d,J = 8.45 Hz) | 3372, 1468, 1407 (KBr) |

TABLE 3

| Re. Ex. No. | Structure | Appearance | FABMS(m/z) |
|---|---|---|---|
| ref. 9 | 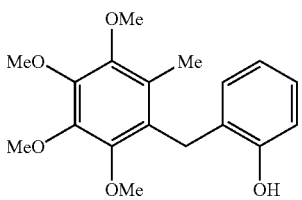 | colorless powder 7.25–7.45° C. | 318(M+, 100) |
| ref. 10a | 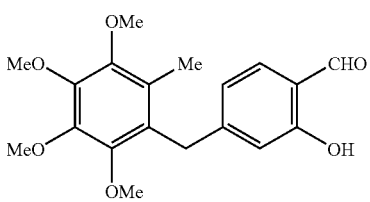 | colorless oil | 346(M+, 100) |

TABLE 3-continued

| Ref. | Structure | Appearance | |
|---|---|---|---|
| ref. 10b | [structure: trimethoxy-methyl-benzyl linked to hydroxy-CHO-phenyl] | colorless powder 95–98° C. | 346(M⁺, 100) |
| ref. 11 | [structure: trimethoxy-methyl-benzyl linked to OH-CHO-phenyl] | colorless powder 72–73.5 | 346(M⁺, 100) |

| NMR(CDCl₃, δ) | IR (cm⁻¹) |
|---|---|
| 2.25 (3H,s), 3.74 (3H,s), 3.87 (2H,s), 3.90 (6H, s), 3.96 (3H,s), 6.79–6.85 (2H,m), 7.10 (1H,t, J = 7.60 Hz), 7.21 (1H,d,J = 7.48 Hz), 7.63 (1H,br s) | 3348, 1466, 1407 (KBr) |
| 2.06 (3H,s), 3.72 (3H,s), 3.79 (3H,s), 3.92 (3H, s) 3.95 (3H,s), 4.02 (2H,s), 6.68 (1H,s), 6.81 (1H,d,J = 7.83 Hz), 7.43 (1H,d,J = 7.97 Hz), 9.82 (1H,s), 11.04 (1H,s) | 3200, 1659, 1627 (KBr) |
| 2.06 (3H,s), 3.67 (3H,s), 3.81 (3H,s), 3.91 (3H, s) 3.96 (3H,s), 4.35 (2H,s), 6.28 (1H,d,J = 7.6 Hz), 6.80 (1H,d,J = 8.4 Hz), 7.31 (1H,t,J = 8.0 Hz), 10.59 (1H,s) | 3400, 1655 (KBr) |
| 2.10 (3H,s), 3.73 (3H,s), 3.79 (3H,s), 3.93 (3H, s) 3.94 (3H,s), 3.96 (2H,s), 6.89 (1H,d,J = 8.53 Hz), 7.24 (1H,s-like), 7.32 (1H,d-like), 9.81 (1H, s), 10.84 (1H,br s) | 3232, 1664, 1486 (KBr) |

TABLE 4

| Re. Ex. No. | Structure | Appearance | FABMS(m/z) |
|---|---|---|---|
| ref. 12 | [structure: trimethoxy-methyl-benzyl linked to CHO-OH-phenyl] | colorless powder 93–95° C. | 346(M⁺, 100) |
| ref. 13 | [structure: trimethoxy-methyl-benzyl linked to CHO-O-benzyl-phenyl] | colorless powder 95–98° C. | 436(M⁺) 154(100) |
| ref. 14 | [structure: trimethoxy-methyl-benzyl linked to CHO-O-benzyl-phenyl] | colorless powder 68–70° C. | 436(M⁺) 91(100) |

TABLE 4-continued

| ref. 15 | [Structure: benzyl-protected trimethoxy-methyl-benzyl aldehyde] | colorless oil | 436(M⁺+1) 91(100) |

| NMR(CDCl₃, δ) | IR (cm⁻¹) |
|---|---|
| 2.03 (3H,s), 3.72 (3H,s), 3.80 (3H,s), 3.93 (3H, s) 3.96 (3H,s), 4.00 (2H,s), 6.86 (1H,t,J = 7.56 Hz), 6.93 (1H,d,J = 7.08 Hz), 7.39 (1H,d, J = 7.28 Hz), 9.91 (1H,s), 11.46 (1H,s) | 3446, 1661, 1468 (KBr) |
| 2.03 (3H,s), 3.64 (3H,s), 3.79 (3H,s), 3.91 (3H, s), 3.96 (3H,s), 4.01 (2H,s), 5.10 (2H,s), 6.76 (1H,s), 6.79 (1H,d,J = 8.1 Hz), 7.20–7.50 (5H, m), 7.73 (1H,d,J = 7.9 Hz), 10.47 (1H,s) | 1688, 1605 (KBr) |
| 1.97 (3H,s), 3.68 (3H,s), 3.79 (3H,s), 3.92 (3H, s), 3.96 (3H,s), 4.40 (2H,s), 5.17 (2H,s), 6.35 (1H,d,J = 7.8 Hz), 6.89 (1H,d,J = 8.3 Hz), 7.20– 7.50 (6H,m), 10.85 (1H,s) | 1684, 1654 (KBr) |
| 2.07 (3H,s), 3.71 (3H,s), 3.78 (3H,s), 3.92 (3H, s), 3.94 (3H,s), 3.95 (2H,s), 5.15 (2H,s), 6.93 (1H,d,J = 8.60 Hz), 7.15–7.50 (6H,m), 7.64 (1H, d,J = 2.23 Hz), 10.52 (1H,s) | 2936, 1682, 1608 (KBr) |

TABLE 5

| Re. Ex. No. | Structure | Appearance | FABMS(m/z) |
|---|---|---|---|
| ref. 16 | [Structure with OMe groups and OBn-aldehyde] | colorless oil | 436(M⁺) 91(100) |
| ref. 17 | [Structure with OMe groups and OMe-aldehyde] | colorless oil | 360(M⁺, 100) |
| ref. 18 | [Structure with OMe groups and O-isopropyl-aldehyde] | colorless oil | 388(M⁺, 100) |

| NMR(CDCl₃, δ) | IR (cm⁻¹) |
|---|---|

TABLE 5-continued

| | |
|---|---|
| 2.03 (3H,s), 3.69 (3H,s), 3.79 (3H,s), 3.92 (3H,s) 3.95 (3H,s), 4.06 (2H,s), 5.11 (2H,s), 7.00 (1H,d,J = 7.26 Hz), 7.09 (1H,t,J = 7.64 Hz), 7.37–7.49 (5H,m), 7.69 (1H,d,J = 7.60 Hz), 10.33 (1H,s) | 2935, 1687, 1467 (NaCl) |
| 2.07 (3H,s), 3.72 (3H,s), 3.78 (3H,s), 3.88 (3H,s), 3.92 (3H,s), 3.94 (3H,s), 3.96 (2H,s), 6.88 (1H,d,J = 8.60 Hz), 7.27 (1H,d,J = 8.52 Hz), 7.62 (1H,d,J = 2.28 Hz), 10.43 (1H,s) | 1609, 1464 (NaCl) |
| 1.37 (6H,d,J = 6.00 Hz), 2.07 (3H,s), 3.72 (3H,s), 3.78 (3H,s), 3.92 (3H,s), 3.94 (3H,s), 3.95 (2H,s), 4.59–4.62 (1H,m), 6.87 (1H,d,J = 8.64 Hz), 7.24 (1H,d,J = 8.48 Hz), 7.61 (1H,s), 10.44 (1H,s) | 1684, 1468 (NaCl) |

TABLE 6

| Ex. No. | Structure | Appearance | FABMS(m/z) |
|---|---|---|---|
| 1 | 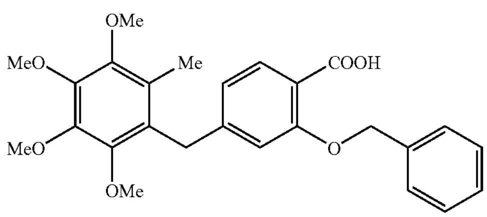 | colorless powder 104–105° C. | 452(M$^+$) 154(100) |
| 2 | 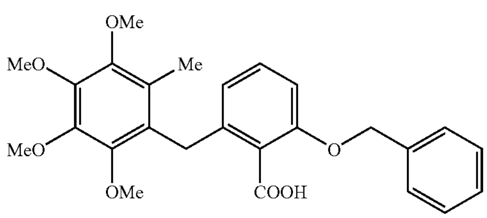 | colorless oil | 452(M$^+$) 91(100) |
| 3 | 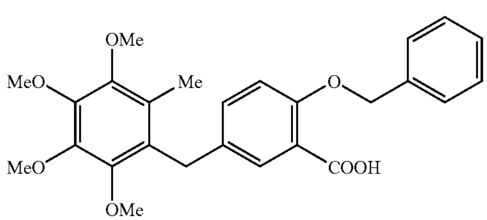 | colorless powder 70.0–71.5° C. | 452(M$^+$) 91(100) |
| 4 | 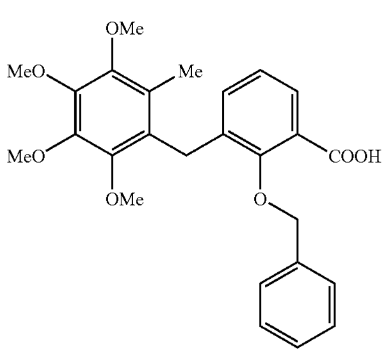 | colorless oil | 452(M$^+$) 91(100) |

TABLE 6-continued

| NMR(CDCl$_3$, δ) | IR (cm$^{-1}$) |
| --- | --- |
| 2.04 (3H,s), 3.67 (3H,s), 3.80 (3H,s), 3.92 (3H, s), 3.96 (3H,s), 4.02 (2H,s), 5.20 (2H,s), 6.84 (1H,s), 6.90 (1H,d,J = 8.1 Hz), 7.20–7.45 (5H, m), 8.06 (1H,d,J = 8.0 Hz) | 3428, 1698, 1609 (KBr) |
| 2.04 (3H,s), 3.65 (3H,s), 3.78 (3H,s), 3.90 (3H, s), 3.95 (3H,s), 4.14 (2H,s), 5.16 (2H,s), 6.40 (1H,d,J = 7.85 Hz), 6.82 (1H,d,J = 8.29 Hz), 7.10–7.50 (6H,m) | 3200, 1732, 1704 (NaCl) |
| 2.07 (3H,s), 3.73 (3H,s), 3.78 (3H,s), 3.92 (3H, s), 3.94 (3H,s), 3.98 (2H,s), 5.24 (2H,s) 7.00 (1H,d,J = 8.60 Hz), 7.23 (1H,d,J = 8.52 Hz), 7.41 (5H,s), 8.03 (1H,s), 10.52–10.87 (1H,br) | 3300, 1736, 1466 (NaCl) |
| 1.98 (3H,s), 3.69 (3H,s), 3.79 (3H,s), 3.93 (3H, s), 3.95 (3H,s), 4.08 (2H,s), 5.14 (2H,s), 6.97 (1H,d,J = 7.52 Hz), 7.09 (1H,t,J = 7.68 Hz), 7.35–7.43 (3H,m), 7.55 (2H,d,J = 7.20 Hz), 7.91 (1H, d,J = 7.64 Hz) | 3064, 1694, 1469 (NaCl) |

TABLE 7

| Ex. No. | Structure | Appearance | FABMS(m/z) |
| --- | --- | --- | --- |
| 5 | 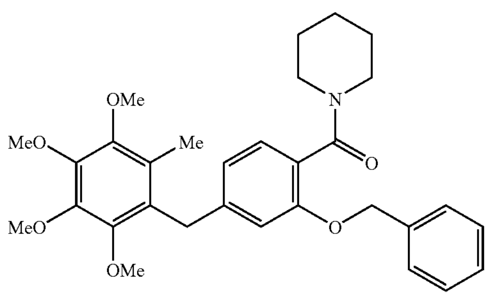 | colorless oil | 520(M$^+$) 91(100) |
| 6 | 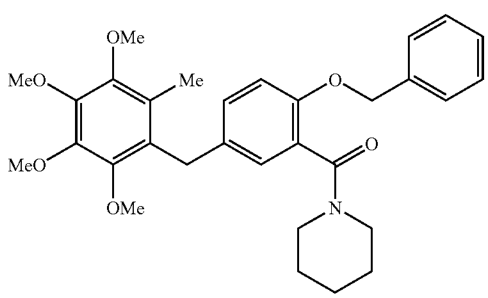 | colorless oil | 520(M$^+$ +1) 91(100) |
| 7 | 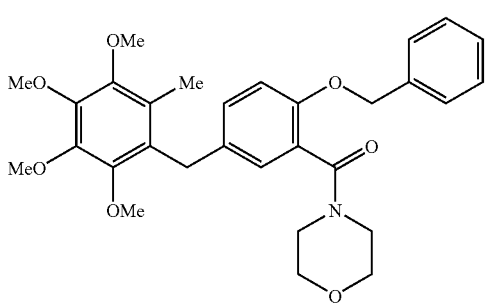 | colorless oil | 522(M$^+$ +1) 91(100) |

TABLE 7-continued
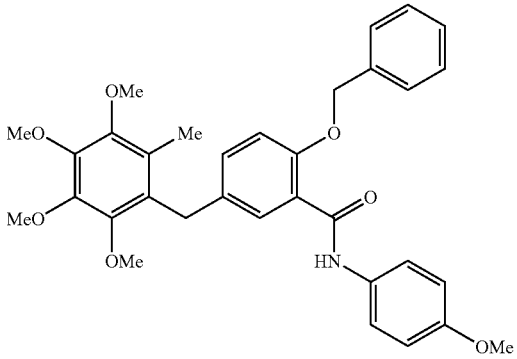
| NMR(CDCl₃, δ) | IR (cm⁻¹) |
|---|---|
| 1.25–1.65 (6H,m), 2.02 (3H,s), 3.10–3.25 (2H, m), 3.60–3.80(2H,m), 3.66 (3H,s), 3.78 (3H, s), 3.91 (3H,s), 3.95 (3H,s), 3.96 (2H,s), 5.01 (2H,q,J = 11.8 and 19.5 Hz), 6.68 (1H,s), 6.72 (1H,d,J = 7.8 Hz), 7.11 (1H,d = 7.7 Hz), 7.20–7.40 (5H,m) | 1609 (CH3Cl) |
| 1.26–1.56 (6H,m), 2.08 (3H,s), 3.70–3.76 (7H, m), 3.77 (3H,s), 3.91 (3H,s), 3.93 (3H,s), 3.94 (2H,s), 5.03 (1H,d 12.08 Hz), 5.08 (1H,d, J = 12.08 Hz), 6.82 (1H,d,J = 9.12 Hz), 7.00–7.02 (2H,m), 7.28–7.38 (5H,m) | 1635, 1471, 1406 (NaCl) |
| 2.07 (3H,s), 3.20–3.26 (2H,m), 3.45–3.47 (2H, m), 3.59–3.82 (4H,m), 3.71 (3H,s), 3.77 (3H,s), 3.91 (3H,s), 3.93 (3H,s), 3.94 (2H,s), 5.04 (2H, s like), 6.84 (1H,d,J = 8.40 Hz), 7.02–7.06 (2H, m), 7.28–7.38 (5H,m) | 1634, 1464, 1406 (NaCl) |
| 2.10 (3H,s), 3.74 (3H,s), 3.77 (3H,s), 3.78 (3H, s), 3.93 (3H,s), 3.94 (3H,s), 4.02 (2H,s), 5.17 (2H,s), 6.75 (2H,d,J = 9.00 Hz), 7.00 (1H,d, J = 8.40 Hz), 7.14–7.25 (5H,m), 7.44–7.50 (4H, m), 8.17–8.18 (1H,br) | 3345, 1663, 1513, 1464, 1239 (KBr) |
TABLE 8
| Ex. No. | Structure | Appearance | FABMS(m/z) |
|---|---|---|---|
| 9 | 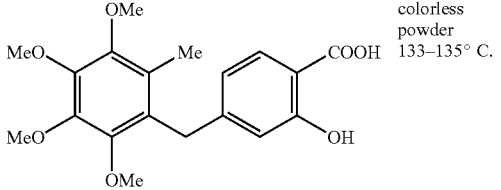 | colorless powder 133–135° C. | 362(M⁺) 154(100) |
| 10 | 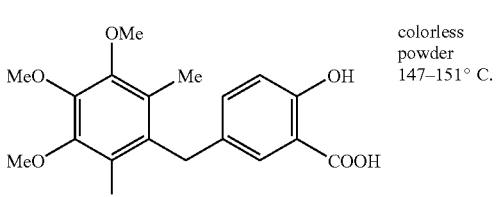 | colorless powder 147–151° C. | 362(M⁺) 154(100) |

TABLE 8-continued

| Ex. No. | Structure | Appearance | FABMS(m/z) |
|---|---|---|---|
| 11 | (MeO, MeO, OMe, OMe, Me)-C6-CH2-C6H3(OH)(COOH) | colorless crystals 87–90° C. | 362(M+, 100) |
| 12 | (MeO, MeO, OMe, OMe, Me)-C6-CH2-C6H3(OAc)(COOH) | colorless powder 83–85° C. | 404(M+, 100) |

| NMR(CDCl$_3$, δ) | IR (cm$^{-1}$) |
|---|---|
| 2.05 (3H,s), 3.70 (3H,s), 3.78 (3H,s), 3.91 (3H,s) 3.93 (3H,s), 3.98 (2H,s), 6.60–6.75 (2H,m), 7.73 (1H,d,J = 8.2 Hz) | 1659, 1622 (KBr) |
| 2.09 (3H,s), 3.73 (3H,s), 3.78 (3H,s), 3.92 (3H,s), 3.94 (5H,s), 6.88 (1H,d,J = 8.60 Hz), 7.24–7.25 (1H,m), 7.65 (1H,s) | 3426, 1672, 1456 (KBr) |
| 2.04 (3H,s), 3.73 (3H,s), 3.81 (3H,s), 3.94 (3H,s), 3.96 (3H,s), 4.01 (2H,s), 6.76 (1H,t,J = 7.72 Hz), 6.90 (1H,d,J = 7.02 Hz), 7.76 (1H,d,J = 7.16 Hz), 10.91 (1H,s) | 3084, 1674, 1468 (NaCl) |
| 2.08 (3H,s), 2.30 (3H,s), 3.69 (3H,s), 3.79 (3H,s), 3.91 (3H,s), 3.94 (3H,s), 4.04 (2H,s), 6.86 (1H,s), 7.07 (1H,d,J = 8.4 Hz), 7.96 (1H,t, J = 8.1 Hz) | 3200, 1772, 1617 (KBr) |

TABLE 9

| Ex. No. | Structure | Appearance | FABMS(m/z) |
|---|---|---|---|
| 13 | (MeO, MeO, OMe, OMe, Me)-C6-CH2-C6H3(OAc)(COOH) | colorless oil | 404(M+, 100) |
| 14 | (MeO, MeO, OMe, OMe, Me)-C6-CH2-C6H3(COOH)(OAc) | colorless oil | 404(M+, 100) |
| 15 | (MeO, MeO, OMe, OMe, Me)-C6-CH2-C6H3(OH)(COOMe) | colorless crystals 74–76° C. | 376(M+ +1, 100) |

TABLE 9-continued

| 16 | ![structure: benzene with OMe, MeO, MeO, OMe, Me substituents linked via CH2 to benzene with OMe and COOH] | colorless oil | 376(M+) 54(100) |

| NMR(CDCl₃, δ) | IR (cm⁻¹) |
|---|---|
| 2.10 (3H,s), 2.30 (3H,s), 3.73 (3H,s), 3.79 (3H, s), 3.92 (3H,s), 3.94 (3H,s), 4.02 (2H,s), 6.99 (1H,d,J = 8.36 Hz), 7.31 (1H,d,J = 8.32 Hz), 7.90 (1H,s) | 3200, 1770, 1716 (NaCl) |
| 2.02 (3H,s), 2.39 (3H,s), 3.67 (3H,s), 3.80 (3H, s), 3.92 (3H,s), 3.93 (3H,s), 3.95 (2H,s), 7.03 (1H,d,J = 7.56 Hz), 7.17 (1H,t,J = 7.72 Hz), 7.93 (1H,d,J = 7.68 Hz), 10.30–11.00 (1H,br,s) | 3150, 1772, 1467 (NaCl) |
| 2.09 (3H,s), 3.71 (3H,s), 3.78 (3H,s), 3.91 (3H, s),3.92 (5H,s), 3.94 (3H,s), 6.86 (1H,d, J = 8.55 Hz), 7.19 (1H,dd,J = 8.51 and 2.11 Hz), 7.59 (1H,d,J = 1.98 Hz), 10.57 (1H,s) | 3426, 1672, 1469(KBr) |
| 2.07 (3H,s), 3.73 (3H,s), 3.78 (3H,s), 3.92 (3H, s), 3.93 (3H,s), 3.98 (2H,s), 4.03 (3H,s), 6.93 (1H,d,J = 8.56 Hz), 7.23 (1H,d,J = 8.60 Hz), 8.01 (1H,s), 10.72 (1H,br s) | 3274, 1733, 1465 (NaCl) |

TABLE 10

| Ex. No. | Structure | Appearance | FABMS(m/z) |
|---|---|---|---|
| 17 | ![structure with OMe, MeO, MeO, OMe, Me substituents, CH2 linker to benzene with O-iPr and COOH] | colorless oil | 404(M+, 100) |
| 18 | ![structure with OMe, MeO, MeO, OMe, Me substituents, CH2 linker to benzene with OPh and COOMe] | colorless oil | 452(M+ +1, 100) |
| 19 | ![structure with OMe, MeO, MeO, OMe, Me substituents, CH2 linker to benzene with O-(3-methoxyphenyl) and COOMe] | colorless oil | 482(M+) 73(100) |

TABLE 10-continued

| 20 | (structure: trimethoxy-methyl-benzyl linked to methoxybenzoate with pyridin-3-ylmethoxy group) | colorless oil | 467(M⁺) 89(100) |

| NMR(CDCl₃, δ) | IR (cm⁻¹) |
|---|---|
| 1.45 (6H,d,J = 6.08 Hz), 2.07 (3H,s), 3.73 (3H, s), 3.78 (3H,s), 3.92 (3H,s), 3.94 (3H,s), 3.98 (2H,s), 4.76–4.80 (1H,m), 6.92 (1H,d,J = 8.60 Hz), 7.22 (1H,d,J = 8.60 Hz), 8.01 (1H,s), 11.23 (1H,br s) | 3244, 1738, 1467 (NaCl) |
| 2.11 (3H,s), 3.74 (3H,s), 3.75 (3H,s), 3.79 (3H, s), 3.92 (3H,s), 3.93 (3H,s), 4.01 (2H,s), 6.87–6.92 (3H,m), 7.02 (1H,t,J = 7.40 Hz), 7.17 (1H, dd,J = 8.44 and 2.08 Hz), 7.26 (2H,t,J = 8.80 Hz), 7.71 (1H,d,J = 2.00 Hz) | 2936, 1735, 1486, 1243 (NaCl) |
| 2.10 (3H,s), 3.73 (3H,s), 3.75 (3H,s), 3.77 (3H, s), 3.79 (3H,s), 3.92 (3H,s), 3.94 (3H,s), 4.00 (2H,s), 6.41–6.50 (2H,m), 6.59 (1H,dd,J = 8.22 and 2.16 Hz), 6.89 (1H,d,J = 8.44 Hz), 7.09–7.19 (2H,m), 7.71 (1H,d,J = 1.96 Hz) | 1712, 1599, 1486, 1147 (NaCl) |
| 2.09 (3H,s), 3.71 (3H,s), 3.78 (3H,s), 3.87 (3H, s), 3.92 (3H,s), 3.94 (3H,s), 3.96 (2H,s), 5.12 (2H,s), 6.90 (1H,d,J = 8.56 Hz), 7.15 (1H,dd, J = 8.56 and 2.00 Hz), 7.28–7.32 (1H,m), 7.64 (1H,d,J = 2.04 Hz), 7.86 (1H,d,J = 7.80 Hz), 8.55 (1H,d,J = 4.32 Hz), 8.69 (1H, br s) | 1727, 1465, 1406, 1259 (NaCl) |

TABLE 11

| Ex. No. | Structure | Appearance | FABMS(m/z) |
|---|---|---|---|
| 21 | (structure: trimethoxy-methyl-benzyl linked to methoxybenzoate with pyridin-4-ylmethoxy group) | colorless oil | 468(M⁺ +1) 179(100) |
| 22 | (structure: trimethoxy-methyl-benzyl linked to methoxybenzoate with tert-butoxycarbonylmethoxy group) | colorless oil | 490(M⁺) 54(100) |

TABLE 11-continued

| Ex. No. | Structure | Appearance | FABMS(m/z) |
|---|---|---|---|
| 23 | (3,4,5-trimethoxy-2-methoxy-6-methylbenzyl linked to 2-phenoxybenzoic acid) | colorless oil | 438(M$^+$ +1, 100) |
| 24 | (3,4,5-trimethoxy-2-methoxy-6-methylbenzyl linked to 2-(3-methoxyphenoxy)benzoic acid) | colorless oil | 468(M$^+$) 69(100) |

| NMR(CDCl$_3$, δ) | IR (cm$^{-1}$) |
|---|---|
| 2.09 (3H,s), 3.72 (3H,s), 3.78 (3H,s), 3.89 (3H, s), 3.92 (3H,s), 3.93 (3H,s), 3.96 (2H,s), 5.10 (2H,s), 6.84 (1H,d,J = 8.56 Hz), 7.15 (1H,dd, J = 8.48 and 2.00 Hz), 7.42 (2H,d,J = 5.48 Hz), 7.67 (1H,d,J = 1.96 Hz), 8.59 (2H,d,J = 5.72 Hz) | 1727, 1467, 1406, 1260 (NaCl) |
| 1.35 (9H,s), 1.98 (3H,s), 3.60 (3H,s), 3.67 (3H, s), 3.77 (3H,s), 3.81 (3H,s), 3.83 (3H,s), 3.85 (2H,s), 4.45 (2H,s), 6.65 (1H,d,J = 8.56 Hz), 7.03 (1H,dd,J = 8.48 and 1.40 Hz), 7.51 (1H,d like) | 1732, 1467, 1155 (NaCl) |
| 2.08 (3H,s), 3.74 (3H,s), 3.78 (3H,s), 3.91 (3H, s), 3.93 (3H,s), 4.00 (2H,s), 6.73 (1H,d,J = 8.56 Hz), 7.05 (2H,d,J = 7.88 Hz), 7.15 (1H,dd, J= 8.60 and 2.20 Hz), 7.19 (1H,t,J = 7.40 Hz), 7.37 (2H,t,J = 7.88 Hz), 7.98 (1H,d,J = 1.96 Hz) | 3300, 1698, 1486, 1241 (NaCl) |
| 2.07 (3H,s), 3.71 (3H,s), 3.72 (3H,s), 3.77 (3H, s), 3.90 (3H,s), 3.92 (3H,s), 3.97 (2H,s), 6.54–6.57 (2H,m), 6.44 (1H,d,J = 8.52 Hz), 6.74 (1H, d,J = 8.48 Hz), 7.09 (1H,d,J = 8.24 Hz), 7.16 (1H, t,J = 8.12 Hz), 7.89 (1H,d like) | 3450, 1698, 1605, 14586 1140 (NaCl) |

TABLE 12

| Ex. No. | Structure | Appearance | FABMS(m/z) |
|---|---|---|---|
| 25 | (3,4,5-trimethoxy-2-methoxy-6-methylbenzyl linked to 2-(pyridin-3-ylmethoxy)benzoic acid) | colorless crystals 129–132° C. | 453(M$^+$) 90(100) |

TABLE 12-continued

| # | Structure | Appearance / mp | MS |
|---|---|---|---|
| 26 | (3,4,5-trimethoxy-6-methylbenzyl group; 2-(pyridin-4-ylmethoxy)benzoic acid) | colorless crystals 174–176° C. | 454(M⁺ +1) 179(100) |
| 27 | (3,4,5-trimethoxy-6-methylbenzyl; 2-hydroxy-5-position; piperidinyl amide) | colorless crystals 184–188° C. | 430(M⁺ +1) 69(100) |
| 28 | (3,4,5-trimethoxy-6-methylbenzyl; 2-hydroxy; morpholinyl amide) | colorless crystals 185–188° C. | 432(M⁺ +1) 154(100) |

| NMR(CDCl$_3$, δ) | IR (cm$^{-1}$) |
|---|---|
| 2.08 (3H,s), 3.72 (3H,s), 3.78 (3H,s), 3.92 (3H, s), 3.94 (3H,s), 3.99 (2H,s), 5.23 (2H,s), 6.96 (1H,d,J = 8.48 Hz), 7.19 (1H,d,J = 7.80 Hz), 7.30–7.39 (1H,m), 7.77 (1H,d,J = 7.64 Hz), 7.95 (1H, br s), 8.60–8.75 (1H,br), 8.90–9.00 (1H,br) | 3475, 1700, 1467, 1251 (KBr) |
| 2.07 (3H,s), 3.73 (3H,s), 3.78 (3H,s), 3.91 (3H, 3.93 (3H,s), 3.98 (2H,s), 5.26 (2H,s), 6.87 (1H,d,J = 8.56 Hz), 7.19 (1H,d,J = 8.44 Hz), 7.39 (2H,d,J = 5.24 Hz), 7.98 (1H,br s), 8.66 (2H,d, J = 5.56 Hz) | 3427, 1691, 1468, 1257 (NaCl) |
| 1.53–1.56 (4H,m), 1.62–1.65 (2H,m), 2.07 (3H, s), 3.52–3.54 (4H,m), 3.70 (3H,s), 3.78 (3H,s), 3.90 (3H,s). 3.92 (5H,s like), 6.85 (1H,s), 6.90 (1H,d,J = 8.40 Hz), 7.15 (1H,d,J = 8.36 Hz), 9.49 (1H,br s) | 3430, 1558, 1469, 1408 (KBr) |
| 2.07 (3H,s), 3.64 (8H,m), 3.72 (3H,s), 3.78 (3H, s), 3.91 (2H,s), 3.92 (3H,s), 3.93 (3H,s), 6.86 (1H,s), 6.91 (1H,d,J = 8.44 Hz), 7.15 (1H,dd, J = 8.36 and 2.12 Hz), 9.31 (1H,br s) | 3448, 1570, 1466 (KBr) |

TABLE 13
| Ex. No. | Structure | Appearance | FABMS(m/z) |
|---|---|---|---|
| 29 | 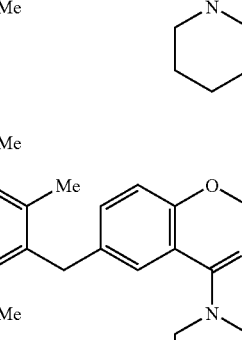 | colorless oil | 522(M⁺ +1, 100) |
| 30 | 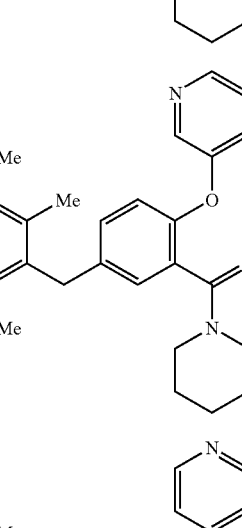 | colorless oil | 521(M⁺ +1) 69(100) |
| 31 | 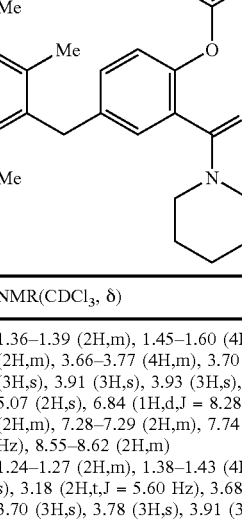 | colorless oil | 507(M⁺,100) |
| 32 | 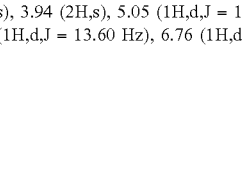 | colorless oil | 507(M⁺) 69(100) |
| NMR(CDCl$_3$, δ) | IR (cm$^{-1}$) |
|---|---|
| 1.36–1.39 (2H,m), 1.45–1.60 (4H,m), 3.14–3.17 (2H,m), 3.66–3.77 (4H,m), 3.70 (3H,s), 3.78 (3H,s), 3.91 (3H,s), 3.93 (3H,s), 3.95 (2H,s), 5.07 (2H,s), 6.84 (1H,d,J = 8.28 Hz), 7.01–7.04 (2H,m), 7.28–7.29 (2H,m), 7.74 (1H,d,J = 7.88 Hz), 8.55–8.62 (2H,m) | 2936, 1624, 1472, 1405 (NaCl) |
| 1.24–1.27 (2H,m), 1.38–1.43 (4H,m), 2.07 (3H, s), 3.18 (2H,t,J = 5.60 Hz), 3.68–3.89 (2H,m), 3.70 (3H,s), 3.78 (3H,s), 3.91 (3H,s), 3.93 (3H, s), 3.94 (2H,s), 5.05 (1H,d,J = 13.56 Hz), 5.10 (1H,d,J = 13.60 Hz), 6.76 (1H,d,J = 9.16 Hz), | 2937, 1624, 1467 (NaCl) |

TABLE 13-continued

| | | |
|---|---|---|
| 7.00–7.02 (2H,m), 7.31 (2H,d,J = 5.56 Hz), 8.58 (2H,d,J = 5.44 Hz) | | |
| 1.55–1.63 (6H,m), 2.09 (3H,s), 3.22–3.26 (2H, m), 3.59–3.63 (2H,m), 3.73 (3H,s), 3.79 (3H,s), 3.92 (3H,s), 3.94 (3H,s), 3.99 (2H,s), 6.81 (1H, d,J = 8.40 Hz), 7.08 (1H,d,J = 8.40 Hz), 7.12 (1H, s), 7.20–7.28 (2H,m), 8.32 (1H,d,J = 3.96 Hz), 8.38 (1H,d,J = 2.36 Hz) | 2936, 1630, 1468 (NaCl) | |
| 1.43–1.62 (6H,m), 2.10 (3H,s), 3.20–3.21 (2H, m), 3.55–3.57 (2H,m), 3.74 (3H,s), 3.80 (3H,s), 3.92 (3H,s), 3.94 (3H,s), 4.02 (2H,s), 6.82 (2H, d,J = 5.72 Hz), 6.94 (1H,d,J = 6.04 Hz), 7.14–7.16 (2H,m), 8.43 (2H,d,J = 5.56 Hz) | 2935, 1631, 1467 (NaCl) | |

15

TABLE 14

| Ex. No. | Structure | Appearance | FABMS (m/z) | NMR(CDCl$_3$, δ) | IR (cm$^{-1}$) |
|---|---|---|---|---|---|
| 33 | 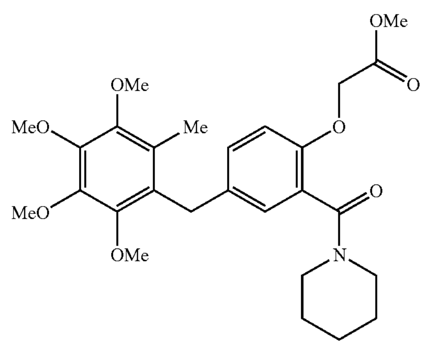 | colorless oil | 502 (M$^+$ + 1) 54(100) | 1.26–1.63(6H, m), 2.07(3H, s), 3.18–3.26(2H, m), 3.29–3.75(2H, m), 3.70(3H, s), 3.75(3H, s), 3.77(3H, s), 3.91(3H, s), 3.93(5H, s), 4.61–4.62 (2H, m), 6.65(1H, d, J=9.00 Hz), 7.00–7.02(2H, m) | 1760, 1626, 1468, 1207 (NaCl) |
| 34 | 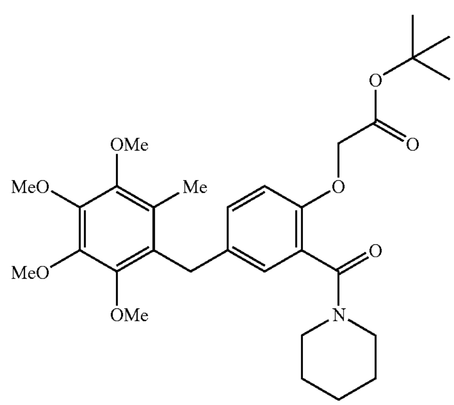 | colorless oil | 544 (M$^+$ + 1) 54(100) | 1.38–1.63(6H, m), 1.46(9H, s), 2.07(3H, s), 3.17–3.29(2H, m), 3.61–3.81(2H, m), 3.69(3H, s), 3.77(3H, s), 3.91(3H, s), 3.93(5H, s), 4.44 (1H, d, J=16.24 Hz), 5.01(1H, d, J=16.08 Hz), 6.62(1H, d, J=8.80 Hz), 6.99–7.01(2H, m) | 1751, 1628, 1468, 1156 (NaCl) |
| 35 | 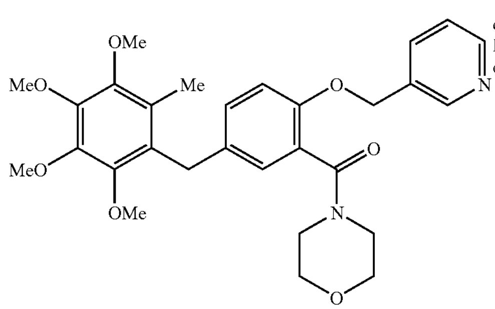 | colorless oil | 522 (M$^+$) 431 (100) | 2.07(3H, s), 3.21–3.23(2H, m), 3.46–3.49(2H, m), 3.60–3.75(4H, m), 3.71(3H, s), 3.78(3H, s), 3.91(3H, s), 3.93(3H, s), 3.95(2H, s), 5.07(2H, s), 6.86(1H, d, J=9.12 Hz), 7.05–7.07(2H, m), 7.29–7.30(1H, m), 7.73(1H, d, J=7.80 Hz), 8.56 (1H, d, J=4.44 Hz), 8.62(1H, s) | 2934, 1636, 1465 (NaCl) |

TABLE 14-continued

| Ex. No. | Structure | Appearance | FABMS (m/z) | NMR(CDCl₃, δ) | IR (cm⁻¹) |
|---|---|---|---|---|---|
| 36 | 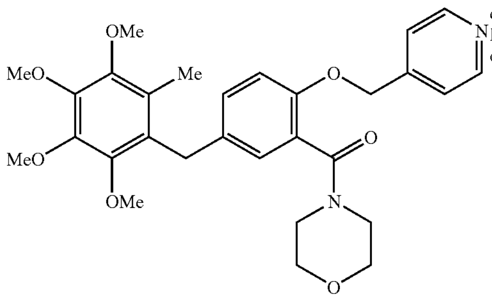 | colorless oil | 523 (M⁺ + 1) 93(100) | 2.07(3H, s), 3.24–3.29(2H, m), 3.51–3.54(2H, m), 3.71–3.82(4H, m), 3.71(3H, s), 3.78(3H, s), 3.92(3H, s), 3.93(3H, s), 3.95(2H, s), 5.08–5.09 (2H, m), 6.78(1H, d, J=8.36 Hz), 7.04–7.06(2H, m), 7.30(2H, d, J=5.52 Hz), 8.59 (2H, d, J=5.60 Hz) | 2935, 1645, 1484 (NaCl) |

TABLE 15

| Ex. No. | Structure | Appearance | FABMS (m/z) | NMR(CDCl₃, δ) | IR (cm⁻¹) |
|---|---|---|---|---|---|
| 37 | 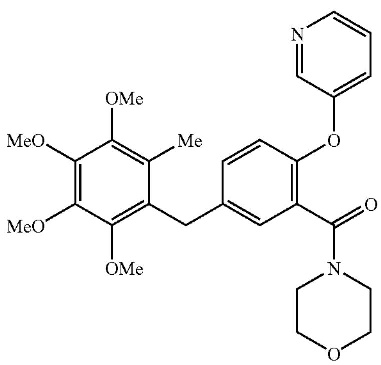 | colorless oil | 509 (M⁺ + 1) 73 (100) | 2.02(3H, s), 3.25–3.28(2H, m), 3.53–3.72(6H, m), 3.67(3H, s), 3.72(3H, s), 3.84(3H, s). 3.86 (3H, s), 3.92(2H, s), 6.74(1H, d, J=8.40 Hz), 7.02(1H, d, J=8.42 Hz), 7.08(1H, s), 7.16–7.19 (2H, m), 8.27(1H, d like), 8.29(1H, d like) | 2933, 1631, 1468 (NaCl) |
| 38 | 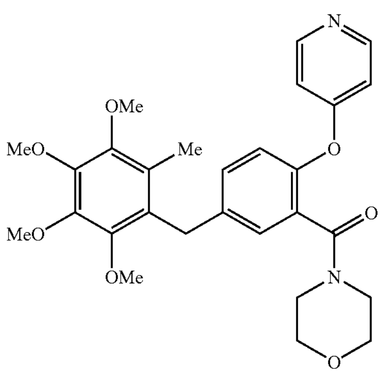 | colorless oil | 509 (M⁺ + 1) 52 (100) | 2.10(3H, s), 3.29–3.31(2H, m), 3.59–3.70(6H, m), 3.75(3H, s), 3.80(3H, s), 3.93(3H, s), 3.94 (3H, s), 4.02(2H, s), 6.81(2H, d, J=6.12 Hz), 6.96(1H, d, J=8.24 Hz), 7.17–7.20(2H, m), 8.44 (2H, d, J=5.64 Hz) | 2931, 1631, 1467 (NaCl) |
| 39 | 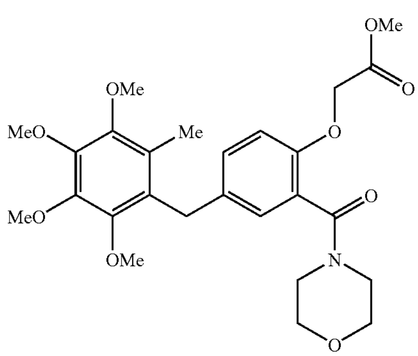 | colorless oil | 504 (M⁺ + 1, 100) | 2.07(3H, s), 3.23–3.76(8H, m), 3.71(3H, s), 3.76 (3H, s), 3.78(3H, s), 3.91(3H, s), 3.93(5H, s), 4.64(2H, s), 6.63(1H, d, J=8.52 Hz), 7.05(1H, d like), 7.30(1H, s) | 1758, 1632, 1466, 1209 (NaCl) |

TABLE 15-continued

| Ex. No. | Structure | Appearance | FABMS (m/z) | NMR(CDCl$_3$, δ) | IR (cm$^{-1}$) |
|---|---|---|---|---|---|
| 40 | 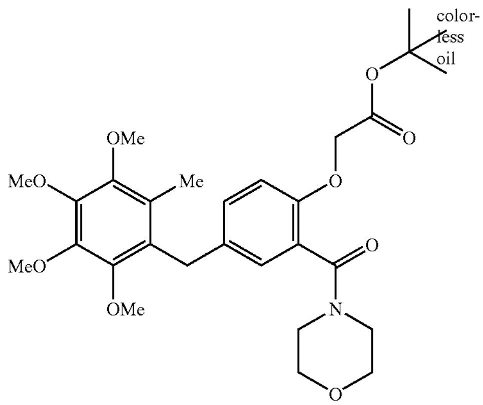 | colorless oil | 545(M$^+$) 54 (100) | 1.46(9H, s), 2.07(3H, s), 3.20–3.78(8H, m), 3.70 (3H, s), 3.78(3H, s), 3.91(3H, s), 3.93(5H, s), 4.50–4.51(2H, m), 6.61(1H, d, J=8.52 Hz), 7.01–7.07(2H, m) | 1749, 1633, 1467, 1222 (NaCl) |

TABLE 16

| Ex. No. | Structure | Appearance | FABMS (m/z) | NMR(CDCl$_3$, δ) | IR (cm$^{-1}$) |
|---|---|---|---|---|---|
| 41 | 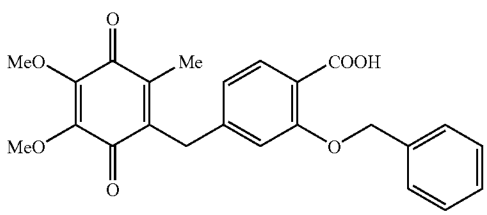 | yellow powder 139–140° C. | 423 (M$^+$ + 1) 154 (100) | 2.03(3H, s), 3.85(2H, s), 4.00(3H, s), 4.01(3H, s), 5.27(2H, s), 6.90–7.00(2H, m), 7.30–7.50 (5H, m), 8.08(1H, d, J=8.2) | 3450, 1703, 1644, 1605 (KBr) |
| 42 | 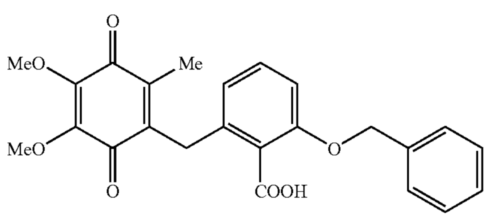 | yellow powder 129–130° C. | 423 (M$^+$ + 1) 154 (100) | 2.01(3H, s), 3.96(3H, s), 4.01(3H, s), 4.03(2H, s), 5.17(2H, s), 6.59(1H, d, J=7.8 Hz), 6.88(1H, d, J=8.3 Hz), 7.20–7.50(6H, m) | 3436, 1648, 1610 (KBr) |
| 43 | 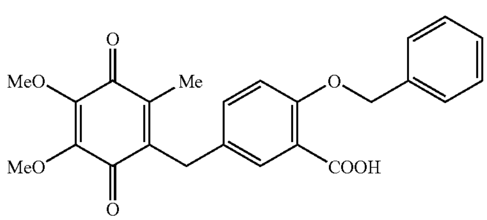 | yellow crystals 93.0–94.0° C. | 423 (M$^+$ + 1) 154 (100) | 2.09(3H, s), 3.83(2H, s), 3.99(3H, s), 4.00(3H, s), 5.26(2H, s), 7.04(1H, d, J=8.00 Hz), 7.36–7.39(1H, m), 7.39–7.42(5H, m), 7.97(1H, d, J=2.40 Hz) | 3448, 1736, 1654, 1612 (KBr) |
| 44 | 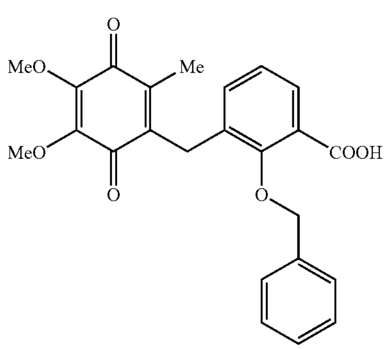 | yellow crystals 154–156° C. | 423 (M$^+$ + 1) 91 (100) | 1.92(3H, s), 3.91(2H, s), 3.97(3H, s), 4.00(3H, s), 5.13(2H, s), 7.13–7.17(2H, m), 7.35–7.49 (5H, m), 7.92–7.93(1H, m) | 3206, 1723, 1647, 1619 (KBr) |

TABLE 17

| Ex. No. | Structure | Appearance | FABHS(m/z) | NMR(CDCl$_3$, δ) | IR(cm$^{-1}$) |
|---|---|---|---|---|---|
| 45 | (structure) | yellow crystals 80–81° C. | 375(M$^+$ + 1) 154(100) | 20.9(3H, s), 2.32(3H, s), 3.89(2H, s), 4.00(6H, s), 6.94(1H, s), 7.16(1H, d, J=8.1 Hz), 8.00(1H, d, J=8.1 Hz) | 3100, 1145, 1690, 1667, 1609(KBr) |
| 46 | (structure) | red crystals 108–110° C. | 375(M$^+$ + 1) 154(100) | 2.12(3H, s), 2.32(3H, s), 3.88(2H, s), 4.00(6H, s), 7.03(1H, d, J=8.28 Hz), 7.44(1H, dd, J=8.32 and 2.16 Hz), 7.91(1H, d, J=2.08 Hz) | 3428, 1772, 1687, 1612 (KBr) |
| 47 | (structure) | red crystals 83–85° C. | 375(M$^+$ + 1) 154(100) | 1.97(3H, s), 2.32(3H, s), 3.80(2H, s), 3.99(3H, s), 4.00(3H, s), 7.21–7.32(2H, m), 7.93(1H, d, J=7.56 Hz), 9.30–9.80(1H, br) | 3400, 1767, 1654, 1612 (KBr) |
| 48 | (structure) | yellow powder 157–158° C. | 333(M$^+$ + 1) 154(100) | 2.02(3H, s), 3.81(2H, s), 3.96(3H, s), 3.97(3H, s), 6.55–6.70(2H, s), 7.74(1H, d, J=8.0 Hz) | 3464, 1646 (KBr) |

TABLE 18

| Ex. No. | Structure | Appearance | FABMS (m/z) | NMR(CDCl$_3$, δ) | IR (cm$^{-1}$) |
|---|---|---|---|---|---|
| 49 | (structure) | yellow crystals 206–207° C. | 333 (M$^+$ + 1) 154(100) | 2.06(3H, s), 3.78(2H, s), 3.95(3H, s), 3.96(3H, s), 6.76(1H, d, J=8.48 Hz), 7.20(1H, dd, J=8.44 and 2.00 Hz), 7.63(1H, d, J=1.76 Hz) (in CD30OD) | 3402, 1652, 1611 (KBr) |
| 50 | (structure) | yellow crystals 109–11.5° C. | 333 (M$^+$ + 1) 154(100) | 1.99(3H, s), 3.82(2H, s), 4.00(3H, s), 4.01(3H, s), 723–7.27(1H, m), 7.34–7.36(1H, m), 7.98 (1H, d, J=7.64 Hz) | 3450, 1653, 1614 (KBr) |
| 51 | (structure) | yellow crystals 127–129° C. | 347 (M$^+$ + 1) 154(100) | 2.09(3H, s), 3.83(2H, s), 3.98(3H, s), 3.99(3H, s), 4.05(3H, s), 6.97(1H, d, J=8.60 Hz), 7.41 (1H, dd, J=8.52 and 2.40 Hz), 7.95(1H, d, J=2.32 Hz), 10.40–11.20(1H, br) | 3446, 1699, 1650, 1605 (KBr) |

TABLE 18-continued

| Ex. No. | Structure | Appearance | FABMS (m/z) | NMR(CDCl$_3$, δ) | IR (cm$^{-1}$) |
|---|---|---|---|---|---|
| 52 | (structure) | yellow oil | 375 (M$^+$ + 1) 154(100) | 1.46(6H, d, J=6.12 Hz), 2.09(3H, s), 3.82(2H, s), 3.99(6H, s), 4.79–4.85(1H, m), 6.96(1H, d, J=8.64 Hz), 7.38(1H, dd, J=8.48 and 2.36 Hz), 7.96(1H, d, J=2.36 Hz), 11.16(1H, brs) | 3246, 1736, 1648, 1611 (NaCl) |

TABLE 19

| Ex. No. | Structure | Appearance | FABMS (m/z) | NMR(CDCl$_3$, δ) | IR (cm$^{-1}$) |
|---|---|---|---|---|---|
| 53 | (structure) | yellow crystals 102–105° C. | 409 (M$^+$ + 1) 154 (100) | 2.09(3H, s), 3.83(2H, s), 3.98(3H, s), 3.99(3H, s), 6.77(1H, d, J=8.56 Hz), 7.04(2H, d, J=7.88 Hz), 7.19(2H, t, J=7.36 Hz), 7.28(1H, d, J=8.56 Hz), 7.37(2H, t, J=7.60 Hz), 7.92(1H, brs) | 3415, 1652, 1613, 1487 (KBr) |
| 54 | (structure) | yellow crystals 142–144° C. | 439 (M$^+$ + 1) 154 (100) | 2.10(3H, s), 3.80(3H, s), 3.84(2H, s), 3.98(3H, s), 3.99(3H, s), 6.63–6.66(2H, m), 6.78–6.81 (2H, m), 7.25–7.32(2H, m), 7.95–7.98(1H, m) | 3428, 1706, 1649, 1608, 1490 (KBr) |
| 55 | (structure) | yellow crystals 187–190° C. | 424 (M$^+$ + 1) 154 (100) | 2.11(3H, s), 3.84(2H, s), 3.99 6H, s), 5.26(2H, s), 7.02(1H, d, J=8.56 Hz), 7.38–7.44(2H, m), 7.78(1H, d, J=7.96 Hz), 7.94(1H, d, J=2.24 Hz), 8.77(1H, d, J=4.32 Hz), 8.98(1H, brs) | 3430, 1648, 1612 (KBr) |
| 56 | (structure) | yellow crystals 178–181° C. | 424 (M$^+$ + 1) 154 (100) | 1.98(3H, s), 3.77(2H, s), 3.88(3H, s), 3.89(3H, s), 5.35(2H, s), 7.07(1H, d, J=8.60 Hz), 7.30 (1H, d, J=8.40 Hz), 7.53(1H, d, J=1.56 Hz), 7.77–7.78(2H, d like), 8.74–8.75(2H, d like) | 3414, 1718, 1658, 1612 (KBr) |

TABLE 20

| Ex. No. | Structure | Appearance | FABMS (m/z) | NMR(CDCl$_3$, δ) | IR (cm$^{-1}$) |
|---|---|---|---|---|---|
| 57 | 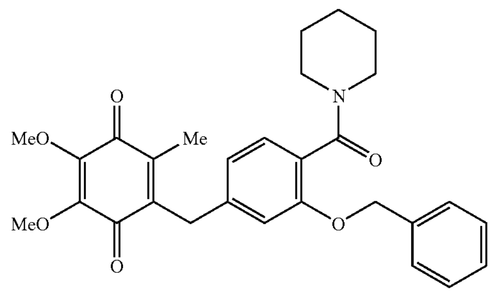 | yellow oil | 490 (M$^+$ + 1) 154 (100) | 1.20–1.90(6H, m), 1.99(3H, s), 3.05–3.30(2H, m), 3.60–3.85(2H, m), 3.79(2H, s), 3.99(3H, s), 4.00(3H, s), 5.00–5.15(2H, m), 6.73(1H, s), 6.78(1H, d, J=7.7 Hz), 7.13(1H, d, J=7.7 Hz), 7.20–7.45(5H, m) | 1608 (NaCl) |
| 58 | 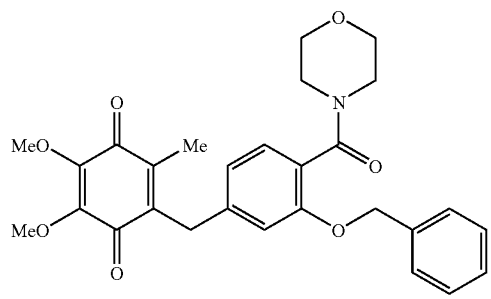 | yellow powder 58–60° C. | 492 (M$^+$ + 1) 154 (100) | 2.01(3H, s), 3.10–3.35(2H, m), 3.40–3.55(2H, m), 3.55–3.90(4H, m), 3.80(2H, s), 3.99(3H, s), 4.00(3H, s), 5.07(2H, s), 6.77(1H, s), 6.80(1H, d, J=7.7 Hz), 7.17(1H, d, J=7.7 Hz), 7.20–7.45(5H, m) | 1644, 1609 (KBr) |
| 59 | 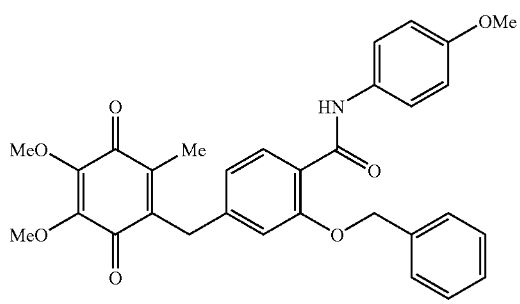 | yellow powder 149–150° C. | 528 (M$^+$ + 1) 154 (100) | 2.09(3H, s), 3.76(3H, s), 3.89(2H, s), 4.01(6H, s), 5.20(2H, s), 6.75(2H, d, J=8.9 Hz), 6.93(1H, d, J=8.1 Hz), 6.98(1H, s). 7.19(2H, d), 7.35–7.55(5H, m), 8.21(1H, d, J=8.0 Hz), 9.78(1H, s) | 1654, 1608 (KBr) |
| 60 | 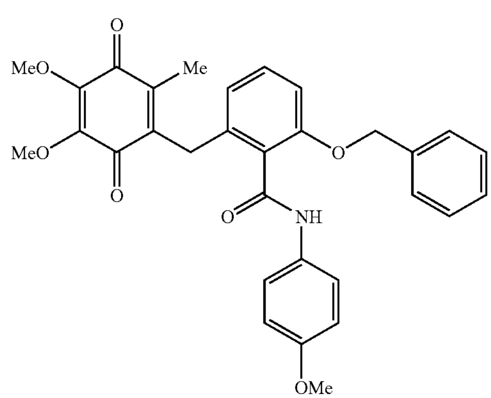 | yellow powder 129–130° C. | 528 (M$^+$ + 1) 154 (100) | 2.09(3H, s), 3.82(3H, s), 3.95(3H, s), 3.96(2H, s), 3.99(3H, s), 5.13(2H, s), 6.58(1H, d), 6.80–6.95(3H, m), 7.19(1H, t), 7.20–7.45(5H, m), 7.51(2H, d), 8.18(1H, s) | 1643, 1611 (KBr) |

TABLE 21

| Ex. No. | Structure | Appearance | FABMS (m/z) | NMR(CDCl$_3$, δ) | IR (cm$^{-1}$) |
|---|---|---|---|---|---|
| 61 | 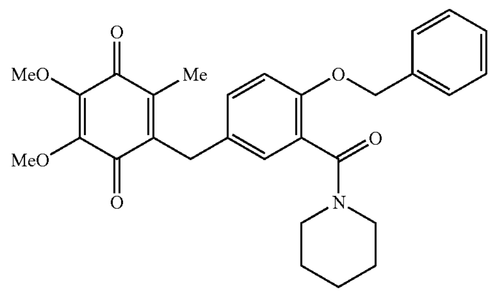 | red-yellow oil | 490 (M$^+$ + 1) 154 (100) | 1.38–1.90(6H, m), 2.06(3H, s), 3.11–3.21(2H, m), 3.56–3.84(4H, m), 3.98(3H, s), 3.99(3H, s), 5.04(1H, d, 12.04 Hz), 5.09(1H, d, J=12.12 Hz), 6.82(1H, d, J=8.52 Hz), 7.03(1H, d, J=2.12 Hz), 7.11(1H, dd, J=8.48 and 2.12 Hz), 7.27–7.38(5H, m) | 1644, 1614, 1456 (NaCl) |
| 62 | 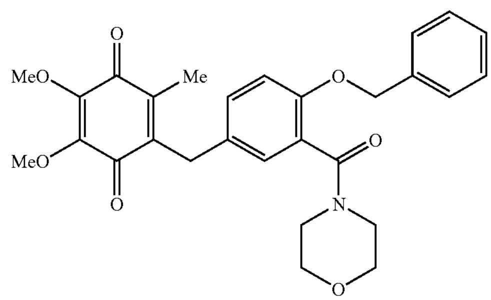 | red-yellow oil | 492 (M$^+$ + 1) 91 (100) | 1.99(3H, s), 3.12–3.18(2H, m), 3.40–3.42(2H, m), 3.53–3.75(6H, m), 3.91(3H, s), 3.92(3H, s), 4.98(2H, s), 6.79(1H, d, J=8.48 Hz), 7.00 (1H, d, J=2.20 Hz), 7.08(1H, dd, J=8.52 and 2.16 Hz), 7.24–7.29(5H, m) | 1640, 1612, 1440 (NaCl) |
| 63 | 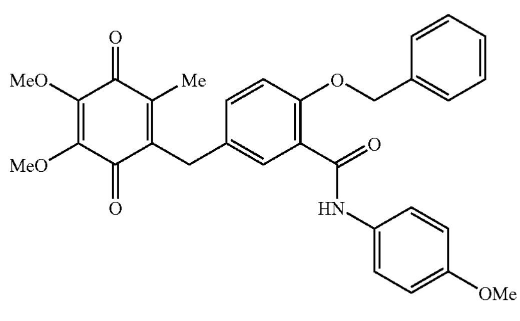 | yellow crystals 113–115° C. | 528 (M$^+$ + 1) 154 (100) | 2.11(3H, s), 3.76(3H, s), 3.85(2H, s), 3.98(3H, s), 3.99(3H, s), 5.17–5.18(2H, m), 6.74(2H, d, J=9.04 Hz), 7.03(1H, d, J=8.52 Hz), 7.18(2H, d, J=9.04 Hz), 7.33(1H, d, J=8.44 Hz), 7.44–7.50(5H m), 8.11(1H, s), 9.84(1H, brs) | 3356, 1664, 1611, 1512 (KBr) |
| 64 | 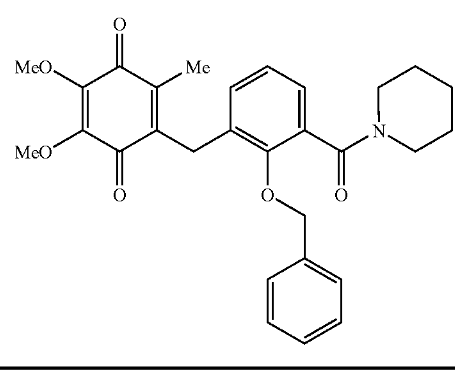 | yellow oil | 490 (M$^+$ + 1) 154 (100) | 1.38–1.62(6H, m), 1.90(3H, s), 3.14–3.19(2H, m), 3.57–3.78(2H, m), 3.79–3.90(2H, m), 3.97 (3H, s), 3.99(3H, s), 4.98(1H, d, 11.00 Hz), 5.09(1H, d, J=11.04 Hz), 6.94(1H, d, J=7.16 Hz), 7.05(1H, t, J=7.60 Hz), 7.17(1H, d, J=7.20 Hz), 7.32–7.43(5H, m) | 1628, 1610, 1436, 1267 (NaCl) |

TABLE 22

| Ex. No. | Structure | Appearance | FABMS (m/z) | NMR(CDCl₃, δ) | IR (cm⁻¹) |
|---|---|---|---|---|---|
| 65 | 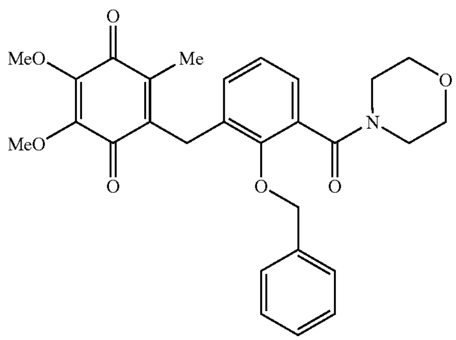 | yellow oil | 492 (M⁺ + 1) 91 (100) | 1.92(3H, s), 3.16–3.22(2H, m), 3.48–3.85 (6H, m), 3.78–3.95(2H, m), 3.98(3H, s), 4.00(3H, s), 5.03(2H, s), 6.96(1H, d, J=7.48 Hz), 7.08(1H, t, J=7.64 Hz), 7.20(1H, d, J=7.40 Hz), 7.34–7.43(5H, m) | 1634, 1611, 1434 (NaCl) |
| 66 | 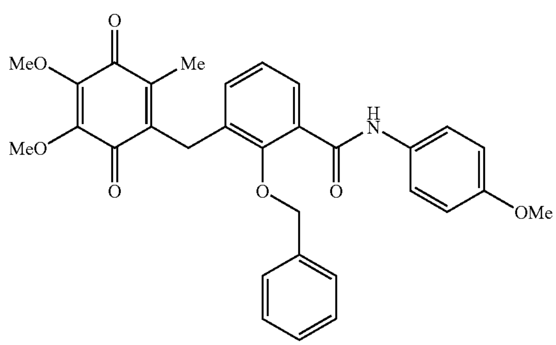 | yellow crystals 138.5–140° C. | 528 (M⁺ + 1) 154 (100) | 1.93(3H, s), 3.72(3H, s), 3.89(2H, s), 3.92 (3H, s), 3.95(3H, s), 5.01(2H, s), 6.75(2H, d, J=8.92 Hz), 6.98(1H, d, J=7.40 Hz), 7.11(1H, d, J=7.69 Hz), 7.29–7.35(7H, m), 7.94(1H, d, J=7.28 Hz), 9.38(1H, brs) | 3286, 1649, 1611, 1516 (KBr) |
| 67 | 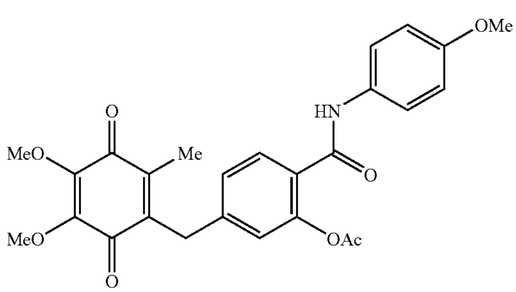 | yellow crystals 147–148° C. | 480 (M⁺ + 1) 154 (100) | 2.10(3H, s), 2.33(3H, s), 3.82(3H, s), 3.88 (2H, s), 4.00(6H, s), 6.88(2H, d), 6.97 (1H, s), 7.17(1H, d), 7.47(2H, d), 7.76 (1H, d), 8.86(1H, s) | 1767, 1654, 1611 (KBr) |
| 68 | 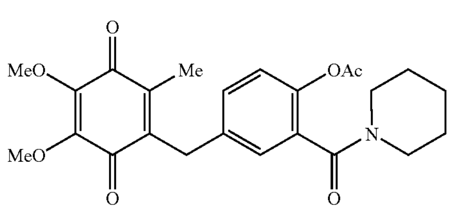 | red oil | 442 (M⁺ + 1) 154 (100) | 1.24–1.87(6H, m), 2.07(3H, s), 2.25(3H, s), 3.18–3.20(2H, m), 3.56–3.98(4H, m), 3.99(3H, s), 4.00(3H, s)6.84–7.10(2H, m), 7.21(1H, d, J=8.00 Hz) | 1766, 1650, 1614 (NaCl) |

TABLE 23

| Ex. No. | Structure | Appearance | FABMS (m/z) | NMR(CDCl$_3$, δ) | IR (cm$^{-1}$) |
|---|---|---|---|---|---|
| 69 | (structure) | red oil | 444 (M$^+$ + 1) 154 (100) | 2.09(3H, s), 2.67(3H, s), 3.20–3.30(2H, m), 3.56–3.84(8H, m), 3.99(3H, s), 4.00 (3H, s), 7.05(1H, d, J=8.40 Hz), 7.11(1H, d, J=1.84 Hz), 7.24(1H, dd, J=8.34 and 1.88 Hz) | 1766, 1644, 1612 (NaCl) |
| 70 | (structure) | yellow crystals 170–171.5° C. | 480 (M$^+$ + 1) 154 (100) | 2.10(3H, s), 2.31(3H, s), 3.80(3H, s), 3.86(2H, s), 3.99(6H, s), 6.89(2H, d, J= 8.80 Hz), 7.05(1H, d, J=8.40 Hz), 7.32 (1H, dd, J=8.24 and 1.72 Hz), 7.48(2H, d, J=8.80 Hz), 7.64(1H, s), 7.96(1H, brs) | 3496, 1766, 1644, 1612 (KBr) |
| 71 | (structure) | yellow oil | 442 (M$^+$ + 1) 136 (100) | 1.50–1.63(6H, m), 1.97(3H, s), 2.28(3H, s), 3.15–3.25(2H, m), 3.60–3.70(2H, m), 3.76(2H, s), 4.00(3H, s), 4.01(3H, s), 7.06–7.18(3H, m) | 1766, 1636, 1610 (NaCl) |
| 72 | (structure) | yellow oil | 444 (M$^+$ + 1) 154 (100) | 1.98(3H, s), 2.29(3H, s), 3.31–3.39(2H, m), 3.59–3.83(6H, m), 3.77(2H, S), 3.99(3H, s), 4.00(3H, s), 7.09–7.19(3H, m) | 1766, 1644, 1613 (NaCl) |

TABLE 24

| Ex. No. | Structure | Appearance | FABMS (m/z) | NMR(CDCl$_3$, δ) | IR (cm$^{-1}$) |
|---|---|---|---|---|---|
| 73 | (structure) | red crystals 73–74° C. | 479 (M$^+$ + 1) 154 (100) | 1.98(3H, s), 2.29(3H, s), 3.78(2H, s), 3.79(3H, s), 3.98(3H, S), 4.00(3H, s), 6.88(2H, d, J=8.84 Hz), 7.17–7.21(2H, m), 7.47(2H, d, J=8.60 Hz), 7.55(1H, d, J=7.00 Hz), 7.71(1H, brs) | 3332, 1766, 1648, 1612 (KBr) |
| 74 | (structure) | yellow crystals 131–134° C. | 400 (M$^+$ + 1) 69 (100) | 1.60–1.72(6H, m), 2.10(3H, s), 3.60–3.63(4H, m), 3.75(2H, s), 3.98(6H, s), 6.89(1H, d, J=8.40 Hz), 7.07(1H, d, J=1.80 Hz), 7.14(1H, dd, J=8.48 and 1.88 Hz), 9.49(1H brs) | 3198, 1642, 1607 (KBr) |

TABLE 24-continued

| Ex. No. | Structure | Appearance | FABMS (m/z) | NMR(CDCl$_3$, δ) | IR (cm$^{-1}$) |
|---|---|---|---|---|---|
| 75 | 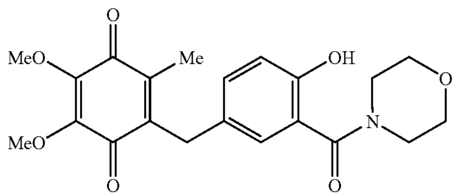 | yellow crystals 145–146° C. | 402 (M$^+$ + 1) 154 (100) | 2.11(3H, s), 3.70–3.74(10H, m), 3.98(3H, s), 3.99(3H, s), 6.91(1H, d, J=8.40 Hz), 7.10–7.17(2H, m), 9.37(1H, brs) | 3150, 1648, 1611 (KBr) |
| 76 | 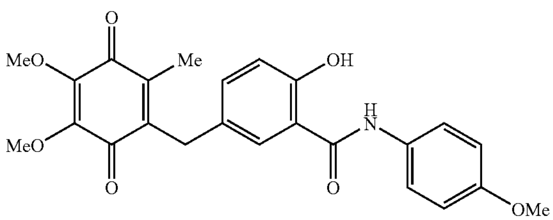 | yellow crystals 121–122° C. | 438 (M$^+$ + 1) 154 (100) | 2.02(3H, s), 3.66(2H, s), 3.72(3H, s), 3.86(3H, S), 3.87(3H, s), 6.78–6.82(3H, m), 7.10(1H, dd, J=8.40 and 1.68 Hz), 7.33(2H, d. J=8.88 Hz), 7.38(1H, d, J=1.44 Hz), 8.22(1H, brs) | 3322, 3076, 1648, 1610 (KBr) |

TABLE 25

| Ex. No. | Structure | Appearance | FABMS (m/z) | NMR(CDCl$_3$, δ) | IR (cm$^{-1}$) |
|---|---|---|---|---|---|
| 77 | 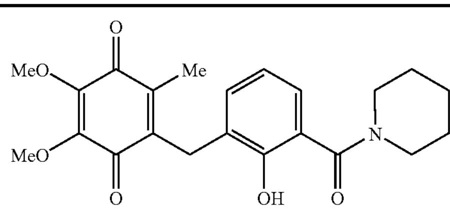 | yellow oil | 400 (M$^+$ + 1) 154 (100) | 1.51–1.71(6H, m), 2.06(3H, s), 3.62–3.77(4H, m), 3.86(3H, s), 3.98(2H, s), 3.99(3H, s), 6.72–6.75(1H, m), 7.09–7.24(2H, m), 9.99(1H, brs) | 3300, 1650, 1610 (NaCl) |
| 78 | 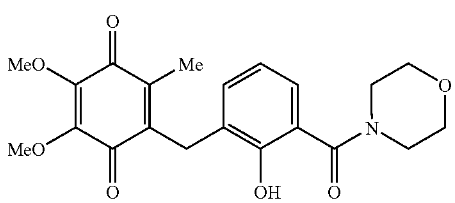 | yellow crystals 128–129° C. | 402 (M$^+$ + 1) 54 (100) | 2.07(3H, s), 3.72(8H, s), 3.86(2H, s), 3.98(3H, s), 4.00(3H, s), 6.76(1H, t, J=7.68 Hz), 7.09(1H, d, J=7.20 Hz), 7.15(1H, d, J=7.50 Hz), 9.85(1H, brs) | 3692, 1645, 1612 (KBr) |
| 79 | 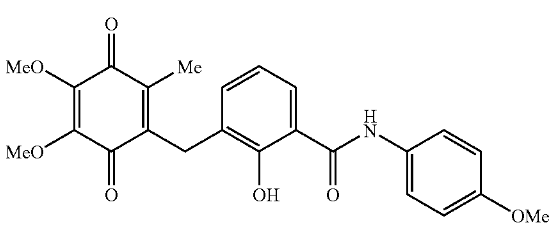 | yellow crystals 109–110.5° C. | 438 (M$^{+\cdot}$ + 1) 154 (100) | 2.06(3H, s), 3.81(3H, s), 3.89(2H, s), 3.98(3H, s), 3.99(3H, s), 6.80(1H, t, J=7.76 Hz), 6.92(2H, d, J=7.92 Hz), 7.24(1H, d, J=8.84 Hz), 7.38(1H, d, J=7.72 Hz), 7.45(2H, d, J=8.96 Hz), 7.91(1H, brs) | 3372, 1639, 1610 (KBr) |
| 80 | 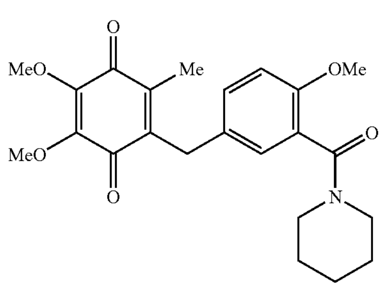 | red-yellow oil | 414 (M$^+$ + 1, 100) | 1.26–1.64(6H, m), 2.06(3H, s), 3.12–3.17(2H, m), 3.71–3.84(4H, m), 3.78(3H, s), 3.98(3H, s), 3.99(3H, s), 6.79(1H, d, J=8.48 Hz), 7.00(1H, d, J=2.20 Hz), 7.14(1H, dd, J=8.50 and 2.24 Hz) | 1645, 1610, 1260 (NaCl) |

TABLE 26

| Ex.No. | Structure | Appearance |
|---|---|---|
| 81 | (structure: 2,3-dimethoxy-5-methyl-1,4-benzoquinone with CH2 linker to 4-methoxyphenyl bearing morpholine carboxamide) | red-yellow oil |
| 82 | (structure: 2,3-dimethoxy-5-methyl-1,4-benzoquinone with CH2 linker to 4-methoxyphenyl bearing N-(4-methoxyphenyl)carboxamide) | red-yellow oil |
| 83 | (structure: 2,3-dimethoxy-5-methyl-1,4-benzoquinone with CH2 linker to 4-isopropoxyphenyl bearing piperidine carboxamide) | red-yellow oil |
| 84 | (structure: 2,3-dimethoxy-5-methyl-1,4-benzoquinone with CH2 linker to 4-isopropoxyphenyl bearing morpholine carboxamide) | red-yellow oil |

| Ex.No. | FABMS(m/z) | NMR(CDCl$_3$, δ) | IR (cm$^{-1}$) |
|---|---|---|---|
| 81 | 416(M$^+$ + 1) 154(100) | 2.07(3H, s), 3.21–3.24(2H, m), 3.57–3.59(2H, m), 3.61–3.82(6H, m), 3.80(3H, s), 3.98(3H, s), 3.99(3H, s), 6.80(1H, d, J=8.52 Hz), 7.04(1H, d, J=2.12 Hz), 7.17(1H, dd, J=8.40 and 2.24 Hz) | 1644, 1611, 1263(NaCl) |
| 82 | 452(M$^+$ + 1) 154(100) | 2.11(3H, s), 3.81(3H, s), 3.85(2H, s), 3.98(6H, s), 4.01(3H, s), 6.88–6.95(3H, m), 7.32(1H, dd, J=8.56 and 2.40 Hz), 7.55(2H, dd, J=6.94 and 2.08 Hz), 8.07(1H, d, J=2.36 Hz), 9.63(1H br s) | 3356, 1654, 1610, 1512, 1245(NaCl) |

TABLE 26-continued

| | | | |
|---|---|---|---|
| 83 | 442(M⁺ + 1, 100) | 1.26–1.62(6H, m), 1.60–1.64(6H, m), 2.06(3H, s), 3.10–3.19(2H, m), 3.70–3.82(4H, m), 3.98(3H, s), 3.99(3H, s), 4.45–4.49(1H, m), 6.77(1H, d, J=8.56 Hz), 6.99(1H, d, J=2.20 Hz), 7.11(1H, dd, J=8.36 and 2.12 Hz) | 1636, 1610, 1265(NaCl) |
| 84 | 444(M⁺ + 1) 154(100) | 1.27–1.33(6H, m), 2.07(3H, s), 3.18–3.27(2H, m), 3.57–3.85(8H, m), 3.98(3H, s), 3.99(3H, s), 4.47–4.53(1H, m), 6.78(1H, d, J=8.56 Hz), 7.03(1H, d, J=2.20 Hz), 7.14(1H, dd, J=8.50 and 2.20 Hz) | 3346, 1645, 1611, 1264(NaCl) |

TABLE 27

| Ex.No. | Structure | Appearance |
|---|---|---|
| 85 | 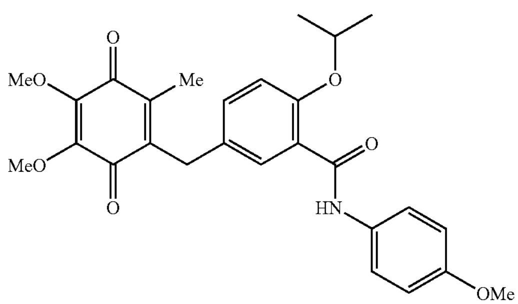 | red-yellow oil |
| 86 | 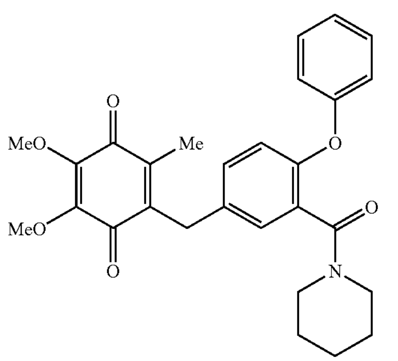 | yellow oil |
| 87 | 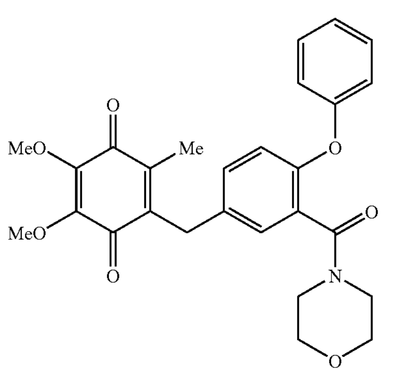 | yellow oil |

TABLE 27-continued

| 88 | [Structure: dimethoxy-methyl-benzoquinone linked via CH2 to phenyl ring bearing OPh and C(O)NH-(4-methoxyphenyl)] | yellow oil |

| Ex.No. | FABMS(m/z) | NMR(CDCl$_3$, δ) | IR (cm$^{-1}$) |
| --- | --- | --- | --- |
| 85 | 480(M$^+$ + 1) 154(100) | 1.48(6H, d, J=6.04 Hz), 2.11(3H, s), 3.81(3H, s), 3.84(2H, s), 3.99(6H, s), 4.73–4.79(1H, m), 6.88–6.93(3H, m), 7.29(1H, d, J=8.52 Hz), 7.57(2H, d, J=8.96 Hz), 8.07(1H, d, J=2.36 Hz), 10.05(1H br s) | 1662, 1610, 1511, 1260(NaCl) |
| 86 | 476(M$^+$ + 1, 100) | 1.47–1.62(6H, m), 2.08(3H, s), 3.21–3.24(2H, m), 3.57–3.75(2H, m), 3.75–3.88(2H, m), 3.99(3H, s), 4.00(3H, s), 6.76(1H, d, J=9.12 Hz), 6.97(2H, d, J=7.92 Hz), 7.07–7.13(3H, m), 7.27–7.33(2H, m) | 1636, 1612, 1485(NaCl) |
| 87 | 478(M$^+$ + 1) 154(100) | 2.08(3H, s), 3.33–3.47(2H, m), 3.61–3.88(8H, m), 3.99(3H, s), 4.00(3H, s), 6.79(1H, d, J=8.28 Hz), 6.95(2H, d, J=8.12 Hz), 7.10–7.17(3H, m), 7.30–7.35(2H, m) | 1645, 1610, 1484(NaCl) |
| 88 | 514(M$^+$ + 1, 100) | 2.12(3H, s), 3.78(3H, s), 3.87(2H, s), 3.99(6H, s), 6.80(1H, d, J=8.44 Hz), 6.85(1H, d, J=8.84 Hz), 7.08(2H, d, J=8.04 Hz), 7.19–7.27(3H, m), 7.39(2H, d, J=8.04 Hz), 7.48(2H, d, J=8.92 Hz), 8.10(1H, d, J=1.84 Hz), 9.48(1H, br s) | 3374, 1659, 1610, 1512(NaCl) |

TABLE 28

| Ex.No. | Structure | Appearance |
| --- | --- | --- |
| 89 | [Structure: dimethoxy-methyl-benzoquinone linked via CH2 to phenyl bearing O-(3-methoxyphenyl) and C(O)-piperidine] | yellow oil |

TABLE 28-continued

| Ex.No. | FABMS(m/z) | NMR(CDCl$_3$, δ) | IR (cm$^{-1}$) |
| --- | --- | --- | --- |
| 89 | 506(M$^+$ + 1) 54(100) | 1.43–1.63(6H, m), 2.08(3H, s), 3.21–3.33(2H, m), 3.57–3.71(2H, m), 3.76(3H, s), 3.71–3.82(2H, m), 3.99(3H, s), 4.00(3H, s), 6.54–6.56(2H, m), 6.64(1H, d, J=7.72 Hz), 6.80(1H, d, J=5.68 Hz), 7.12–7.14(2H, m), 7.19(1H, t, J=7.18 Hz) | 1642, 1609, 1484(NaCl) |
| 90 | 507(M$^+$) 154(100) | 2.09(3H, s), 3.31–3.39(2H, m), 3.57–3.84(8H, m) 3.76(3H, s), 3.99(3H, s), 4.00(3H, s), 6.52–6.54(2H, m), 6.65(1H, dd, J=7.72 and 2.32 Hz), 6.82(1H, dd, J=5.68 and 3.52 Hz), 7.14–7.23(3H, m) | 1643, 1610, 1485(NaCl) |
| 91 | 544(M$^+$ + 1) 154(100) | 2.12(3H, s), 3.78(3H, s), 3.79(3H, s), 3.88(2H, s), 3.99(6H, s), 6.62–6.66(2H, m), 7.75(1H, d, J=8.40 Hz), 6.82–6.87(3H, m), 7.24–7.31(2H, m), 7.48(2H, d, J=8.88 Hz), 8.09(1H, d, J=2.12 Hz), 9.42(1H, br s) | 3376, 1684, 1608, 1513(KBr) |

TABLE 28-continued

| 92 | 491(M⁺ + 1) 154(100) | 1.40–1.41(2H, m), 1.57–1.59(4H, m), 2.06(3H, s), 3.13–3.15(2H, m), 3.68–3.70(2H, m), 3.71–3.85(2H, m), 3.98(3H, s), 3.99(3H, m), 5.08(2H, s), 6.85(1H, d, J=8.48 Hz), 7.04(1H, d, J=2.08 Hz), 7.14(1H, dd, J=8.48 and 2.04 Hz), 7.30–7.32(1H, m), 7.73(1H, d, J=7.80 Hz), 8.56(1H, d, J=3.72 Hz), 8.62(1H, d, J=1.24 Hz) | 1650, 1611, 1266(NaCl) |

TABLE 29

| Ex.No. | Structure | Appearance |
|---|---|---|
| 93 | 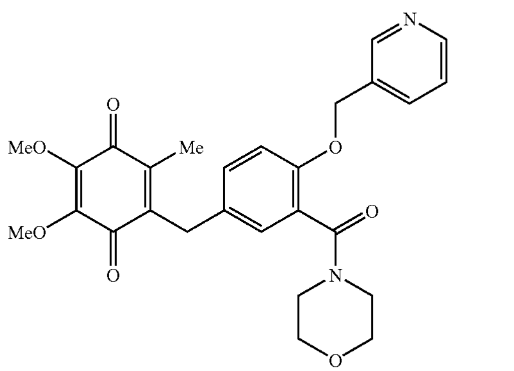 | yellow oil |
| 94 | 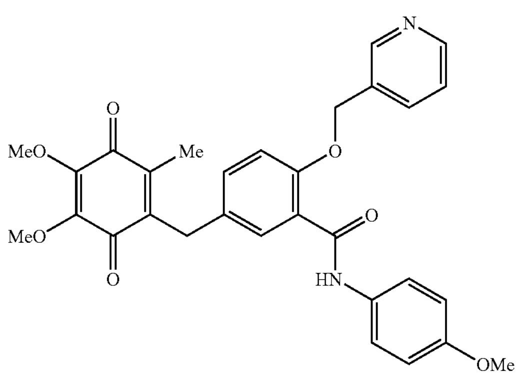 | yellow crystals 128–130° C. |
| 95 | 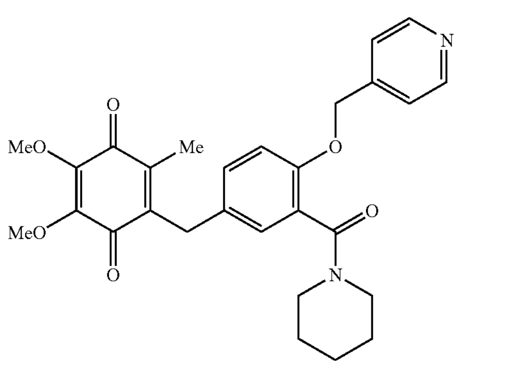 | yellow oil |

TABLE 29-continued

| | | | |
|---|---|---|---|
| 96 | | | yellow oil |

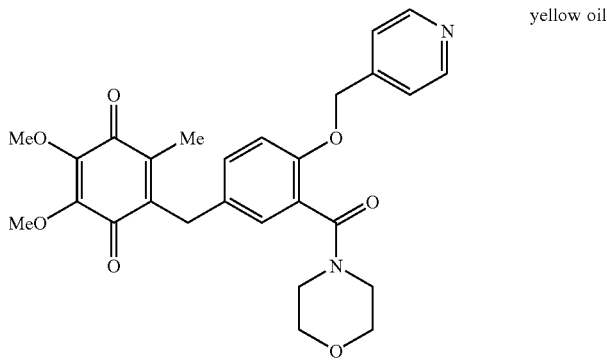

| Ex.No. | FABMS(m/z) | NMR(CDCl$_3$, δ) | IR (cm$^{-1}$) |
|---|---|---|---|
| 93 | 493(M$^+$ + 1)<br>154(100) | 2.07(3H, s), 3.21–3.24(2H, m), 3.47–<br>3.64(2H, m), 3.66–3.84(6H, m),<br>3.98(3H, s), 3.99(3H, m),<br>5.08(2H, s), 6.88(1H, d, J=8.52 Hz),<br>7.08(1H, d, J=2.12 Hz),<br>7.18(1H, dd, J=8.52 and 2.20 Hz),<br>7.30–7.33(1H, m),<br>7.73(1H, d, J=7.88 Hz),<br>8.58(1H, dd, J=4.72 and 1.24 Hz),<br>8.63(1H, d, J=1.76 Hz) | 1644, 1611, 1265(NaCl) |
| 94 | 529(M$^+$ + 1)<br>154(100) | 2.12(3H, s), 3.77(3H, s), 3.86(2H, s),<br>3.99(6H, s), 5.23(2H, s),<br>6.78(2H, d, J=8.92 Hz),<br>7.03(1H, d, J=8.52 Hz),<br>7.23(2H, dd, J=9.00 Hz),<br>7.34–7.41(2H, m),<br>7.83(1H, d, J=7.84 Hz),<br>8.09(1H, d, J=7.84 Hz),<br>8.70(1H, d, J=4.80 Hz),<br>8.78(1H, br s), 9.55(1H, br s) | 3357, 1658, 1611,<br>1513(KBr) |
| 95 | 491(M$^+$ + 1)<br>154(100) | 1.42–1.44(2H, m), 1.60–1.64(4H, m),<br>2.07(3H, s), 3.16–3.20(2H, m),<br>3.72–3.74(2H, m), 3.74–<br>3.85(2H, m), 3.99(3H, s),<br>4.00(3H, s), 5.07–5.09(2H, m),<br>6.78(1H, d, J=8.48 Hz),<br>7.05(1H, d, J=2.00 Hz),<br>7.13(1H, dd, J=8.52 and 2.12 Hz),<br>7.30(2H, d, J=5.56 Hz),<br>8.59(2H, d, J=5.92 Hz) | 1660, 1610, 1265(NaCl) |
| 96 | 493(M$^+$ + 1)<br>154(100) | 2.07(3H, s), 3.25–3.28(2H, m),<br>3.53–3.55(2H, m), 3.70–3.84(6H, m),<br>3.98(3H, s), 3.99(3H, m),<br>5.09(2H, s), 6.80(1H, d, J=8.52 Hz),<br>7.09(1H, d, J=1.44 Hz),<br>7.16(1H, d, J=8.48 Hz),<br>7.29(2H, d, J=6.56 Hz),<br>8.61(2H, d, J=5.56 Hz) | 1660, 1610, 1265(NaCl) |

TABLE 30

| Ex.No. | Structure | Appearance |
|---|---|---|
| 97 | 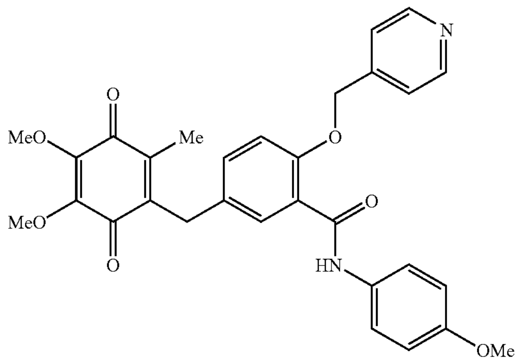 | yellow crystals 131–134° C. |
| 98 | 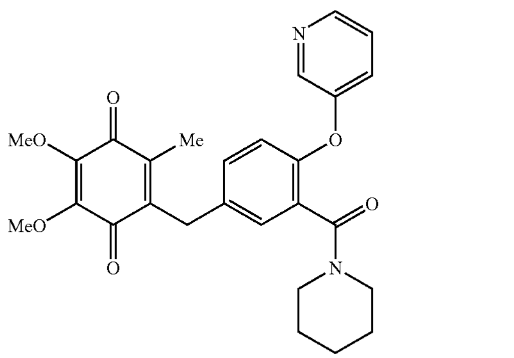 | yellow oil |
| 99 | 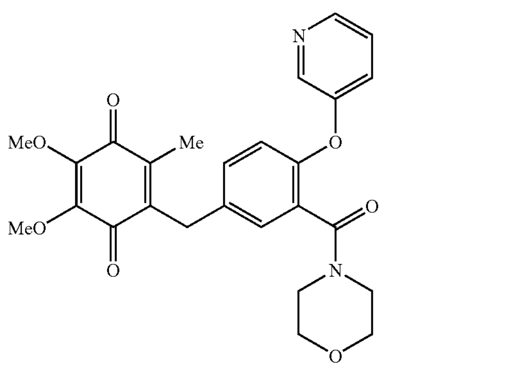 | yellow oil |
| 100 | 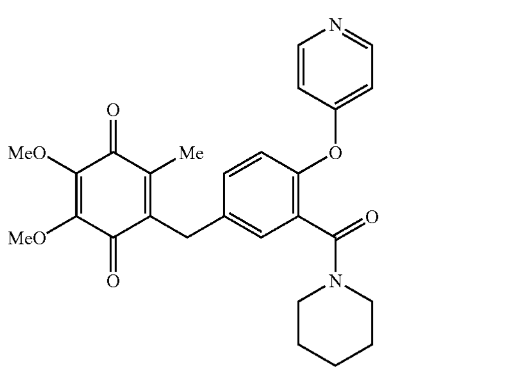 | yellow oil |

| Ex.No. | FABMS(m/z) | NMR(CDCl$_3$, δ) | IR (cm$^{-1}$) |
|---|---|---|---|
| 97 | 529(M$^+$ + 1) 69(100) | 2.11(3H, s), 3.78(3H, s), 3.86(2H, s), 3.99(6H, s), 5.23(2H, s), 6.82(2H, d, J=8.92 Hz), 6.94(1H, d, J=8.48 Hz), 7.31– | 3374, 1654, 1608, 1512(KBr) |

TABLE 30-continued

|  |  | 7.34(3H, m), 7.40(2H, d, J=5.68 Hz), 8.08(1H, d, J=2.32 Hz), 8.69(2H, d, J=5.76 Hz), 9.50(1H, br s) |  |
|---|---|---|---|
| 98 | 477(M⁺ + 1) 52(100) | 1.40–1.62(6H, m), 2.11(3H, s), 3.19–3.23(2H, m), 3.54–3.60(2H, m), 3.86(2H, d, J=14.24 Hz), 4.00(3H, s), 4.01(3H, s), 6.82(2H, d, J=6.08 Hz), 6.97(1H, d, J=8.36 Hz), 7.18(1H, d, J=2.04 Hz), 7.24–7.26(1H, m), 8.44(2H, d, J=5.36 Hz) | 1640, 1611, 1264(NaCl) |
| 99 | 479(M⁺ + 1) 52(100) | 2.12(3H, s), 3.25–3.40(2H, m), 3.60–3.69(6H, m), 3.85–3.88(2H, m), 4.00(3H, s), 4.01(3H, s), 6.81(2H, d, J=5.50 Hz), 6.98(1H, d, J=8.36 Hz), 7.23(1H, d, J=2.08 Hz), 7.26–7.30(1H, m), 8.46(2H, d, J=5.68 Hz) | 1638, 1611, 1263(NaCl) |
| 100 | 477(M⁺ + 1) 52(100) | 1.50–1.72(6H, m), 2.09(3H, s), 3.23–3.29(2H, m), 3.60–3.65(2H, m), 3.83(2H, d, J=14.12 Hz), 3.99(3H, s), 4.00(3H, s), 6.81(1H, d, J=8.32 Hz), 7.14–7.17(4H, m), 8.35(1H, dd, J=5.56 and 2.11 Hz), 8.39(1H, d, J=1.92 Hz) | 1636, 1611, 1264(NaCl) |

TABLE 31

| Ex.No. | Structure | Appearance |
|---|---|---|
| 101 | 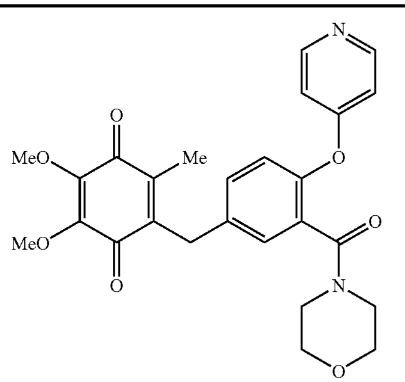 | yellow oil |
| 102 | 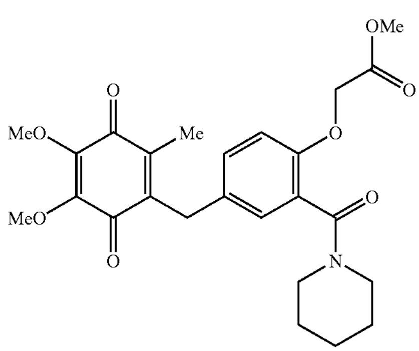 | yellow crystals 89–92° C. |

TABLE 31-continued
| 103 | 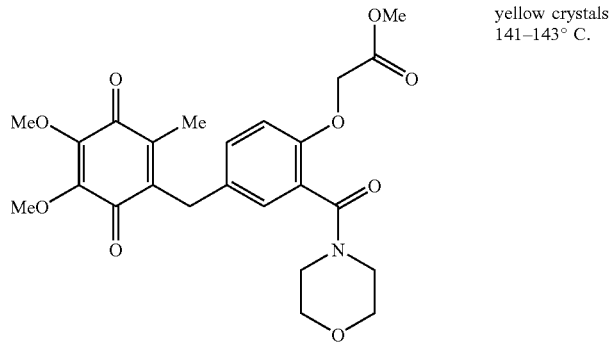 | yellow crystals 141–143° C. |
|---|---|---|
| 104 | 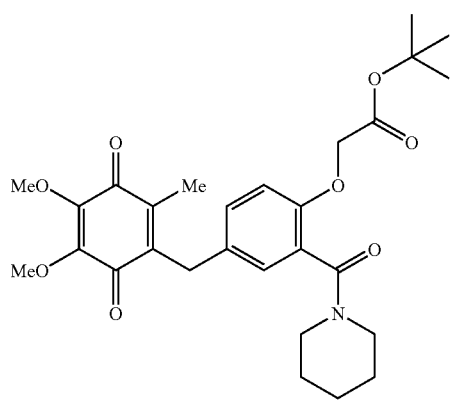 | yellow oil |
| Ex.No. | FABMS(m/z) | NMR(CDCl$_3$, δ) | IR (cm$^{-1}$) |
|---|---|---|---|
| 101 | 479(M$^+$ + 1) 154(100) | 2.10(3H, s), 3.33–3.37(2H, m), 3.61–3.85(8H, m), 3.99(3H, s), 4.00(3H, s), 6.82(1H, d, J=8.24 Hz), 7.19–7.26(5H, m), 8.37(1H, d, J=8.08 Hz) | 1641, 1611, 1263(NaCl) |
| 102 | 472(M$^+$ + 1) 154(100) | 1.40–1.60(6H, m), 2.06(3H, s), 3.14–3.30(2H, m), 3.70–3.84(4H, m), 3.77(3H, s), 3.98(3H, s), 3.99(3H, s), 4.60–4.63(2H, m), 6.65(1H, d, J=8.48 Hz), 7.04(1H, d, J=2.12 Hz), 7.12(1H, d, 8.56 and 2.20 Hz) | 1748, 1649, 1630, 1610(KBr) |
| 103 | 474(M$^+$ + 1) 154(100) | 2.03(3H, s), 3.23–3.26(1H, m), 3.39–3.43(1H, m), 3.57–3.99(8H, m), 3.77(3H, s), 3.99(3H, s), 4.00(3H, s), 4.64(2H, s), 6.64(1H, d, J=8.56 Hz), 7.08(1H, d, J=2.04 Hz), 7.15(1H, dd, J=8.52 and 2.08 Hz) | 1751, 1668, 1634, 1610(KBr) |
| 104 | 514(M$^+$ + 1) 54(100) | 1.45–1.64(6H, m), 1.47(9H, s), 2.06(3H, s), 3.18–3.29(2H, m), 3.66–3.84(4H, m), 3.98(3H, s), 3.99(3H, s), 4.43–4.54(2H, m), 6.63(1H, d, J=8.52 Hz), 7.04(1H, br s), 7.12(1H, d, J=8.40 Hz) | 1748, 1646, 1456, 1264(NaCl) |

TABLE 32

| Ex.No. | Structure | Appearance |
|---|---|---|
| 105 | (structure) | yellow oil |
| 106 | (structure) | yellow oil |
| 107 | (structure) | yellow oil |
| 108 | (structure) | yellow crystals 176–179° C. |

| Ex.No. | FABMS(m/z) | NMR(CDCl$_3$, δ) | IR (cm$^{-1}$) |
|---|---|---|---|
| 105 | 516(M$^+$ + 1) 154(100) | 1.47(9H, s), 2.07(3H, s), 3.20–3.25(1H, m), 3.43–3.47(1H, m), 3.56–3.84(8H, m), 3.98(3H, s), 3.99(3H, s), 4.50–4.52(2H, m), 6.62(1H, d, J=8.56 Hz), 7.08(1H, d, J=2.12 Hz), 7.15(1H, dd, J=8.56 and 2.12 Hz) | 1750, 1641, 1611, 1267(NaCl) |
| 106 | 539(M$^+$ + 1) 183(100) | 2.10(3H, s), 2.32(3H, s), 3.83(3H, s), 3.87(6H, s), 3.99(3H, s), 4.00(3H, s), 6.80–6.90(2H, m), 7.05(1H, d, J=8.36 Hz), 7.33(1H, dd, J=8.28 and 1.88 Hz), 7.61(1H, s), 7.94(1H, br s) | 3300, 1766, 1652, 1609(NaCl) |

TABLE 32-continued

| 107 | 510(M⁺ + 1) 154(100) | 2.11(3H, s), 2.32(3H, s), 3.88(6H, s), 3.91(2H, s), 3.99(3H, s), 4.00(3H, s), 6.83(1H, d, J=8.60 Hz), 6.89(1H, dd, J=8.60 and 2.24 Hz), 7.05(1H, d, J=8.32 Hz), 7.34(1H, dd, J=8.32 and 2.04 Hz), 7.46(1H, d, J=1.96 Hz), 7.64(1H, d, J=1.56 Hz), 7.92(1H, br s) | 3338, 1766, 1649, 1610(NaCl) |
| --- | --- | --- | --- |
| 108 | 492(M⁺ + 1) 154(100) | 2.11(3H, s), 2.32(3H, s), 2.59(3H, s), 3.88(2H, s), 3.99(6H, s), 7.07(1H, d, J=8.40 Hz), 7.36(1H, dd, J=8.32 and 2.12 Hz), 7.66–7.71(3H, m), 7.97(2H, d, J=8.64 Hz), 8.27(1H, br s) | 3322, 1766, 1652, 1594(NaCl) |

TABLE 33

| Ex.No. | Structure | Appearance |
| --- | --- | --- |
| 109 | [Structure: trimethoxy-methyl-benzoquinone linked via CH₂ to benzamide with OAc and N-H-(4-chlorophenyl)] | yellow oil |
| 110 | [Structure: trimethoxy-methyl-benzoquinone linked via CH₂ to benzamide with OAc and N-H-(4-morpholinophenyl)] | yellow crystals 173–177° C. |
| 111 | [Structure: trimethoxy-methyl-benzoquinone linked via CH₂ to benzamide with OAc and N-H-(4-cyanophenyl)] | yellow oil |
| 112 | [Structure: trimethoxy-methyl-benzoquinone linked via CH₂ to benzamide with OAc and N-H-(4-trifluoromethylphenyl)] | yellow crystals 127–128° C. |

| Ex.No. | FABMS(m/z) | NMR(CDCl₃, δ) | IR (cm⁻¹) |
| --- | --- | --- | --- |
| 109 | 484(M⁺ + 1) 69(100) | 2.09(3H, s), 2.30(3H, s), 3.85(2H, s), 3.98(6H, s), 7.06(1H, d, J=8.90 Hz), 7.26–7.34(3H, m), 7.53(2H, d, J=8.60 Hz), 7.62(1H, s), 8.13(1H, br s) | 3320, 1766, 1648, 1610(NaCl) |

TABLE 33-continued

| 110 | 535(M⁺ + 1) 154(100) | 2.11(3H, s), 2.31(3H, s), 3.10–3.15(4H, m), 3.84–3.88(6H, m), 3.99(3H, s), 4.00(3H, s), 6.90(2H, d, J=8.88 Hz), 7.04(1H, d, J=8.40 Hz), 7.32(1H, dd, J=8.24 and 1.88 Hz), 7.48(2H, d, J=8.88 Hz), 7.65(1H, s), 7.89(1H, br s) | 3300, 1766, 1650, 1611(NaCl) |
|---|---|---|---|
| 111 | 475(M⁺ + 1) 154(100) | 2.11(3H, s), 2.31(3H, s), 3.87(2H, s), 3.99(6H, s), 7.07(1H, d, J=8.44 Hz), 7.36(1H, d, J=8.32 Hz), 7.61–7.66(3H, m), 7.69–7.76(2H, m), 8.28(1H, br s) | 3323, 2224, 1767, 1648, 1610(NaCl) |
| 112 | 518(M⁺ + 1) 476(100) | 2.13(3H, s), 2.32(3H, s), 3.89(2H, s), 4.00(3H, s), 4.01(3H, s), 7.08(1H, d, J=8.32 Hz), 7.37(1H, dd, J=8.32 and 2.20 Hz), 7.62(2H, d, J=8.60 Hz), 7.66(1H, s), 7.72(2H, d, J=8.56 Hz), 8.17(1H, br, s) | 3320, 1767, 1648, 1610, 1322(NaCl) |

TABLE 34

| Ex.No. | Structure | Appearance |
|---|---|---|
| 113 | (MeO, MeO, Me-substituted benzoquinone)-CH₂-(phenyl with OAc)-C(=O)NH-(3,5-bis(CF₃)phenyl) | yellow crystals 127–129° C. |
| 114 | (MeO, MeO, Me-substituted benzoquinone)-CH₂-(phenyl with OH)-C(=O)NH-(3,4,5-trimethoxyphenyl) | yellow crystals 68–70° C. |
| 115 | (MeO, MeO, Me-substituted benzoquinone)-CH₂-(phenyl with OH)-C(=O)NH-(3,4-dimethoxyphenyl) | yellow crystals 72–75° C. |
| 116 | (MeO, MeO, Me-substituted benzoquinone)-CH₂-(phenyl with OH)-C(=O)NH-(4-acetylphenyl) | yellow crystals 158–160° C. |

TABLE 34-continued

| Ex.No. | FABMS(m/z) | NMR(CDCl$_3$, δ) | IR (cm$^{-1}$) |
|---|---|---|---|
| 113 | 586(M$^+$ + 1) 544(100) | 2.12(3H, s), 2.33(3H, s), 3.88(2H, s), 3.99(3H, s), 4.00(3H, s), 7.09(1H, d, J=8.32 Hz), 7.37(1H, dd, J=8.36 and 2.12 Hz), 7.60–7.65(2H, m), 8.10(2H, d like), 8.35(1H, br s) | 3339, 1768, 1649, 1612, 1382(NaCl) |
| 114 | 498(M$^+$ + 1) 183(100) | 2.15(3H, s), 3.79(2H, s), 3.85(3H, s), 3.89(6H, s), 3.98(3H, s), 3.99(3H, s), 6.87(1H, s), 6.92(1H, d, J=8.52 Hz), 7.20(1H, d, J=8.28 Hz), 7.27(1H, s), 7.44(1H, s), 8.02(1H, br s), 11.81(1H, br s) | 3300, 1648, 1610(NaCl) |
| 115 | 468(M$^+$ + 1) 154(100) | 2.15(3H, s), 3.79(2H, s), 3.90(3H, s), 3.92(3H, s), 3.98(3H, s), 3.99(3H, s), 6.86–6.94(2H, m), 7.00(1H, dd, J=8.60 and 2.40 Hz), 7.21(1H, dd, J=8.48 and 1.92 Hz), 7.26–7.27(1H, m), 7.42(1H, d, J=1.56 Hz), 7.95(1H, s), 11.91(1H, s) | 3350, 1647, 1610(NaCl) |
| 116 | 450(M$^+$ + 1) 154(100) | 2.16(3H, s), 2.61(3H, s), 3.80(2H, s), 3.98(3H, s), 3.99(3H, s), 6.94(1H, d, J=8.52 Hz), 7.24(1H, d, J=8.52 Hz), 7.48(1H, d, J=1.72 Hz), 7.73(2H, d, J=8.68 Hz), 8.01(2H, d, J=8.68 Hz), 8.22(1H, br s), 11.56(1H, br s) | 3326, 1651, 1610(NaCl) |

TABLE 35

| Ex.No. | Structure | Appearance |
|---|---|---|
| 117 | [Structure: 2,3-dimethoxy-5-methyl-1,4-benzoquinone with CH$_2$ linker to 2-hydroxy-benzamide N-(4-chlorophenyl)] | yellow crystals 138–141° C. |
| 118 | [Structure: 2,3-dimethoxy-5-methyl-1,4-benzoquinone with CH$_2$ linker to 2-hydroxy-benzamide N-(4-morpholinophenyl)] | yellow crystals 184–186° C. |
| 119 | [Structure: 2,3-dimethoxy-5-methyl-1,4-benzoquinone with CH$_2$ linker to 2-hydroxy-benzamide N-(4-cyanophenyl)] | yellow crystals 149–151° C. |

TABLE 35-continued

| Ex.No. | Structure | Appearance |
|---|---|---|
| 120 | 2,3-dimethoxy-5-methyl-6-[(4-hydroxy-3-{[4-(trifluoromethyl)phenyl]carbamoyl}benzyl)]-1,4-benzoquinone | yellow crystals 169.5–173° C. |

| Ex.No. | FABMS(m/z) | NMR(CDCl₃, δ) | IR (cm⁻¹) |
|---|---|---|---|
| 117 | 442(M⁺ + 1) 154(100) | 2.13(3H, s), 3.76(2H, s), 3.95(3H, s), 3.96(3H, s), 6.90(1H, d, J=8.48 Hz), 7.20(1H, dd, J=8.48 and 1.88 Hz), 7.33(2H, d, J=8.48 Hz), 7.46(1H, d, J=1.68 Hz), 7.52(2H, d, J=8.84 Hz), 8.26(1H, br s), 11.55–11.85(1H, br) | 3250, 1647, 1609(NaCl) |
| 118 | 493(M⁺ + 1) 154(100) | 2.15(3H, s), 3.15–3.18(4H, m), 3.79(2H, s), 3.79–3.89(4H, m), 3.98(3H, s), 3.99(3H, s), 6.90–6.95(3H, m), 7.21(1H, dd, J=8.52 and 1.96 Hz), 7.40–7.47(3H, m), 7.87(1H, br s), 11.96(1H, s) | 3250, 1647, 1610(NaCl) |
| 119 | 433(M⁺ + 1) 154(100) | 2.16(3H, s), 3.79(2H, s), 3.98(3H, s), 3.99(3H, s), 6.94(1H, d, J=8.52 Hz), 7.23–7.26(1H, m), 7.49(1H, s), 7.68(2H, d, J=8.56 Hz), 7.77(2H, d, J=8.60 Hz), 8.32(1H, br s), 11.28–11.36(1H, br) | 3326, 2224, 1648, 1610(NaCl) |
| 120 | 476(M⁺ + 1) 154(100) | 2.16(3H, s), 3.80(2H, s), 3.98(3H, s), 3.99(3H, s), 6.92(1H, d, J=8.52 Hz), 7.24(1H, dd, J=8.60 and 1.96 Hz), 7.48(1H, d, J=1.56 Hz), 7.65(2H, d, J=8.60 Hz), 7.74(2H, d, J=8.56 Hz), 8.21(1H, br s), 11.56(1H, s) | 3250, 1648, 1610(NaCl) |

TABLE 36

| Ex.No. | Structure | Appearance |
|---|---|---|
| 121 | 2,3-dimethoxy-5-methyl-6-[(4-hydroxy-3-{[3,5-bis(trifluoromethyl)phenyl]carbamoyl}benzyl)]-1,4-benzoquinone | yellow crystals 168–171° C. |
| 122 | 2,3-dimethoxy-5-methyl-6-[(4-hydroxy-3-{[(1S)-1-phenylethyl]carbamoyl}benzyl)]-1,4-benzoquinone | yellow crystals 54–56° C. |

TABLE 36-continued

| Ex.No. | Structure | Appearance |
|---|---|---|
| 123 | (MeO, MeO, Me, quinone, CH2, 2-hydroxyphenyl, C(=O)NH-CH(Me)-Ph) | yellow crystals 53–55° C. |
| 124 | (MeO, MeO, Me, quinone, CH2, 2-phenoxyphenyl, C(=O)-N(tetrahydroquinoline)) | yellow oil |

| Ex.No. | FABMS(m/z) | NMR(CDCl$_3$, δ) | IR (cm$^{-1}$) |
|---|---|---|---|
| 121 | 544(M$^+$ + 1) 154(100) | 2.16(3H, s), 3.80(2H, s), 3.97(3H, s), 3.99(3H, s), 6.95(1H, d, J=8.52 Hz), 7.24–7.27(1H, m), 7.51(1H s), 7.70(1H, s), 8.14(2H, s), 8.44(1H, br s), 11.32(1 H, s) | 3250, 1648, 1611, 1381(NaCl) |
| 122 | 436(M$^+$ + 1) 154(100) | 1.63(3H, d, J=6.92 Hz), 2.11(3H, s), 3.75(2H, s), 3.96(3H, s), 3.98(3H, s), 5.20–5.23(1H, m), 6.48(1H, d, J=7.36 Hz), 6.87(1H, d, J=8.52 Hz), 7.14(1H, dd, J=8.56 and 1.92 Hz), 7.27–7.39(6H, m), 12.14(1H, br s) | 3300, 1644, 1610(NaCl) |
| 123 | 436(M$^+$ + 1) 154(100) | 1.63(3H, d, J=6.84 Hz), 2.11(3H, s), 3.75(2H, s), 3.96(3H, s), 3.97(3H, s), 5.22–5.33(1H, m), 6.50(1H, d, J=6.64 Hz), 6.87(1H, d, J=8.52 Hz), 7.14(1H, d, J=8.48 Hz), 7.26–7.39(6H, m), 12.15(1H, br s) | 3358, 1643, 1611(NaCl) |
| 124 | 524(M$^+$ + 1, 100) | 1.54–1.97(2H, m), 2.05(3H, s), 2.41–2.75(2H, br), 3.32–3.64(1H, br), 3.81(2H, s), 4.00(3H, s), 4.01(3H, s), 4.20–4.59(1H, br), 6.26–6.89(6H, m), 6.90–7.10(4H, m), 7.11–7.26(2H, m), 7.27–7.33(1H, br) | 1645, 1610, 1486, 1264(NaCl) |

TABLE 37

| Ex.No. | Structure | Appearance |
|---|---|---|
| 125 | (MeO, MeO, Me, quinone, CH2, 2-phenoxyphenyl, C(=O)-N(2-methylpiperidine)) | yellow oil |

TABLE 37-continued
| | | |
|---|---|---|
| 126 | 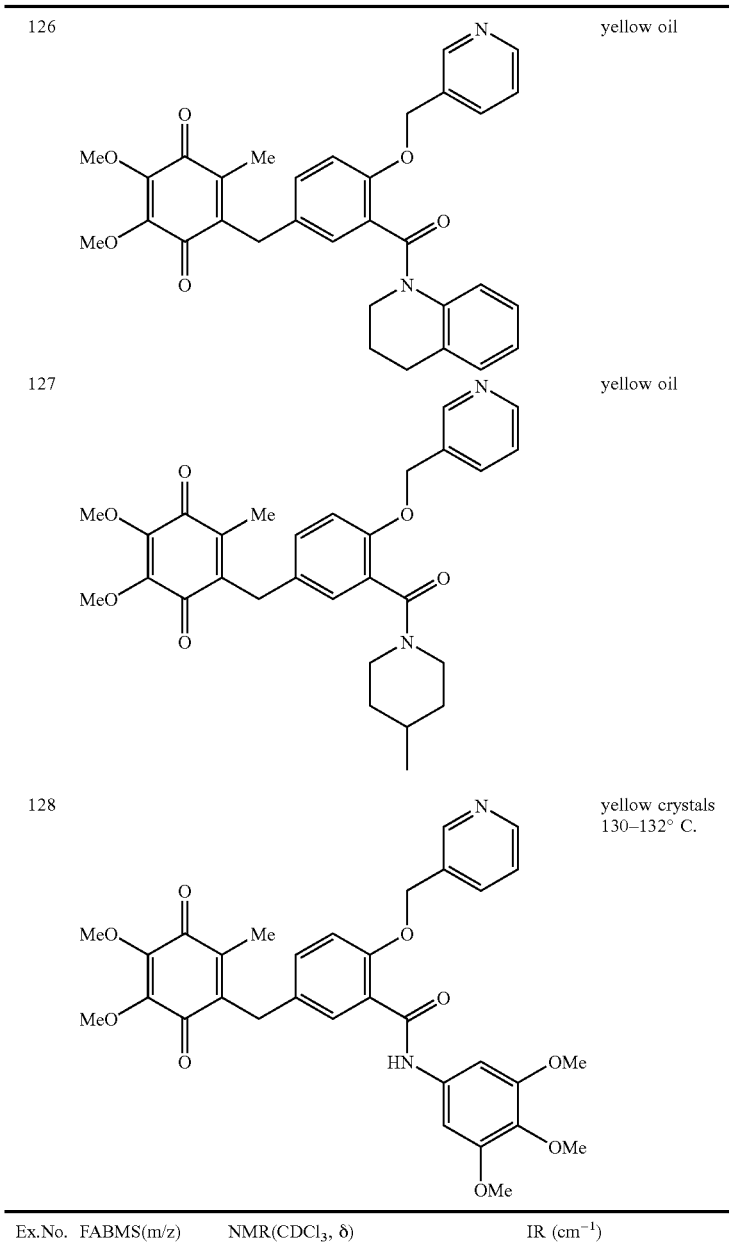 | yellow oil |
| 127 | | yellow oil |
| 128 | | yellow crystals 130–132° C. |
| Ex.No. | FABMS(m/z) | NMR(CDCl$_3$, δ) | IR (cm$^{-1}$) |
|---|---|---|---|
| 125 | 490(M$^+$ + 1) 154(100) | 1.03–1.72(8H, m), 2.07–2.09(3H, m), 2.77–3.19(2H m), 3.35–3.94(1H, m), 3.74–3.95(2H, m), 3.90–4.00(6H, m), 4.54–4.98(1H, m), 6.72–6.94(1H, m), 6.97–7.00(2H, m), 7.04–7.21(3H, m), 7.26–7.33(2H, m) | 1650, 1612, 1485, 1266(NaCl) |
| 126 | 539(M$^+$ + 1) 92(100) | 1.70–1.96(4H, br), 2.02(3H, s), 2.37–2.68(1H, br), 3.38–3.56(1H, br), 3.78(3H, s), 3.99(3H, s), 4.00(3H, s), 4.12–4.52(1H, br), 4.73–5.03(1H, br), 6.22–6.51(1H, br), 6.51–6.81(2H, br), 6.89–7.08(2H br), 7.11(1H, d, J=8.12 Hz), 7.18(1H, d, J=2.04 Hz), 7.20–7.27(1H, m), 7.42–7.60(1H, br), 8.30–8.48(1H, br), 8.56(1H, d, J=4.12 Hz) | 1648, 1610, 1492, 1265(NaCl) |

TABLE 37-continued

| | | | |
|---|---|---|---|
| 127 | 505(M⁺ + 1) 219(100) | 0.72–1.99(8H, m), 2.07(3H, s), 2.63–2.95(2H, m), 3.39–3.43(1H, m), 3.70–3.85(2H, m), 3.99(3H, s), 4.00(3H, s), 4.60–4.71(1H, m), 5.07(2H, s), 6.80–6.89(1H, m), 7.01–7.07(1H, m), 7.13–7.17(1H, m), 7.28–7.33(1H, m), 7.69–7.79(1H, m), 8.50–8.64(2H, m) | 1650, 1612, 1451, 1265(NaCl) |
| 128 | 589(M⁺ + 1) 154(100) | 2.12(3H, s), 3.74(3H, s), 3.79(3H, s), 3.88(3H, s), 4.00(6H, s), 5.22(2H, s), 6.62(2H, s), 7.07(1H, d, J=8.52 Hz), 7.36–7.42(2H, m), 7.38–7.44(2H, m), 7.86(1H, d, J=7.80 Hz), 8.11(1H, d, J=2.20 Hz), 8.68(1H, dd, J=4.68 and 1.16 Hz), 8.84(1H, d, J=1.52 Hz), 9.63(1H, br s) | 3356, 1654, 1608, 1508(NaCl) |

TABLE 38

| Ex.No. | Structure | Appearance |
|---|---|---|
| 129 | (structure shown) | yellow crystals 152–155° C. |
| 130 | (structure shown) | yellow oil |

| Ex.No. | FABMS(m/z) | NMR(CDCl₃, δ) | IR (cm⁻¹) |
|---|---|---|---|
| 129 | 541(M⁺ + 1) 92(100) | 2.13(3H, s), 3.55(3H, s), 3.88(2H, s), 4.00(6H, s), 5.24(2H, s), 7.06(1H, d, J=8.52 Hz), 7.32(2H, d, J=8.68 Hz), 7.38–7.44(2H, m), 7.83–7.86(3H, m), 8.10(1H, d, J=2.20 Hz), 8.45(1H, dd, J=4.64 and 1.28 Hz), 8.81(1H, d, J=1.64 Hz), 9.90(1H, br s) | 3340, 1673, 1609, 1530(NaCl) |
| 130 | 461(M⁺ + 1) 405(100) | 1.47(9H, s), 2.08(3H, s), 3.79(2H, s), 3.89(3H, s), 3.99(6H, s), 4.56(2H, s), 6.75(1H, d, J=8.60 Hz), 7.25(1H, dd, J=8.64 and 1.64 Hz), 7.61(1H, d, J=1.56 Hz) | 1731, 1648, 1611, 1264(NaCl) |

TABLE 39

| Ex.No. | Structure | Appearance |
|---|---|---|
| 131 | 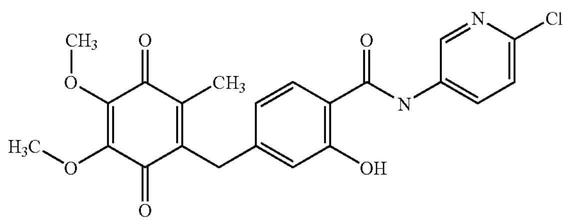 | orange crystals |
| 132 | 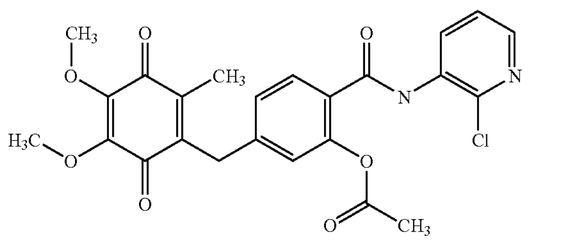 | orange crystals |
| 133 | 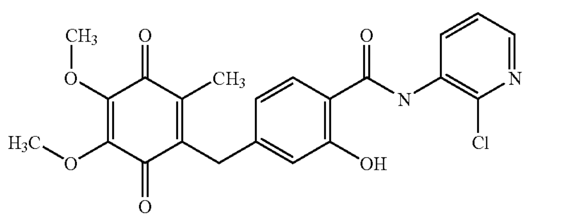 | orange crystals |
| 134 | 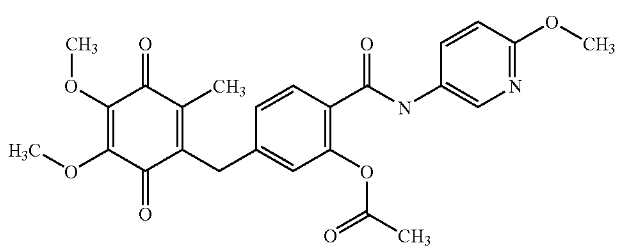 | orange crystals |

| Ex.No. | mp (° C.) | IR (cm-) | NMR (ppm) | FAB MS |
|---|---|---|---|---|
| 131 | 200.2–201.9 | 3334, 1684, 1652, 1612, 1552, 1497, 1265(KBr) | 2.08(3H, s), 3.85(2H, s), 4.00(6H, s), 6.79(1H, s), 6.80(1H, s), 7.37(1H, d, J=8.70 Hz), 7.44(1H, d, J=8.7 Hz), 7.96(1H, s), 8.17(1H, dd, J=8.7, 2.8 Hz), 8.47(1H, d, J=2.7 Hz), 11.78(1H, s) | 443(M+ + 1) |
| 132 | 113.5–115.1 | 1782, 1649, 1611, 1586, 1521, 1389, 1268(KBr) | 2.11(3H, s), 2.40(3H, s), 3.91(2H, s), 4.00(6H, s), 6.82(1H, s), 7.03(1H, s), 7.90(1H, d, J=8.2 Hz), 8.17–8.18(1H, m), 8.78–8.79(1H, m), 8.92(1H, dd, J=8.2, 1.6 Hz) | 485(M+ + 1) |
| 133 | 200.2–202.6 | 3280, 1649, 1611, 1586, 1534, 1432, 1267(KBr) | 2.09(3H, s), 3.87(2H, s), 4.01(6H, s), 6.82(1H, s), 6.84(1H, s), 7.33–7.34(1H, m), 7.47(1H, d, J=8.3 Hz), 8.19(1H, d, J=4.7 Hz), 8.50(1H, s), 8.78(1H, d, J=8.2 Hz), 11.77(1H, s) | 443(M+ + 1) |
| 134 | 124.7–125.5 | 1768, 1654, 1611, 1529, 1500, 1269(KBr) | 2.03(3H, s), 2.26(3H, s), 3.82(2H, s), 3.87(3H, s), 3.93(6H, s), 6.70–6.71(1H, m), 6.92(1H, s), 7.12(1H, d, J=7.9 Hz), 7.68–7.69(1H, m), 7.82–7.83(1H, m), 7.84–7.85(1H, m), 8.13(1H, s) | 481(M+ + 1) |

TABLE 40

| Ex.No. | Structure | Appearance |
|---|---|---|
| 135 | 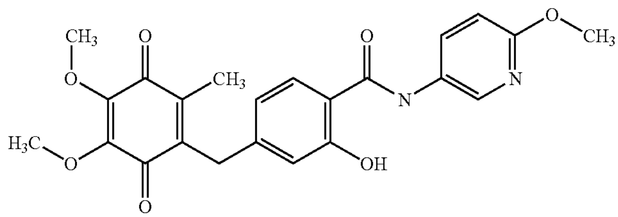 | orange crystals |
| 136 | 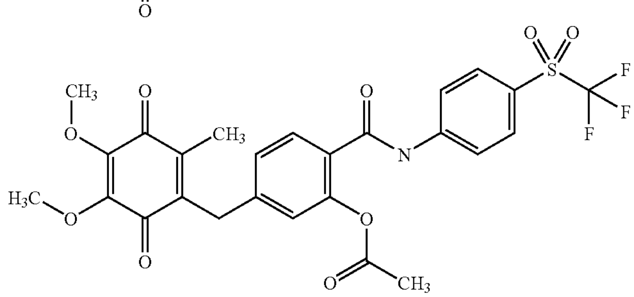 | orange amorphous |
| 137 | 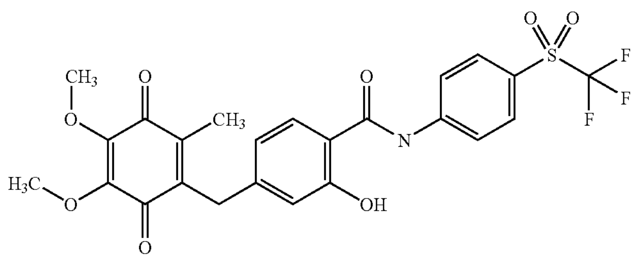 | orange crystals |
| 138 | 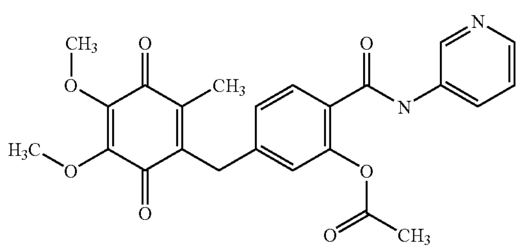 | orange crystals |

| Ex.No. | mp (° C.) | IR (cm-) | NMR (ppm) | FAB MS |
|---|---|---|---|---|
| 135 | 194.3–196.5 | 3335, 1651, 1612, 1552, 1497, 1266(KBr) | 2.08(3H, s), 3.85(2H, s), 3.96(3H, s), 4.00(3H, s), 4.01(3H, s), 6.73–6.82(3H, m), 7.48(1H, d, J=8.6 Hz), 7.91–8.00(2H, m), 8.28(1H, s), 11.91(1H, br s) | 439(M+ + 1) |
| 136 | | 1773, 1652, 1612, 1588, 1526, 1365, 1267, 1217(KBr) | 2.11(3H, s), 2.34(3H, s), 3.91(2H, s), 4.00(6H, s), 7.02(1H, s), 7.22(1H, d, J=8.0 Hz), 7.76(1H, d, J=8.0 Hz), 7.91(2H, d, J=8.9 Hz), 8.02(2H, d, J=8.8 Hz), 8.37(1H, s) | 582(M+ + 1) |
| 137 | 186.9–187.5 | 3138, 1679, 1652, 1612, 1438, 1341, 1292, 1264(KBr) | 2.09(3H, s), 3.86(2H, s), 4.00(3H, s), 4.01(3H, s), 6.81(1H, d, J=8.8 Hz), 6.82(1H, s), 7.46(1H, d, J=8.8 Hz), 7.93(2H, d, J=8.8 Hz), 8.05(2H, d, J=8.8 Hz), 8.23(1H, s), 11.35(1H, s) | 540(M+ + 1) |
| 138 | 158.2–160.0 | 1769, 1654, 1611, 1530, 1500, 1272, 1206(KBr) | 2.07(3H, s), 2.34(3H, s), 3.85(2H, s), 4.00(3H, s), 4.01(3H, s), 6.78–6.80(1H, m), 6.80(1H, s), 7.38–7.40(1H, m), 7.59(1H, d, J=8.2 Hz), 8.29–8.31(1H, m), 8.32–8.39(2H, m), 8.78(1H, s) | 451(M+ + 1) |

TABLE 41

| Ex.No. | Structure | Appearance |
|---|---|---|
| 139 | 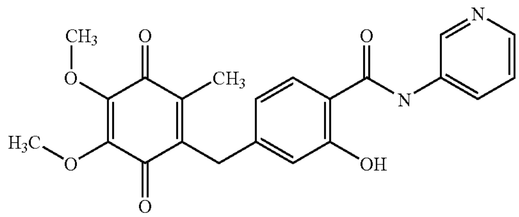 | orange crystals |
| 140 | 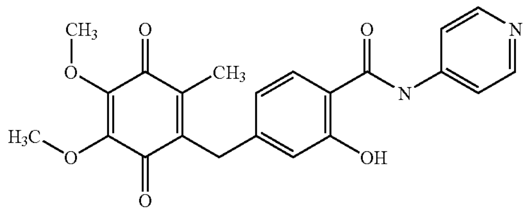 | orange crystals |
| 141 | 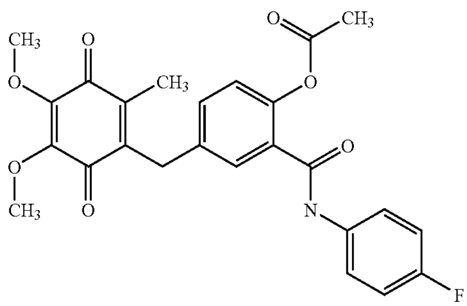 | yellow crystals |
| 142 | 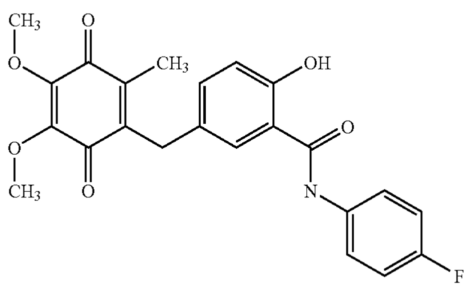 | yellow crystals |

| Ex.No. | mp (° C.) | IR (cm-) | NMR (ppm) | FAB MS |
|---|---|---|---|---|
| 139 | 138.1–139.7 | 3297, 1648, 1611, 1544, 1430, 1267(KBr) | 2.07(3H, s), 3.88(2H, s), 4.00(3H, s), 4.01(3H, s), 6.80(1H, s), 6.84(1H, d, J=8.4 Hz), 7.63–7.70(1H, m), 8.10(1H, d, J=8.3 Hz), 8.35–8.38(1H, m), 9.00(1H, d, J=9.3 Hz), 9.49(1H, s), 9.99(1H, s), 11.58–11.80(1H, br s) | 409(M+ + 1) |
| 140 | 181.4–183.3 | 3298, 1648, 1611, 1542, 1430, 1266(KBr) | 2.11(3H, s), 3.97(2H, s), 4.01(3H, s), 4.02(3H, s), 7.19–7.21(2H, m), 7.60–7.71(2H, m), 8.09–8.11(2H, m), 8.87–8.90(2H, m), 10.78–11.31(1H, br s) | 409(M+ + 1) |
| 141 | 128.5–130.5 | 1751, 1651, 1611, 1515, 1268(KBr) | 2.11(3H, s), 2.31(3H, s), 3.87(2H, s), 3.99(3H, s), 4.00(3H, s), 7.03–7.08(3H, m), 7.25–7.56(2H, m), 7.34(1H, dd, J=8.32, 2.16 Hz), 7.64–7.65(1H, m), 7.96(1H br s) | 468(M+ + 1), 154(100) |
| 142 | 125–127 | 3359, 1648, 1615, 1511, 1266(KBr) | 2.15(3H, s), 3.79(2H, s), 3.98(3H, s), 3.99(3H, s), 7.08(1H, d, J=2.08 Hz), 7.10–7.13(2H, m), 7.22(1H, dd, J=8.56 and 1.84 Hz), 7.43(1H, d, J=1.64 Hz), 7.51–7.55(2H, m), 7.93(1H br s), 11.75(1H, s) | 426(M+ + 1, 100) |

TABLE 42

| Ex.No. | Structure | Appearance |
|---|---|---|
| 143 | 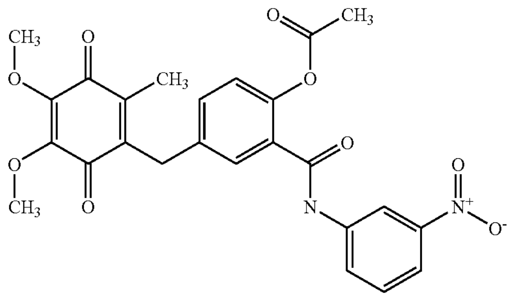 | yellow crystals |
| 144 | 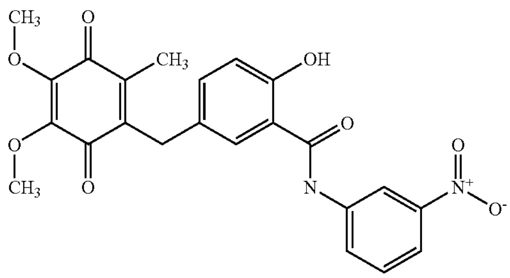 | yellow crystals |
| 145 | 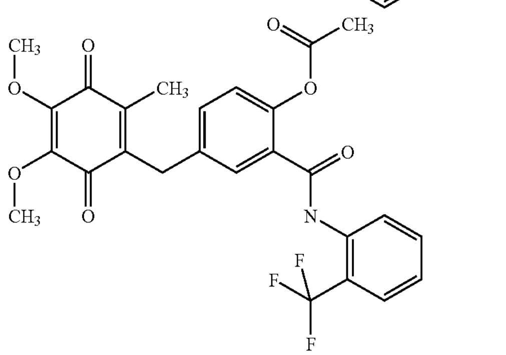 | yellow crystals |
| 146 | 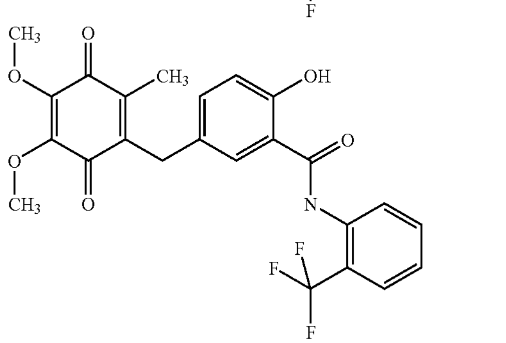 | yellow crystals |

| Ex.No. | mp (° C.) | IR (cm-) | NMR (ppm) | FAB MS |
|---|---|---|---|---|
| 143 | 152–153.5 | 1764, 1654, 1612, 1530, 1268(KBr) | 2.12(3H, s), 2.34(3H, s), 3.89(2H, s), 3.99(3H, s), 4.00(3H, s), 7.09(1H, d, J=8.32 Hz), 7.38(1H, dd, J=8.28, 2.04 Hz), 7.54(1H, t, J=8.16 Hz), 7.66(1H, d, J=1.72 Hz), 7.98–8.02(2H, m), 8.26–8.27(1H, m), 8.45(1H br s) | 495(M+ + 1), 154(100) |
| 144 | 153–154 | 3337, 1642, 1610, 1549, 1530, 1271(KBr) | 2.16(3H, s), 3.81(2H, s), 3.96(3H, s), 3.98(3H, s), 7.09(1H, d, J=8.52 Hz), 7.24–7.27(1H, m), 7.52(1H, d, J=1.68 Hz), 7.57(1H, t, J=8.24 Hz), 8.00–8.06(2H, m), 8.36(1H br s), 8.44–8.45(1H, m), 11.46(1H, s) | 453(M+ + 1), 154(100) |

TABLE 42-continued

| 145 | 57.5–60 | 1768, 1660, 1610, 1548, 1337, 1268(KBr) | 2.12(3H, s), 2.31(3H, s), 3.89(2H, s), 3.99(3H, s), 4.00(3H, s), 7.09(1H, d, J=8.32 Hz), 7.26–7.29(1H, m), 7.40(1H, m), 7.58–7.71(3H, m), 8.30–8.32(1H, m), 8.39(1H br s) | 518(M+ + 1), 476(100) |
| 146 | 111–114 | 3056, 1653, 1610, 1555, 1336, 1270(KBr) | 2.15(3H, s), 3.80(2H, s), 3.98(3H, s), 3.99(3H, s), 6.94(1H, d, J=8.56 Hz), 7.23–7.26(1H, m), 7.46–7.55(3H, m), 7.80(1H, d, J=7.88 Hz), 7.88–7.89(1H, m), 8.12(1H br s), 11.57(1H, s) | 476(M+ + 1, 100) |

TABLE 43

| Ex.No. | Structure | Appearance |
|---|---|---|
| 147 | [structure] | yellow crystals |
| 148 | [structure] | yellow crystals |
| 149 | [structure] | yellow crystals |

TABLE 43-continued

| | | | | |
|---|---|---|---|---|
| 150 | | | | yellow crystals |

| Ex.No. | mp (° C.) | IR (cm-) | NMR (ppm) | FAB MS |
|---|---|---|---|---|
| 147 | 154–156.5 | 1749, 1713, 1652, 1609, 1278, 1203(KBr) | 1.40(3H, t, J=7.08 Hz), 2.12(3H, s), 2.31(3H, s), 3.88(2H, s), 3.98(3H, s), 3.99(3H, s), 4.37(2H, q, J=14.24, 7.08 Hz), 7.07(1H, d, J=8.32 Hz), 7.36(1H, dd, J=8.40, 2.08 Hz), 7.65–7.68(3H, m), 8.05(2H, d, J=8.60 Hz), 8.19(1H br s) | 522(M+ + 1), 120(100) |
| 148 | 176–179 | 3351, 1702, 1648, 1608, 1534, 1285(KBr) | 1.41(3H, t, J=7.12 Hz), 2.15(3H, s), 3.79(2H, s), 3.97(3H, s), 3.98(3H, s), 4.39(2H, q, J=14.24, 7.12 Hz), 6.93(1H, d, J=8.52 Hz), 7.22–7.26(1H, m), 7.47(1H, d, J=1.44 Hz), 7.69(2H, d, J=8.64 Hz), 8.08(2H, d, J=8.64 Hz), 8.17(1H br s), 11.58(1H, s) | 480(M+ + 1), 154(100) |
| 149 | 125–128 | 2946, 1762, 1656, 1612, 1518, 1268, 1206(KBr) | 2.11(3H, s), 2.31(3H, s), 3.74(2H, s), 3.88(2H, s), 3.99(3H, s), 4.00(3H, s), 7.06(1H, d, J=8.32 Hz), 7.31–7.36(3H, m), 7.60–7.65(3H, m), 8.05(1H br s) | 489(M+ + 1), 154(100) |
| 150 | 164.5–166 | 3380, 2950, 1648, 1611, 1538, 1518, 1265(KBr) | 2.15(3H, s), 3.77(2H, s), 3.80(2H, s), 3.98(3H, s), 3.99(3H, s), 6.93(1H, d, J=8.56 Hz), 7.23(1H, dd, J=8.60 1.88 Hz), 7.36(2H, d, J=8.40 Hz), 7.44(1H, d, J=1.64 Hz), 7.61(2H, d, J=8.44 Hz), 8.03(1H br s), 11.70(1H, s) | 447(M+ + 1), 154(100) |

TABLE 44

| Ex.No. | Structure | Appearance |
|---|---|---|
| 151 | 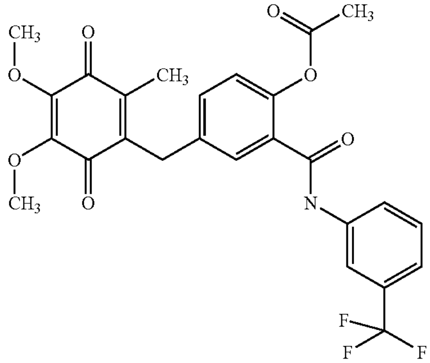 | yellow crystals |

TABLE 44-continued
| | | |
|---|---|---|
| 152 | 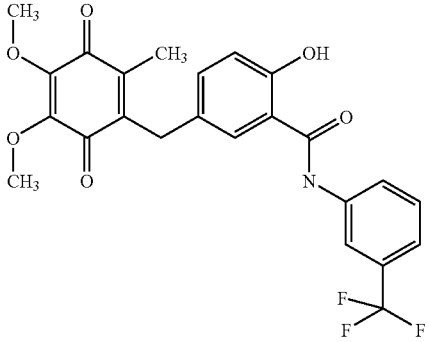 | yellow crystals |
| 153 | 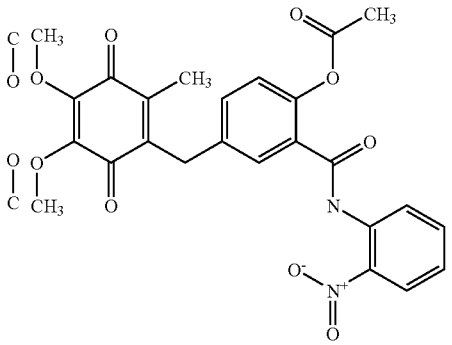 | yellow crystals |
| 154 | 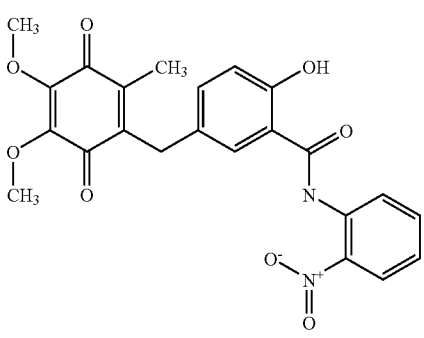 | yellow crystals |
| Ex.No. | mp (° C.) | IR (cm-) | NMR (ppm) | FAB MS |
|---|---|---|---|---|
| 151 | 98–100 | 1757, 1654, 1612, 1529, 1322, 1271(KBr) | 2.12(3H, s), 2.32(3H, s), 3.89(2H, s), 3.99(3H, s), 4.00(3H, s), 7.09(1H, d, J=8.40 Hz), 7.26–7.30(1H, m), 7.40(1H, dd, J=8.40, 2.20 Hz), 7.58–7.66(2H, m), 7.70–7.71(1H, m), 8.30–8.32(1H, m), 8.39(1H br s) | 518(M+ + 1), 476(100) |
| 152 | 127.5–130 | 3310, 1655, 1612, 1540, 1332, 1271(KBr) | 2.14(3H, s), 3.82(2H, s), 3.99(3H, s), 4.00(3H, s), 6.97(1H, d, J=8.56 Hz), 7.27–7.35(3H, m), 7.63(1H, t, J=8.04 Hz), 7.69(1H, d, J=7.84 Hz), 8.25–8.29(2H, m), 11.53(1H, s) | 476(M+ + 1, 100) |
| 153 | 97.5–100 | 1780, 1666, 1613, 1500, 1341, 1265(KBr) | 2.13(3H, s), 2.33(3H, s), 3.91(2H, s), 4.00(3H, s), 4.01(3H, s), 7.12(1H, d, J=8.36 Hz), 7.21–7.25(1H, m), 7.42(1H, d, J=8.36 Hz), 7.67–7.73(2H, m), 8.23(1H, d, J=8.36 Hz), 8.87(1H, d, J=8.90 Hz), 11.04(1H br s) | 495(M+ + 1), 154(100) |

TABLE 44-continued

| 154 | 155–156 | 3334, 1654, 1612, 1502, 1349, 1269(KBr) | 2.14(3H, s), 3.86(2H, s), 4.01(3H, s), 4.02(3H, s), 6.98(1H, d, J=8.48 Hz), 7.24–7.42(3H, m), 7.72(1H, t, J=7.90 Hz), 8.28(1H, dd, J=8.52, 1.40 Hz), 8.86(1H, d, J=7.88 Hz), 11.94(1H br s), 11.59(1H, s) | 453(M+ + 1), 154(100) |

TABLE 45

| Ex.No. | Structure | Appearance |
|---|---|---|
| 155 | 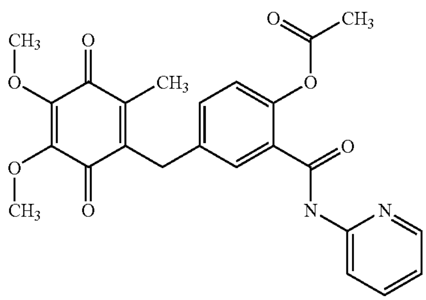 | yellow crystals |
| 156 | 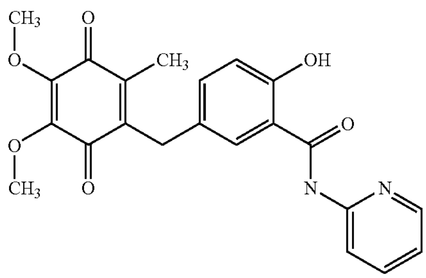 | yellow crystals |
| 157 | 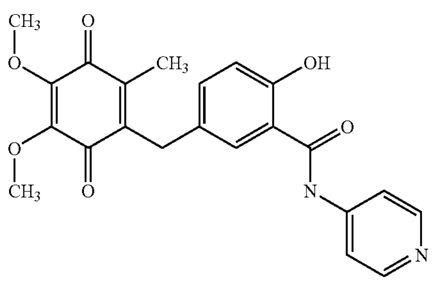 | yellow crystals |
| 158 | 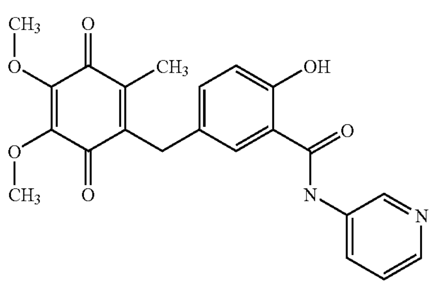 | yellow crystals |

| Ex.No. | mp (° C.) | IR (cm-) | NMR (ppm) | FAB MS |
|---|---|---|---|---|
| 155 | 124–126.5 | 1764, 1655, 1612, 1436, 1267, 1204(KBr) | 2.12(3H, s), 2.39(3H, s), 3.89(2H, s), 3.99(3H s), 4.00(3H, s), 7.05–7.11(2H, m), 7.38(1H, d, J=8.28 Hz), 7.71–7.80(2H, m), 8.27–8.32(2H, m), 8.95(1H br s) | 451(M+ + 1, 100) |

TABLE 45-continued

| 156 | 180–183 | 3281, 1683, 1665, 1610, 1439, 1309, 1264(KBr) | 2.13(3H, s), 3.80(2H, s), 3.98(3H, s), 3.99(3H, s), 6.91(1H, d, J=8.56 Hz), 7.11–7.15(1H, m), 7.21–7.26(1H, m), 7.56–7.57(1H, m), 7.77–7.80(1H, m), 8.32–8.34(2H, m), 9.07–9.08(1H, m), 11.99(1H br s) | 409(M+ + 1, 100) |
| --- | --- | --- | --- | --- |
| 157 | 171–172.5 | 3446, 1650, 1611, 1510, 1266, 1206(KBr) | 2.15(3H, s), 3.79(2H, s), 3.98(3H, s), 3.99(3H, s), 6.94(1H, d, J=8.52 Hz), 7.22–7.26(1H, m), 7.58(1H, s like), 7.64(2H, dd, J=4.88, 1.44 Hz), 8.56(2H, dd, J=4.80, 1.44 Hz), 8.78(1H, br s) | 409(M+ + 1), 154(100) |
| 158 | 119–122.5 | 3430, 1651, 1611, 1547, 126, 1206(KBr) | 2.14(3H, s), 3.79(2H, s), 3.98(3H, s), 3.99(3H, s), 6.94(1H, d, J=8.52 Hz), 7.22–7.26(1H, m), 7.34–7.38(1H, m), 7.56(1H, d, J=1.80 Hz), 8.20–8.22(1H, m), 8.41–8.43(1H, m), 8.64(1H br s), 8.69(1H, d, J=2.40 Hz) | 409(M+ + 1), 154(100) |

TABLE 46

| Ex.No. | Structure | Appearance |
| --- | --- | --- |
| 159 | 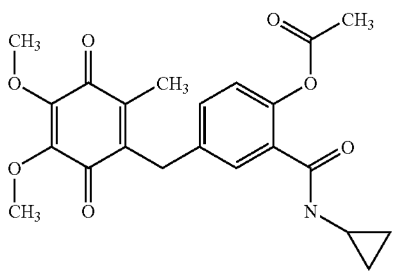 | yellow crystals |
| 160 | 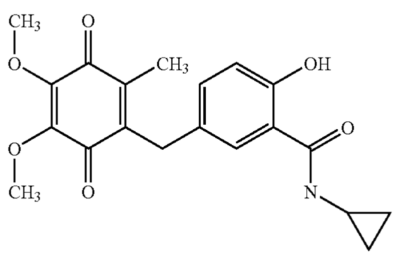 | yellow crystals |
| 161 | 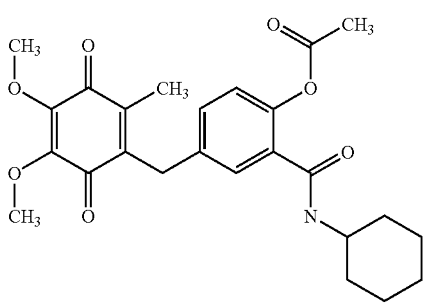 | yellow crystals |

TABLE 46-continued

| Ex.No. | Structure | Appearance |
|---|---|---|
| 162 | (2,3-dimethoxy-5-methyl-1,4-benzoquinone linked via CH2 to 2-hydroxy-5-substituted benzamide with N-cyclohexyl) | yellow crystals |

| Ex.No. | mp (° C.) | IR (cm-) | NMR (ppm) | FAB MS |
|---|---|---|---|---|
| 159 | 95.5–98 | 1759, 1642, 1611, 1264, 1208(KBr) | 0.53–0.57(2H, m), 0.83–0.89(2H, m), 2.09(3H, s), 2.30(3H, s), 2.83–2.87(1H, m), 3.84(2H, s), 3.99(3H, s), 4.00(3H, s), 6.28–6.29(1H, m), 6.98(1H, d, J=8.32 Hz), 7.26–7.28(1H, m), 7.51–7.52(1H, m) | 414(M+ + 1), 154(100) |
| 160 | 111–112 | 3365, 1642, 1611, 1536, 1268(KBr) | 0.65–0.69(2H, m), 0.88–0.93(2H, m), 2.12(3H, s), 2.83–2.87(1H, m), 3.73(2H, s), 3.98(3H, s), 3.99(3H, s), 6.40–6.42(1H, m), 6.87(1H, d, J=9.04 Hz), 7.14–7.17(2H, m), 12.20(1H, s) | 372(M+ + 1), 154(100) |
| 161 | 137.5–140 | 1766, 1638, 1610, 1534, 1265, 1218(KBr) | 1.31–1.46(5H, m), 1.55–1.75(3H, m), 1.98–2.01(2H, m), 2.09(3H, s), 2.31(3H, s), 3.84(2H, s), 3.80–3.95(1H, m), 3.99(3H, s), 4.00(3H, s), 6.07–6.10(1H, m), 6.98(1H, d, J=8.32 Hz), 7.25–7.27(1H, m), 7.53(1H, d, J=2.00 Hz) | 456(M+ + 1), 154(100) |
| 162 | 107–109 | 3372, 1644, 1615, 1543, 1265(KBr) | 1.20–1.48(5H, m), 1.66–1.82(3H, m), 2.00–2.04(2H, m), 2.13(3H, s), 3.75(2H, s), 3.93–3.97(1H, m), 3.99(3H, s), 4.00(3H, s), 6.08–6.10(1H, m), 6.86(1H, d, J=8.48 Hz), 7.13(1H, dd, J=8.52, 1.92 Hz), 7.20(1H, d, J=1.76 Hz), 12.30(1H, s) | 414(M+ + 1), 154(100) |

TABLE 47

| Ex.No. | Structure | Appearance |
|---|---|---|
| 163 | (2,3-dimethoxy-5-methyl-1,4-benzoquinone linked via CH2 to 2-acetoxy-substituted benzamide with N-methyl-N-(4-methoxyphenyl)) | yellow oil |
| 164 | (2,3-dimethoxy-5-methyl-1,4-benzoquinone linked via CH2 to 2-hydroxy-substituted benzamide with N-methyl-N-(4-methoxyphenyl)) | yellow oil |

TABLE 47-continued

| Ex.No. | Structure | Appearance |
|---|---|---|
| 165 | (structure) | yellow crystals |
| 166 | (structure) | yellow crystals |

| Ex.No. | mp (° C.) | IR (cm-) | NMR (ppm) | FAB MS |
|---|---|---|---|---|
| 163 | | 1766, 1646, 1610, 1511, 1249(NaCl) | 1.85(3H, s), 2.30(3H, s), 3.39(3H, s like), 3.59(2H, s), 3.71(3H, s like), 3.99(3H, s), 4.01(3H, s), 6.63–6.74(3H, m), 6.91–7.08(4H, m) | 494(M+ + 1), 154(100) |
| 164 | | 3350, 1647, 1610, 1510, 1248(NaCl) | 1.76(3H, s), 3.38–3.40(5H, m), 3.77(3H, s), 3.98(3H, s), 4.00(3H, s), 6.50(1H, d, J=1.76 Hz), 6.74(2H, d, J=8.88 Hz), 6.84(1H, d, J=8.44 Hz), 6.95(2H, d, J=8.84 Hz), 7.04(1H, dd, J=8.48, 2.12 Hz), 10.68(1H, s) | 452(M+ + 1), 154(100) |
| 165 | 163–166 | 1764, 1667, 1614, 1533, 1319(KBr) | 2.00(3H, s), 2.31(3H, s), 3.79(2H, s), 4.00(3H, s), 4.01(3H, s), 7.21–7.29(2H, m), 7.56–7.63(3H, m), 7.71(2H, d, J=8.52 Hz), 7.87(1H br s) | 518(M+ + 1), 154(100) |
| 166 | 129–131.5 | 3384, 1640, 1608, 1537, 1336(KBr) | 2.10(3H, s), 3.89(2H, s), 3.99(3H, s), 4.00(3H, s), 6.86(1H, t, J=7.76 Hz), 7.29–7.31(1H, m), 7.48(1H, d, J=7.64 Hz), 7.65(2H, d, J=8.60 Hz), 7.74(2H, d, J=8.52 Hz), 8.32(1H br s), 11.93(1H, s) | 476(M+ + 1), 154(100) |

TABLE 48

| Ex.No. | Structure | Appearance |
|---|---|---|
| 167 | (structure) | yellow crystals |

TABLE 48-continued
| 168 | 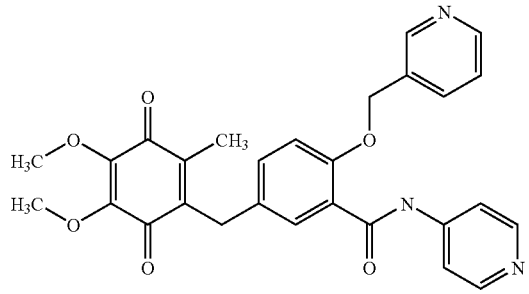 | yellow crystals |
| 169 | 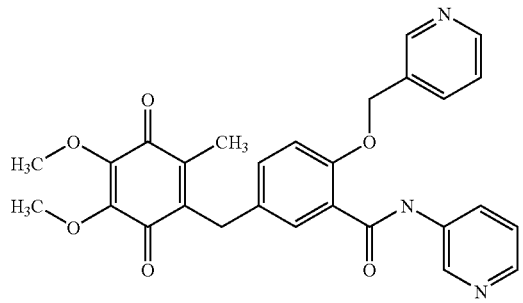 | yellow crystals |
| 170 | 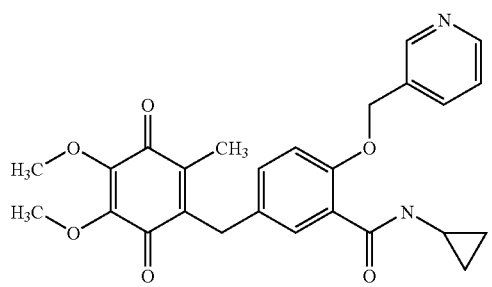 | yellow crystals |
| Ex.No. | mp (° C.) | IR (cm-) | NMR (ppm) | FAB MS |
|---|---|---|---|---|
| 167 | 83–85.5 | 1710, 1654, 1610, 1537, 1277(KBr) | 1.38(3H, t, J=7.08 Hz), 2.12(3H, s), 3.87(2H, s), 3.99(3H, s), 4.00(3H, s), 4.32–4.37(2H, m), 5.24(2H, s), 7.06(1H, d, J=8.52 Hz), 7.30(2H, d, J=8.60 Hz), 7.38–7.43(2H, m), 7.84–7.93(3H, m), 8.10(1H, d, J=1.56 Hz), 8.74–8.80(2H, m), 9.87(1H, br s) | 571(M+ + 1), 154(100) |
| 168 | 116–119 | 1677, 1648, 1610, 1590, 1517, 1264(KBr) | 2.13(3H, s), 3.87(2H, s), 3.99(3H, s), 4.00(3H, s), 5.24(2H, s), 7.07(1H, d, J=8.56 Hz), 7.14(2H, d, J=5.16 Hz), 7.40–7.45(2H, m), 7.83–7.86(1H, m), 8.08(1H, s like), 8.40(2H, d, J=5.32 Hz), 8.76(1H, d, J=4.72 Hz), 8.81(1H, br s), 9.82(1H br s) | 500(M+ + 1), 154(100) |
| 169 | 135–137 | 1672, 1609, 1543, 1425, 1264(KBr) | 2.12(3H, s), 3.88(2H, s), 3.99(3H, s), 4.00(3H, s), 5.25(2H, s), 7.06(1H, d, J=8.48 Hz), 7.20–7.24(1H, m), 7.38–7.45(2H, m), 7.85(1H, d, J=7.76 Hz), 8.09–8.11(3H, m), 8.29(1H, d, J=4.52 Hz), 8.73–8.79(2H m), 9.75(1H, br s) | 500(M+ + 1), 154(100) |
| 170 | 87–89.5 | 1651, 1610, 1498, 1264(KBr) | 0.27–0.29(2H, m), 0.71–0.73(2H, m), 2.10(3H, s), 2.84–2.87(1H, m), 3.83(2H, s), 3.98(3H, s), 3.99(3H, s), 5.13(2H, s), 6.94(1H, d, J=8.48 Hz), 7.26–7.40(2H, m), 7.70–7.76(2H, m), 8.00(1H, s like), 8.67–8.69(2H, m) | 463(M+ + 1), 154(100) |

TABLE 49

| Ex.No. | Structure | Appearance |
|---|---|---|
| 171 | 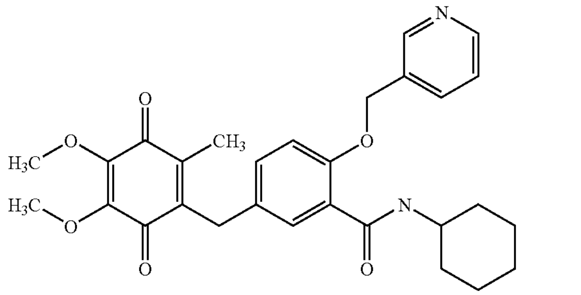 | yellow crystals |
| 172 | 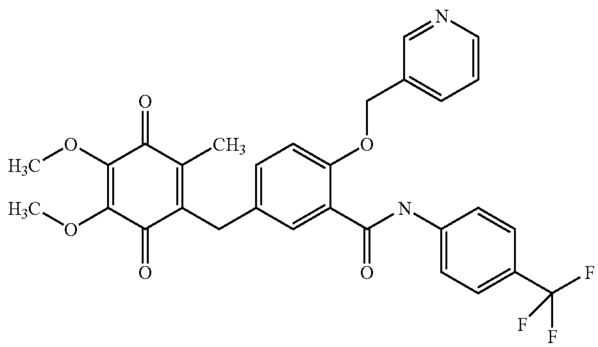 | yellow crystals |
| 173 | 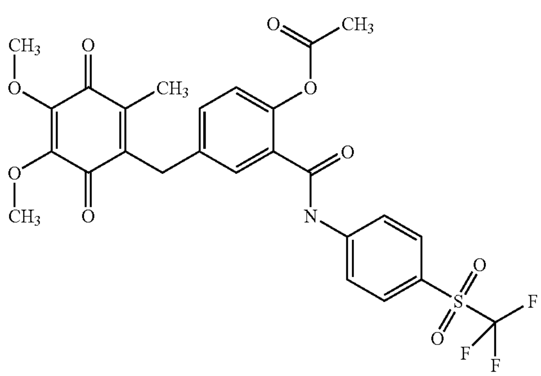 | yellow crystals |
| 174 | 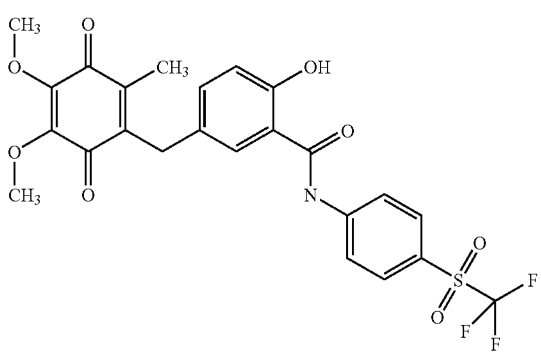 | yellow crystals |

| Ex.No. | mp (° C.) | IR (cm-) | NMR (ppm) | FAB MS |
|---|---|---|---|---|
| 171 | 115–118 | 2933, 1630, 1610, 1289(KBr) | 0.94–1.47(8H, m), 1.77–1.80(2H, m), 2.10(3H, s), 3.84(2H, s), 3.84–3.98(1H, m), 3.99(3H, s), 4.00(3H, s), 5.13(2H, s), 6.96(1H, d, J=8.52 Hz), 7.26–7.39(2H, m), 7.58–7.60(1H, m), 7.78(1H, d, J=7.76 Hz), 8.00(1H, d, J=2.32 Hz), 8.66–8.73(2H, m) | 505(M+ + 1, 100) |

TABLE 49-continued

| 172 | 173–176 | 1676, 1610, 1541, 1324, 1265(KBr) | 2.13(3H, s), 3.88(2H, s), 3.99(3H, s), 4.00(3H, s), 5.24(2H, s), 7.06(1H, d, J=8.48 Hz), 7.34–7.49(6H, m), 7.82–7.85(1H, m), 8.10(1H, d, J=2.36 Hz), 8.74–8.81(2H, m), 9.85(1H, br s) | 567(M+ + 1), 154(100) |
| --- | --- | --- | --- | --- |
| 173 | 84.5–87 | 1770, 1652, 1612, 1588, 1525, 1217(KBr) | 2.13(3H, s), 2.33(3H, s), 3.88(2H, s), 3.99(3H, s), 4.00(3H, s), 7.09(1H, d, J=8.40 Hz), 7.39(1H, dd, J=8.40, 2.16 Hz), 7.65(1H, d, J=2.16 Hz), 7.90(2H, d, J=8.92 Hz), 8.02(2H, d, J=8.76 Hz), 8.42(1H, br s) | 582(M+ + 1), 540(100) |
| 174 | 223–225.5 | 3325, 1656, 1613, 1584, 1537, 1211(KBr) | 2.17(3H, s), 3.80(2H, s), 3.99(3H, s), 4.00(3H, s), 6.95–6.97(1H, m), 7.50–7.52(1H, m), 7.97(2H, d, J=8.52 Hz), 8.06(2H, d, J=8.76 Hz), 8.40–8.42(1H, m), 11.00(1H, br s) | 540(M+ + 1), 154(100) |

TABLE 50

| Ex. No. | Structure | Appearance | mp (°C.) | IR (cm-) | NMR (ppm) | FAB MS |
| --- | --- | --- | --- | --- | --- | --- |
| 175 | [structure] | yellow crystals | 87–89 | 1770, 1653, 1612, 1589, 1365, 1216, (KBr) | 2.01 (3H, s), 2.33 (3H, s), 3.80 (2H, s), 3.99 (3H, s), 4.02 (3H, s), 724–730 (2H, m), 7.58 (1H, d, J=7.36 Hz), 7.90 (2H, d, J=8.88 Hz), 8.01 (2H, d J=8.76 Hz), 8.19 (1H, br s) | 582 (M+ +1), 154 (100) |
| 176 | [structure] | yellow oil | | 1769, 1651, 1610, 1507, 1269, 1194 (KBr) | 2.01 (3H, s), 2.35 (3H, s), 3.80(2H, s), 3.99 (3H, s), 4.00 (3H, s), 721–731 (3H, m), 7.42 (1H, d, J=2.36 Hz), 7.65 (1H, d, J=7.56 Hz), 8.29 (1H, br s), 8.48 (1H, d, J=8.92 Hz) | 519 (M+ +1), 154 (100) |
| 177 | [structure] | yellow crystals | 147–150 | 3422, 1651, 1610, 1590, 1529, 1269, (KBr) | 2.09 (3H, s), 3.89 (2H, s), 3.99 (3H, s), 4.00 (3H, s), 6.87 (1H, t, J=7.76 Hz), 7.29–7.33 (2H, m), 7.45–7.48 (2H, m), 8.39 (1H, d, J=8.88 Hz), 8.66 (1H, br s), 12.00 (1H, s) | 477 (M+ +1), 154 (100) |
| 178 | [structure] | yellow crystals | 168–171 | 1762, 1650, 1612, 1451, 1269 (KBr) | 2.00 (3H, s), 2.31 (3H, s), 3.12–3.15 (4H, m), 3.78 (2H, s), 3.85–3.88 (4H, M0, 4.00 (3H, s), 4.01 (3H, s), 6.89–6.92 (2H, m), 7.19–7.25 (2H, m), 7.46–7.49 (2H, m), 7.56–7.60 (2H, m) | 534 (M+), 154 (100) |

TABLE 51

| Ex.No. | Structure | Appearance |
|---|---|---|
| 179 | [structure: 2,3-dimethoxy-5-methyl-1,4-benzoquinone linked via CH2 to 2-hydroxy-benzamide with N-(4-morpholinophenyl)] | yellow crystals |
| 180 | [structure: 2,3-dimethoxy-5-methyl-1,4-benzoquinone linked via CH2 to 2-acetoxy-benzamide with N-(6-methoxypyridin-3-yl)] | yellow crystals |
| 181 | [structure: 2,3-dimethoxy-5-methyl-1,4-benzoquinone linked via CH2 to 2-hydroxy-benzamide with N-(6-methoxypyridin-3-yl)] | yellow crystals |
| 182 | [structure: 2,3-dimethoxy-5-methyl-1,4-benzoquinone linked via CH2 to 2-acetoxy-benzamide with N-(2,6-dimethoxypyridin-3-yl)] | yellow oil |

| Ex.No. | mp (° C.) | IR (cm-) | NMR (ppm) | FAB MS |
|---|---|---|---|---|
| 179 | 177.5–180.5 | 3422, 1648, 1611, 1518, 1266(KBr) | 2.07(3H, s), 3.14–3.17(4H, m), 3.85–3.89(6H, m), 3.99(3H, s), 4.00(3H, s), 6.81(1H, t, J=7.84 Hz), 6.93(1H, d, J=8.96 Hz), 7.24–7.26(1H, m), 7.38(1H, d J=7.88 Hz), 7.44(2H, d, J=8.92 Hz), 7.89(1H, br s), 12.44(1H, s) | 492(M+), 154(100) |

TABLE 51-continued

| 180 | 104.5–107.5 | 1761, 1654, 1612, 1495, 1286, 1205(KBr) | 2.11(3H, s), 2.32(3H, s), 3.87(2H, s), 3.93(3H, s), 3.99(3H, s), 4.00(3H, s), 6.77(1H, d, J=8.80 Hz), 7.06(1H, d, J=8.32 Hz), 7.34(1H, dd, J=8.32, 1.96 Hz), 7.66(1H, br s), 7.95–8.03(2H, m), 8.20(1H, d, J=2.40 Hz) | 481(M+ + 1), 154(100) |
|---|---|---|---|---|
| 181 | 169–170 | 3134, 1639, 1608, 1492, 1267(KBr) | 2.14(3H, s), 3.78(2H, s), 3.95(3H, s), 3.97(3H, s), 3.98(3H, s), 6.79(1H, d, J=8.84 Hz), 6.92(1H, d, J=8.56 Hz), 7.22(1H, dd, J=8.56, 1.72 Hz), 7.46(1H, d, J=1.32 Hz), 7.87(1H, dd, J=8.80, 2.64 Hz), 8.06(1H, s like), 8.23(1H, d, J=2.60 Hz), 11.77(1H, s) | 439(M+ + 1), 154(100) |
| 182 | | 1773, 1663, 1610, 1522, 1265(KBr) | 2.12(3H, s), 2.38(3H, s), 3.89(2H, s), 3.91(3H, s), 3.99(3H, s), 4.00(3H, s), 4.03(3H, s), 6.35(1H, d, J=8.52 Hz), 7.08(1H, d, J=8.36 Hz), 7.35(1H, dd, J=8.36, 2.24 Hz), 7.81(1H, d, J=2.04 Hz), 8.60(1H, br s), 8.66(1H, d, J=8.56 Hz) | 510(M+), 154(100) |

TABLE 52

| Ex.No. | Structure | Appearance |
|---|---|---|
| 183 | 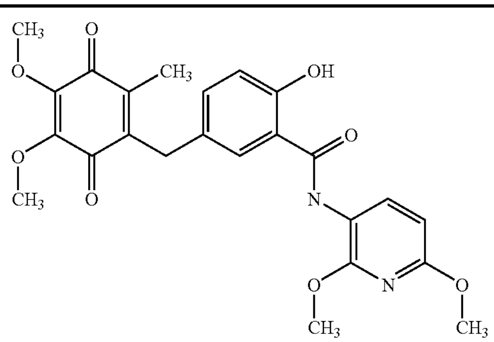 | yellow crystals |
| 184 | 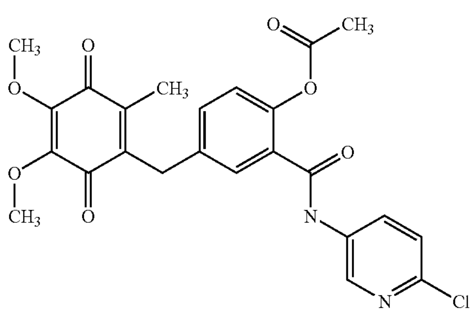 | yellow crystals |
| 185 | 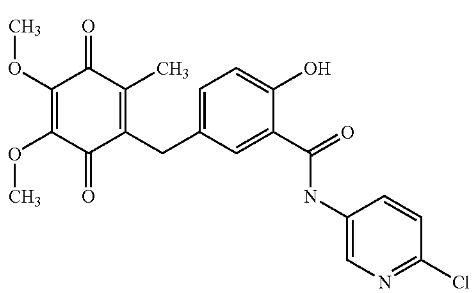 | yellow crystals |

TABLE 52-continued
| 186 | 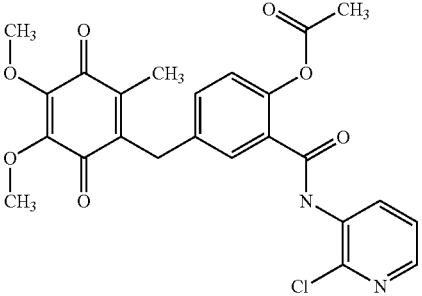 | yellow crystals |
| Ex.No. | mp (° C.) | IR (cm-) | NMR (ppm) | FAB MS |
|---|---|---|---|---|
| 183 | 119–121.5 | 3234, 1651, 1611, 1563, 1265(KBr) | 2.17(3H, s), 3.82(2H, s), 3.92(3H, s), 3.99(3H, s), 4.00(3H, s), 4.07(3H, s), 6.36(1H, d, J=8.52 Hz), 6.92(1H, d, J=8.56 Hz), 7.24(1H, d, J=1.60 Hz), 7.34(1H, br s), 8.20(1H, br s), 8.46(1H, br s), 11.85(1H, s) | 469(M+ + 1), 154(100) |
| 184 | 74.5–77.5 | 1768, 1649, 1611, 1525, 1464, 1203(KBr) | 2.12(3H, s), 2.33(3H, s), 3.88(2H, s), 3.99(3H, s), 4.00(3H, s), 7.08(1H, d, J=8.36 Hz), 7.33–7.38(2H, m), 7.66(1H, br s), 8.14–8.26(2H, m), 8.41(1H, br s) | 485(M+ + 1), 154(100) |
| 185 | 166–169 | 3451, 1651, 1611, 1537, 1464, 1268(KBr) | 2.16(3H, s), 3.80(2H, s), 3.98(3H, s), 3.99(3H, s), 6.94(1H, d, J=8.56 Hz), 7.24–7.26(1H, m), 7.38(1H, d, J=8.64 Hz), 7.48(1H, br s), 8.12–8.18(2H, m), 8.52(1H, br s), 11.40(1H, br s) | 443(M+ + 1), 154(100) |
| 186 | 128.5–130 | 1770, 1669, 1609, 1517, 1273, 1201(KBr) | 2.13(3H, s), 2.39(3H, s), 3.90(2H, s), 3.99(3H, s), 4.00(3H, s), 7.11(1H, d, J=8.40 Hz), 7.26–7.40(1H, m), 7.42(1H, d, J=2.12 Hz), 7.79(1H, d, J=2.04 Hz), 8.14–8.16(1H, m), 8.81(1H, br s), 8.91(1H, dd, J=8.16, 1.36 Hz) | 485(M+ + 1), 154(100) |
TABLE 53
| Ex.No. | Structure | Appearance |
|---|---|---|
| 187 | 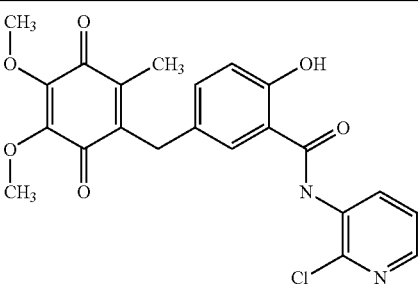 | yellow crystals |

TABLE 53-continued
| 188 | 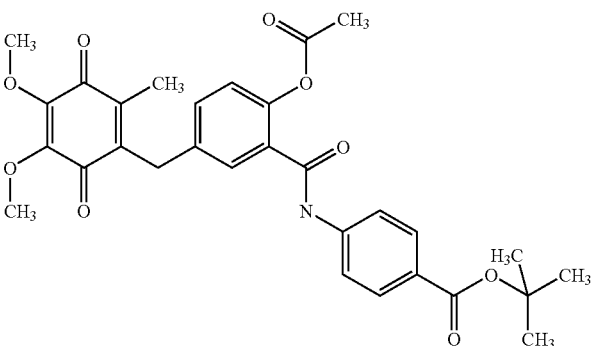 | yellow crystals |
| 189 | 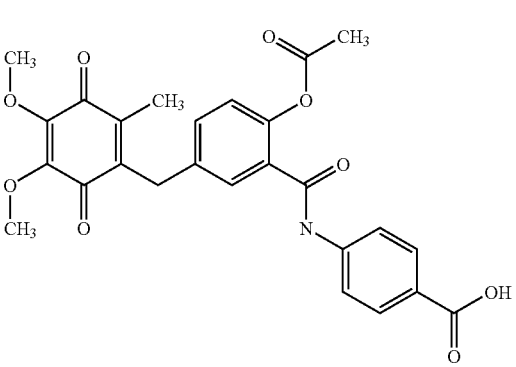 | yellow crystals |
| 190 | 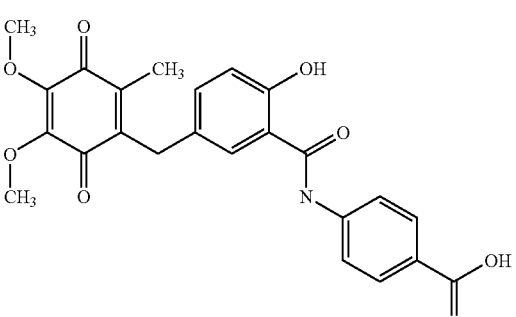 | yellow crystals |
| Ex.No. | mp (° C.) | IR (cm-) | NMR (ppm) | FAB MS |
|---|---|---|---|---|
| 187 | 152–154 | 3280, 1652, 1612, 1534, 1502, 1267, 1209(KBr) | 2.15(3H, s), 3.83(2H, s), 3.99(3H, s), 4.00(3H, s), 6.96(1H, d, J=8.56 Hz), 7.31–7.35(2H, m), 7.43(1H, s like), 8.19(1H, dd, J=4.56, 1.44 Hz), 8.60(1H, br s), 8.80(1H, dd, J=8.16, 1.48 Hz), 11.33(1H, br s) | 443(M+ + 1), 154(100) |
| 188 | 78.5–81 | 1769, 1709, 1651, 1611, 1529, 1294, 1164(KBr) | 1.60(9H, s), 2.12(3H, s), 2.31(3H, s), 3.88(2H, s), 3.99(3H, s), 4.00(3H, s), 7.07(1H, d, J=8.32 Hz), 7.35(1H, dd, J=8.40, 2.08 Hz), 7.63–7.67(3H, m), 7.99(2H, d, J=8.60 Hz), 8.16(1H, br s) | 550(M+ + 1), 154(100) |
| 189 | 199–201.5 | 3256, 1749, 1720, 1653, 1608, 1533, 1270, 1202(KBr) | 2.12(3H, s), 2.33(3H, s), 3.88(2H, s), 3.99(3H, s), 4.00(3H, s), 7.08(1H, d, J=8.48 Hz), 7.36(1H, dd, J=8.52, 1.64 Hz), 7.66–7.72(3H, m), 8.11(2H, d, J=8.20 Hz), 8.28(1H, br s) | 494(M+ + 1), 154(100) |

TABLE 53-continued
| 190 | 257–260 | 3139, 1700, 1641, 1611, 1552, 1431, 1263(KBr) | 2.00(3H, s), 3.76(2H, s), 3.88(3H, s), 3.89(3H, s), 6.91(1H, d, J=8.36 Hz), 7.20(1H, d, J=8.08 Hz), 7.67(1H, br s), 7.82(2H, d, J=8.44 Hz), 7.93(2H, d, J=8.48 Hz), 10.56(1H, br s), 11.28(1H, br s), 12.76(1H, br s) | 452(M+ + 1), 154(100) |
TABLE 54
| Ex.No. | Structure | Appearance |
|---|---|---|
| 191 | 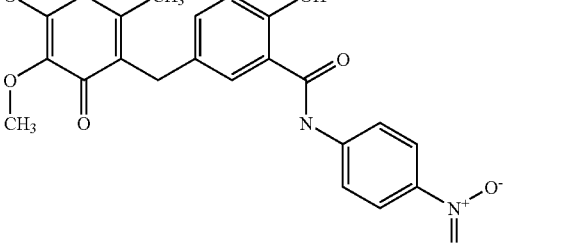 | yellow crystals |
| 192 | 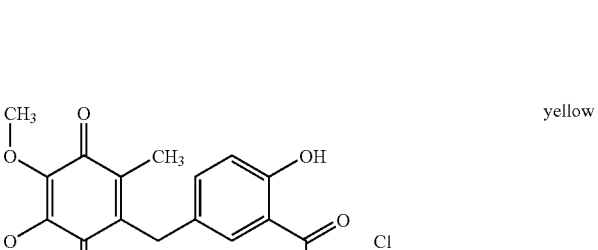 | yellow crystals |
| 193 | 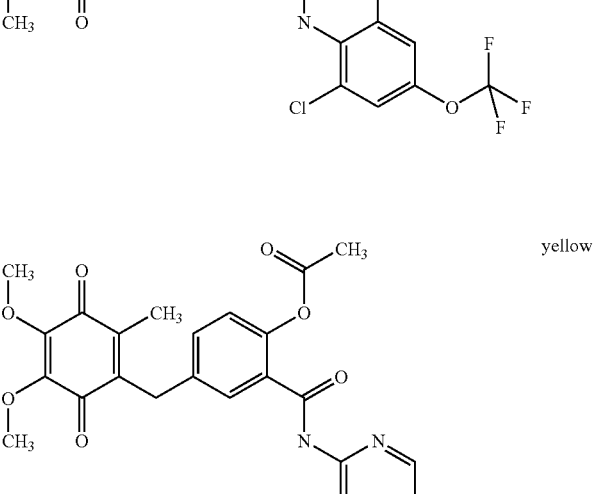 | yellow oil |

TABLE 54-continued
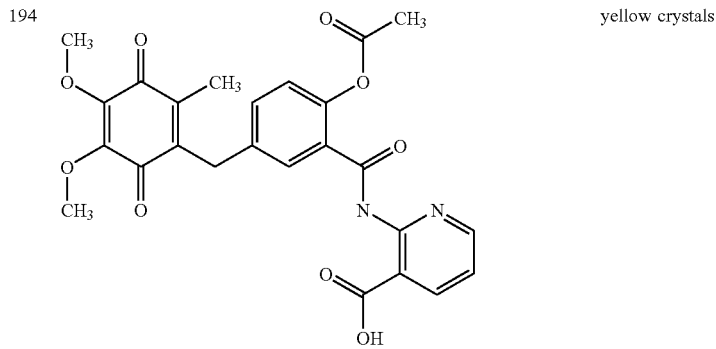
| 194 | | yellow crystals |
| Ex.No. | mp (° C.) | IR (cm-) | NMR (ppm) | FAB MS |
|---|---|---|---|---|
| 191 | 213.5–215.5 | 3328, 1651, 1614, 1560, 1503, 1332(KBr) | 2.17(3H, s), 3.81(2H, s), 3.99(3H, s), 4.00(3H, s), 6.95(1H, d, J=8.52 Hz), 7.25–7.26(1H, m), 7.50(1H, s like), 7.83(2H, d, J=9.04 Hz), 8.29(2H, d, J=9.04 Hz), 8.35(1H, br s), 11.32(1H, br s) | 453(M+ + 1), 154(100) |
| 192 | 138–141 | 3324, 1651, 1610, 1510, 1268, 1224(KBr) | 2.16(3H, s), 3.82(2H, s), 3.98(3H, s), 3.99(3H, s), 6.96(1H, d, J=8.56 Hz), 7.28–7.36(3H, m), 7.53(1H, d, J=1.48 Hz), 7.72(1H, br s), 11.37(1H, s) | 560(M+), 154(100) |
| 193 | | 1764, 1712, 1651, 1610, 1306, 1265, 1123(NaCl) | 1.64(9H, s), 2.14(3H, s), 2.29(3H, s), 3.89(2H, s), 3.98(3H, s), 3.99(3H, s), 6.94–7.15(3H, m), 7.37–7.71(2H, m), 8.26–8.70(2H, m) | 551(M+ + 1), 154(100) |
| 194 | 148–151 | 3402, 1768, 1654, 1610, 1492, 1266, 1201(KBr) | 2.02(3H, s), 2.16(3H, s), 3.85(2H, s), 3.89(3H, s), 3.90(3H, s), 7.10–7.16(2H, m), 7.36(1H, d, J=6.72 Hz), 7.56(1H, br s), 8.22(1H, d, J=6.32 Hz), 8.35–8.36(1H, m) | 495(M+ + 1), 154(100) |
TABLE 55
| Ex.No. | Structure | Appearance |
|---|---|---|
| 195 | 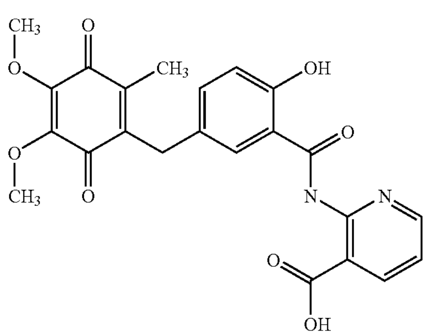 | yellow crystals |

TABLE 55-continued

| Ex.No. | mp (° C.) | IR (cm-) | NMR (ppm) | FAB MS |
|---|---|---|---|---|
| 195 | 134–136.5 | 3410, 2951, 1656, 1609, 1268(KBr) | 2.01(3H, s), 3.76(2H, s), 3.88(3H, s), 3.89(3H, s), 6.93(1H, d, J=8.36 Hz), 7.25(1H, d, J=8.48 Hz), 7.32–7.36(1H, m), 7.75(1H, br s), 8.24(1H, d, J=7.68 Hz), 8.57(1H, d, J=4.68 Hz), 11.58(1H, br s) | 453(M+ + 1), 154(100) |
| 196 | | 2980, 1769, 1687, 1650, 1610, 1448, 1265, 1140(NaCl) | 1.60(9H, s), 2.12(3H, s), 2.39(3H, s), 3.88(2H, s), 3.98(3H, s), 3.99(3H, s), 7.11(1H, d, J=8.36 Hz), 7.39(1H, dd, J=8.28, 1.64 Hz), 7.81(1H, d, J=1.60 Hz), 8.26–8.38(2H, m), 8.82–8.84(1H, m), 8.29(1H, br s) | 551(M+ + 1), 154(100) |
| 197 | 123–125 | 3410, 2948, 1769, 1698, 1654, 1612, 1267(KBr) | 2.02(3H, s), 2.18(3H, s), 3.85(2H, s), 3.89(3H, s), 3.90(3H, s), 7.14(1H, d, J=8.36 Hz), 7.38(1H, dd, J=8.40, 1.92 Hz), 7.52(1H, d, J=1.88 Hz), 8.18–8.30(2H, m), 8.83–8.84(1H, m), 11.08(1H, s), 12.90–13.50(1H, br s) | 495(M+ + 1), 154(100) |

TABLE 55-continued

| 198 | 238–241 | 3280, 2954, 1654, 1611, 1533, 1311, 1267(KBr) | 2.00(3H, s), 3.77(2H, s), 3.88(3H, s), 3.89(3H, s), 6.98(1H, d, J=8.36 Hz), 7.25–7.28(1H, m), 7.82(1H, d J=1.88 Hz), 8.30–8.38(2H, m), 8.84(1H, s), 11.16(1H, br s), 11.60–11.80(1H, m), 13.17–13.20(1H, m) | 453(M+ + 1), 154(100) |

TABLE 56

| Ex.No. | Structure | Appearance |
|---|---|---|
| 199 | 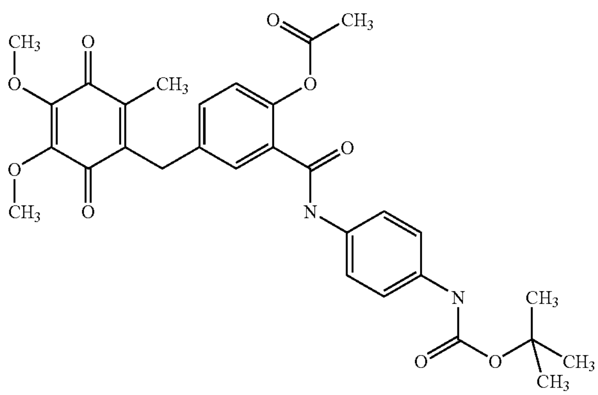 | yellow crystals |
| 200 | 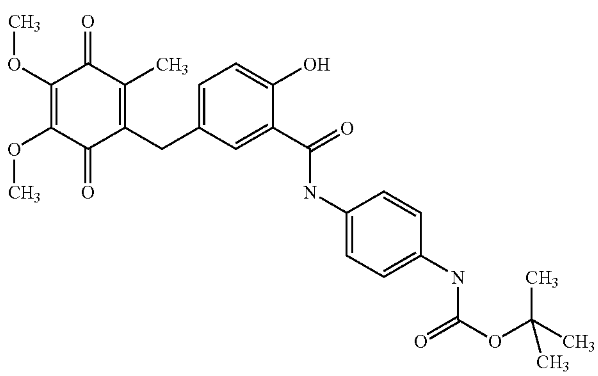 | yellow crystals |
| 201 | 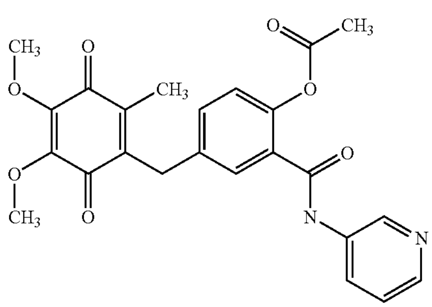 | yellow oil |

TABLE 56-continued

| Ex.No. | mp (° C.) | IR (cm-) | NMR (ppm) | FAB MS |
|---|---|---|---|---|
| 199 | 188.5–191 | 1764, 1654, 1611, 1520, 1268, 1163(KBr) | 1.59(9H, s), 2.14(3H, s), 2.29(3H, s), 3.89(2H, s), 3.98(3H, s), 3.99(3H, s), 7.07–7.12(2H, m), 7.39(1H, dd, J=8.32, 1.88 Hz), 7.70(1H, d, J=1.76 Hz), 8.27(1H, dd, J=7.80, 1.68 Hz), 8.64–8.66(1H, m), 11.48(1H, br s) | 565(M+ + 1), 154(100) |
| 200 | 127–129 | 3352, 1699, 1648, 1610, 1520, 1269, 1159(KBr) | 1.53(9H, s), 2.14(3H, s), 3.79(2H, s), 3.98(3H, s), 3.99(3H, s), 6.50(1H, br s), 6.89–6.92(1H, m), 7.19–7.25(1H, m), 7.38–7.50(5H, m), 7.97(1H, br s), 11.86(1H, s) | 523(M+ + 1), 154(100) |
| 201 |  | 1764, 1651, 1609, 1538, 1264(NaCl) | 2.10(3H, s), 2.32(3H, s), 3.87(2H, s), 3.98(3H, s), 3.99(3H, s), 7.06–7.09(1H, m), 7.27–7.36(2H, m), 7.65(1H, br s), 8.25–8.38(3H, m), 8.57–8.58(1H, m) | 451(M+ + 1), 154(100) |
| 202 | 149.5–152 | 3416, 3080, 1672, 1649, 1612, 1549, 1150(KBr) | 2.11(3H, s), 2.94(3H, s), 3.85(2H, s), 3.98(3H, s), 3.99(3H, s), 6.91(1H, d, J=8.56 Hz), 7.16(1H, d, J=7.32 Hz), 7.79–7.83(1H, m), 8.02(1H, br s), 8.41(1H, d, J=4.72 Hz), 9.24(1H, d, J=8.88 Hz), 9.53(1H, br s), 11.04(1H,br s) | 409(M+ + 1), 154(100) |

TABLE 57

| Ex.No. | Structure | Appearance |
|---|---|---|
| 203 | 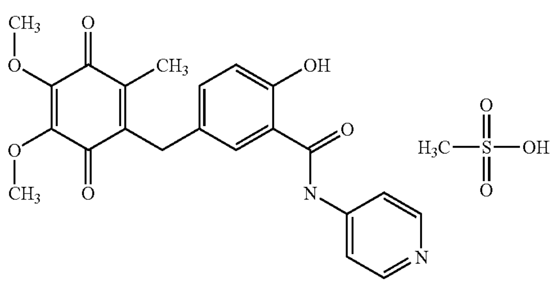 | yellow crystals |
| 204 | 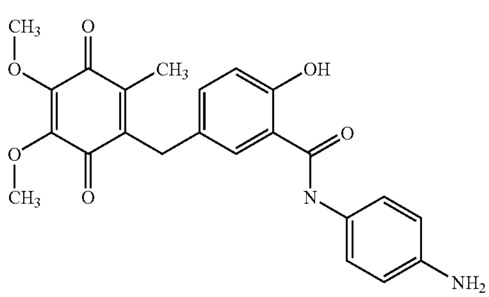 | yellow oil |

TABLE 57-continued

| Ex.No. | Structure | Appearance |
|---|---|---|
| 205 | [structure: 2,3-dimethoxy-5-methyl-1,4-benzoquinone with CH2 linker to 2-hydroxy-5-substituted benzamide, N-(4-aminophenyl), HCl salt] | yellow crystals |
| 206 | [structure: 2,3-dimethoxy-6-methyl-1,4-benzoquinone with CH2 linker to 2-acetoxy benzamide, N-(pyridin-3-yl)] | yellow oil |

| Ex.No. | mp (° C.) | IR (cm−) | NMR (ppm) | FAB MS |
|---|---|---|---|---|
| 203 | 199.5–201.5 | 3246, 2948, 1702, 1613, 1513, 1139(KBr) | 1.99(3H, s), 2.29(3H, s), 3.76(2H, s), 3.88(3H, s), 3.89(3H, s), 6.95(1H, d, J=8.48 Hz), 7.25–7.27(1H, m), 7.53(1H, br s), 8.16(2H, d, J=6.76 Hz), 8.71(2H, d, J=6.88 Hz) | 409(M+ + 1), 154(100) |
| 204 |  | 3366, 2944, 1648, 1609, 1516, 1265(KBr) | 2.10(3H, s), 3.75(2H, s), 3.93(3H, s), 3.94(3H, s), 6.66(2H, d, J=8.68 Hz), 6.88(1H, d, J=8.48 Hz), 7.16–7.27(3H, m), 7.43(1H, d, J=1.16 Hz), 8.14(1H, br s) | 423(M+ + 1), 108(100) |
| 205 | 162–164 | 3366, 2940, 1650, 1613, 1513, 1268(KBr) | 2.07(3H, s), 3.84(2H, s), 3.96(3H, s), 3.97(3H, s), 6.89(1H, d, J=8.28 Hz), 7.24–7.38(3H, m), 7.78–7.85(3H, m) | 423(M+ + 1), 108(100) |
| 206 |  | 1760, 1648,) 1610, 1540, 1196(NaCl) | 2.00(3H, s), 2.31(3H, s), 3.79(2H, s), 3.98(3H, s), 4.01(3H, s), 7.19–7.33(3H, m) 7.57(1H, d, J=7.04 Hz), 8.15(1H, br s), 8.24(1H, d, J=8.04 Hz), 8.37(1H, d, J=4.68 Hz), 8.58(1H, d, J=2.20 Hz) | 451(M+ + 1), 154(100) |

TABLE 58

| Ex.No. | Structure | Appearance |
|---|---|---|
| 207 | [structure: 2,3-dimethoxy-6-methyl-1,4-benzoquinone with CH2 linker to 2-hydroxy benzamide, N-(pyridin-3-yl)] | yellow crystals |

TABLE 58-continued

| 208 | [structure: 2,3-dimethoxy-5-methyl-1,4-benzoquinone-6-CH2- linked to phenyl bearing OC(O)CH3 and C(O)NH-(4-imidazol-1-yl-phenyl)] | yellow crystals |
| 209 | [structure: 2,3-dimethoxy-5-methyl-1,4-benzoquinone-6-CH2- linked to phenyl bearing OH and C(O)NH-(4-imidazol-1-yl-phenyl)] | yellow crystals |
| 210 | [structure: 2,3-dimethoxy-5-methyl-1,4-benzoquinone-6-CH2- linked to phenyl bearing OC(O)CH3 and C(O)NH-(4-pyrazol-3-yl-phenyl)] | yellow oil |

| Ex.No. | mp (° C.) | IR (cm-) | NMR (ppm) | FAB MS |
|---|---|---|---|---|
| 207 | 169–171 | 3258, 1651, 1611, 1544, 1269(KBr) | 2.10(3H, s), 3.89(2H s) 3.99(3H, s), 4.00(3H, s), 6.86(1H, t, J=7.76 Hz), 7.29–7.37(2H, m), 7.50(1H, d, J=7.00 Hz), 8.20(1H, dd, J=8.20, 1.60 Hz), 8.28(1H, br s), 8.43(1H, d, J=3.72 Hz), 8.68(1H, d, J=2.44 Hz), 11.95(1H, s) | 409(M+ + 1), 154(100) |
| 208 | 116.5–118.5 | 3135, 1767, 1653, 1611, 1523, 1267(KBr) | 2.12(3H, s), 2.33(3H, s), 3.89(2H, s), 3.99(3H, s), 4.00(3H, s), 7.06–7.09(1H, m), 7.20–7.27(2H, m), 7.34–7.44(3H, m), 7.66(1H, br s), 7.72(2H, d, J=8.80 Hz), 7.75–7.83(1H, m), 8.18(1H, br s) | 516(M+ + 1), 154(100) |
| 209 | 119–121.5 | 3324, 3124, 1651, 1611, 1522, 1267(KBr) | 2.16(3H, s), 3.81(2H, s), 3.99(3H, s), 4.00(3H, s), 6.95(1H, d, J=8.56 Hz), 7.22–7.29(3H, m), 7.43(2H, d, J=8.76 Hz), 7.53(1H, d, J=1.76 Hz), 7.74(2H, d, J=8.80 Hz), 7.87(1H, s), 8.42(1H, s), 11.50–11.90(1H, br s) | 474(M+ + 1), 154(100) |
| 210 | | 3346, 1768, 1648, 1611, 1267, 1188(KBr) | 2.12(3H, s), 2.34(3H, s), 3.90(2H, s), 3.97(3H, s), 3.99(3H, s), 6.82–6.84(1H, m), 7.07(1H, d, J=8.28 Hz), 7.20–7.46(2H, m), 7.62–7.81(5H, m), 8.10–8.20(1H, m), 8.38(1H, br s) | 516(M+ + 1), 154(100) |

TABLE 59

| Ex.No. | Structure | Appearance |
|---|---|---|
| 211 | (structure) | yellow crystals |
| 212 | (structure) | yellow oil |
| 213 | (structure) | yellow oil |
| 214 | (structure) | yellow crystals |

| Ex.No. | mp (° C.) | IR (cm-) | NMR (ppm) | FAB MS |
|---|---|---|---|---|
| 211 | 182–185.5 | 3200, 2946, 1653, 1610, 1540, 1268(KBr) | 2.01(3H, s), 3.77(2H, s), 3.89(3H, s), 3.90(3H, s), 6.68–6.69(1H, m), 6.90(1H, d, J=8.40 Hz), 7.18–7.21(1H, m), 7.72–7.82(5H, m), 10.39–10.41(1H, br s), 11.48–11.49(1H, br s), 12.80–12.83(1H, br s) | 474(M+ + 1), 154(100) |

TABLE 59-continued

| 212 | | 1767, 1636, 1611, 1325, 1125(NaCl) | 1.89(3H, s), 2.29(3H, s), 3.44(3H, s), 3.63(2H, s), 3.99(3H, s), 4.00(3H, s), 6.88–6.89(1H, m), 6.97(1H, d, J=8.36 Hz), 7.11–7.13(1H, m), 7.26–7.29(2H, m), 7.49(2H, d, J=8.16 Hz) | 532(M+ + 1), 154(100) |
|---|---|---|---|---|
| 213 | | 3322, 1636, 1610, 1325, 1126(NaCl) | 1.76(3H, s), 3.35(2H, s), 3.48(3H, s), 3.96(3H, s), 3.98(3H, s), 6.53(1H, d, J=1.80 Hz), 6.86(1H, d, J=8.56 Hz), 7.02(1H, dd, J=8.56, 1.96 Hz), 7.20(2H, d, J=8.32 Hz), 7.58(2H, d, J=8.36 Hz), 10.24(1H, s) | 490(M+ + 1, 100) |
| 214 | 200.5–202 | 3322, 2982, 1706, 1653, 1610, 1297, 1268(KBr) | 1.61(9H, s), 2.15(3H, s), 3.79(2H, s), 3.97(3H, s), 3.98(3H, s), 6.93(1H, d, J=8.56 Hz), 7.22(1H, dd, J=8.56, 1.88 Hz), 7.47(1H, d, J=1.68 Hz), 7.66(2H, d, J=8.64 Hz), 8.01(2H, d, J=8.64 Hz), 8.20(1H, s like), 11.60–11.62(1H, br s) | 508(M+ + 1), 154(100) |

TABLE 60

| Ex.No. | Structure | Appearance |
|---|---|---|
| 215 | 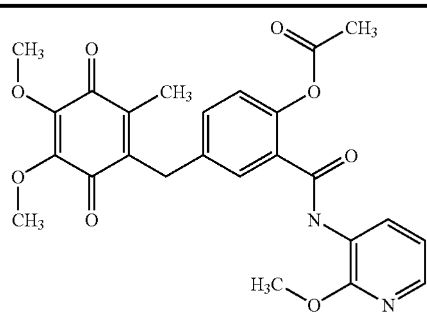 | yellow crystals |
| 216 | 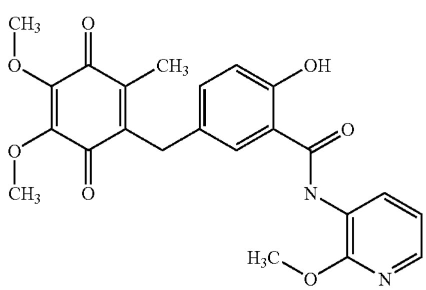 | yellow crystals |
| 217 | 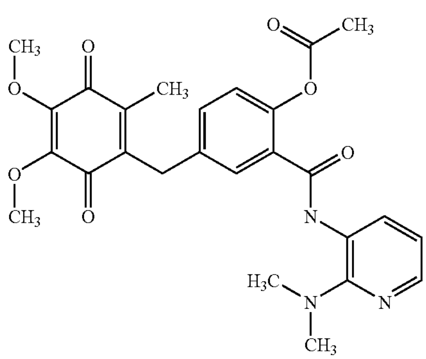 | yellow oil |

TABLE 60-continued

| 218 | [structure: 2,3-dimethoxy-5-methyl-1,4-benzoquinone with CH2 linker to 2-hydroxy-5-position of benzamide; amide N connected to 3-position of 2-(N,N-dimethylamino)pyridine] | yellow oil |

| Ex.No. | mp (° C.) | IR (cm-) | NMR (ppm) | FAB MS |
|---|---|---|---|---|
| 215 | 111–112 | 1773, 1666, 1611, 1526, 1266(NaCl) | 2.12(3H, s), 2.36(3H, s), 3.89(2H, s), 3.99(3H, s), 4.00(3H, s), 4.05(3H, s), 6.93–6.96(1H, m), 7.09(1H, d, J=8.36 Hz), 7.37(1H, d, J=8.44 Hz), 7.81(1H, s like), 7.89(1H, d, J=5.04 Hz), 8.75(1H, d, J=7.72 Hz), 8.88(1H, s like) | 481(M+ + 1), 184(100) |
| 216 | 112–114 | 3186, 1654, 1632, 1611, 1250(KBr) | 2.17(3H, s), 3.82(2H, s), 3.99(3H, s), 4.00(3H, s), 4.11(3H, s), 6.93–6.97(2H, m), 7.26–7.29(1H, m), 7.36(1H, s like), 7.92–7.94(1H, m), 8.52(1H, s like), 8.60(1H, d, J=7.88 Hz), 11.70(1H, s) | 439(M+ + 1), 154(100) |
| 217 | | 1773, 1665, 1611, 1508, 1266(NaCl) | 2.13(3H, s), 2.36(3H, s), 2.76(6H, s), 3.90(2H, s), 3.99(3H, s), 4.00(3H, s), 7.04–7.11(2H, m), 7.38(1H, d, J=8.36 Hz), 7.84(1H, s like), 8.10–8.12(1H, m), 8.68(1H, d, J=8.00 Hz), 9.10(1H, s like) | 494(M+ + 1), 315(100) |
| 218 | | 3284, 1648, 1610, 1522, 1266(NaCl) | 2.16(3H, s), 2.82(6H, s), 3.82(2H, s), 3.99(3H, s), 4.00(3H, s), 6.95(1H, d, J=8.52 Hz), 7.07–7.10(1H, m), 7.30–7.39(2H, m), 8.14(1H, d, J=4.88 Hz), 8.59(1H, d, J=1.44 Hz), 8.61(1H, d, J=1.48 Hz), 9.04–9.06(1H, br s) | 452(M+ + 1), 136(100) |

TABLE 61

| Ex.No. | Structure | Appearance |
|---|---|---|
| 219 | [structure: 2,3-dimethoxy-5-methyl-1,4-benzoquinone with CH2 linker to benzamide bearing 2-acetoxy group; amide N connected to 2,5-dimethoxyphenyl] | yellow crystals |

TABLE 61-continued

| 220 | [structure: 2,3-dimethoxy-5-methyl-1,4-benzoquinone linked via CH₂ to a 2-hydroxyphenyl group with C(=O)NH to a 2,5-dimethoxyphenyl] | yellow crystals |
| 221 | [structure: 2,3-dimethoxy-5-methyl-1,4-benzoquinone linked via CH₂ to a 2-methoxyphenyl group with C(=O)NH to a 2-chloropyridin-3-yl] | yellow crystals |
| 222 | [structure: 2,3-dimethoxy-5-methyl-1,4-benzoquinone linked via CH₂ to a 2-acetoxyphenyl group with C(=O)NH to a 2-morpholinopyridin-3-yl] | yellow oil |

| Ex.No. | mp (° C.) | IR (cm-) | NMR (ppm) | FAB MS |
|---|---|---|---|---|
| 219 | 118.5–120 | 1789, 1660, 1610, 1530, 1486, 1269(KBr) | 2.11(3H, s), 2.34(3H, s), 3.80(3H, s), 3.86(3H, s), 3.88(2H, s), 3.99(3H, s), 4.00(3H, s), 6.59–6.62(1H, m), 6.82(1H, d, J=8.96 Hz), 7.07(1H, d, J=8.36 Hz), 7.33–7.36(1H, m), 7.79(1H, s like), 8.27–8.28(1H, m), 8.91–8.92(1H, m) | 510(M+ + 1), 154(100) |
| 220 | 130–132 | 3324, 1661, 1608, 1540, 1500, 1264(KBr) | 2.17(3H, s), 3.80(3H, s), 3.81(3H, s), 3.94(2H, s), 3.99(3H, s), 4.00(3H, s), 6.64(1H, d, J=8.92 Hz), 6.85(1H, d, J=8.96 Hz), 6.93(1H, d, J=8.52 Hz), 7.26–7.36(2H, m), 8.09–8.11(1H, m), 8.70(1H, s like), 11.90(1H, s) | 468(M+ + 1), 154(100) |
| 221 | 178–180 | 1673, 1612, 1530, 1494, 1271(KBr) | 2.12(3H, s), 3.86(2H, s), 3.99(3H, s), 4.00(3H, s), 4.08(3H, s), 6.98(1H, d, J=8.52 Hz), 7.26–7.40(2H, m), 8.07–8.12(2H, m), 9.00(1H, d, J=8.16 Hz), 10.68(1H, s like) | 457(M+ + 1), 154(100) |
| 222 |  | 1768, 1653, 1611, 1508, 1266, 1200(KBr) | 2.14(3H, s), 2.31(3H, s), 3.08–3.12(4H, m), 3.86–3.90(6H, m), 3.99(3H, s), 4.00(3H, s), 7.07–7.12(2H, m), 7.38(1H, dd, J=8.32, 2.08 Hz), 7.73(1H, d, J=1.68 Hz), 8.14(1H, dd, J=4.80, 1.56 Hz), 8.68(1H, d, J=7.72 Hz), 8.88(1H, s like) | 536(M+ + 1), 154(100) |

TABLE 62

| Ex.No. | Structure | Appearance |
|---|---|---|
| 223 | (structure) | yellow crystals |
| 224 | (structure) | yellow oil |
| 225 | (structure) | yellow crystals |
| 226 | (structure) | yellow oil |

| Ex.No. | mp (° C.) | IR (cm-) | NMR (ppm) | FAB MS |
|---|---|---|---|---|
| 223 | 210–212.5 | 3296, 1648, 1609, 1518, 1266(KBr) | 2.17(3H, s), 3.12–3.15(4H, m), 3.82(2H, s), 3.98–4.02(10H, m), 6.95(1H, d, J=8.52 Hz), 7.12–7.16(1H, m), 7.26–7.30(1H, m), 7.49(1H, s like), 8.18(1H, dd, J=4.80, 1.44 Hz), 8.64(1H, dd, J=8.00, 1.32 Hz), 9.07(1H, s like), 11.94(1H, s) | 494(M+ + 1), 154(100) |

TABLE 62-continued

| 224 | | 3313, 1768, 1654, 1611, 1526, 1492(KBr) | 2.09(3H, s), 2.31(3H, s), 3.45–3.48(4H, m), 3.80–3.96(6H, m), 3.98(3H, s), 3.99(3H, s), 6.65(1H, d, J=9.12 Hz), 7.05(1H, d, J=8.36 Hz), 7.31(1H, d, J=8.40 Hz), 7.64(1H, s like), 7.98–8.01(1H, m), 8.13–8.20(2H, m) | 536(M+ + 1), 154(100) |
|---|---|---|---|---|
| 225 | 102.5–105 | 3400, 1646, 1611, 1495, 1266(KBr) | 2.15(3H, s), 3.49–3.53(4H, m), 3.81–3.98(6H, m), 3.98(3H, s), 3.99(3H, s), 6.68(1H, d, J=9.04 Hz), 6.92(1H, d, J=8.60 Hz), 7.20–7.25(1H, m), 7.43(1H, s like), 7.80–7.84(2H, m), 8.25(1H, s like), 11.83(1H, s) | 494(M+ + 1), 154(100) |
| 226 | | 1768, 1648, 1612, 1582, 1267, 1200(KBr) | 2.10(3H, s), 2.33(3H, s), 3.86(2H, s), 3.98(3H, s), 3.99(3H, s), 7.07(1H, d, J=8.44 Hz), 7.35–7.42(2H, m), 7.61(1H, s like), 7.70(1H, s like), 8.28(1H, d, J=5.56 Hz), 8.40–8.42(1H, br s) | 485(M+ + 1), 154(100) |

TABLE 63

| Ex.No. | Structure | Appearance |
|---|---|---|
| 227 | 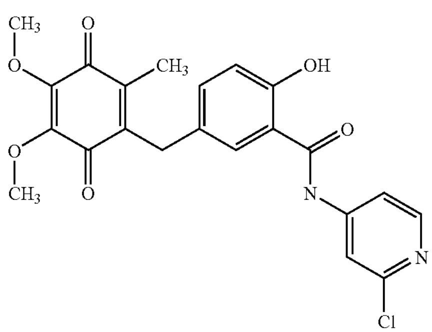 | yellow crystals |
| 228 | 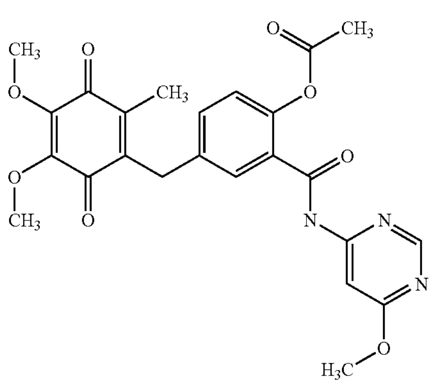 | yellow crystals |

TABLE 63-continued
229 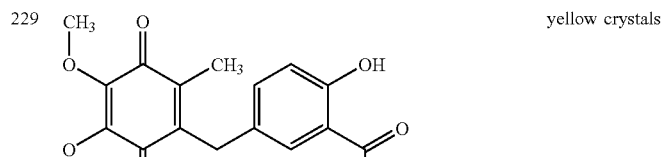 yellow crystals
230 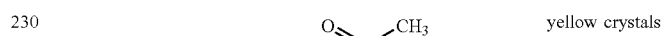 yellow crystals
| Ex.No. | mp (° C.) | IR (cm-) | NMR (ppm) | FAB MS |
|---|---|---|---|---|
| 227 | 142–144 | 3272, 1653, 1611, 1582, 1501, 1266(KBr) | 2.15(3H, s), 3.79(2H, s), 3.97(3H, s), 3.99(3H, s), 6.95(1H, d, J=8.52 Hz), 7.26–7.28(1H, m), 7.48–7.50(2H, m), 7.74(1H, s like), 8.27(1H, s like), 8.35(1H, d, J=5.60 Hz), 11.16(1H, s) | 443(M+ + 1), 154(100) |
| 228 | 138.5–141 | 1772, 1700, 1653, 1611, 1570, 1517, 1267, 1207(KBr) | 2.12(3H, s), 2.40(3H, s), 3.89(2H, s), 3.99(9H, s like), 7.11(1H, d, J=8.40 Hz), 7.39(1H, dd, J=8.40, 2.24 Hz), 7.66(1H, s like), 7.79(1H, d, J=2.16 Hz), 8.46(1H, s like), 9.00–9.02(1H, br s) | 482(M+ + 1), 154(100) |
| 229 | 209.5–211.5 | 2920, 1686, 1612, 1590, 1500, 1269, 1194(KBr) | 2.13(3H, s), 3.80(2H, s), 3.98(3H, s), 3.99(3H, s), 4.02,(3H, s), 6.93(1H, d, J=8.56 Hz), 7.24–7.26(1H, m), 7.31(1H, s like), 7.50–7.51(1H, m), 8.52(1H, s like), 8.88–8.90(1H, br s), 11.4–11.51(1H, br s) | 439(M+), 154(100) |
| 230 | 138–140.5 | 1773, 1701, 1650, 1611, 1570, 1267, 1206(KBr) | 2.12(3H, s), 2.40(3H, s), 3.89(2H, s), 3.99–4.01(9H, m), 7.11(1H, d, J=8.48 Hz), 7.26–7.27(1H, m), 7.39(1H, d, J=8.36 Hz), 7.66(1H, s like), 7.79(1H, s like), 8.46(1H, s like), 8.98–8.99(1H, br s) | 481(M+ + 1), 154(100) |

TABLE 64

| Ex.No. | Structure | Appearance |
|---|---|---|
| 231 | (structure) | yellow crystals |
| 232 | (structure) | white crystals |
| 233 | (structure) | yellow crystals |
| 234 | (structure) | yellow crystals |

| Ex.No. | mp (° C.) | IR (cm-) | NMR (ppm) | FAB MS |
|---|---|---|---|---|
| 231 | 218–220.5 | 3269, 1686, 1611, 1567, 1503, 1195(KBr) | 2.13(3H, s), 3.80(2H, s), 3.98(3H, s), 3.99(3H, s), 4.02(3H, s), 6.93(1H, d, J=8.48 Hz), 7.23–7.26(1H, m), 7.51(1H, s like), 7.66(1H, s like), 8.52(1H, s like), 8.85–8.87(1H, br s), 11.50–11.52(1H, br s) | 439(M+ + 1), 154(100) |
| 232 | 110–112 | 2992, 2827, 1770, 1695, 1210(KBr) | 2.11(3H, s), 2.21(3H, s), 2.22(3H, s), 2.30(3H, s), 3.57(3H, s), 3.64(3H, s), 4.08(2H, s), 6.97(1H, d, J=8.32 Hz), 7.27(1H, d, J=2.00 Hz), 7.89(1H, d, J=1.76 Hz) | 372(M+, 100) |
| 233 | 157–159.5 | 2951, 1756, 1683, 1648, 1213(KBr) | 2.02(3H, s), 2.03(3H, s), 2.13(3H, s), 2.32(3H, s), 3.89,(2H, s), 7.02(1H, d, J=8.28 Hz), 7.44(1H, dd, J=8.32, 1.48 Hz), 7.91(1H, d, J=2.08 Hz) | 343(M+ + 1), 154(100) |

TABLE 64-continued

| 234 | 180–181 | 1758, 1668, 1644, 1526, 1327(KBr) | 2.02(3H, s), 2.03(3H, s), 2.12(3H, s), 2.31(3H, s), 3.90(2H, s), 7.06(1H, d, J=8.40 Hz), 7.36(1H, dd, J=8.24, 2.04 Hz), 7.06–7.65(3H, m), 7.71(2H, d, J=8.56 Hz), 8.16(1H, s) | 486(M+ + 1), 154(100) |

TABLE 65

| Ex.No. | Structure | Appearance |
|---|---|---|
| 235 | 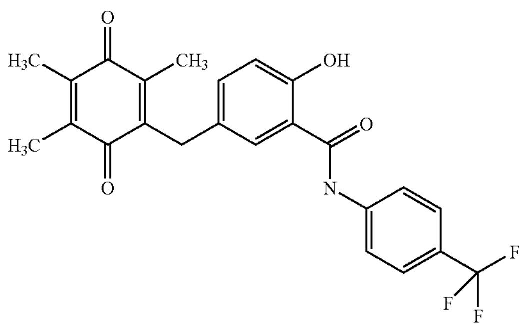 | yellow crystals |
| 236 | 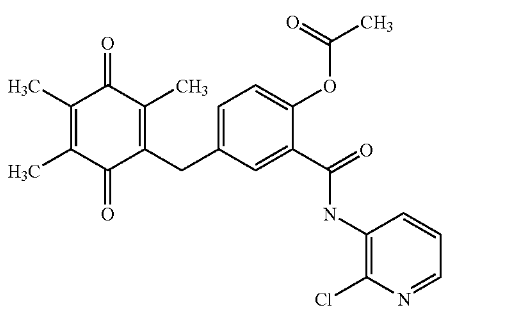 | yellow crystals |
| 237 | 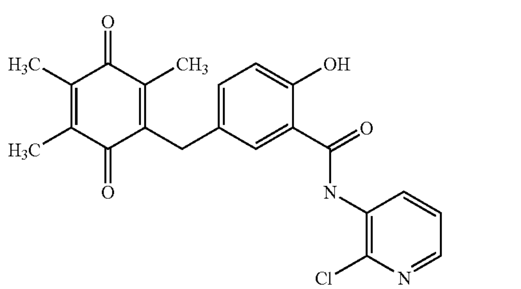 | yellow crystals |
| 238 | 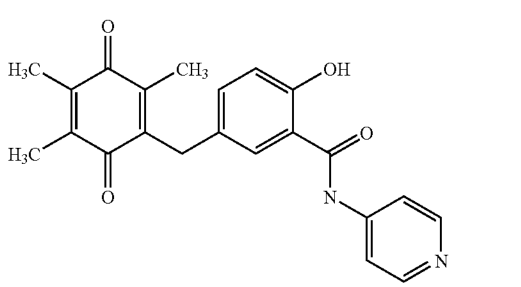 | yellow crystals |

| Ex.No. | mp (° C.) | IR (cm-) | NMR (ppm) | FAB MS |
|---|---|---|---|---|

TABLE 65-continued

| 235 | 233–235 | 3168, 1676, 1642, 1544, 1321(KBr) | 2.02(3H, s), 2.03(3H, s), 2.17(3H, s), 3.82(2H, s), 6.93(1H, d, J=8.56 Hz), 7.22–7.26(1H, m), 7.46(1H, d, J=1.44 Hz), 7.66(2H, d, J=8.56 Hz), 7.75(2H, d, J=8.52 Hz), 8.16(1H, s), 11.52(1H, s) | 444(M+ + 1), 154(100) |
| --- | --- | --- | --- | --- |
| 236 | 130–131 | 1768, 1670, 1648, 1518, 1302(KBr) | 2.02(3H, s), 2.03(3H, s), 2.14(3H, s), 2.39(3H, s), 3.92(2H, s), 7.10(1H, d, J=8.40 Hz), 7.29–7.33(1H, m), 7.40(1H, dd, J=8.36 1.44 Hz), 7.78(1H, d, J=1.92 Hz), 8.15(1H, dd, J=4.64, 1.64 Hz), 8.78–8.80(1H, br s), 8.91(1H, dd, J=8.12, 1.08 Hz) | 453(M+ + 1), 154(100) |
| 237 | 199–201 | 3270, 1675, 1639, 1531, 1505, 1310(KBr) | 2.03(3H, s), 2.04(3H, s), 2.15(3H, s), 3.85(2H, s), 6.96(1H, d, J=8.52 Hz), 7.31–7.35(2H, m), 7.42(1H, d, J=1.52 Hz), 8.18(1H, dd, J=4.68 1.64 Hz), 8.57(1H, s like), 8.80(1H, dd, J=8.16, 1.64 Hz), 11.32(1H, s) | 411(M+ + 1), 154(100) |
| 238 | 245–247 | 3250, 2414, 1676, 1642, 1589, 1513, 1302(KBr) | 1.95(3H, s), 1.96(3H, s), 2.02(3H, s), 3.78(2H, s), 6.91(1H, d, J=8.44 Hz), 7.20(1H, d, J=8.40 Hz), 7.61–7.70(3H, m), 8.46(2H, d, J=5.96 Hz), 10.58–10.59(1H, br s), 11.16–11.18(1H, br s) | 377(M+ + 1), 154(100) |

EXPERIMENT 1

Effect on Human Lung Cancer-Derived Cell A549 (A549/NF-κBluc) Containing Stably Introduced Luciferase Plasmid (pNFκB-Luc, Stratagene. U.S.A.) Regulated by NF-κB Binding Sequence Using Lipofectamine (Lifetech Oriental, Tokyo), pNFκB-Luc and pSV2neo (Clontech, U.S.A.) were co-transfected into the A549 cell (ATCC CCL185) and G418 sulfate (1 mg/ml, Lifetech Oriental) was added to the culture medium to select cells containing stably introduced pNFκB-Luc A549/NF-κBLuc.

The compound obtained in Examples each was added to A549/NF-κBLuc and one hour after that, IL-1β capable of activating NF-κB was added. The incubation was further continued for 3 hours. As indexed by the luciferase activity, the compounds obtained in Examples were revealed to suppress the activation of NF-κB stimulated with of IL-1β. The $IC_{50}$ values thereof are shown in Table below.

NF-κB Inhibitory Activity ($IC_{50}$) of Substituted Benzoic Acid Derivitives:

| Example 57 | 29 μM |
| --- | --- |
| Example 60 | 19 μM |
| Example 61 | 31 μM |
| Example 64 | 33 μM |
| Example 65 | 37 μM |
| Example 70 | 15 μM |
| Example 71 | 36 μM |
| Example 72 | 43 μM |
| Example 73 | 31 μM |
| Example 76 | 7 μM |
| Example 77 | 35 μM |
| Example 78 | 57 μM |
| Example 79 | 27 μM |
| Example 80 | 82 μM |
| Example 82 | 84 μM |
| Example 84 | 63 μM |
| Example 85 | 65 μM |
| Example 86 | 27 μM |
| Example 87 | 19 μM |
| Example 89 | 45 μM |
| Example 92 | 49 μM |
| (HCl) | 46 μM |
| Example 94 | 45 μM |
| Example 95 | 35 μM |
| (pTsOH) | 51 μM |
| Example 104 | 29 μM |
| Example 106 | 70 μM |
| Example 107 | 84 μM |
| Example 108 | 67 μM |
| Example 109 | 46 μM |
| Example 110 | 34 μM |
| Example 111 | 25 μM |
| Example 112 | 14 μM |
| Example 114 | 48 μM |
| Example 115 | 36 μM |
| Example 116 | 17 μM |
| Example 117 | 20 μM |
| Example 118 | 8.3 μM |
| Example 119 | 13 μM |
| Example 120 | 1.7 μM |
| Example 121 | 64 μM |
| Example 124 | 46 μM |
| Example 125 | 19 μM |
| Example 126 | 24 μM |
| Example 127 | 24 μM |
| Example 128 | 19 μM |
| Example 130 | 59 μM |
| Example 142 | 9 μg/ml |
| Example 146 | 11 μg/ml |
| Example 147 | 19 μg/ml |
| Example 148 | 3 μg/ml |
| Example 149 | 25 μg/ml |
| Example 150 | 4 μg/ml |

-continued

| | |
|---|---|
| Example 157 | 7 μg/ml |
| Example 158 | 7 μg/ml |
| Example 163 | 30 μg/ml |
| Example 164 | 20 μg/ml |
| Example 171 | 26 μg/ml |
| Example 173 | 9 μg/ml |
| Example 174 | 6 μg/ml |
| Example 180 | 23 μg/ml |
| Example 181 | 11 μg/ml |
| Example 184 | 56 μg/ml |
| Example 185 | 11 μg/ml |
| Example 186 | 2 μg/ml |
| Example 187 | 2 μg/ml |
| Example 188 | 9 μg/ml |
| Example 191 | 4 μg/ml |
| Example 199 | 16 μg/ml |
| Example 200 | 17 μg/ml |
| Example 201 | 16 μg/ml |
| Example 202 | 20 μg/ml |
| Example 203 | 30 μg/ml |
| Example 204 | 47 μg/ml |
| Example 205 | 50 μg/ml |
| Example 206 | 87 μg/ml |
| Example 207 | 98 μg/ml |
| Example 208 | 19 μg/ml |
| Example 214 | 10 μg/ml |
| Example 216 | 10 μg/ml |
| Example 220 | 66 μg/ml |
| Example 221 | 46 μg/ml |
| Example 222 | 77 μg/ml |
| Example 223 | 81 μg/ml |
| Example 224 | 24 μg/ml |
| Example 225 | 24 μg/ml |
| Example 226 | 19 μg/ml |
| Example 227 | 20 μg/ml |
| Example 228 | 64 μg/ml |
| Example 229 | 59 μg/ml |
| Example 235 | 5 μg/ml |
| Example 237 | 5 μg/ml |

EXPERIMENT 2

Effect on In Vivo Sepsis Model

A mixed solution of N-acetyl galactosamine (GalN, 20 mg, Sigma) and lipopolysaccharide (LPS, 5 μg, Sigma) was intraperitoneally administered as a stimulant to a 7-week-old C3H/HeN female mice and immediately thereafter, the compound of Example 112 suspended in a vehicle (0.5% hydroxypropyl cellulose (HPC), produced by Nippon Soda Co., Ltd.) was intraperitoneally administered to give a dose of 10 mg/kg, 30 mg/kg or 100 mg/kg. The TNF-α mRNA levels and the IL-1β mRNA levels in liver 60 minutes after the administration of stimulant each was measured by the real-time PCR method, and the TNF-α levels in plasma after 90 minutes were measured using the mouse TNF-α ELISA kit (Biosource). In the real-time PCR using PRISM7700 (PE Biosystems Japan) according to the protocol of PCR quantitative System (PE Biosystems Japan), mRNA was extracted from the liver and the TNF-α and IL-1β were detected with cDNA obtained by SuperScript Preamplification System (Lifetech Orient) as a template. For the detection, the following primers and TaqMan probes were used.

TNF-α
  Forward: CAT CTT CTC AAA ATT GGA GTG ACA A
  Reverse: TGG GAG TAG ACA AGG TAC AAC CC
  Probe: CAC GTC GTA GCA AAC CAC CAA GTG GA
IL-1β
  Forward: CAA CCA ACA AGT GAT ATT CTC CAT G
  Reverse: GAT CCA CAC TCT CCA GCT GCA
  Probe: CTG TGT AAT GAA AGA CGG CAC ACC CAC C The RNA level in each sample was corrected by the expression level of glyceraldehyde 3-phosphate dehydrogenase (GAPDH) gene.

ELISA was performed according to the manual included in the kit. The comparison with the vehicle group was performed by the Dunnett's Multiple Comparison test using Stat-View (SAS Institute).

As shown in FIG. 1, in the vehicle group, the TNF-α mRNA levels in liver were markedly increased and the TNF-α levels in plasma were also increased. Furthermore, the IL-1β mRNA levels in liver were increased. On the other hand, in the group administered with the compound of Example 112, the TNF-α mRNA in liver and the TNF-α levels in plasma were suppressed dose dependently. Also, the IL-1β mRNA levels in liver were suppressed.

EXPERIMENT 3

Effect on Sepsis Model in Oral Administration

Similarly to Experiment 2, a mixed solution of GalN (20 mg) and LPS (2 μg) was intraperitoneally administered as a stimulant to a 7-week-old C3H/HeN female mice. Ten minutes before that, the compound of Example 112 or the compound of Example 157 each suspended in a vehicle (0.5% HPC) was orally administered to give a dose of 10 mg/kg, 30 mg/kg or 100 mg/kg. The TNF-α mRNA levels in liver 60 minutes after the administration of stimulant were measured by the real-time PCR method, and the TNF-α levels in plasma after 90 minutes were measured using the mouse TNF-α ELISA kit. The comparison with the vehicle group was performed by the Dunnett's Multiple Comparison test using Stat-View.

Figure 2:
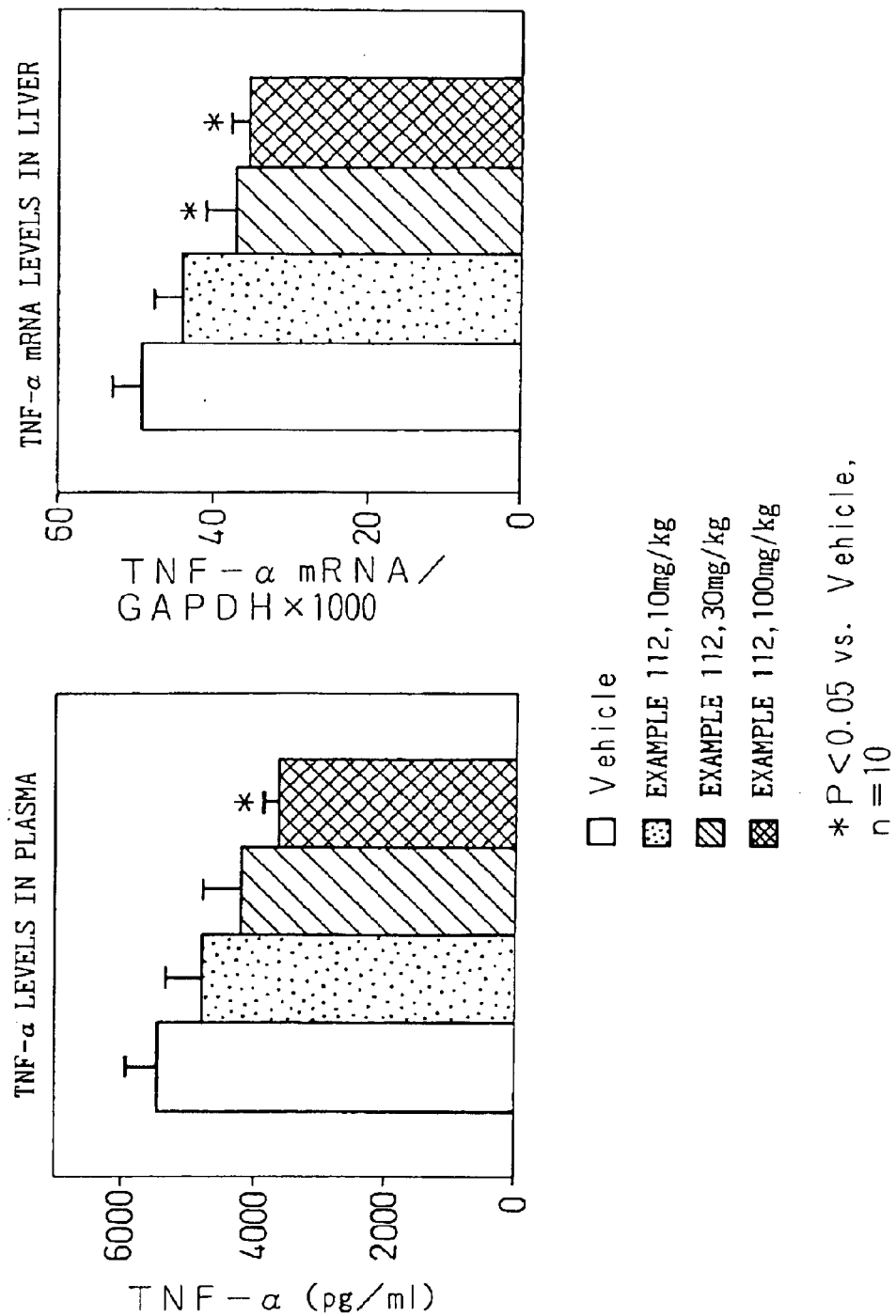
FIG. 2 shows the results when a 7-week-old C3H/HeN female mouse was intraperitoneally administered with GalN/LPS and, 10 minutes before this, administered with the compound of Example 112, the liver was removed 60 minutes after the stimulation and the TNF-α mRNA levels were measured (right in the Figure) and, 90 minutes after the stimulation, blood was collected from the heart and the TNF-α levels (left in the Figure) in plasma were also measured.
Figure 3:
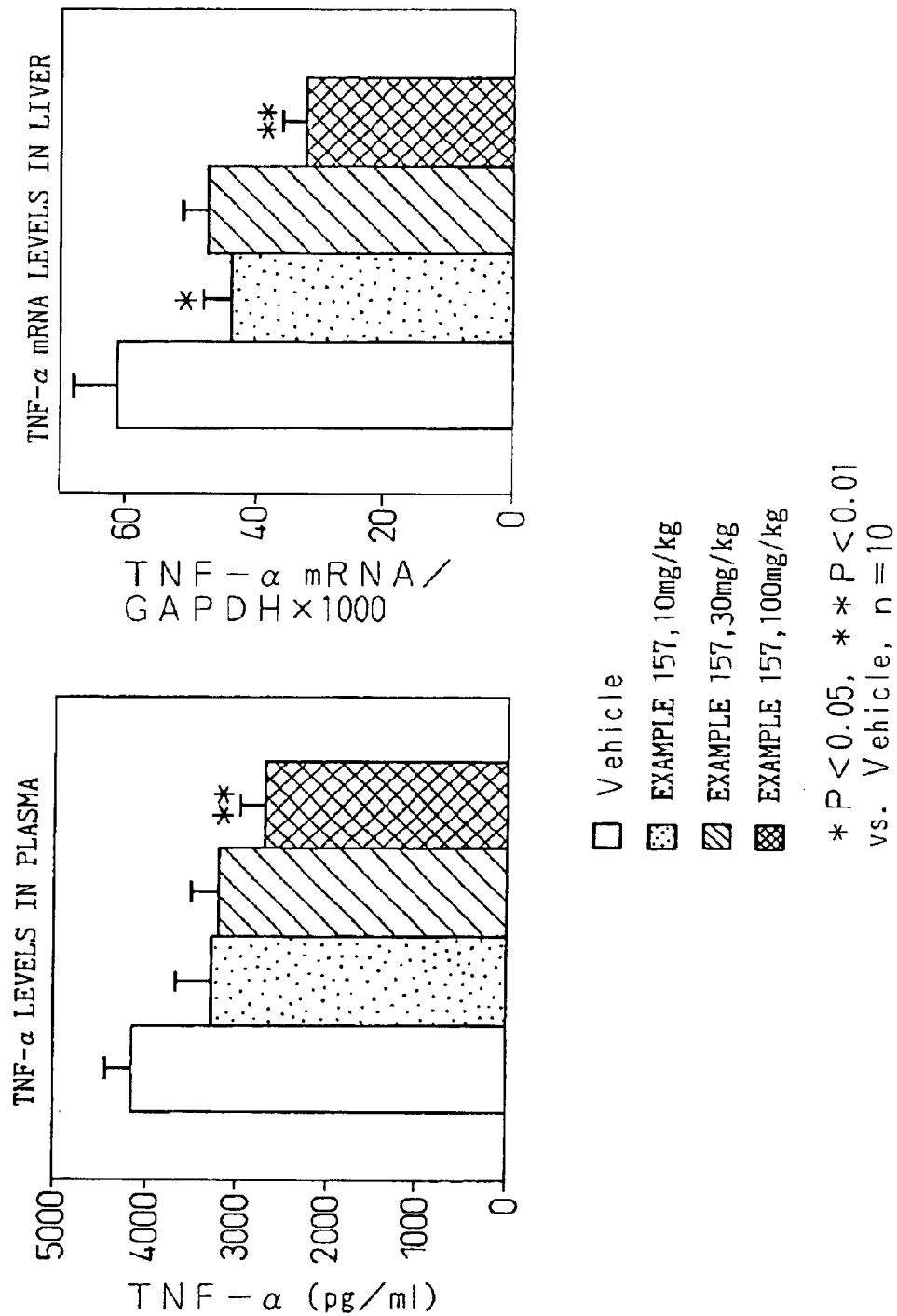
FIG. 3 shows the results when a 7-week-old C3H/HeN female mouse was intraperitoneally administered with GalN/LPS and, 10 minutes before this, administered with the compound of Example 157, the liver was removed 60 minutes after the stimulation and the TNF-α mRNA levels were measured (right in the Figure) and, 90 minutes after the stimulation, blood was collected from the heart and the TNF-α levels (left in the Figure) in plasma were also measured.

Also in the group where the compound of Example 112 (FIG. 2) or the compound of Example 157 (FIG. 3) was orally administered, the TNF-α mRNA levels in liver and the TNF-α levels in plasma were suppressed dose dependently.

EXPERIMENT 4

Effect on Acute Inflammation in Oral Administration Model

On the footpad of the right hind leg of a 5-week-old Wister male rat, 0.1 ml of 1 w/v % λ-carrageenin (Sigma) was subcutaneously administered. Immediately thereafter, the compound of Example 112 or the compound of Example 157 each suspended in a vehicle (0.5% HPC) was orally administered to give a dose of 100 mg/kg. As a positive control, indomethacin (sigma) was orally administered to give a dose of 10 mg/kg. The foot edema ratio was calculated according to the formula: (volume of foot 2 hours after administration of carrageenin−volume of foot before administration)/volume of foot before administration×100, using a volume meter (TK-101, manufactured by Unicom). For the comparison between the vehicle group and the drug administered group, a variance test was performed by the F-test and thereafter, Student's t test was performed when the variance was equal, or Aspin-Welch's t test was performed when the variance was not equal.

Figure 4:
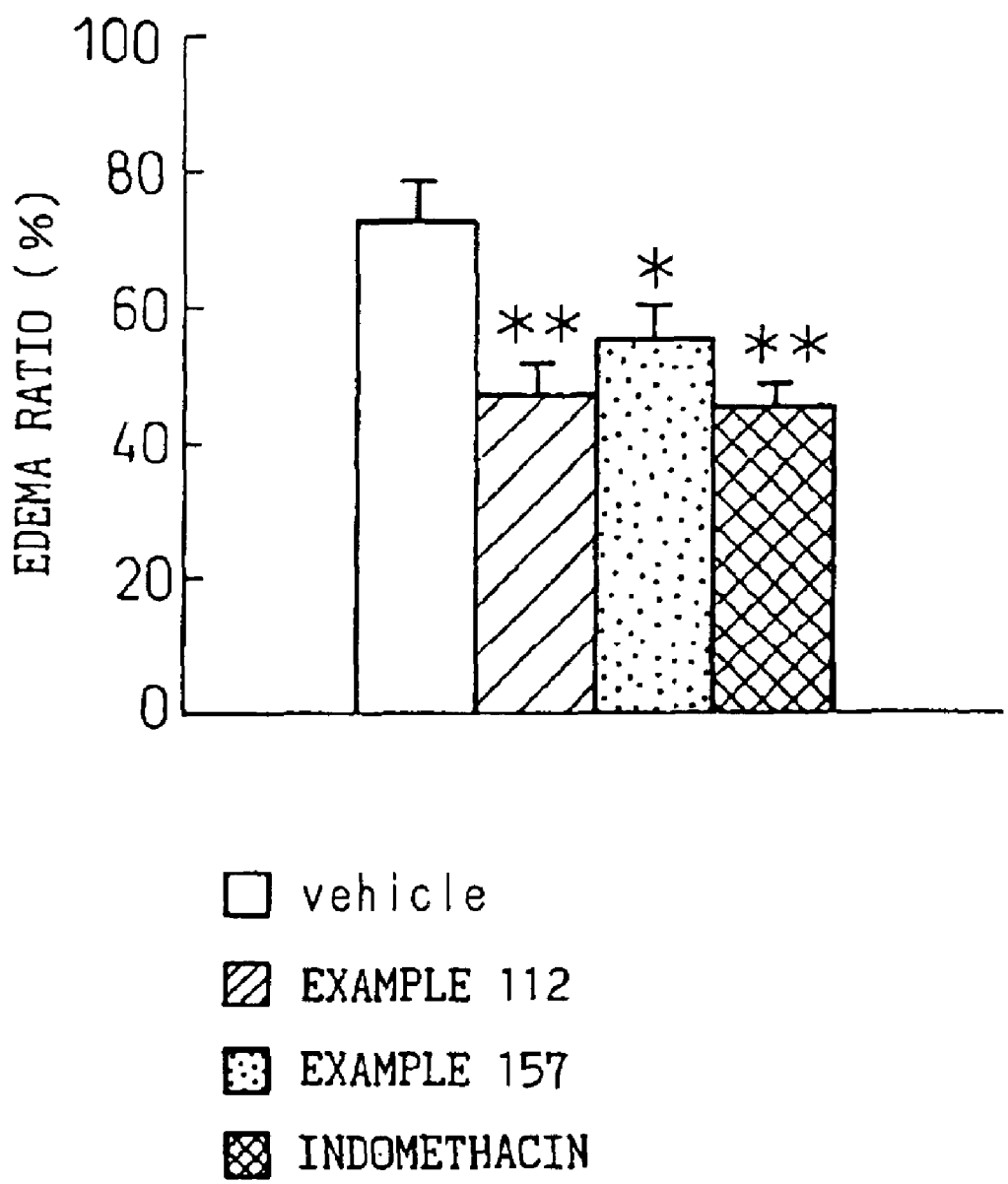
FIG. 4 shows the foot edema ratio when carrageenin was subcutaneously administered to the foot pat of the right hind leg of rat and immediately thereafter, 100 mg/kg of the compound of Example 112 or Example 157 was orally administered or 10 mg/kg of indomethacin as a positive control was also orally administered. The foot edma ratio was calculated according to the formula: (volume of foot after administration of carrageenin–volume of foot before administration)/volume of foot before administration×100, and shown by the average of foot edma ratio +/–SE.

As shown in FIG. 4, the compound of Example 112 and the compound of Example 157 significantly suppressed the acute inflammation (foot edema) caused by carrageenin through their oral administration.

What is claimed is:

1. A substituted benzoic acid derivative represented by the following formula (I):

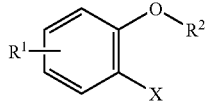 (I)

wherein $R^1$ is the following formula (II):

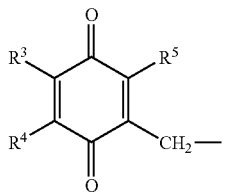 (II)

or the following formula (III):

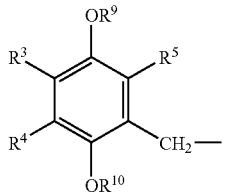 (III)

wherein $R^3$, $R^4$ and $R^5$ each independently represents an alkyl group having from 1 to 6 carbon atoms, or an alkoxy group having from 1 to 6 carbon atoms;

$R^9$ and $R^{10}$ each independently represents a hydrogen atom, an alkyl group having from 1 to 6 carbon atoms, or an acyl group having from 2 to 11 carbon atoms;

$R^2$ represents a hydrogen atom, a optionally substituted lower alkyl group having from 1 to 6 carbon atoms, an optionally substituted aryl group having from 6 to 12 carbon atoms, an optionally substituted heteroaryl group having from 4 to 11 carbon atoms, an optionally substituted aralkyl group having from 7 to 14 carbon atoms, an optionally substituted heteroarylalkyl group having from 5 to 13 carbon atoms, or an optionally substituted acyl group having from 2 to 11 carbon atoms; and X represents a carboxyl group which may be esterified or amidated.

2. The substituted benzoic acid derivative according to claim 1, wherein $R^1$ is the following formula

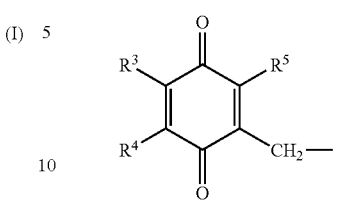 (II)

wherein $R^3$ and $R^4$ each independently represents a atom, a methyl group or a methoxy group.

3. The substituted benzoic acid derivative according to claim 1, wherein $R^1$ is the following formula (II):

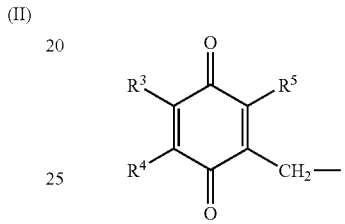 (II)

wherein $R^5$ represents or a methyl group.

4. The substituted benzoic acid derivative according to claim 1, wherein $R^2$ is selected from the group consisting of a hydrogen atom, a methyl group, an isopropyl group, a phenyl group, a 3-methoxyphenyl group, a 3-pyridyl group, a 4-pyridyl group, a benzyl group, a 3-pyridylmethyl group, a 4-pyridylmethyl group, an acetyl group, a carboxymethyl group, a methoxycarbonylmethyl group and a tert-butoxycarbonylmethyl group.

5. The substituted benzoic acid derivative according to claim 1, wherein X is a group —COOR$^6$, wherein $R^6$ represents a hydrogen atom, an optionally substituted alkyl group having from 1 to 6 carbon atoms, or an optionally substituted aralkyl group having from 7 to 14 carbon atoms.

6. The substituted benzoic acid derivative according to claim 1, wherein X is a group —CONR$^7$ R$^8$, wherein $R^7$ and $R^8$ each independently represents a substituent selected from the group consisting of a hydrogen atom, an optionally substituted alkyl group having from 1 to 6 carbon atoms, an optionally substituted aryl group having from 6 to 12 carbon atoms, an optionally substituted heteroaryl group having from 4 to 11 carbon atoms, an optionally substituted aralkyl group having from 7 to 14 carbon atoms, and an optionally substituted heteroarylalkyl group having from 5 to 13 carbon atoms, or $R^7$ and $R^8$, together with the nitrogen atom to which they are attached, represent a heteroeyclic ring which may further contain a nitrogen atom, an oxygen atom, and/or a sulfur atom or may be condensed.

7. The substituted benzoic acid derivative according to claim 1, wherein X is a group —CONR$^7$ R$^8$ wherein $R^7$ and $R^8$, together with the nitrogen atom to which they are attached, represent a 5- to 8-membered nitrogen-containing heterocyclic ring which optionally has from 1 to 3 heteroatoms selected from the group consisting of a nitrogen atom, an oxygen atom and a sulfur atom, in addition to the carbon atom and the nitrogen atom which nitrogen atom is optionally substituted, wherein the carbon atom or sulfur atom on the ring is optionally present in an oxide form.

8. The substituted benzoic acid derivative according to claim 1, wherein in the following formula (I):

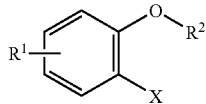

$R^1$ is the following formula (II):

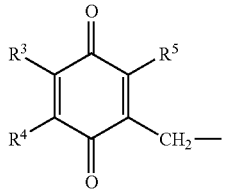

wherein $R^3$ and $R^4$ each independently represents a methyl group or a methoxy group, and $R^5$ represents a methyl group; $R^2$ represents a hydrogen atom, a methyl group, an isopropyl group, a phenyl group, a 3-methoxyphenyl group, a 3-pyridyl group, a 4-pyridyl group, a benzyl group, a 3-pyridylmethyl group, a 4-pyridylmethyl group, an acetyl group, a carboxymethyl group, a methoxycarbonylmethyl group or a tert-butoxycarbonylmethyl group; and X represents a carboxyl group which is optionally esterified or amidated.

9. An NF-κB inhibitor comprising the substituted benzoic acid derivative according to claim 1, or a hydroquinone form or pharmaceutically acceptable salt thereof as an active ingredient.

10. A pharmaceutical composition of matter comprising a substituted benzoic acid derivative represented by the following formula (I):

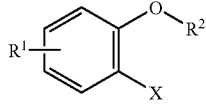

wherein $R^1$ is the following formula (II):

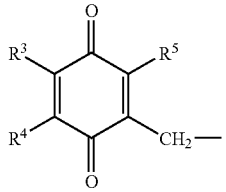

or the following formula (III):

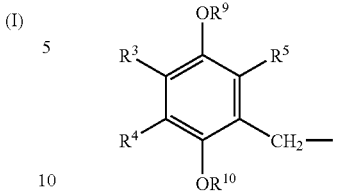

wherein $R^3$, $R^4$ and $R^5$ each independently represents an alkyl group having from 1 to 6 carbon atoms or an alkoxy group having from 1 to 6 carbons, and $R^9$ and $R^{10}$ each independently represents a hydrogen atom, an alkyl group having from 1 to 6 carbon atoms or an acyl group having from 2 to 11 carbon atoms;

$R^2$ represents a substituent selected from the group consisting of hydrogen atom, an optionally substituted lower alkyl group having from 1 to 6 carbon atoms, an optionally substituted aryl group having from 6 to 12 carbon atoms, an optionally substituted heteroaryl group having from 4 to 11 carbon atoms, an optionally substituted aralkyl group having from 7 to 14 carbon atoms, an optionally substituted heteroarylalkyl group having from 5 to 13 carbon atoms, end an acyl group having from 2 to 11 carbon atoms; and X represents a carboxyl group which is optionally esterified or amidated, or a hydroquinone form, or a pharmaceutically acceptable salt thereof, and a pharmaceutically acceptable carrier therefor.

11. The substituted benzoic acid derivative according to claim 1, wherein the optionally substituted substituents of $R^2$ are optionally substituted with a substituent selected from the group consisting of an aryl group, a heteroaryl group, a hydroxy group, an alkoxy group, an acyloxy group, a carboxyl group, an alkoxycarbonyl group, an aryloxycarbonyl group, an optionally substituted carbamoyl group, an optionally substituted amino group, a cyano group and a halogen atom.

12. A substituted benzoic acid derivative selected from the group consisting of:

4-(3,4,5,6-tetramethoxy-2-methylbenzyl)-2-benzyloxybenzoic acid, 6-(3,4,5,6-tetramethoxy-2-methylbenzyl)-2-benzyloxybenzoic acid, 5-(3,4,5,6-tetramethoxy-2-methylbenzyl)-2-benzyloxybenzoic acid, 3-(3,4,5,6-tetramethoxy-2-methylbenzyl)-2-benzyloxybenzoic acid, N-[4-(3,4,5,6-tetramethoxy-2-methylbenzyl)-2-benzyloxybenzoyl]piperidine, N-[5-(3,4,5,6-tetramethoxy-2-methylbenzyl)-2-benzyloxybenzoyl]piperidine, N-[5-(3,4,5,6-tetramethoxy-2-methylbenzyl)-2-benzyloxybenzoyl]morpholine, N-[5-(3,4,5,6-tetramethoxy-2-methylbenzyl)-2-benzyloxybenzoyl]-4-methoxyaniline, 4-(3,4,5,6-tetramethoxy-2-methylbenzyl)-2-hydroxybenzoic acid, 5-(3,4,5,6-tetramethoxy-2-methylbenzyl)-2-hydroxybenzoic acid, 3-(3,4,5,6-tetramethoxy-2-methylbenzyl)-2-hydroxybenzoic acid, 4-(3,4,5,6-tetramethoxy-2-methylbenzyl)-2-acetoxybenzoic acid,
5-(3,4,5,6-tetramethoxy-2-methylbenzyl)-2-acetoxybenzoic acid,
3-(3,4,5,6-tetramethoxy-2-methylbenzyl)-2-acetoxybenzoic acid,
methyl 5-(3,4,5,6-tetramethoxy-2-methylbenzyl)-2-hydroxybenzoate,
5-(3,4,5,6-tetramethoxy-2-methylbenzyl)-2-methoxybenzoic acid,
5-(3,4,5,6-tetramethoxy-2-methylbenzyl)-2-isopropoxybenzoic acid,
methyl 5-(3,4,5,6-tetramethoxy-2-methylbenzyl)-2-phenoxybenzoate,
methyl 5-(3,4,5,6-tetramethoxy-2-methylbenzyl)-2-(3-methoxyphenoxy)benzoate,
methyl 5-(3,4,5,6-tetramethoxy-2-methylbenzyl)-2-(3-pyridylmethyloxy)benzoate,
methyl 5-(3,4,5,6-tetramethoxy-2-methylbenzyl)-2-(4-pyridylmethyloxy)benzoate,
methyl 5-(3,4,5,6-tetramethoxy-2-methylbenzyl)-2-(tert-butoxycarbonylmethyloxy)benzoate,
5-(3,4,5,6-tetramethoxy-2-methylbenzyl)-2-phenoxybenzoic acid,
5-(3,4,5,6-tetramethoxy-2-methylbenzyl)-2-(3-methoxyphenoxy)benzoic acid,
5-(3,4,5,6-tetramethoxy-2-methylbenzyl)-2-(3-pyridylmethyloxy)benzoic acid,
5-(3,4,5,6-tetramethoxy-2-methylbenzyl)-2-(3-pyridylmethyloxy)benzoic acid,
N-[5-(3,4,5,6-tetramethoxy-2-methylbenzyl)-2-hydroxybenzoyl]piperidine,
N-[5-(3,4,5,6-tetramethoxy-2-methylbenzyl)-2-hydroxybenzoyl]morpholine,
N-[5-(3,4,5,6-tetramethoxy-2-methylbenzyl)-2-(3-pyridylmethyloxy)benzoyl]piperidine,
N-[5-(3,4,5,6-tetramethoxy-2-methylbenzyl)-2-(4-pyridylmethyloxy)benzoyl]piperidine,
N-[5-(3,4,5,6-tetramethoxy-2-methylbenzyl)-2-(3-pyridyloxy)benzoyl]piperidine,
N-[5-(3,4,5,6-tetramethoxy-2-methylbenzyl)-2-(4-pyridyloxy)benzoyl]piperidine,
N-[5-(3,4,5,6-tetramethoxy-2-methylbenzyl)-2-(methoxycarbonylmethyloxy)benzoyl]piperidine,
N-[5-(3,4,5,6-tetramethoxy-2-methylbenzyl)-2-(3-tert-butoxycarbonylmethyloxy)benzoyl]piperidine.
N-[5-(3,4,5,6-tetramethoxy-2-methylbenzyl)-2-(3-pyridylmethyloxy)benzoyl]morpholine,
N-[5-(3,4,5,6-tetramethoxy-2-methylbenzyl)-2-(4-(pyridylmethyloxy)benzoyl]morpholine.
N-[5-(3,4,5,6-tetramethoxy-2-methylbenzyl)-2-(3-pyridyloxy)benzoyl]morpholine,
N-[5-(3,4,5,6-tetramethoxy-2-methylbenzyl)-2-(4-pyridyloxy)benzoyl]morpholine,
N-[5-(3,4,5,6-tetramethoxy-2-methylbenzyl)-2-(methoxycarbonylmethyloxy)benzoyl]morpholine,
N-[5-(3,4,5,6-tetramethoxy-2-methylbenzyl)-2-(tert-butoxycarbonylmethyloxy)benzoyl]morpholine,
4-(5,6-dimethoxy-3-methyl-1,4-benzoquinon-2-yl)methyl-2-benzyloxybenzoic acid,
6-(5,6-dimethoxy-3-methyl-1,4-benzoquinon-2-yl)methyl-2-benzyloxybenzoic acid,
5-(5,6-dimethoxy-3-methyl-1,4-benzoquinon-2-yl)methyl-2-benzyloxybenzoic acid,
3-(5,6-dimethoxy-3-methyl-1,4-benzoquinon-2-yl)methyl-2-benzyloxybenzoic acid,
4-(5,6-dimethoxy-3-methyl-1,4-benzoquinon-2-yl)methyl-2-acetoxybenzoic acid,
5-(5,6-dimethoxy-3-methyl-1,4-benzoquinon-2-yl)methyl-2-acetoxybenzoic acid,
3-(5,6-dimethoxy-3-methyl-1,4-benzoquinon-2-yl)methyl-2-acetoxybenzoic acid,
4-(5,6-dimethoxy-3-methyl-1,4-benzoquinon-2-yl)methyl-2-hydroxybenzoic acid,
5-(5,6-dimethoxy-3-methyl-1,4-benzoquinon-2-yl)methyl-2-hydroxybenzoic acid,
3-(5,6-dimethoxy-3-methyl-1,4-benzoquinon-2-yl)methyl-2-hydroxybenzoic acid,
5-(5,6-dimethoxy-3-methyl-1,4-benzoquinon-2-yl)methyl-2-methoxybenzoic acid,
5-(5,6-dimethoxy-3-methyl-1,4-benzoquinon-2-yl)methyl-2-isopropoxybenzoic acid,
5-(5,6-dimethoxy-3-methyl-1,4-benzoquinon-2-yl)methyl-2-phenoxybenzoic acid,
5-(5,6-dimethoxy-3-methyl-1,4-benzoquinon-2-yl)methyl-2-(3-methoxyphenoxy)benzoic acid,
5-(5,6-dimethoxy-3-methyl-1,4-benzoquinon-2-yl)methyl-2-(3-pyridylmethyloxy)benzoic acid,
5-(5,6-dimethoxy-3-methyl-1,4-benzoquinon-2-yl)methyl-2-(4-pyridylmethyloxy)benzoic acid,
N-[4-(5,6-dimethoxy-3-methyl-1,4-benzoquinon-2-yl)methyl-2-benzyloxybenzoyl]piperidine,
N-[4-(5,6-dimethoxy-3-methyl-1,4-benzoquinon-2-yl)methyl-2-benzyloxybenzoyl]morpholine,
N-[4-(5,6-dimethoxy-3-methyl-1,4-benzoquinon-2-yl)methyl-2-benzyloxybenzoyl]-4-methoxyaniline,
N-[6-(5,6-dimethoxy-3-methyl-1,4-benzoquinon-2-yl)methyl-2-benzyloxybenzoyl]-4-methoxyaniline,
N-[5-(5,6-dimethoxy-3-methyl-1,4-benzoquinon-2-yl)methyl-2-benzyloxybenzoyl]piperidine,
N-[5-(5,6-dimethoxy-3-methyl-1,4-benzoquinon-2-yl)methyl-2-benzyloxybenzoyl]morpholine,
N-[5-(5,6-dimethoxy-3-methyl-1,4-benzoquinon-2-yl)methyl-2-benzyloxybenzoyl]-4-methoxyaniline,
N-[3-(5,6-dimethoxy-3-methyl-1,4-benzoquinon-2-yl)methyl-2-benzyloxybenzoyl]piperidine,
N-[3-(5,6-dimethoxy-3-methyl-1,4-benzoquinon-2-yl)methyl-2-benzyloxybenzoyl]morpholine,
N-[3-(5,6-dimethoxy-3-methyl-1,4-benzoquinon-2-yl)methyl-2-benzyloxybenzoyl]-4-methoxyaniline,
N-[4-(5,6-dimethoxy-3-methyl-1,4-benzoquinon-2-yl)methyl-2-acetoxybenzoyl]-4-methoxyaniline,
N-[5-(5,6-dimethoxy-3-methyl-1,4-benzoquinon-2-yl)methyl-2-acetoxybenzoyl]piperidine,
N-[5-(5,6-dimethoxy-3-methyl-1,4-benzoquinon-2-yl)methyl-2-acetoxybenzoyl]morpholine,
N-[5-(5,6-dimethoxy-3-methyl-1,4-benzoquinon-2-yl)methyl-2-acetoxybenzoyl]-4-methoxyaniline,
N-[3-(5,6-dimethoxy-3-methyl-1,4-benzoquinon-2-yl)methyl-2-acetoxybenzoyl]piperidine,
N-[3-(5,6-dimethoxy-3-methyl-1 4-benzoquinon-2-yl)methyl-2-acetoxybenzoyl]morpholine,
N-[3-(5,6-dimethoxy-3-methyl-1,4-benzoquinon-2-yl)methyl-2-acetoxybenzoyl]-4-methoxyaniline,
N-[5-(5,6-dimethoxy-3-methyl-1,4-benzoquinon-2-yl)methyl-2-hydroxybenzoyl]piperidine,
N-[5-(5,6-dimethoxy-3-methyl-1,4-benzoquinon-2-yl)methyl-2-hydroxybenzoyl]morpholine, N-[5-(5,6-dimethoxy-3-methyl-1,4-benzoquinon-2-yl)methyl-2-hydroxybenzoyl]-4-methoxyaniline,
N-[3-(5,6-dimethoxy-3-methyl-1,4-benzoquinon-2-yl)methyl-2-hydroxybenzoyl]piperidine,
N-[3-(5,6-dimethoxy-3-methyl-1,4-benzoquinon-2-yl)methyl-2-hydroxybenzoyl]morpholine,
N-[3-(5,6-dimethoxy-3-methyl-1,4-benzoquinon-2-yl)methyl-2-hydroxybenzoyl]-4-methoxyaniline,
N-[5-(5,6-dimethoxy-3-methyl-1,4-benzoquinon-2-yl)methyl-2-methoxybenzoyl]piperidine,
N-[5-(5,6-dimethoxy-3-methyl-1,4-benzoquinon-2-yl)methyl-2-methoxybenzoyl]morpholine,
N-[5-(5,6-dimethoxy-3-methyl-1,4-benzoquinon-2-yl)methyl-2-methoxybenzoyl]-4-methoxyaniline,
N-[5-(5,6-dimethoxy-3-methyl-1,4-benzoquinon-2-yl)methyl-2-isopropoxybenzoyl]piperidine,
N-[5-(5,6-dimethoxy-3-methyl-1,4-benzoquinon-2-yl)methyl-2-isopropoxybenzoyl]morpholine,
N-[5-(5,6-dimethoxy-3-methyl-1,4-benzoquinon-2-yl)methyl-2-isopropoxybenzoyl]-4-methoxyaniline,
N-[5-(5,6-dimethoxy-3-methyl-1,4-benzoquinon-2-yl)methyl-2-phenoxybenzoyl]piperidine,
N-[5-(5,6-dimethoxy-3-methyl-1,4-benzoquinon-2-yl)methyl-2-phenoxybenzoyl]morpholine,
N-[5-(5,6-dimethoxy-3-methyl-1,4-benzoquinon-2-yl)methyl-2-phenoxybenzoyl]-4-methoxyaniline,
N-[5-(5,6-dimethoxy-3-methyl-1,4-benzoquinon-2-yl)methyl-2-(3-methoxyphenoxy)benzoyl]piperidine,
N-[5-(5,6-dimethoxy-3-methyl-1,4-benzoquinon-2-yl)methyl-2-(3-methoxyphenoxy)benzoyl]morpholine,
N-[5-(5,6-dimethoxy-3-methyl-1,4-benzoquinon-2-yl)methyl-2-(3-methoxyphenoxy)benzoyl]-4-methoxyaniline,
N-[5-(5,6-dimethoxy-3-methyl-1,4-benzoquinon-2-yl)methyl-2-(3-pyridylmethyloxy)benzoyl]piperidine,
N-[5-(5,6-dimethoxy-3-methyl-1,4-benzoquinon-2-yl)methyl-2-(3-pyridylmethyloxy)benzoyl]morpholine,
N-[5-(5,6-dimethoxy-3-methyl-1,4-benzoquinon-2-yl)methyl-2-(3-pyridylmethyloxy)benzoyl]-4-methoxyaniline,
N-[5-(5,6-dimethoxy-3-methyl-1,4-benzoquinon-2-yl)methyl-2-(4-pyridylmethyloxy)benzoyl]piperidine,
N-[5-(5,6-dimethoxy-3-methyl-1,4-benzoquinon-2-yl)methyl-2-(4-pyridylmethyloxy)benzoyl]morpholine,
N-[5-(5,6-dimethoxy-3-methyl-1,4-benzoquinon-2-yl)methyl-2-(4-pyridylmethyloxy)benzoyl]-4-methoxyaniline,
N-[5-(5,6-dimethoxy-3-methyl-1,4-benzoquinon-2-yl)methyl-2-(3-pyridyloxy)benzoyl]piperidine,
N-[5-(5,6-dimethoxy-3-methyl-1,4-benzoquinon-2-yl)methyl-2-(3-pyridyloxy)benzoyl]morpholine,
N-[5-(5,6-dimethoxy-3-methyl-1,4-benzoquinon-2-yl)methyl-2-(4-pyridyloxy)benzoyl]piperidine,
N-[5-(5,6-dimethoxy-3-methyl-1,4-benzoquinon-2-yl)methyl-2-(4-pyridyloxy)benzoyl]morpholine,
N-[5-(5,6-dimethoxy-3-methyl-1,4-benzoquinon-2-yl)methyl-2-(methoxycarbonylmethyloxy)benzoyl]piperidine,
N-[5-(5,6-dimethoxy-3-methyl-1,4-benzoquinon-2-yl)methyl-2-(methoxycarbonylmethyloxy)benzoyl]morpholine,
N-[5-(5,6-dimethoxy-3-methyl-1,4-benzoquinon-2-yl)methyl-2-(tert-butoxycarbonylmethyloxy)benzoyl]piperidine,
N-[5-(5,6-dimethoxy-3-methyl-1,4-benzoquinon-2-yl)methyl-2-(tert-butoxycarbonylmethyloxy)benzoyl]morpholine,
N-[5-(5,6-dimethoxy-3-methyl-1,4-benzoquinon-2-yl)methyl-2-acetoxybenzoyl]-3,4-dimethoxyaniline,
N-[5-(5,6-dimethoxy-3-methyl-1,4-benzoquinon-2-yl)methyl-2-acetoxybenzoyl]-3,4,5-trimethoxyaniline,
N-[5-(5,6-dimethoxy-3-methyl-1,4-benzoquinon-2-yl)methyl-2-acetoxybenzoyl]-4-acetylaniline,
N-[5-(5,6-dimethoxy-3-methyl-1,4-benzoquinon-2-yl)methyl-2-acetoxybenzoyl]-4-chloroaniline,
N-[5-(5,6-dimethoxy-3-methyl-1,4-benzoquinon-2-yl)methyl-2-acetoxybenzoyl]-4-morpholinoaniline,
N-[5-(5,6-dimethoxy-3-methyl-1,4-benzoquinon-2-yl)methyl-2-acetoxybenzoyl]-4-cyanoaniline,
N-[5-(5,6-dimethoxy-3-methyl-1,4-benzoquinon-2-yl)methyl-2-acetoxybenzoyl]-4-trifluoromethylaniline,
N-[5-(5,6-dimethoxy-3-methyl-1,4-benzoquinon-2-yl)methyl-2-acetoxybenzoyl]-3,5-bistrifluoromethylaniline,
N-[5-(5,6-dimethoxy-3-methyl-1,4-benzoquinon-2-yl)methyl-2-hydroxybenzoyl]-3,4-dimethoxyaniline,
N-[5-(5,6-dimethoxy-3-methyl-1,4-benzoquinon-2-yl)methyl-2-hydroxybenzoyl]-3,4,5-trimethoxyaniline,
N-[5-(5,6-dimethoxy-3-methyl-1,4-benzoquinon-2-yl)methyl-2-hydroxybenzoyl]-4-acetylaniline,
N-[5-(5,6-dimethoxy-3-methyl-1,4-benzoquinon-2-yl)methyl-2-hydroxybenzoyl]-4-chloroaniline,
N-[5-(5,6-dimethoxy-3-methyl-1,4-benzoquinon-2-yl)methyl-2-hydroxybenzoyl]-4-morpholinoaniline,
N-[5-(5,6-dimethoxy-3-methyl-1,4-benzoquinon-2-yl)methyl-2-hydroxybenzoyl]-4-cyanoaniline,
N-[5-(5,6-dimethoxy-3-methyl-1,4-benzoquinon-2-yl)methyl-2-hydroxybenzoyl]-4-trifluoromethylaniline,
N-[5-(5,6-dimethoxy-3-methyl-1,4-benzoquinon-2-yl)methyl-2-hydroxybenzoyl]-3,5-bistrifluoromethylaniline,
N-[5-(5,6-dimethoxy-3-methyl-1,4-benzoquinon-2-yl)methyl-2-hydroxybenzoyl]-(S)-1-phenylethylamine,
N-[5-(5,6-dimethoxy-3-methyl-1,4-benzoquinon-2-yl)methyl-2-hydroxybenzoyl]-(R)-1-phenylethylamine,
N-[5-(5,6-dimethoxy-3-methyl-1,4-benzoquinon-2-yl)methyl-2-phenoxybenzoyl]-1,2,3,4-tetrahydroquinoline,
N-[5-(5,6-dimethoxy-3-methyl-1,4-benzoquinon-2-yl)methyl-2-phenoxybenzoyl]-2-methylpiperidine,
N-[5-(5,6-dimethoxy-3-methyl-1,4-benzoquinon-2-yl)methyl-2-(3-pyridylmethyloxy)benzoyl]-1,2,3,4-tetrahydroquinoline,
N-[5-(5,6-dimethoxy-3-methyl-1,4-benzoquinon-2-yl)methyl-2-(3-pyridylmethyloxy)benzoyl]-4-methylpiperidine,
N-[5-(5,6-dimethoxy-3-methyl-1,4-benzoquinon-2-yl)methyl-2-(3-pyridylmethyloxy)benzoyl]-3,4,5-trimethoxyaniline,
N-[5-(5,6-dimethoxy-3-methyl-1,4-benzoquinon-2-yl)methyl-2-(3-pyridylmethyloxy)benzoyl]-4-acetylaniline,
methyl 5-(5,6-dimethoxy-3-methyl-1,4-benzoquinon-2-yl)methyl-2-(tert-butoxycarbonylmethyloxy)benzoate,
N-(6-chloropyridin-3-yl)-4-(5,6-dimethoxy-3-methyl-1,4-benzoquinon-2-yl)methyl-2-hydroxybenzamide,
N-(2-chloropyridin-3-yl)-4-(5,6-dimethoxy-3-methyl-1,4-benzoquinon-2-yl)methyl-2-acetoxybenzamide,
N-(2-chloropyridin-3-yl)-4-(5,6-dimethoxy-3-methyl-1,4-benzoquinon-2-yl)methyl-2-hydroxybenzamide,
N-(6-methoxypyridin-3-yl)-4-(5,6-dimethoxy-3-methyl-1,4-benzoquinon-2-yl)methyl-2-acetoxybenzamide, N-(6-methoxypyridin-3-yl)-4-(5,6-dimethoxy-3-methyl-1,4-benzoquinon-2-yl)methyl-2-hydroxybenzamide,
N-[4-(5,6-dimethoxy-3-methyl-1,4-benzoquinon-2-yl)methyl-2-acetoxybenzoyl]-4-(trifluoromethylsulfonyl)aniline,
N-[4-(5,6-dimethoxy-3-methyl-1,4-benzoquinon-2-yl)methyl-2-hydroxybenzoyl]-4-(trifluoromethylsulfonyl)aniline,
N-(pyridin-3-yl)-4-(5,6-dimethoxy-3-methyl-1,4-benzoquinon-2-yl)methyl-2-acetoxybenzamide,
N-(pyridin-3-yl)-4-(5,6-dimethoxy-3-methyl-1,4-benzoquinon-2-yl)methyl-2-hydroxybenzamide,
N-(pyridin-4-yl)-4-(5,6-dimethoxy-3-methyl-1,4-benzoquinon-2-yl)methyl-2-hydroxybenzamide,
N-[5-(5,6-dimethoxy-3-methyl-1,4-benzoquinon-2-yl)methyl-2-acetoxybenzoyl]-4-fluoroaniline,
N-[5-(5,6-dimethoxy-3-methyl-1,4-benzoquinon-2-yl)methyl-2-hydroxybenzoyl]-4-fluoroaniline,
N-[5-(5,6-dimethoxy-3-methyl-1,4-benzoquinon-2-yl)methyl-2-acetoxybenzoyl]-3-nitroaniline,
N-[5-(5,6-dimethoxy-3-methyl-1,4-benzoquinon-2-yl)methyl-2hydroxybenzoyl]-3-nitroaniline,
N-[5-(5,6-dimethoxy-3-methyl-1,4-benzoquinon-2-yl)methyl-2-acetoxybenzoyl]-2-trifluoromethylaniline,
N-[5-(5,6-dimethoxy-3-methyl-1,4-benzoquinon-2-yl)methyl-2-hydroxybenzoyl]-2-trifluoromethylaniline,
ethyl N-[5-(5,6-dimethoxy-3-methyl-1,4-benzoquinon-2-yl)methyl-2-acetoxybenzoyl]-4-aminobenzoate,
ethyl N-[5-(5 6-dimethoxy-3-methyl-1,4-benzoquinon-2-yl)methyl-2-hydroxybenzoyl]-4-aminobenzoate,
N-[5-(5,6-dimethoxy-3-methyl-1,4-benzoquinon-2-yl)methyl-2-acetoxybenzoyl]-4-cyanomethylaniline,
N-[5-(5,6-dimethoxy-3-methyl-1,4-benzoquinon-2-yl)methyl-2-hydroxybenzoyl]-4-cyanomethylaniline,
N-[5-(5,6-dimethoxy-3-methyl-1,4-benzoquinon-2-yl)methyl-2-acetoxybenzoyl]-3-trifluoromethylaniline,
N-[5-(5,6-dimethoxy-3-methyl-1,4-benzoquinon-2-yl)methyl-2-hydroxybenzoyl]-3-trifluoromethylaniline,
N-[5-(5,6-dimethoxy-3-methyl-1,4-benzoquinon-2-yl)methyl-2-acetoxybenzoyl]-2-nitroaniline,
N-[5-(5,6-dimethoxy-3-methyl-1,4-benzoquinon-2-yl)methyl-2-hydroxybenzoyl]-2-nitroaniline,
N-(pyridin-2-yl)-5-(5,6-dimethoxy-3-methyl-1,4-benzoquinon-2-yl)methyl-2-acetoxybenzamide,
N-(pyridin-2-yl)-5-(5,6-dimethoxy-3-methyl-1,4-benzoquinon-2-yl)methyl-2-hydroxybenzamide,
N-(pyridin-4-yl)-5-(5,6-dimethoxy-3-methyl-1,4-benzoquinon-2-yl)methyl-2-hydroxybenzamide,
N-(pyridin-3-yl)-5-(5,6-dimethoxy-3-methyl-1,4-benzoquinon-2-yl)methyl-2-hydroxybenzamide,
N-cyclopropyl-5-(5,6-dimethoxy-3-methyl-1,4-benzoquinon-2-yl)methyl-2-acetoxybenzamide,
N-cyclopropyl-5-(5,6-dimethoxy-3-methyl-1,4-benzoquinon-2-yl)methyl-2-hydroxybenzamide,
N-cyclohexyl-5-(5,6-dimethoxy-3-methyl-1,4-benzoquinon-2-yl)methyl-2-acetoxybenzamide
N-cyclohexyl-5-(5,6-dimethoxy-3-methyl-1,4-benzoquinon-2-yl)methyl-2-hydroxybenzamide
N-methyl-N-[5-(5,6-dimethoxy-3-methyl-1,4-benzoquinon-2-yl)methyl-2-acetoxybenzoyl]-4-methoxyaniline,
N-methyl-N-[5-(5,6-dimethoxy-3-methyl-1,4-benzoquinon-2-yl)methyl-2-hydroxybenzoyl]-4-methoxyaniline,
N-[3-(5,6-dimethoxy-3-methyl-1,4-benzoquinon-2-yl)methyl-2-acetoxybenzoyl]-4-trifluoromethylaniline,
N-[3-(5,6-dimethoxy-3-methyl-1,4-benzoquinon-2-yl)methyl-2-hydroxybenzoyl]-4-trifluoromethylaniline,
ethyl N-[5-(5,6-dimethoxy-3-methyl-1,4-benzoquinon-2-yl)methyl-2-(3-pyridyimethyloxy)benzoyl]-4-aminobenzoate,
N-(pyridin-4-yl)-5-(5,6-dimethoxy-3-methyl-1,4-benzoquinon-2-yl)methyl-2-(3-pyridylmethyloxy)benzamide,
N-(pyridin-3-yl)-5-(5,6-dimethoxy-3-methyl-1,4-benzoquinon-2-yl)methyl-2-(3-pyridylmethyloxy)benzamide,
N-cyclopropyl-5-(5,6-dimethoxy-3-methyl-1,4-benzoquinon-2-yl)methyl-2-(3-pyridylmethyloxy)benzamide,
N-cyclohexyl-5-(5,6-dimethoxy-3-methyl-1,4-benzoquinon-2-yl)methyl-2-(3-pyridyimethyloxy)benzamide,
N-[5-(5,6-dimethoxy-3-methyl-1,4-benzoquinon-2-yl)methyl-2-(3-pyridyimethyloxy)benzoyl]-4-trifluoromethylaniline,
N-[5-(5,6-dimethoxy-3-methyl-1,4-benzoquinon-2-yl)methyl-2-acetoxybenzoyl]-4-(trifluoromethylsulfonyl)aniline,
N-[5-(5,6-dimethoxy-3-methyl-1,4-benzoquinon-2-yl)methyl-2-hydroxybenzoyl]-4-(trifluoromethylsulfonyl)aniline,
N-[3-(5,6-dimethoxy-3-methyl-1,4-benzoquinon-2-yl)methyl-2-acetoxybenzoyl]-4-(trifluoromethylsulfonyl)aniline,
N-[3-(5,6-dimethoxy-3-methyl-1,4-benzoquinon-2-yl)methyl-2-acetoxybenzoyl]-2,4-dichloroaniline,
N-[3-(5,6-dimethoxy-3-methyl-1,4-benzoquinon-2-yl)methyl-2-hydroxybenzoyl]-2,4-dichloroaniline,
N-[3-(5,6-dimethoxy-3-methyl-1,4-benzoquinon-2-yl)methyl-2-acetoxybenzoyl]-4-morpholinoaniline,
N-[3-(5,6-dimethoxy-3-methyl-1,4-benzoquinon-2-yl)methyl-2-hydroxybenzoyl]-4-morpholinoaniline,
N-(6-methoxypyridin-3-yl)-5-(5,6-dimethoxy-3-methyl-1,4-benzoquinon-2-yl)methyl-2-acetoxybenzamide,
N-(6-methoxypyridin-3-yl)-5-(5,6-dimethoxy-3-methyl-1,4-benzoquinon-2-yl)methyl-2-hydroxybenzamide,
N-(2,6-dimethoxypyridin-3-yl)-5-(5,6-dimethoxy-3-methyl-1,4-benzoquinon-2-yl)methyl-2-acetoxybenzamide,
N-(2,6-dimethoxypyridin-3-yl)-5-(5,6-dimethoxy-3-methyl-1,4-benzoquinon-2-yl)methyl-2-hydroxybenzamide,
N-(6-chloropyridin-3-yl)-5-(5,6-dimethoxy-3-methyl-1,4-benzoquinon-2-yl)methyl-2-acetoxybenzamide,
N-(6-chloropyridin-3-yl)-5-(5,6-dimethoxy-3-methyl-1,4-benzoquinon-2-yl)methyl-2-hydroxybenzamide,
N-(2-chloropyridin-3-yl)-5-(5,6-dimethoxy-3-methyl-1,4-benzoquinon-2-yl)methyl-2-acetoxybenzamide,
N-(2-chloropyridin-3-yl)-5-(5,6-dimethoxy-3-methyl-1,4-benzoquinon-2-yl)methyl-2-hydroxybenzamide,
tert-butyl N-[5-(5,6-dimethoxy-3-methyl-1,4-benzoquinon-2-yl)methyl-2-acetoxybenzoyl]-4-aminobenzoate,
N-[5-(5,6-dimethoxy-3-methyl-1,4-benzoquinon-2-yl)methyl-2-acetoxybenzoyl]-4-aminobenzoic acid,
N-[5-(5,6-dimethoxy-3-methyl-1,4-benzoquinon-2-yl)methyl-2-hydroxybenzoyl]-4-aminobenzoic acid,
N-[5-(5,6-dimethoxy-3-methyl-1,4-benzoquinon-2-yl)methyl-2-hydroxybenzoyl]-4-nitroaniline,
N-[5-(5,6-dimethoxy-3-methyl-1,4-benzoquinon-2-yl)methyl-2-hydroxybenzoyl]-2,6-dichloro-4-trifluoromethoxyaniline, N-(3-tert-butoxycarbonylpyridin-2-yl)-5-(5,6-dimethoxy-3-methyl-1,4-benzoquinon-2-yl)methyl-2-acetoxybenzamide, N-(3-hydroxycarbonylpyridin-2-yl)-5-(5,6-dimethoxy-3-methyl-1,4-benzoquinon-2-yl)methyl-2-acetoxybenzamide, N-(3-hydroxycarbonylpyridin-2-yl)-5-(5,6-dimethoxy-3-methyl-1,4-benzoquinon-2-yl)methyl-2-hydroxybenzamide, N-(5-tert-butoxycarbonylpyridin-2-yl)-5-(5,6-dimethoxy-3-methyl-1,4-benzoquinon-2-yl)methyl-2-acetoxybenzamide, N-(5-hydroxycarbonylpyridin-2-yl)-5-(5,6-dimethoxy-3-methyl-1,4-benzoquinon-2-yl)methyl-2-acetoxybenzamide, N-(5-hydroxycarbonylpyridin-2-yl)-5-(5,6-dimethoxy-3-methyl-1,4-benzoquinon-2-yl)methyl-2-hydroxybenzamide, N-[5-(5,6-dimethoxy-3-methyl-1,4-benzoquinon-2-yl)methyl-2-acetoxybenzoyl]-4-tert-butoxycarbonylaminoaniline, N-[5-(5,6-dimethoxy-3-methyl-1,4-benzoquinon-2-yl)methyl-2-hydroxybenzoyl]-4-tert-butoxycarbonylaminoaniline, N-(pyridin-3-yl)-5-(5,6-dimethoxy-3-methyl-1,4-benzoquinon-2-yl)methyl-2-acetoxybenzamide, N-(pyridin-3-yl)-5-(5,6-dimethoxy-3-methyl-1,4-benzoquinon-2-yl)methyl-2-hydroxybenzamide (methanesulfonate), N-(pyridin-4-yl)-5-(5,6-dimethoxy-3-methyl-1,4-benzoquinon-2-yl)methyl-2-hydroxybenzamide (methanesulfonate), N-[5-(5,6-dimethoxy-3-methyl-1,4-benzoquinon-2-yl)methyl-2-hydroxybenzoyl]-p-phenylenediamine, N-[5-(5,6-dimethoxy-3-methyl-1,4-benzoquinon-2-yl)methyl-2-hydroxybenzoyl]-p-phenylenediamine (hydrochloride), N-(pyridin-3-yl)-3-(5,6-dimethoxy-3-methyl-1,4-benzoquinon-2-yl)methyl-2-acetoxybenzamide, N-(pyridin-3-yl)-3-(5,6-dimethoxy-3-methyl-1,4-benzoquinon-2-yl)methyl-2-hydroxybenzamide, N-[5-(5,6-dimethoxy-3-methyl-1,4-benzoquinon-2-yl)methyl-2-acetoxybenzoyl]-4-(imidazol-1-yl)aniline, N-[5-(5,6-dimethoxy-3-methyl-1,4-benzoquinon-2-yl)methyl-2-hydroxybenzoyl]-4-(imidazol-1-yl)aniline, N-[5-(5,6-dimethoxy-3-methyl-1,4-benzoquinon-2-yl)methyl-2-acetoxybenzoyl]-4-(1H-pyrazol-3-yl)aniline, N-(5-(5,6-dimethoxy-3-methyl-1,4-benzoquinon-2-yl)methyl-2-hydroxybenzoyl]-4-(1H-pyrazol-3-yl)aniline, N-methyl-N-[5-(5,6-dimethoxy-3-methyl-1,4-benzoquinon-2-yl)methyl-2-acetoxybenzoyl]-4-trifluoromethylaniline, N-methyl-N-[5-(5,6-dimethoxy-3-methyl-1,4-benzoquinon-2-yl)methyl-2-hydroxybenzoyl]-4-trifluoromethylaniline, t-butyl N-[5-(5,6-dimethoxy-3-methyl-1,4-benzoquinon-2-yl)methyl-2-hydroxybenzoyl]-4-aminobenzoate, N-(2-methoxypyridin-3-yl)-5-(5,6-dimethoxy-3-methyl-1,4-benzoquinon-2-yl)methyl-2-acetoxybenzamide, N-(2-methoxypyridin-3-yl)-5-(5,6-dimethoxy-3-methyl-1,4-benzoquinon-2-yl)methyl-2-hydroxybezamide, N-(2-dimethylaminopyridin-3-yl)-5-(5,6-dimethoxy-3-methyl-1,4-benzoquinon-2-yl)methyl-2-acetoxybenzamide, N-(2-dimethylaminopyridin-3-yl)-5-(5,6-dimethoxy-3-methyl-1,4-benzoquinon-2-yl)methyl-2-hydroxybezamide, N-(5-(5,6-dimethoxy-3-methyl-1,4-benzoquinon-2-yl)methyl-2-acetoxybenzoyl]-2,5-dimethoxyaniline, N-[5-(5,6-dimethoxy-3-methyl-1,4-benzoquinon-2-yl)methyl-2-hydroxybenzoyl]-2,5-dimethoxyaniline, N-(2-chloropyridin-3-yl)-5-(5,6-dimethoxy-3-methyl-1,4-benzoquinon-2-yl)methyl-2-methoxybenzamide, N-(2-morpholinopyridin-3-yl)-5-(5,6-dimethoxy-3-methyl-1,4-benzoquinon-2-yl)methyl-2-acetoxybenzamide, N-(2-morpholinopyridin-3-yl)-5-(5,6-dimethoxy-3-methyl-1,4-benzoquinon-2-yl)methyl-2-hydroxybenzamide, N-(6-morpholinopyridin-3-yl)-5-(5,6-dimethoxy-3-methyl-1,4-benzoquinon-2-yl)methyl-2-acetoxybenzamide, N-(6-morpholinopyridin-3-yl)-5-(5,6-dimethoxy-3-methyl-1,4-benzoquinon-2-yl)methyl-2-hydroxybenzamide, N-(2-chloropyridin-4-yl)-5-(5,6-dimethoxy-3-methyl-1,4-benzoquinon-2-yl)methyl-2-acetoxybenzamide, N-(2-chloropyridin-4-yl)-5-(5,6-dimethoxy-3-methyl-1,4-benzoquinon-2-yl)methyl-2-hydroxybenzamide, N-(6-methoxypyrimidin-4-yl)-5-(5,6-dimethoxy-3-methyl-1,4-benzoquinon-2-yl)methyl-2-acetoxybenzamide, N-(6-methoxypyrimidin-4-yl)-5-(5,6-dimethoxy-3-methyl-1,4-benzoquinon-2-yl)methyl-2-hydroxybenzamide, N-(2-methoxypyridin-4-yl)-5-(5,6-dimethoxy-3-methyl-1,4-benzoquinon-2-yl)methyl-2-acetoxybenzamide, N-(2-methoxypyridin-4-yl)-5-(5,6-dimethoxy-3-methyl-1,4-benzoquinon-2-yl)methyl-2-hydroxybenzamide, 5-(2,5-dimethoxy-3,4,6-trimethylbenzyl)-2-acetoxybenzoic acid, 5-(3,5,6-trimethyl-1,4-benzoquinon-2-yl)methyl-2-acetoxybenzoic acid, N-[5-(3,5,6-trimethyl-1,4-benzoquinon-2-yl)methyl-2-acetoxybenzoyl]-4-trifluoromethylaniline, N-[5-(3,5,6-trimethyl-1,4-benzoquinon-2-yl)methyl-2-hydroxybenzoyl]-4-trifluoromethylaniline, N-(2-chloropyridin-3-yl)-5-(3,5,6-trimethyl-1,4-benzoquinon-2-yl)methyl-2-acetoxybenzamide, N-(2-chloropyridin-3-yl)-5-(3,5,6-trimethyl-1,4-benzoquinon-2-yl)methyl-2-hydroxybenzamide, N-(pyridin-4-yl)-5-(3,5,6-trimethyl-1,4-benzoquinon-2-yl)methyl-2-hydroxybenzamide.

* * * * *